US012698493B2

(12) United States Patent
Kurakata et al.

(10) Patent No.: US 12,698,493 B2
(45) Date of Patent: Aug. 4, 2026

(54) GLUCOAMYLASE VARIANTS AND POLYNUCLEOTIDES ENCODING SAME

(71) Applicant: Novozymes A/S, Bagsvaerd (DK)

(72) Inventors: Yuma Kurakata, Chiba (JP); Aki Tomiki-Hashizume, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 487 days.

(21) Appl. No.: 18/250,372

(22) PCT Filed: Nov. 2, 2021

(86) PCT No.: PCT/EP2021/080338

§ 371 (c)(1),
(2) Date: Apr. 25, 2023

(87) PCT Pub. No.: WO2022/090564

PCT Pub. Date: May 5, 2022

(65) Prior Publication Data

US 2023/0399632 A1 Dec. 14, 2023

(30) Foreign Application Priority Data

Nov. 2, 2020 (DK) ................................ 2020 01234

(51) Int. Cl.
*C12N 9/34* (2006.01)
*C12P 19/14* (2006.01)

(52) U.S. Cl.
CPC ............ *C12N 9/2428* (2013.01); *C12P 19/14* (2013.01)

(58) Field of Classification Search
CPC ................... C12N 9/2428; C12P 19/14; C12Y 302/01003
See application file for complete search history.

(56) References Cited

U.S. PATENT DOCUMENTS 10,676,751 B2 * 6/2020 Daniell .......... C12Y 302/01021
2003/0082595 A1 5/2003 Jiang et al.
2009/0325240 A1 12/2009 Daniell
2019/0032039 A1 1/2019 Slupska et al.

FOREIGN PATENT DOCUMENTS

WO 2013/005801 A1 1/2013
WO 2013053801 A1 4/2013
WO 2014/085439 A1 6/2014
WO 2016/210238 A1 12/2016
WO 2018/164737 A1 9/2018
WO 2019/070883 A1 4/2019
WO 2019/113413 A1 6/2019
WO 2020/010101 A2 1/2020

OTHER PUBLICATIONS

Banerjee et al., Improving enzymes for biomass conversion: A basic research perspective. Bioenerg. Res., 2010, vol. 3: 82-92. (Year: 2010).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Fill et al., 2017, UniProt Accession No. A0A1S9RV34.
Horn et al., 2015, UniProt Accession No. A0A0F7TFI1.
Liu et al., 2013, UniProt Accession No. S7ZIW0.
Vries et al., 2017, UniProt Accession No. A0A1Q5TJS7.

* cited by examiner

*Primary Examiner* — Ganapathirama Raghu
(74) *Attorney, Agent, or Firm* — Yoshimi D. Barron

(57) ABSTRACT

The present invention relates to glucoamylase variants having improved thermostability and compositions comprising such variants. The present invention further relates to polynucleotides encoding such variants, vectors and host cells comprising genes encoding such variants, which may also enable the production of such variants. The present invention also relates to methods of liquefying starch-containing materials using or applying the variants or compositions, as well as the saccharification thus produced by the method. The present invention also relates to methods of saccharifying starch-containing materials using or applying the variants or compositions, as well as the saccharides thus produced by the method. The present invention further relates to processes for producing fermentation products from starch-containing or cellulosic-containing material, as well as an enzyme blend or composition, or a recombinant host cell or fermenting organism suitable for use in processes of the invention.

16 Claims, 2 Drawing Sheets

Specification includes a Sequence Listing.

```
PoAMG         ----------------------RPDPKGGNLTPFIHKEGERSLQGILDNLGGRGKKTPGTA
AMGNL         ----------------------RPDPKGGNLTPFIHKEGERSLQGILDNLGGRGKKTPGTA
AMGanPAV498   ----------------------RNDSKGGNLTFFIHKEGERSLQGILDNLGGRGKKTPGTA
AMGJPO001     ----------------------ANDSKGGNLTFFIHKEGERSLQGILDNLGGRGKKTPGTA
PmAMG         MRYTVLTSIASVLCVGPLASANPTSKDAKMASYISKEGQRSIVGITENLGGKGSKTPGTA
PrAMG         ------------------------SKDGNLASYIAKEGQRSIVGITENLGGKGSKTPGTA
PgAMG         ------------------------NPFNSLDSFILKEGARSYQGIIDNLGNKGVKAPGTA
                                          .:  :* *** **  ** :***..* *:****

PoAMG         AGLFIASPNTENPNYYYTWTRDSALTAKCLIDLFEDSRAVFPIDRKYLETGIRDYVSSQA
AMGNL         AGLFIASPNTENPNYYYTWTRDSALTAKCLIDLFEDSRAVFPIDRKYLETGIRDYVSSQA
AMGanPAV498   AGLFIASPNTENPNYYYTWTRDSALAAKCLIDLFEDSRAVFPIDRKYLETGIRDYVSSQA
AMGJPO001     AGLFIASPNTENPNYYYTWTRDSALAAKCLIDLFEDSRAVFPIDRKYLETGIRDYVSSQA
PmAMG         AGLFIASPNMANPNYYYTWTRDSALTFKCLIDLFETSDQDY-ISRKELETDIRNYVSSQA
PrAMG         AGLFIASPNMANPNYYYTWTRDSALTFKCLIDLFETSDQDY-ISRKELETDIRNYVSSQA
PgAMG         AGLFVASPNTANPDYFYTWTRDSALTFKCLIDLFDGGSTEFGLKNSELETDIRNYVSSQA
              ****:****  **:*:*********: *******: .   : :... ***.**:******

PoAMG         ILQSVSNPSGTLKDGSGLGEPKFEIDLNPFSGAWGRPQRDGPALRATAMITYANYLISHG
AMGNL         ILQSVSNPSGTLKDGSGLGEPKFEIDLNPFSGAWGRPQRDGPALRATAMITYANYLISHG
AMGanPAV498   ILQSVSNPSGTLKDGSGLGEPKFEIDLNPFSGAWGRPQRDGPALRATAMITYANYLISHG
AMGJPO001     ILQSVSNPSGTLKDGSGLGEPKFEIDLNPFSGAWGRPQRDGPALRATAMITYANYLISHG
PmAMG         VLQNVSNPSGTLKDGSGLGEPKFEIDLNPFSGSWGRPQRDGPALRATAMITYADWLISHG
PrAMG         VLQNVSNPSGTLKDGSGLGEPKFEIDLNPFSGSWGRPQRDGPALRATAMITYADWLVSHG
PgAMG         VLQNVSNPSGTLEDGTGLGEPKFEVDLNPFTGSWGRPQRDGPALRATALITYTNYLLSQG
              :**.********:**:********:*****:*:***************:***:::*:*:*

PoAMG         QKSDVSQVMWPIIANDLAYVGQYWNNTGFDLWEEVDGSSFFTIAVQHRALVEGSQLAKKL
AMGNL         QKSDVSQVMWPIIANDLAYVGQYWNNTGFDLWEEVDGSSFFTIAVQHRALVEGSQLAKKL
AMGanPAV498   QKSDVSQVMWPIIANDLAYVGQYWNNTGFDLWEEVDGSSFFTIAVQHRALVEGSQLAKKL
AMGJPO001     QKSDVSQVMWPIIANDLAYVGQYWNNTGFDLWEEVDGSSFFTIAVQHRALVEGSQLAKKL
PmAMG         SKSEAANIMWPIIANDLAYVGQYWNNTGFDLWEEVDGSSFFTLAVQHRSLVQGASLAKKL
PrAMG         QKSEATNIMWPIIANDLAYVGQYWNKTGFDLWEEVDGSSFYTLAVQHRALVQGASLAKKL
PgAMG         QKSEAVNIMWPIISNDLAYVGQYWNDTGFDLWEETDGSSFFTLAVQHRALVQGATLAQKL
              .**:. ::*****:***********.********.*****:*:*****:**:*: **:**

PoAMG         GKSCDACDSQPPQILCFLQSFWNGKYITSNINTQASRSGIDLDSVLGSIHTFDPEAACDD
AMGNL         GKSCDACDSQPPQILCFLQSFWNGKYITSNINTQASRSGIDLDSVLGSIHTFDPEAACDD
AMGanPAV498   GKSCDACDSQPPQILCFLQSFWNGKYITSNINTQASRSGIDLDSVLGSIHTFDPEAACDD
AMGJPO001     GKSCDACDSQPPQILCFLQSFWNGKYITSNINTQASRSGIDLDSVLGSIHTFDPEAACDD
PmAMG         GKSCPACVSQAPQILCFLQSFWNGNYITANINLDTSRSGIDLNSILGSIHTFDPEASCDD
PrAMG         GKSCTACVSQAPQILCFLQSFWNGNYITANINLDTSRSGIDLNSILGSIHTFDPEASCDD
PgAMG         GKSCAACSSQAPQILCFLQSFWNGKYITANINLDTSRTGIDANTLLGSIHTFDPEAACDD
              **** ** **.*************:***:*** ::**:*** :::***********:***

PoAMG         ATFQPCSARALANHKVYVDSFRSIYKINAGLAEGSAANVGRYPEDVYQGGNPWYLATLGA
AMGNL         ATFQPCSARALANHKVYVDSFRSIYKINAGLAEGSAANVGRYPEDVYQGGNPWYLATLGA
AMGanPAV498   ATFQPCSARALANHKVYVDSFRSIYKINAGLAEGSAANVGRYPEDVYFGGNPWYLATLGA
AMGJPO001     ATFQPCSARALANHKVYVDSFRSIYKINAGLAEGSAANVGRYPEDVYFGGNPWYLATLGA
PmAMG         STFQPCSARALANHKVYVDAFRSIYKVNAGLSNGSAANVGRYPEDVYQGGNPWYLATLAS
PrAMG         STFQPCSARALANHKVYVDAFRSIYGVNAGLSNGTAANVGRYPEDVYQGGNPWYLATLAA
PgAMG         STFQPCSARALANHKVYVDAFRSIYKINSGIAEGSPANVGRYPEDVYQGGNPWYLTTLAS
              :******************:***** :*:*:::*:.*********** *******:**.:
```

```
PoAMG          SELLYDALYQWDRLGKLEVSETSLSFFKDFDATVKIGSYSRNSKTYKKLTQSIKSYADGF
AMGNL          SELLYDALYQWDRLGKLEVSETSLSFFKDFDATVKIGSYSRNSKTYKKLTQSIKSYADGF
AMGanPAV498    SELLYDALYQWDRLGKLEVSETSLSFFKDFDATVKIGSYSRNSKTYKKLTQSIKSYADGF
AMGJPO001      SELLYDALYQWDRLGKLEVSETSLSFFKDFDATVKIGSYSRNSKTYKKLTQSIKSYADGF
PmAMG          AELLYDALYQWSKIGKLDVTKTSLAFFKDFDMAVKTGTYSAHSSTYKSLTSAIRTYADDF
PrAMG          AELLYDALYQWNQIGKLDVTKTSLAFFKDFDAAVKTGTYSAHSSAYRTLTSAIRTYADDF
PgAMG          AELLYDALYQWNKIGGLDVTETSLAFFKDFHSSVKTGSYSAHSQTYKTLTSAIRTYADGF
               :**********..:* *:*::***:*****  :** *:** :*.:*..**.:*.:***.*

PoAMG          IQLVQQYTPSNGSLAEQYDRNTAAPLSANDLTWSFASFLTATQRRDAVVPPSWGAKSANK
AMGNL          IQLVQQYTPSNGSLAEQYDRNTAAPLSANDLTWSFASFLTATQRRDAVVPPSWGAKSANK
AMGanPAV498    IQLVQQYTPSNGSLAEQYDRNTAAPLSANDLTWSFASFLTATQRRDAVVPPSWGAKSANK
AMGJPO001      IQLVQQYTPSNGSLAEQYDRNTAAPLSANDLTWSFASFLTATQRRDAVVPPSWGAKSANK
PmAMG          IGLVQDYTPSNGSLAEQYDRNTGIPLSANDLTWSYASFITAIQRRASVVPASWGEKSANV
PrAMG          ISLVQHYTPSNGSLAEQYDRDTGIPLSANDLTWSYASFITAIERRASVVPASWGEKSANV
PgAMG          VGLVQKYTPANGSLAEQYNRNTSVPLSANDLTWSFASFLTAIQRRESIVPGSWGEKSANT
               : *** ***:********:*:*. **********:***:** :** ::** *** ****

PoAMG          VPTTCSASPVVGTYKAPTATFSSKT-KCVPAKDIVPITFYLIENTYYGENVFMSGNITAL
AMGNL          VPTTCSASPVVGTYKAPTATFSSKT-KCVPAKDIVPITFYLIENTYYGENVFMSGNITAL
AMGanPAV498    VPTTCSASPVVGTYKAPTATFSSKT-KCVPAKDIVPITFYLIENTYYGENVFMSGNITAL
AMGJPO001      VPTTCSASPVVGTYKAPTATFSSKT-KCVPAKDIVPITFYLIENTYYGENVFMSGNITAL
PmAMG          VPTICSASPVTGTYQAAPSVFPTTT-GCVPATSIVPITFYLTETTFYGENVYMTGNISAL
PrAMG          VPTTCSASPVTGTYVAATSVFPTTT-GCVPATSIVPITFYLTESTFYGENVYMTGNISAL
PgAMG          VPTTCSASPVTGTYKAATSTFPTSTAGCVPATDW-PITFYLIENTYYGENVYMTGNISAL
               *** ******.*** *..:.*.:.*  ****..  ****** *.*:*****:*:***:**

PoAMG          GNWDAKKGFPLTANLYTQDQNLWFASVEFIPAGTPFEYKYYKVEPNGDITWEKGPNRVFV
AMGNL          GNWDAKKGFPLTANLYTQDQNLWFASVEFIPAGTPFEYKYYKVEPNGDITWEKGPNRVFV
AMGanPAV498    GNWDAKKGFPLTANLYTQDQNLWFASVEFIPAGTPFEYKYYKVEPNGDITWEKGPNRVFV
AMGJPO001      GNWDAKKGFPLTANLYTQDQNLWFASVEFIPAGTPFEYKYYKVEPNGDITWEKGPNRVFV
PmAMG          GNWDTNNGFPLTANLYTDSDHLWFASVELVPAGTPFEYKYYKVEPNGTVIWENGENRVYV
PrAMG          GNWDTSSGFPLTANLYTDSDHLWFASVELVPAGTPFEYKYYKVEPNGTVIWENGENRVYV
PgAMG          GNWDTSDGLALDAGLYTETDNLWFGTLELVTAGTPFEYKYYKIEPNGTVTWESGDNRVSV
               ****:..*:.* *.***: ::***.::*::.***********:**** : **.* *** *

PoAMG          APTGCPVQPHSNDVWQF
AMGNL          APTGCPVQPHSNDVWQF
AMGanPAV498    APTGCPVQPHSNDVWQF
AMGJPO001      APTGCPVQPHSNDVWQF
PmAMG          APTGCPIQPSQTDVWR-
PrAMG          APTGCPIQPSQTDIWR-
PgAMG          VPTGCPIQPSLHDVWRS
               .*****:**   *:*.
```

(Cont.)

SEQUENCE LISTING

```
<160> NUMBER OF SEQ ID NOS: 42

<210> SEQ ID NO 1
<211> LENGTH: 595
<212> TYPE: PRT
<213> ORGANISM: Penicillium oxalicum

<400> SEQUENCE: 1

Ala Asn Asp Ser Lys Gly Gly Asn Leu Thr Phe Phe Ile His Lys Glu
1               5                   10                  15

Gly Glu Arg Ser Leu Gln Gly Ile Leu Asp Asn Leu Gly Gly Arg Gly
            20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
    50                  55                  60

Ala Ala Lys Cys Leu Ile Asp Leu Phe Glu Asp Ser Arg Ala Val Phe
65                  70                  75                  80

Pro Ile Asp Arg Lys Tyr Leu Glu Thr Gly Ile Arg Asp Tyr Val Ser
                85                  90                  95

Ser Gln Ala Ile Leu Gln Ser Val Ser Asn Pro Ser Gly Thr Leu Lys
```

-continued

```
            100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
    130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
        195                 200                 205

Leu Val Glu Gly Ser Gln Leu Ala Lys Lys Leu Gly Lys Ser Cys Asp
    210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
    290                 295                 300

Lys Ile Asn Ala Gly Leu Ala Glu Gly Ser Ala Ala Asn Val Gly Arg
305                 310                 315                 320

Tyr Pro Glu Asp Val Tyr Phe Gly Gly Asn Pro Trp Tyr Leu Ala Thr
                325                 330                 335

Leu Gly Ala Ser Glu Leu Leu Tyr Asp Ala Leu Tyr Gln Trp Asp Arg
            340                 345                 350

Leu Gly Lys Leu Glu Val Ser Glu Thr Ser Leu Ser Phe Phe Lys Asp
        355                 360                 365

Phe Asp Ala Thr Val Lys Ile Gly Ser Tyr Ser Arg Asn Ser Lys Thr
    370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415

Tyr Asp Arg Asn Thr Ala Ala Pro Leu Ser Ala Asn Asp Leu Thr Trp
            420                 425                 430

Ser Phe Ala Ser Phe Leu Thr Ala Thr Gln Arg Arg Asp Ala Val Val
        435                 440                 445

Pro Pro Ser Trp Gly Ala Lys Ser Ala Asn Lys Val Pro Thr Thr Cys
    450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                485                 490                 495

Phe Tyr Leu Ile Glu Asn Thr Tyr Tyr Gly Glu Asn Val Phe Met Ser
            500                 505                 510

Gly Asn Ile Thr Ala Leu Gly Asn Trp Asp Ala Lys Lys Gly Phe Pro
        515                 520                 525
```

```
Leu Thr Ala Asn Leu Tyr Thr Gln Asp Gln Asn Leu Trp Phe Ala Ser
    530                 535                 540

Val Glu Phe Ile Pro Ala Gly Thr Pro Phe Glu Tyr Lys Tyr Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
            580                 585                 590

Trp Gln Phe
        595


<210> SEQ ID NO 2
<211> LENGTH: 604
<212> TYPE: PRT
<213> ORGANISM: Penicillium oxalicum

<400> SEQUENCE: 2

Phe Ala Arg Ala Pro Val Ala Ala Arg Ala Asn Asp Ser Lys Gly Gly
1               5                   10                  15

Asn Leu Thr Phe Phe Ile His Lys Glu Gly Glu Arg Ser Leu Gln Gly
            20                  25                  30

Ile Leu Asp Asn Leu Gly Gly Arg Gly Lys Lys Thr Pro Gly Thr Ala
        35                  40                  45

Ala Gly Leu Phe Ile Ala Ser Pro Asn Thr Glu Asn Pro Asn Tyr Tyr
    50                  55                  60

Tyr Thr Trp Thr Arg Asp Ser Ala Leu Ala Ala Lys Cys Leu Ile Asp
65                  70                  75                  80

Leu Phe Glu Asp Ser Arg Ala Val Phe Pro Ile Asp Arg Lys Tyr Leu
                85                  90                  95

Glu Thr Gly Ile Arg Asp Tyr Val Ser Ser Gln Ala Ile Leu Gln Ser
            100                 105                 110

Val Ser Asn Pro Ser Gly Thr Leu Lys Asp Gly Ser Gly Leu Gly Glu
        115                 120                 125

Pro Lys Phe Glu Ile Asp Leu Asn Pro Phe Ser Gly Ala Trp Gly Arg
    130                 135                 140

Pro Gln Arg Asp Gly Pro Ala Leu Arg Ala Thr Ala Met Ile Thr Tyr
145                 150                 155                 160

Ala Asn Tyr Leu Ile Ser His Gly Gln Lys Ser Asp Val Ser Gln Val
                165                 170                 175

Met Trp Pro Ile Ile Ala Asn Asp Leu Ala Tyr Val Gly Gln Tyr Trp
            180                 185                 190

Asn Asn Thr Gly Phe Asp Leu Trp Glu Glu Val Asp Gly Ser Ser Phe
        195                 200                 205

Phe Thr Ile Ala Val Gln His Arg Ala Leu Val Glu Gly Ser Gln Leu
    210                 215                 220

Ala Lys Lys Leu Gly Lys Ser Cys Asp Ala Cys Asp Ser Gln Pro Pro
225                 230                 235                 240

Gln Ile Leu Cys Phe Leu Gln Ser Phe Trp Asn Gly Lys Tyr Ile Thr
                245                 250                 255

Ser Asn Ile Asn Thr Gln Ala Ser Arg Ser Gly Ile Asp Leu Asp Ser
            260                 265                 270

Val Leu Gly Ser Ile His Thr Phe Asp Pro Glu Ala Ala Cys Asp Asp
        275                 280                 285

Ala Thr Phe Gln Pro Cys Ser Ala Arg Ala Leu Ala Asn His Lys Val
```

-continued

```
    290                 295                 300

Tyr Val Asp Ser Phe Arg Ser Ile Tyr Lys Ile Asn Ala Gly Leu Ala
305                 310                 315                 320

Glu Gly Ser Ala Ala Asn Val Gly Arg Tyr Pro Glu Asp Val Tyr Phe
                325                 330                 335

Gly Gly Asn Pro Trp Tyr Leu Ala Thr Leu Gly Ala Ser Glu Leu Leu
            340                 345                 350

Tyr Asp Ala Leu Tyr Gln Trp Asp Arg Leu Gly Lys Leu Glu Val Ser
        355                 360                 365

Glu Thr Ser Leu Ser Phe Phe Lys Asp Phe Asp Ala Thr Val Lys Ile
    370                 375                 380

Gly Ser Tyr Ser Arg Asn Ser Lys Thr Tyr Lys Lys Leu Thr Gln Ser
385                 390                 395                 400

Ile Lys Ser Tyr Ala Asp Gly Phe Ile Gln Leu Val Gln Gln Tyr Thr
                405                 410                 415

Pro Ser Asn Gly Ser Leu Ala Glu Gln Tyr Asp Arg Asn Thr Ala Ala
            420                 425                 430

Pro Leu Ser Ala Asn Asp Leu Thr Trp Ser Phe Ala Ser Phe Leu Thr
        435                 440                 445

Ala Thr Gln Arg Arg Asp Ala Val Val Pro Pro Ser Trp Gly Ala Lys
    450                 455                 460

Ser Ala Asn Lys Val Pro Thr Thr Cys Ser Ala Ser Pro Val Val Gly
465                 470                 475                 480

Thr Tyr Lys Ala Pro Thr Ala Thr Phe Ser Ser Lys Thr Lys Cys Val
                485                 490                 495

Pro Ala Lys Asp Ile Val Pro Ile Thr Phe Tyr Leu Ile Glu Asn Thr
            500                 505                 510

Tyr Tyr Gly Glu Asn Val Phe Met Ser Gly Asn Ile Thr Ala Leu Gly
        515                 520                 525

Asn Trp Asp Ala Lys Lys Gly Phe Pro Leu Thr Ala Asn Leu Tyr Thr
    530                 535                 540

Gln Asp Gln Asn Leu Trp Phe Ala Ser Val Glu Phe Ile Pro Ala Gly
545                 550                 555                 560

Thr Pro Phe Glu Tyr Lys Tyr Tyr Lys Val Glu Pro Asn Gly Asp Ile
                565                 570                 575

Thr Trp Glu Lys Gly Pro Asn Arg Val Phe Val Ala Pro Thr Gly Cys
            580                 585                 590

Pro Val Gln Pro His Ser Asn Asp Val Trp Gln Phe
        595                 600


<210> SEQ ID NO 3
<211> LENGTH: 625
<212> TYPE: PRT
<213> ORGANISM: Penicillium oxalicum

<400> SEQUENCE: 3

Met Arg Leu Thr Leu Leu Ser Gly Val Ala Gly Val Leu Cys Ala Gly
1               5                   10                  15

Gln Leu Thr Ala Ala Phe Ala Arg Ala Pro Val Ala Ala Arg Ala Asn
            20                  25                  30

Asp Ser Lys Gly Gly Asn Leu Thr Phe Phe Ile His Lys Glu Gly Glu
        35                  40                  45

Arg Ser Leu Gln Gly Ile Leu Asp Asn Leu Gly Gly Arg Gly Lys Lys
    50                  55                  60
```

-continued

Thr Pro Gly Thr Ala Ala Gly Leu Phe Ile Ala Ser Pro Asn Thr Glu
65 70 75 80

Asn Pro Asn Tyr Tyr Tyr Thr Trp Thr Arg Asp Ser Ala Leu Ala Ala
85 90 95

Lys Cys Leu Ile Asp Leu Phe Glu Asp Ser Arg Ala Val Phe Pro Ile
100 105 110

Asp Arg Lys Tyr Leu Glu Thr Gly Ile Arg Asp Tyr Val Ser Ser Gln
115 120 125

Ala Ile Leu Gln Ser Val Ser Asn Pro Ser Gly Thr Leu Lys Asp Gly
130 135 140

Ser Gly Leu Gly Glu Pro Lys Phe Glu Ile Asp Leu Asn Pro Phe Ser
145 150 155 160

Gly Ala Trp Gly Arg Pro Gln Arg Asp Gly Pro Ala Leu Arg Ala Thr
165 170 175

Ala Met Ile Thr Tyr Ala Asn Tyr Leu Ile Ser His Gly Gln Lys Ser
180 185 190

Asp Val Ser Gln Val Met Trp Pro Ile Ile Ala Asn Asp Leu Ala Tyr
195 200 205

Val Gly Gln Tyr Trp Asn Asn Thr Gly Phe Asp Leu Trp Glu Glu Val
210 215 220

Asp Gly Ser Ser Phe Phe Thr Ile Ala Val Gln His Arg Ala Leu Val
225 230 235 240

Glu Gly Ser Gln Leu Ala Lys Lys Leu Gly Lys Ser Cys Asp Ala Cys
245 250 255

Asp Ser Gln Pro Pro Gln Ile Leu Cys Phe Leu Gln Ser Phe Trp Asn
260 265 270

Gly Lys Tyr Ile Thr Ser Asn Ile Asn Thr Gln Ala Ser Arg Ser Gly
275 280 285

Ile Asp Leu Asp Ser Val Leu Gly Ser Ile His Thr Phe Asp Pro Glu
290 295 300

Ala Ala Cys Asp Asp Ala Thr Phe Gln Pro Cys Ser Ala Arg Ala Leu
305 310 315 320

Ala Asn His Lys Val Tyr Val Asp Ser Phe Arg Ser Ile Tyr Lys Ile
325 330 335

Asn Ala Gly Leu Ala Glu Gly Ser Ala Ala Asn Val Gly Arg Tyr Pro
340 345 350

Glu Asp Val Tyr Phe Gly Gly Asn Pro Trp Tyr Leu Ala Thr Leu Gly
355 360 365

Ala Ser Glu Leu Leu Tyr Asp Ala Leu Tyr Gln Trp Asp Arg Leu Gly
370 375 380

Lys Leu Glu Val Ser Glu Thr Ser Leu Ser Phe Phe Lys Asp Phe Asp
385 390 395 400

Ala Thr Val Lys Ile Gly Ser Tyr Ser Arg Asn Ser Lys Thr Tyr Lys
405 410 415

Lys Leu Thr Gln Ser Ile Lys Ser Tyr Ala Asp Gly Phe Ile Gln Leu
420 425 430

Val Gln Gln Tyr Thr Pro Ser Asn Gly Ser Leu Ala Glu Gln Tyr Asp
435 440 445

Arg Asn Thr Ala Ala Pro Leu Ser Ala Asn Asp Leu Thr Trp Ser Phe
450 455 460

Ala Ser Phe Leu Thr Ala Thr Gln Arg Arg Asp Ala Val Val Pro Pro
465 470 475 480

Ser Trp Gly Ala Lys Ser Ala Asn Lys Val Pro Thr Thr Cys Ser Ala

```
                485                 490                 495

Ser Pro Val Val Gly Thr Tyr Lys Ala Pro Thr Ala Thr Phe Ser Ser
            500                 505                 510

Lys Thr Lys Cys Val Pro Ala Lys Asp Ile Val Pro Ile Thr Phe Tyr
        515                 520                 525

Leu Ile Glu Asn Thr Tyr Tyr Gly Glu Asn Val Phe Met Ser Gly Asn
    530                 535                 540

Ile Thr Ala Leu Gly Asn Trp Asp Ala Lys Lys Gly Phe Pro Leu Thr
545                 550                 555                 560

Ala Asn Leu Tyr Thr Gln Asp Gln Asn Leu Trp Phe Ala Ser Val Glu
                565                 570                 575

Phe Ile Pro Ala Gly Thr Pro Phe Glu Tyr Lys Tyr Tyr Lys Val Glu
            580                 585                 590

Pro Asn Gly Asp Ile Thr Trp Glu Lys Gly Pro Asn Arg Val Phe Val
        595                 600                 605

Ala Pro Thr Gly Cys Pro Val Gln Pro His Ser Asn Asp Val Trp Gln
    610                 615                 620

Phe
625


<210> SEQ ID NO 4
<211> LENGTH: 595
<212> TYPE: PRT
<213> ORGANISM: Penicillium oxalicum

<400> SEQUENCE: 4

Arg Asn Asp Ser Lys Gly Gly Asn Leu Thr Phe Phe Ile His Lys Glu
1               5                   10                  15

Gly Glu Arg Ser Leu Gln Gly Ile Leu Asp Asn Leu Gly Gly Arg Gly
            20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
    50                  55                  60

Ala Ala Lys Cys Leu Ile Asp Leu Phe Glu Asp Ser Arg Ala Val Phe
65                  70                  75                  80

Pro Ile Asp Arg Lys Tyr Leu Glu Thr Gly Ile Arg Asp Tyr Val Ser
                85                  90                  95

Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
    130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
        195                 200                 205

Leu Val Glu Gly Ser Gln Leu Ala Lys Lys Leu Gly Lys Ser Cys Asp
    210                 215                 220
```

-continued

```
Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
    290                 295                 300

Lys Ile Asn Ala Gly Leu Ala Glu Gly Ser Ala Ala Asn Val Gly Arg
305                 310                 315                 320

Tyr Pro Glu Asp Val Tyr Phe Gly Gly Asn Pro Trp Tyr Leu Ala Thr
                325                 330                 335

Leu Gly Ala Ser Glu Leu Leu Tyr Asp Ala Leu Tyr Gln Trp Asp Arg
            340                 345                 350

Leu Gly Lys Leu Glu Val Ser Glu Thr Ser Leu Ser Phe Phe Lys Asp
        355                 360                 365

Phe Asp Ala Thr Val Lys Ile Gly Ser Tyr Ser Arg Asn Ser Lys Thr
    370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415

Tyr Asp Arg Asn Thr Ala Ala Pro Leu Ser Ala Asn Asp Leu Thr Trp
            420                 425                 430

Ser Phe Ala Ser Phe Leu Thr Ala Thr Gln Arg Arg Asp Ala Val Val
        435                 440                 445

Pro Pro Ser Trp Gly Ala Lys Ser Ala Asn Lys Val Pro Thr Thr Cys
    450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                485                 490                 495

Phe Tyr Leu Ile Glu Asn Thr Tyr Tyr Gly Glu Asn Val Phe Met Ser
            500                 505                 510

Gly Asn Ile Thr Ala Leu Gly Asn Trp Asp Ala Lys Lys Gly Phe Pro
        515                 520                 525

Leu Thr Ala Asn Leu Tyr Thr Gln Asp Gln Asn Leu Trp Phe Ala Ser
    530                 535                 540

Val Glu Phe Ile Pro Ala Gly Thr Pro Phe Glu Tyr Lys Tyr Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
            580                 585                 590

Trp Gln Phe
        595
```

<210> SEQ ID NO 5
<211> LENGTH: 616
<212> TYPE: PRT
<213> ORGANISM: Penicillium oxalicum

<400> SEQUENCE: 5

-continued

Met Arg Leu Thr Leu Leu Ser Gly Val Ala Gly Val Leu Cys Ala Gly
1               5                   10                  15

Gln Leu Thr Ala Ala Arg Asn Asp Ser Lys Gly Gly Asn Leu Thr Phe
            20                  25                  30

Phe Ile His Lys Glu Gly Glu Arg Ser Leu Gln Gly Ile Leu Asp Asn
        35                  40                  45

Leu Gly Gly Arg Gly Lys Lys Thr Pro Gly Thr Ala Ala Gly Leu Phe
    50                  55                  60

Ile Ala Ser Pro Asn Thr Glu Asn Pro Asn Tyr Tyr Tyr Thr Trp Thr
65                  70                  75                  80

Arg Asp Ser Ala Leu Ala Ala Lys Cys Leu Ile Asp Leu Phe Glu Asp
                85                  90                  95

Ser Arg Ala Val Phe Pro Ile Asp Arg Lys Tyr Leu Glu Thr Gly Ile
            100                 105                 110

Arg Asp Tyr Val Ser Ser Gln Ala Ile Leu Gln Ser Val Ser Asn Pro
        115                 120                 125

Ser Gly Thr Leu Lys Asp Gly Ser Gly Leu Gly Glu Pro Lys Phe Glu
    130                 135                 140

Ile Asp Leu Asn Pro Phe Ser Gly Ala Trp Gly Arg Pro Gln Arg Asp
145                 150                 155                 160

Gly Pro Ala Leu Arg Ala Thr Ala Met Ile Thr Tyr Ala Asn Tyr Leu
                165                 170                 175

Ile Ser His Gly Gln Lys Ser Asp Val Ser Gln Val Met Trp Pro Ile
            180                 185                 190

Ile Ala Asn Asp Leu Ala Tyr Val Gly Gln Tyr Trp Asn Asn Thr Gly
        195                 200                 205

Phe Asp Leu Trp Glu Glu Val Asp Gly Ser Ser Phe Phe Thr Ile Ala
    210                 215                 220

Val Gln His Arg Ala Leu Val Glu Gly Ser Gln Leu Ala Lys Lys Leu
225                 230                 235                 240

Gly Lys Ser Cys Asp Ala Cys Asp Ser Gln Pro Pro Gln Ile Leu Cys
                245                 250                 255

Phe Leu Gln Ser Phe Trp Asn Gly Lys Tyr Ile Thr Ser Asn Ile Asn
            260                 265                 270

Thr Gln Ala Ser Arg Ser Gly Ile Asp Leu Asp Ser Val Leu Gly Ser
        275                 280                 285

Ile His Thr Phe Asp Pro Glu Ala Ala Cys Asp Asp Ala Thr Phe Gln
    290                 295                 300

Pro Cys Ser Ala Arg Ala Leu Ala Asn His Lys Val Tyr Val Asp Ser
305                 310                 315                 320

Phe Arg Ser Ile Tyr Lys Ile Asn Ala Gly Leu Ala Glu Gly Ser Ala
                325                 330                 335

Ala Asn Val Gly Arg Tyr Pro Glu Asp Val Tyr Phe Gly Gly Asn Pro
            340                 345                 350

Trp Tyr Leu Ala Thr Leu Gly Ala Ser Glu Leu Leu Tyr Asp Ala Leu
        355                 360                 365

Tyr Gln Trp Asp Arg Leu Gly Lys Leu Glu Val Ser Glu Thr Ser Leu
    370                 375                 380

Ser Phe Phe Lys Asp Phe Asp Ala Thr Val Lys Ile Gly Ser Tyr Ser
385                 390                 395                 400

Arg Asn Ser Lys Thr Tyr Lys Lys Leu Thr Gln Ser Ile Lys Ser Tyr
                405                 410                 415

```
Ala Asp Gly Phe Ile Gln Leu Val Gln Gln Tyr Thr Pro Ser Asn Gly
            420                 425                 430

Ser Leu Ala Glu Gln Tyr Asp Arg Asn Thr Ala Ala Pro Leu Ser Ala
        435                 440                 445

Asn Asp Leu Thr Trp Ser Phe Ala Ser Phe Leu Thr Ala Thr Gln Arg
    450                 455                 460

Arg Asp Ala Val Val Pro Pro Ser Trp Gly Ala Lys Ser Ala Asn Lys
465                 470                 475                 480

Val Pro Thr Thr Cys Ser Ala Ser Pro Val Val Gly Thr Tyr Lys Ala
                485                 490                 495

Pro Thr Ala Thr Phe Ser Ser Lys Thr Lys Cys Val Pro Ala Lys Asp
            500                 505                 510

Ile Val Pro Ile Thr Phe Tyr Leu Ile Glu Asn Thr Tyr Tyr Gly Glu
        515                 520                 525

Asn Val Phe Met Ser Gly Asn Ile Thr Ala Leu Gly Asn Trp Asp Ala
    530                 535                 540

Lys Lys Gly Phe Pro Leu Thr Ala Asn Leu Tyr Thr Gln Asp Gln Asn
545                 550                 555                 560

Leu Trp Phe Ala Ser Val Glu Phe Ile Pro Ala Gly Thr Pro Phe Glu
                565                 570                 575

Tyr Lys Tyr Tyr Lys Val Glu Pro Asn Gly Asp Ile Thr Trp Glu Lys
            580                 585                 590

Gly Pro Asn Arg Val Phe Val Ala Pro Thr Gly Cys Pro Val Gln Pro
        595                 600                 605

His Ser Asn Asp Val Trp Gln Phe
    610                 615


<210> SEQ ID NO 6
<211> LENGTH: 595
<212> TYPE: PRT
<213> ORGANISM: Penicillium oxalicum

<400> SEQUENCE: 6

Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
            20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
    50                  55                  60

Thr Ala Lys Cys Leu Ile Asp Leu Phe Glu Asp Ser Arg Ala Val Phe
65                  70                  75                  80

Pro Ile Asp Arg Lys Tyr Leu Glu Thr Gly Ile Arg Asp Tyr Val Ser
                85                  90                  95

Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
    130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175
```

-continued

```
Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
        195                 200                 205

Leu Val Glu Gly Ser Gln Leu Ala Lys Lys Leu Gly Lys Ser Cys Asp
    210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
    290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
            340                 345                 350

Leu Gly Lys Leu Glu Val Ser Glu Thr Ser Leu Ser Phe Phe Lys Asp
        355                 360                 365

Phe Asp Ala Thr Val Lys Ile Gly Ser Tyr Ser Arg Asn Ser Lys Thr
    370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415

Tyr Asp Arg Asn Thr Ala Ala Pro Leu Ser Ala Asn Asp Leu Thr Trp
            420                 425                 430

Ser Phe Ala Ser Phe Leu Thr Ala Thr Gln Arg Arg Asp Ala Val Val
        435                 440                 445

Pro Pro Ser Trp Gly Ala Lys Ser Ala Asn Lys Val Pro Thr Thr Cys
    450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                485                 490                 495

Phe Tyr Leu Ile Glu Asn Thr Tyr Tyr Gly Glu Asn Val Phe Met Ser
            500                 505                 510

Gly Asn Ile Thr Ala Leu Gly Asn Trp Asp Ala Lys Lys Gly Phe Pro
        515                 520                 525

Leu Thr Ala Asn Leu Tyr Thr Gln Asp Gln Asn Leu Trp Phe Ala Ser
    530                 535                 540

Val Glu Phe Ile Pro Ala Gly Thr Pro Phe Glu Tyr Lys Tyr Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
            580                 585                 590
```

Trp Gln Phe
        595

<210> SEQ ID NO 7
<211> LENGTH: 616
<212> TYPE: PRT
<213> ORGANISM: Penicillium oxalicum

<400> SEQUENCE: 7

Met Arg Leu Thr Leu Leu Ser Gly Val Ala Gly Val Leu Cys Ala Gly
1               5                   10                  15

Gln Leu Thr Ala Ala Arg Pro Asp Pro Lys Gly Gly Asn Leu Thr Pro
            20                  25                  30

Phe Ile His Lys Glu Gly Glu Arg Ser Leu Gln Gly Ile Leu Asp Asn
        35                  40                  45

Leu Gly Gly Arg Gly Lys Lys Thr Pro Gly Thr Ala Ala Gly Leu Phe
    50                  55                  60

Ile Ala Ser Pro Asn Thr Glu Asn Pro Asn Tyr Tyr Tyr Thr Trp Thr
65                  70                  75                  80

Arg Asp Ser Ala Leu Thr Ala Lys Cys Leu Ile Asp Leu Phe Glu Asp
                85                  90                  95

Ser Arg Ala Val Phe Pro Ile Asp Arg Lys Tyr Leu Glu Thr Gly Ile
            100                 105                 110

Arg Asp Tyr Val Ser Ser Gln Ala Ile Leu Gln Ser Val Ser Asn Pro
        115                 120                 125

Ser Gly Thr Leu Lys Asp Gly Ser Gly Leu Gly Glu Pro Lys Phe Glu
    130                 135                 140

Ile Asp Leu Asn Pro Phe Ser Gly Ala Trp Gly Arg Pro Gln Arg Asp
145                 150                 155                 160

Gly Pro Ala Leu Arg Ala Thr Ala Met Ile Thr Tyr Ala Asn Tyr Leu
                165                 170                 175

Ile Ser His Gly Gln Lys Ser Asp Val Ser Gln Val Met Trp Pro Ile
            180                 185                 190

Ile Ala Asn Asp Leu Ala Tyr Val Gly Gln Tyr Trp Asn Asn Thr Gly
        195                 200                 205

Phe Asp Leu Trp Glu Glu Val Asp Gly Ser Ser Phe Phe Thr Ile Ala
    210                 215                 220

Val Gln His Arg Ala Leu Val Glu Gly Ser Gln Leu Ala Lys Lys Leu
225                 230                 235                 240

Gly Lys Ser Cys Asp Ala Cys Asp Ser Gln Pro Pro Gln Ile Leu Cys
                245                 250                 255

Phe Leu Gln Ser Phe Trp Asn Gly Lys Tyr Ile Thr Ser Asn Ile Asn
            260                 265                 270

Thr Gln Ala Ser Arg Ser Gly Ile Asp Leu Asp Ser Val Leu Gly Ser
        275                 280                 285

Ile His Thr Phe Asp Pro Glu Ala Ala Cys Asp Asp Ala Thr Phe Gln
    290                 295                 300

Pro Cys Ser Ala Arg Ala Leu Ala Asn His Lys Val Tyr Val Asp Ser
305                 310                 315                 320

Phe Arg Ser Ile Tyr Lys Ile Asn Ala Gly Leu Ala Glu Gly Ser Ala
                325                 330                 335

Ala Asn Val Gly Arg Tyr Pro Glu Asp Val Tyr Gln Gly Gly Asn Pro
            340                 345                 350

Trp Tyr Leu Ala Thr Leu Gly Ala Ser Glu Leu Leu Tyr Asp Ala Leu
        355                 360                 365

```
Tyr Gln Trp Asp Arg Leu Gly Lys Leu Glu Val Ser Glu Thr Ser Leu
    370                 375                 380

Ser Phe Phe Lys Asp Phe Asp Ala Thr Val Lys Ile Gly Ser Tyr Ser
385                 390                 395                 400

Arg Asn Ser Lys Thr Tyr Lys Lys Leu Thr Gln Ser Ile Lys Ser Tyr
                405                 410                 415

Ala Asp Gly Phe Ile Gln Leu Val Gln Gln Tyr Thr Pro Ser Asn Gly
            420                 425                 430

Ser Leu Ala Glu Gln Tyr Asp Arg Asn Thr Ala Ala Pro Leu Ser Ala
        435                 440                 445

Asn Asp Leu Thr Trp Ser Phe Ala Ser Phe Leu Thr Ala Thr Gln Arg
    450                 455                 460

Arg Asp Ala Val Val Pro Pro Ser Trp Gly Ala Lys Ser Ala Asn Lys
465                 470                 475                 480

Val Pro Thr Thr Cys Ser Ala Ser Pro Val Val Gly Thr Tyr Lys Ala
                485                 490                 495

Pro Thr Ala Thr Phe Ser Ser Lys Thr Lys Cys Val Pro Ala Lys Asp
            500                 505                 510

Ile Val Pro Ile Thr Phe Tyr Leu Ile Glu Asn Thr Tyr Tyr Gly Glu
        515                 520                 525

Asn Val Phe Met Ser Gly Asn Ile Thr Ala Leu Gly Asn Trp Asp Ala
    530                 535                 540

Lys Lys Gly Phe Pro Leu Thr Ala Asn Leu Tyr Thr Gln Asp Gln Asn
545                 550                 555                 560

Leu Trp Phe Ala Ser Val Glu Phe Ile Pro Ala Gly Thr Pro Phe Glu
                565                 570                 575

Tyr Lys Tyr Tyr Lys Val Glu Pro Asn Gly Asp Ile Thr Trp Glu Lys
            580                 585                 590

Gly Pro Asn Arg Val Phe Val Ala Pro Thr Gly Cys Pro Val Gln Pro
        595                 600                 605

His Ser Asn Asp Val Trp Gln Phe
    610                 615


<210> SEQ ID NO 8
<211> LENGTH: 595
<212> TYPE: PRT
<213> ORGANISM: Penicillium oxalicum

<400> SEQUENCE: 8

Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
            20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
    50                  55                  60

Thr Ala Lys Cys Leu Ile Asp Leu Phe Glu Asp Ser Arg Ala Val Phe
65                  70                  75                  80

Pro Ile Asp Arg Lys Tyr Leu Glu Thr Gly Ile Arg Asp Tyr Val Ser
                85                  90                  95

Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
```

-continued 115 120 125

Phe Ser Gly Ala Trp Gly Arg Pro Gln Arg Asp Gly Pro Ala Leu Arg
130 135 140

Ala Thr Ala Met Ile Thr Tyr Ala Asn Tyr Leu Ile Ser His Gly Gln
145 150 155 160

Lys Ser Asp Val Ser Gln Val Met Trp Pro Ile Ile Ala Asn Asp Leu
165 170 175

Ala Tyr Val Gly Gln Tyr Trp Asn Asn Thr Gly Phe Asp Leu Trp Glu
180 185 190

Glu Val Asp Gly Ser Ser Phe Phe Thr Ile Ala Val Gln His Arg Ala
195 200 205

Leu Val Glu Gly Ser Gln Leu Ala Lys Lys Leu Gly Lys Ser Cys Asp
210 215 220

Ala Cys Asp Ser Gln Pro Pro Gln Ile Leu Cys Phe Leu Gln Ser Phe
225 230 235 240

Trp Asn Gly Lys Tyr Ile Thr Ser Asn Ile Asn Thr Gln Ala Ser Arg
245 250 255

Ser Gly Ile Asp Leu Asp Ser Val Leu Gly Ser Ile His Thr Phe Asp
260 265 270

Pro Glu Ala Ala Cys Asp Asp Ala Thr Phe Gln Pro Cys Ser Ala Arg
275 280 285

Ala Leu Ala Asn His Lys Val Tyr Val Asp Ser Phe Arg Ser Ile Tyr
290 295 300

Lys Ile Asn Ala Gly Leu Ala Glu Gly Ser Ala Ala Asn Val Gly Arg
305 310 315 320

Tyr Pro Glu Asp Val Tyr Gln Gly Gly Asn Pro Trp Tyr Leu Ala Thr
325 330 335

Leu Gly Ala Ser Glu Leu Leu Tyr Asp Ala Leu Tyr Gln Trp Asp Arg
340 345 350

Leu Gly Lys Leu Glu Val Ser Glu Thr Ser Leu Ser Phe Phe Lys Asp
355 360 365

Phe Asp Ala Thr Val Lys Ile Gly Ser Tyr Ser Arg Asn Ser Lys Thr
370 375 380

Tyr Lys Lys Leu Thr Gln Ser Ile Lys Ser Tyr Ala Asp Gly Phe Ile
385 390 395 400

Gln Leu Val Gln Gln Tyr Thr Pro Ser Asn Gly Ser Leu Ala Glu Gln
405 410 415

Tyr Asp Arg Asn Thr Ala Ala Pro Leu Ser Ala Asn Asp Leu Thr Trp
420 425 430

Ser Phe Ala Ser Phe Leu Thr Ala Thr Gln Arg Arg Asp Ala Val Val
435 440 445

Pro Pro Ser Trp Gly Ala Lys Ser Ala Asn Lys Val Pro Thr Thr Cys
450 455 460

Ser Ala Ser Pro Val Val Gly Thr Tyr Lys Ala Pro Thr Ala Thr Phe
465 470 475 480

Ser Ser Lys Thr Lys Cys Val Pro Ala Lys Asp Ile Val Pro Ile Thr
485 490 495

Phe Tyr Leu Ile Glu Asn Thr Tyr Tyr Gly Glu Asn Val Phe Met Ser
500 505 510

Gly Asn Ile Thr Ala Leu Gly Asn Trp Asp Ala Lys Lys Gly Phe Pro
515 520 525

Leu Thr Ala Asn Leu Tyr Thr Gln Asp Gln Asn Leu Trp Phe Ala Ser
530 535 540

Val Glu Phe Ile Pro Ala Gly Thr Pro Phe Glu Tyr Lys Tyr Tyr Lys
545 550 555 560

Val Glu Pro Asn Gly Asp Ile Thr Trp Glu Lys Gly Pro Asn Arg Val
565 570 575

Phe Val Ala Pro Thr Gly Cys Pro Val Gln Pro His Ser Asn Asp Val
580 585 590

Trp Gln Phe
595

<210> SEQ ID NO 9
<211> LENGTH: 592
<212> TYPE: PRT
<213> ORGANISM: Penicillum glabrum

<400> SEQUENCE: 9

Asn Pro Phe Asn Ser Leu Asp Ser Phe Ile Leu Lys Glu Gly Ala Arg
1 5 10 15

Ser Tyr Gln Gly Ile Ile Asp Asn Leu Gly Asn Lys Gly Val Lys Ala
20 25 30

Pro Gly Thr Ala Ala Gly Leu Phe Val Ala Ser Pro Asn Thr Ala Asn
35 40 45

Pro Asp Tyr Phe Tyr Thr Trp Thr Arg Asp Ser Ala Leu Thr Phe Lys
50 55 60

Cys Leu Ile Asp Leu Phe Asp Gly Gly Ser Thr Glu Phe Gly Leu Lys
65 70 75 80

Asn Ser Glu Leu Glu Thr Asp Ile Arg Asn Tyr Val Ser Ser Gln Ala
85 90 95

Val Leu Gln Asn Val Ser Asn Pro Ser Gly Thr Leu Glu Asp Gly Thr
100 105 110

Gly Leu Gly Glu Pro Lys Phe Glu Val Asp Leu Asn Pro Phe Thr Gly
115 120 125

Ser Trp Gly Arg Pro Gln Arg Asp Gly Pro Ala Leu Arg Ala Thr Ala
130 135 140

Leu Ile Thr Tyr Thr Asn Tyr Leu Leu Ser Gln Gly Gln Lys Ser Glu
145 150 155 160

Ala Val Asn Ile Met Trp Pro Ile Ile Ser Asn Asp Leu Ala Tyr Val
165 170 175

Gly Gln Tyr Trp Asn Asp Thr Gly Phe Asp Leu Trp Glu Glu Thr Asp
180 185 190

Gly Ser Ser Phe Phe Thr Leu Ala Val Gln His Arg Ala Leu Val Gln
195 200 205

Gly Ala Thr Leu Ala Gln Lys Leu Gly Lys Ser Cys Ala Ala Cys Ser
210 215 220

Ser Gln Ala Pro Gln Ile Leu Cys Phe Leu Gln Ser Phe Trp Asn Gly
225 230 235 240

Lys Tyr Ile Thr Ala Asn Ile Asn Leu Asp Thr Ser Arg Thr Gly Ile
245 250 255

Asp Ala Asn Thr Leu Leu Gly Ser Ile His Thr Phe Asp Pro Glu Ala
260 265 270

Ala Cys Asp Asp Ser Thr Phe Gln Pro Cys Ser Ala Arg Ala Leu Ala
275 280 285

Asn His Lys Val Tyr Val Asp Ala Phe Arg Ser Ile Tyr Lys Ile Asn
290 295 300

Ser Gly Ile Ala Glu Gly Ser Pro Ala Asn Val Gly Arg Tyr Pro Glu

-continued 305 310 315 320

Asp Val Tyr Gln Gly Gly Asn Pro Trp Tyr Leu Thr Thr Leu Ala Ser
325 330 335

Ala Glu Leu Leu Tyr Asp Ala Leu Tyr Gln Trp Asn Lys Ile Gly Gly
340 345 350

Leu Asp Val Thr Glu Thr Ser Leu Ala Phe Phe Lys Asp Phe His Ser
355 360 365

Ser Val Lys Thr Gly Ser Tyr Ser Ala His Ser Gln Thr Tyr Lys Thr
370 375 380

Leu Thr Ser Ala Ile Arg Thr Tyr Ala Asp Gly Phe Val Gly Leu Val
385 390 395 400

Gln Lys Tyr Thr Pro Ala Asn Gly Ser Leu Ala Glu Gln Tyr Asn Arg
405 410 415

Asn Thr Ser Val Pro Leu Ser Ala Asn Asp Leu Thr Trp Ser Phe Ala
420 425 430

Ser Phe Leu Thr Ala Ile Gln Arg Arg Glu Ser Ile Val Pro Gly Ser
435 440 445

Trp Gly Glu Lys Ser Ala Asn Thr Val Pro Thr Thr Cys Ser Ala Ser
450 455 460

Pro Val Thr Gly Thr Tyr Lys Ala Ala Thr Ser Thr Phe Pro Thr Ser
465 470 475 480

Thr Ala Gly Cys Val Pro Ala Thr Asp Trp Pro Ile Thr Phe Tyr Leu
485 490 495

Ile Glu Asn Thr Tyr Tyr Gly Glu Asn Val Tyr Met Thr Gly Asn Ile
500 505 510

Ser Ala Leu Gly Asn Trp Asp Thr Ser Asp Gly Leu Ala Leu Asp Ala
515 520 525

Gly Leu Tyr Thr Glu Thr Asp Asn Leu Trp Phe Gly Thr Leu Glu Leu
530 535 540

Val Thr Ala Gly Thr Pro Phe Glu Tyr Lys Tyr Tyr Lys Ile Glu Pro
545 550 555 560

Asn Gly Thr Val Thr Trp Glu Ser Gly Asp Asn Arg Val Ser Val Val
565 570 575

Pro Thr Gly Cys Pro Ile Gln Pro Ser Leu His Asp Val Trp Arg Ser
580 585 590

<210> SEQ ID NO 10
<211> LENGTH: 588
<212> TYPE: PRT
<213> ORGANISM: Penicillium brasilianum

<400> SEQUENCE: 10

Asn Val Asp Leu Ala Ser Phe Ile Ser Lys Glu Gly Gln Arg Ser Ile
1 5 10 15

Leu Gly Ile Thr Glu Asn Leu Gly Gly Lys Gly Ser Lys Thr Pro Gly
20 25 30

Thr Ala Ala Gly Leu Phe Ile Ala Ser Pro Asn Met Ala Asn Pro Asn
35 40 45

Tyr Tyr Tyr Thr Trp Thr Arg Asp Ser Ala Leu Thr Ile Lys Cys Leu
50 55 60

Ile Asp Leu Phe Glu Ser Ser Gly Gly Gly Phe Ser Thr Ser Ser Lys
65 70 75 80

Glu Leu Glu Thr Asp Ile Arg Asn Tyr Val Ser Ala Gln Ala Val Leu
85 90 95

-continued

```
Gln Asn Val Ser Asn Pro Ser Gly Thr Leu Gln Asp Gly Ser Gly Leu
            100                 105                 110

Gly Glu Pro Lys Phe Glu Val Asp Leu Asn Pro Phe Ser Gly Ser Trp
        115                 120                 125

Gly Arg Pro Gln Arg Asp Gly Pro Ala Leu Arg Ala Thr Ala Met Ile
    130                 135                 140

Thr Tyr Ala Asp Trp Leu Ile Ser His Gly Gln Lys Ser Glu Ala Ala
145                 150                 155                 160

Ser Ile Met Trp Pro Ile Ile Ala Asn Asp Leu Ala Tyr Val Gly Gln
                165                 170                 175

Tyr Trp Asn Asn Thr Gly Phe Asp Leu Trp Glu Glu Val Asp Gly Ser
            180                 185                 190

Ser Phe Phe Thr Leu Ala Val Gln His Arg Ala Leu Val Gln Gly Ser
        195                 200                 205

Ser Leu Ala Gln Lys Leu Gly Lys Ser Cys Pro Ala Cys Lys Ser Gln
    210                 215                 220

Ala Pro Gln Ile Leu Cys Phe Leu Gln Ser Phe Trp Asn Gly Asn Tyr
225                 230                 235                 240

Ile Thr Ala Asn Ile Asn Leu Asp Thr Ser Arg Ser Gly Ile Asp Leu
                245                 250                 255

Asn Ser Ile Leu Gly Ser Ile His Thr Phe Asp Pro Glu Ala Ala Cys
            260                 265                 270

Asp Asp Ser Thr Phe Gln Pro Cys Ser Ala Arg Ala Leu Ala Asn His
        275                 280                 285

Lys Val Tyr Val Asp Ser Phe Arg Ser Ile Tyr Thr Ile Asn Ala Gly
    290                 295                 300

Ile Gly Lys Gly Ser Ala Ala Asn Val Gly Arg Tyr Pro Glu Asp Val
305                 310                 315                 320

Tyr Gln Gly Gly Asn Pro Trp Tyr Leu Ala Thr Leu Ala Ala Ala Glu
                325                 330                 335

Met Leu Tyr Asp Ala Leu Tyr Gln Trp Asn Lys Ile Gly Lys Leu Asp
            340                 345                 350

Val Thr Asp Thr Ser Leu Ala Phe Phe Lys Asp Phe Asp Ala Ser Val
        355                 360                 365

Arg Lys Gly Ser Tyr Ser Ala His Ser Ser Thr Tyr Lys Thr Leu Thr
    370                 375                 380

Ser Ala Ile Arg Thr Tyr Ala Asp Gly Phe Leu Thr Leu Val Gln Glu
385                 390                 395                 400

Tyr Thr Pro Ser Asn Gly Ser Leu Ala Glu Gln Tyr Asn Arg Asn Thr
                405                 410                 415

Ser Val Pro Leu Ser Ala Asn Asp Leu Thr Trp Ser Tyr Ala Ser Phe
            420                 425                 430

Val Thr Ala Val Gln Arg Arg Ser Ser Ile Val Pro Ala Ser Trp Gly
        435                 440                 445

Glu Lys Ser Ala Asn Trp Pro Thr Thr Cys Ser Ala Ser Pro Val Thr
    450                 455                 460

Gly Thr Tyr Gln Ala Val Ser Ser Ala Phe Pro Thr Ser Thr Gly Cys
465                 470                 475                 480

Val Pro Ala Thr Asp Trp Pro Ile Thr Phe Tyr Leu Ile Glu Asn Thr
                485                 490                 495

Phe Tyr Gly Glu Asn Val Phe Met Thr Gly Asn Ile Ser Ala Leu Gly
            500                 505                 510

Asn Trp Asp Thr Ser Asn Gly Phe Pro Leu Thr Ala Asn Leu Tyr Thr
```

515 520 525

Glu Thr Asn Asn Leu Trp Phe Ala Ser Val Glu Leu Val Ala Ala Gly
530 535 540

Thr Pro Phe Glu Tyr Lys Tyr Tyr Lys Val Glu Pro Asn Gly Thr Val
545 550 555 560

Ile Trp Glu Asn Gly Asp Asn Arg Val Tyr Val Ala Pro Thr Gly Cys
565 570 575

Pro Ile Gln Pro Asn Gln His Asp Val Trp Arg Ser
580 585

<210> SEQ ID NO 11
<211> LENGTH: 614
<212> TYPE: PRT
<213> ORGANISM: Penicillium russellii

<400> SEQUENCE: 11

Met Arg Tyr Thr Leu Leu Thr Ser Ile Ala Ser Val Leu Ser Val Gly
1 5 10 15

Pro Leu Ala Ser Ala Ser Pro Thr Ser Lys Asp Gly Asn Leu Ala Ser
20 25 30

Tyr Ile Ala Lys Glu Gly Gln Arg Ser Ile Val Gly Ile Thr Glu Asn
35 40 45

Leu Gly Gly Lys Gly Ser Lys Thr Pro Gly Thr Ala Ala Gly Leu Phe
50 55 60

Ile Ala Ser Pro Asn Met Ala Asn Pro Asn Tyr Tyr Tyr Thr Trp Thr
65 70 75 80

Arg Asp Ser Ala Leu Thr Phe Lys Cys Leu Ile Asp Leu Phe Glu Thr
85 90 95

Ser Asp Gln Asp Tyr Ile Ser Arg Lys Glu Leu Glu Thr Asp Ile Arg
100 105 110

Asn Tyr Val Ser Ser Gln Ala Val Leu Gln Asn Val Ser Asn Pro Ser
115 120 125

Gly Thr Leu Lys Asp Gly Ser Gly Leu Gly Glu Pro Lys Phe Glu Ile
130 135 140

Asp Leu Asn Pro Phe Ser Gly Ser Trp Gly Arg Pro Gln Arg Asp Gly
145 150 155 160

Pro Ala Leu Arg Ala Thr Ala Met Ile Thr Tyr Ala Asp Trp Leu Val
165 170 175

Ser His Gly Gln Lys Ser Glu Ala Thr Asn Ile Met Trp Pro Ile Ile
180 185 190

Ala Asn Asp Leu Ala Tyr Val Gly Gln Tyr Trp Asn Lys Thr Gly Phe
195 200 205

Asp Leu Trp Glu Glu Val Asp Gly Ser Ser Phe Tyr Thr Leu Ala Val
210 215 220

Gln His Arg Ala Leu Val Gln Gly Ala Ser Leu Ala Lys Lys Leu Gly
225 230 235 240

Lys Ser Cys Thr Ala Cys Val Ser Gln Ala Pro Gln Ile Leu Cys Phe
245 250 255

Leu Gln Ser Phe Trp Asn Gly Asn Tyr Ile Thr Ala Asn Ile Asn Leu
260 265 270

Asp Thr Ser Arg Ser Gly Ile Asp Leu Asn Ser Ile Leu Gly Ser Ile
275 280 285

His Thr Phe Asp Pro Glu Ala Ser Cys Asp Asp Ser Thr Phe Gln Pro
290 295 300

```
Cys Ser Ala Arg Ala Leu Ala Asn His Lys Val Tyr Val Asp Ala Phe
305                 310                 315                 320

Arg Ser Ile Tyr Gly Val Asn Ala Gly Leu Ser Asn Gly Thr Ala Ala
                325                 330                 335

Asn Val Gly Arg Tyr Pro Glu Asp Val Tyr Gln Gly Gly Asn Pro Trp
            340                 345                 350

Tyr Leu Ala Thr Leu Ala Ala Ala Glu Leu Leu Tyr Asp Ala Leu Tyr
        355                 360                 365

Gln Trp Asn Gln Ile Gly Lys Leu Asp Val Thr Lys Thr Ser Leu Ala
    370                 375                 380

Phe Phe Lys Asp Phe Asp Ala Ala Val Lys Thr Gly Thr Tyr Ser Ala
385                 390                 395                 400

His Ser Ser Ala Tyr Arg Thr Leu Thr Ser Ala Ile Arg Thr Tyr Ala
                405                 410                 415

Asp Asp Phe Ile Ser Leu Val Gln His Tyr Thr Pro Ser Asn Gly Ser
            420                 425                 430

Leu Ala Glu Gln Tyr Asp Arg Asp Thr Gly Ile Pro Leu Ser Ala Asn
        435                 440                 445

Asp Leu Thr Trp Ser Tyr Ala Ser Phe Ile Thr Ala Ile Glu Arg Arg
    450                 455                 460

Ala Ser Val Val Pro Ala Ser Trp Gly Glu Lys Ser Ala Asn Val Val
465                 470                 475                 480

Pro Thr Thr Cys Ser Ala Ser Pro Val Thr Gly Thr Tyr Val Ala Ala
                485                 490                 495

Thr Ser Val Phe Pro Thr Thr Thr Gly Cys Val Pro Ala Thr Ser Ile
            500                 505                 510

Val Pro Ile Thr Phe Tyr Leu Thr Glu Ser Thr Phe Tyr Gly Glu Asn
        515                 520                 525

Val Tyr Met Thr Gly Asn Ile Ser Ala Leu Gly Asn Trp Asp Thr Ser
    530                 535                 540

Ser Gly Phe Pro Leu Thr Ala Asn Leu Tyr Thr Asp Ser Asp His Leu
545                 550                 555                 560

Trp Phe Ala Ser Val Glu Leu Val Pro Ala Gly Thr Pro Phe Glu Tyr
                565                 570                 575

Lys Tyr Tyr Lys Val Glu Pro Asn Gly Thr Val Ile Trp Glu Asn Gly
            580                 585                 590

Glu Asn Arg Val Tyr Val Ala Pro Thr Gly Cys Pro Ile Gln Pro Ser
        595                 600                 605

Gln Thr Asp Ile Trp Arg
    610
```

<210> SEQ ID NO 12
<211> LENGTH: 590
<212> TYPE: PRT
<213> ORGANISM: Penicillium russellii

<400> SEQUENCE: 12

```
Ser Lys Asp Gly Asn Leu Ala Ser Tyr Ile Ala Lys Glu Gly Gln Arg
1               5                   10                  15

Ser Ile Val Gly Ile Thr Glu Asn Leu Gly Gly Lys Gly Ser Lys Thr
            20                  25                  30

Pro Gly Thr Ala Ala Gly Leu Phe Ile Ala Ser Pro Asn Met Ala Asn
        35                  40                  45

Pro Asn Tyr Tyr Tyr Thr Trp Thr Arg Asp Ser Ala Leu Thr Phe Lys
    50                  55                  60
```

```
Cys Leu Ile Asp Leu Phe Glu Thr Ser Asp Gln Asp Tyr Ile Ser Arg
65                  70                  75                  80

Lys Glu Leu Glu Thr Asp Ile Arg Asn Tyr Val Ser Ser Gln Ala Val
                85                  90                  95

Leu Gln Asn Val Ser Asn Pro Ser Gly Thr Leu Lys Asp Gly Ser Gly
            100                 105                 110

Leu Gly Glu Pro Lys Phe Glu Ile Asp Leu Asn Pro Phe Ser Gly Ser
        115                 120                 125

Trp Gly Arg Pro Gln Arg Asp Gly Pro Ala Leu Arg Ala Thr Ala Met
    130                 135                 140

Ile Thr Tyr Ala Asp Trp Leu Val Ser His Gly Gln Lys Ser Glu Ala
145                 150                 155                 160

Thr Asn Ile Met Trp Pro Ile Ile Ala Asn Asp Leu Ala Tyr Val Gly
                165                 170                 175

Gln Tyr Trp Asn Lys Thr Gly Phe Asp Leu Trp Glu Glu Val Asp Gly
            180                 185                 190

Ser Ser Phe Tyr Thr Leu Ala Val Gln His Arg Ala Leu Val Gln Gly
        195                 200                 205

Ala Ser Leu Ala Lys Lys Leu Gly Lys Ser Cys Thr Ala Cys Val Ser
    210                 215                 220

Gln Ala Pro Gln Ile Leu Cys Phe Leu Gln Ser Phe Trp Asn Gly Asn
225                 230                 235                 240

Tyr Ile Thr Ala Asn Ile Asn Leu Asp Thr Ser Arg Ser Gly Ile Asp
                245                 250                 255

Leu Asn Ser Ile Leu Gly Ser Ile His Thr Phe Asp Pro Glu Ala Ser
            260                 265                 270

Cys Asp Asp Ser Thr Phe Gln Pro Cys Ser Ala Arg Ala Leu Ala Asn
        275                 280                 285

His Lys Val Tyr Val Asp Ala Phe Arg Ser Ile Tyr Gly Val Asn Ala
    290                 295                 300

Gly Leu Ser Asn Gly Thr Ala Ala Asn Val Gly Arg Tyr Pro Glu Asp
305                 310                 315                 320

Val Tyr Gln Gly Gly Asn Pro Trp Tyr Leu Ala Thr Leu Ala Ala Ala
                325                 330                 335

Glu Leu Leu Tyr Asp Ala Leu Tyr Gln Trp Asn Gln Ile Gly Lys Leu
            340                 345                 350

Asp Val Thr Lys Thr Ser Leu Ala Phe Phe Lys Asp Phe Asp Ala Ala
        355                 360                 365

Val Lys Thr Gly Thr Tyr Ser Ala His Ser Ser Ala Tyr Arg Thr Leu
    370                 375                 380

Thr Ser Ala Ile Arg Thr Tyr Ala Asp Asp Phe Ile Ser Leu Val Gln
385                 390                 395                 400

His Tyr Thr Pro Ser Asn Gly Ser Leu Ala Glu Gln Tyr Asp Arg Asp
                405                 410                 415

Thr Gly Ile Pro Leu Ser Ala Asn Asp Leu Thr Trp Ser Tyr Ala Ser
            420                 425                 430

Phe Ile Thr Ala Ile Glu Arg Arg Ala Ser Val Val Pro Ala Ser Trp
        435                 440                 445

Gly Glu Lys Ser Ala Asn Val Val Pro Thr Thr Cys Ser Ala Ser Pro
    450                 455                 460

Val Thr Gly Thr Tyr Val Ala Ala Thr Ser Val Phe Pro Thr Thr Thr
465                 470                 475                 480
```

Gly Cys Val Pro Ala Thr Ser Ile Val Pro Ile Thr Phe Tyr Leu Thr
485 490 495

Glu Ser Thr Phe Tyr Gly Glu Asn Val Tyr Met Thr Gly Asn Ile Ser
500 505 510

Ala Leu Gly Asn Trp Asp Thr Ser Ser Gly Phe Pro Leu Thr Ala Asn
515 520 525

Leu Tyr Thr Asp Ser Asp His Leu Trp Phe Ala Ser Val Glu Leu Val
530 535 540

Pro Ala Gly Thr Pro Phe Glu Tyr Lys Tyr Tyr Lys Val Glu Pro Asn
545 550 555 560

Gly Thr Val Ile Trp Glu Asn Gly Glu Asn Arg Val Tyr Val Ala Pro
565 570 575

Thr Gly Cys Pro Ile Gln Pro Ser Gln Thr Asp Ile Trp Arg
580 585 590

<210> SEQ ID NO 13
<211> LENGTH: 614
<212> TYPE: PRT
<213> ORGANISM: Penicillium miczynskii

<400> SEQUENCE: 13

Met Arg Tyr Thr Val Leu Thr Ser Ile Ala Ser Val Leu Cys Val Gly
1 5 10 15

Pro Leu Ala Ser Ala Asn Pro Thr Ser Lys Asp Ala Lys Met Ala Ser
20 25 30

Tyr Ile Ser Lys Glu Gly Gln Arg Ser Ile Val Gly Ile Thr Glu Asn
35 40 45

Leu Gly Gly Lys Gly Ser Lys Thr Pro Gly Thr Ala Ala Gly Leu Phe
50 55 60

Ile Ala Ser Pro Asn Met Ala Asn Pro Asn Tyr Tyr Tyr Thr Trp Thr
65 70 75 80

Arg Asp Ser Ala Leu Thr Phe Lys Cys Leu Ile Asp Leu Phe Glu Thr
85 90 95

Ser Asp Gln Asp Tyr Ile Ser Arg Lys Glu Leu Glu Thr Asp Ile Arg
100 105 110

Asn Tyr Val Ser Ser Gln Ala Val Leu Gln Asn Val Ser Asn Pro Ser
115 120 125

Gly Thr Leu Lys Asp Gly Ser Gly Leu Gly Glu Pro Lys Phe Glu Ile
130 135 140

Asp Leu Asn Pro Phe Ser Gly Ser Trp Gly Arg Pro Gln Arg Asp Gly
145 150 155 160

Pro Ala Leu Arg Ala Thr Ala Met Ile Thr Tyr Ala Asp Trp Leu Ile
165 170 175

Ser His Gly Ser Lys Ser Glu Ala Ala Asn Ile Met Trp Pro Ile Ile
180 185 190

Ala Asn Asp Leu Ala Tyr Val Gly Gln Tyr Trp Asn Asn Thr Gly Phe
195 200 205

Asp Leu Trp Glu Glu Val Asp Gly Ser Ser Phe Phe Thr Leu Ala Val
210 215 220

Gln His Arg Ser Leu Val Gln Gly Ala Ser Leu Ala Lys Lys Leu Gly
225 230 235 240

Lys Ser Cys Pro Ala Cys Val Ser Gln Ala Pro Gln Ile Leu Cys Phe
245 250 255

Leu Gln Ser Phe Trp Asn Gly Asn Tyr Ile Thr Ala Asn Ile Asn Leu
260 265 270

Asp Thr Ser Arg Ser Gly Ile Asp Leu Asn Ser Ile Leu Gly Ser Ile
275 280 285

His Thr Phe Asp Pro Glu Ala Ser Cys Asp Asp Ser Thr Phe Gln Pro
290 295 300

Cys Ser Ala Arg Ala Leu Ala Asn His Lys Val Tyr Val Asp Ala Phe
305 310 315 320

Arg Ser Ile Tyr Lys Val Asn Ala Gly Leu Ser Asn Gly Ser Ala Ala
325 330 335

Asn Val Gly Arg Tyr Pro Glu Asp Val Tyr Gln Gly Gly Asn Pro Trp
340 345 350

Tyr Leu Ala Thr Leu Ala Ser Ala Glu Leu Leu Tyr Asp Ala Leu Tyr
355 360 365

Gln Trp Ser Lys Ile Gly Lys Leu Asp Val Thr Lys Thr Ser Leu Ala
370 375 380

Phe Phe Lys Asp Phe Asp Met Ala Val Lys Thr Gly Thr Tyr Ser Ala
385 390 395 400

His Ser Ser Thr Tyr Lys Ser Leu Thr Ser Ala Ile Arg Thr Tyr Ala
405 410 415

Asp Asp Phe Ile Gly Leu Val Gln Asp Tyr Thr Pro Ser Asn Gly Ser
420 425 430

Leu Ala Glu Gln Tyr Asp Arg Asn Thr Gly Ile Pro Leu Ser Ala Asn
435 440 445

Asp Leu Thr Trp Ser Tyr Ala Ser Phe Ile Thr Ala Ile Gln Arg Arg
450 455 460

Ala Ser Val Val Pro Ala Ser Trp Gly Glu Lys Ser Ala Asn Val Val
465 470 475 480

Pro Thr Ile Cys Ser Ala Ser Pro Val Thr Gly Thr Tyr Gln Ala Ala
485 490 495

Pro Ser Val Phe Pro Thr Thr Thr Gly Cys Val Pro Ala Thr Ser Ile
500 505 510

Val Pro Ile Thr Phe Tyr Leu Thr Glu Thr Thr Phe Tyr Gly Glu Asn
515 520 525

Val Tyr Met Thr Gly Asn Ile Ser Ala Leu Gly Asn Trp Asp Thr Asn
530 535 540

Asn Gly Phe Pro Leu Thr Ala Asn Leu Tyr Thr Asp Ser Asp His Leu
545 550 555 560

Trp Phe Ala Ser Val Glu Leu Val Pro Ala Gly Thr Pro Phe Glu Tyr
565 570 575

Lys Tyr Tyr Lys Val Glu Pro Asn Gly Thr Val Ile Trp Glu Asn Gly
580 585 590

Glu Asn Arg Val Tyr Val Ala Pro Thr Gly Cys Pro Ile Gln Pro Ser
595 600 605

Gln Thr Asp Val Trp Arg
610

<210> SEQ ID NO 14
<211> LENGTH: 590
<212> TYPE: PRT
<213> ORGANISM: Rasamsonia emersonii

<400> SEQUENCE: 14

Ala Thr Gly Ser Leu Asp Ser Phe Leu Ala Thr Glu Thr Pro Ile Ala
1 5 10 15

Leu Gln Gly Val Leu Asn Asn Ile Gly Pro Asn Gly Ala Asp Val Ala

-continued

```
            20                  25                  30

Gly Ala Ser Ala Gly Ile Val Val Ala Ser Pro Ser Arg Ser Asp Pro
        35                  40                  45

Asn Tyr Phe Tyr Ser Trp Thr Arg Asp Ala Ala Leu Thr Ala Lys Tyr
    50                  55                  60

Leu Val Asp Ala Phe Ile Ala Gly Asn Lys Asp Leu Glu Gln Thr Ile
65                  70                  75                  80

Gln Gln Tyr Ile Ser Ala Gln Ala Lys Val Gln Thr Ile Ser Asn Pro
                85                  90                  95

Ser Gly Asp Leu Ser Thr Gly Gly Leu Gly Glu Pro Lys Phe Asn Val
            100                 105                 110

Asn Glu Thr Ala Phe Thr Gly Pro Trp Gly Arg Pro Gln Arg Asp Gly
        115                 120                 125

Pro Ala Leu Arg Ala Thr Ala Leu Ile Ala Tyr Ala Asn Tyr Leu Ile
    130                 135                 140

Asp Asn Gly Glu Ala Ser Thr Ala Asp Glu Ile Ile Trp Pro Ile Val
145                 150                 155                 160

Gln Asn Asp Leu Ser Tyr Ile Thr Gln Tyr Trp Asn Ser Ser Thr Phe
                165                 170                 175

Asp Leu Trp Glu Glu Val Glu Gly Ser Ser Phe Phe Thr Thr Ala Val
            180                 185                 190

Gln His Arg Ala Leu Val Glu Gly Asn Ala Leu Ala Thr Arg Leu Asn
        195                 200                 205

His Thr Cys Ser Asn Cys Val Ser Gln Ala Pro Gln Val Leu Cys Phe
    210                 215                 220

Leu Gln Ser Tyr Trp Thr Gly Ser Tyr Val Leu Ala Asn Phe Gly Gly
225                 230                 235                 240

Ser Gly Arg Ser Gly Lys Asp Val Asn Ser Ile Leu Gly Ser Ile His
                245                 250                 255

Thr Phe Asp Pro Ala Gly Gly Cys Asp Asp Ser Thr Phe Gln Pro Cys
            260                 265                 270

Ser Ala Arg Ala Leu Ala Asn His Lys Val Val Thr Asp Ser Phe Arg
        275                 280                 285

Ser Ile Tyr Ala Ile Asn Ser Gly Ile Ala Glu Gly Ser Ala Val Ala
    290                 295                 300

Val Gly Arg Tyr Pro Glu Asp Val Tyr Gln Gly Gly Asn Pro Trp Tyr
305                 310                 315                 320

Leu Ala Thr Ala Ala Ala Ala Glu Gln Leu Tyr Asp Ala Ile Tyr Gln
                325                 330                 335

Trp Lys Lys Ile Gly Ser Ile Ser Ile Thr Asp Val Ser Leu Pro Phe
            340                 345                 350

Phe Gln Asp Ile Tyr Pro Ser Ala Ala Val Gly Thr Tyr Asn Ser Gly
        355                 360                 365

Ser Thr Thr Phe Asn Asp Ile Ile Ser Ala Val Gln Thr Tyr Gly Asp
    370                 375                 380

Gly Tyr Leu Ser Ile Val Glu Lys Tyr Thr Pro Ser Asp Gly Ser Leu
385                 390                 395                 400

Thr Glu Gln Phe Ser Arg Thr Asp Gly Thr Pro Leu Ser Ala Ser Ala
                405                 410                 415

Leu Thr Trp Ser Tyr Ala Ser Leu Leu Thr Ala Ser Ala Arg Arg Gln
            420                 425                 430

Ser Val Val Pro Ala Ser Trp Gly Glu Ser Ser Ala Ser Ser Val Pro
        435                 440                 445
```

```
Ala Val Cys Ser Ala Thr Ser Ala Thr Gly Pro Tyr Ser Thr Ala Thr
    450                 455                 460

Asn Thr Val Trp Pro Ser Ser Gly Ser Gly Ser Ser Thr Thr Thr Ser
465                 470                 475                 480

Ala Pro Cys Thr Thr Pro Thr Ser Val Ala Val Thr Phe Asp Glu Ile
                485                 490                 495

Val Ser Thr Ser Tyr Gly Glu Thr Ile Tyr Leu Ala Gly Ser Ile Pro
            500                 505                 510

Glu Leu Gly Asn Trp Ser Thr Ala Ser Ala Ile Pro Leu Arg Ala Asp
        515                 520                 525

Ala Tyr Thr Asn Ser Asn Pro Leu Trp Tyr Val Thr Val Asn Leu Pro
    530                 535                 540

Pro Gly Thr Ser Phe Glu Tyr Lys Phe Phe Lys Asn Gln Thr Asp Gly
545                 550                 555                 560

Thr Ile Val Trp Glu Asp Asp Pro Asn Arg Ser Tyr Thr Val Pro Ala
                565                 570                 575

Tyr Cys Gly Gln Thr Thr Ala Ile Leu Asp Asp Ser Trp Gln
            580                 585                 590


<210> SEQ ID NO 15
<211> LENGTH: 253
<212> TYPE: PRT
<213> ORGANISM: Penicillium emersonii

<400> SEQUENCE: 15

Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
```

225 230 235 240

Ala Thr Tyr Thr Ile Pro Gly Pro Pro Glu Pro Thr Phe
245 250

<210> SEQ ID NO 16
<211> LENGTH: 863
<212> TYPE: PRT
<213> ORGANISM: Aspergillus fumigatus

<400> SEQUENCE: 16

Met Arg Phe Gly Trp Leu Glu Val Ala Ala Leu Thr Ala Ala Ser Val
1 5 10 15

Ala Asn Ala Gln Glu Leu Ala Phe Ser Pro Pro Phe Tyr Pro Ser Pro
20 25 30

Trp Ala Asp Gly Gln Gly Glu Trp Ala Asp Ala His Arg Arg Ala Val
35 40 45

Glu Ile Val Ser Gln Met Thr Leu Ala Glu Lys Val Asn Leu Thr Thr
50 55 60

Gly Thr Gly Trp Glu Met Asp Arg Cys Val Gly Gln Thr Gly Ser Val
65 70 75 80

Pro Arg Leu Gly Ile Asn Trp Gly Leu Cys Gly Gln Asp Ser Pro Leu
85 90 95

Gly Ile Arg Phe Ser Asp Leu Asn Ser Ala Phe Pro Ala Gly Thr Asn
100 105 110

Val Ala Ala Thr Trp Asp Lys Thr Leu Ala Tyr Leu Arg Gly Lys Ala
115 120 125

Met Gly Glu Glu Phe Asn Asp Lys Gly Val Asp Ile Leu Leu Gly Pro
130 135 140

Ala Ala Gly Pro Leu Gly Lys Tyr Pro Asp Gly Gly Arg Ile Trp Glu
145 150 155 160

Gly Phe Ser Pro Asp Pro Val Leu Thr Gly Val Leu Phe Ala Glu Thr
165 170 175

Ile Lys Gly Ile Gln Asp Ala Gly Val Ile Ala Thr Ala Lys His Tyr
180 185 190

Ile Leu Asn Glu Gln Glu His Phe Arg Gln Val Gly Glu Ala Gln Gly
195 200 205

Tyr Gly Tyr Asn Ile Thr Glu Thr Ile Ser Ser Asn Val Asp Asp Lys
210 215 220

Thr Met His Glu Leu Tyr Leu Trp Pro Phe Ala Asp Ala Val Arg Ala
225 230 235 240

Gly Val Gly Ala Val Met Cys Ser Tyr Asn Gln Ile Asn Asn Ser Tyr
245 250 255

Gly Cys Gln Asn Ser Gln Thr Leu Asn Lys Leu Leu Lys Ala Glu Leu
260 265 270

Gly Phe Gln Gly Phe Val Met Ser Asp Trp Ser Ala His His Ser Gly
275 280 285

Val Gly Ala Ala Leu Ala Gly Leu Asp Met Ser Met Pro Gly Asp Ile
290 295 300

Ser Phe Asp Asp Gly Leu Ser Phe Trp Gly Thr Asn Leu Thr Val Ser
305 310 315 320

Val Leu Asn Gly Thr Val Pro Ala Trp Arg Val Asp Asp Met Ala Val
325 330 335

Arg Ile Met Thr Ala Tyr Tyr Lys Val Gly Arg Asp Arg Leu Arg Ile
340 345 350

-continued

```
Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
    610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
    690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
```

770 775 780

Gln Leu Tyr Val Ser Leu Gly Gly Pro Asn Glu Pro Arg Val Val Leu
785 790 795 800

Arg Lys Phe Asp Arg Ile Phe Leu Ala Pro Gly Glu Gln Lys Val Trp
805 810 815

Thr Thr Thr Leu Asn Arg Arg Asp Leu Ala Asn Trp Asp Val Glu Ala
820 825 830

Gln Asp Trp Val Ile Thr Lys Tyr Pro Lys Lys Val His Val Gly Ser
835 840 845

Ser Ser Arg Lys Leu Pro Leu Arg Ala Pro Leu Pro Arg Val Tyr
850 855 860

<210> SEQ ID NO 17
<211> LENGTH: 532
<212> TYPE: PRT
<213> ORGANISM: Aspergillus fumigatus

<400> SEQUENCE: 17

Met Leu Ala Ser Thr Phe Ser Tyr Arg Met Tyr Lys Thr Ala Leu Ile
1 5 10 15

Leu Ala Ala Leu Leu Gly Ser Gly Gln Ala Gln Gln Val Gly Thr Ser
20 25 30

Gln Ala Glu Val His Pro Ser Met Thr Trp Gln Ser Cys Thr Ala Gly
35 40 45

Gly Ser Cys Thr Thr Asn Asn Gly Lys Val Val Ile Asp Ala Asn Trp
50 55 60

Arg Trp Val His Lys Val Gly Asp Tyr Thr Asn Cys Tyr Thr Gly Asn
65 70 75 80

Thr Trp Asp Thr Thr Ile Cys Pro Asp Asp Ala Thr Cys Ala Ser Asn
85 90 95

Cys Ala Leu Glu Gly Ala Asn Tyr Glu Ser Thr Tyr Gly Val Thr Ala
100 105 110

Ser Gly Asn Ser Leu Arg Leu Asn Phe Val Thr Thr Ser Gln Gln Lys
115 120 125

Asn Ile Gly Ser Arg Leu Tyr Met Met Lys Asp Asp Ser Thr Tyr Glu
130 135 140

Met Phe Lys Leu Leu Asn Gln Glu Phe Thr Phe Asp Val Asp Val Ser
145 150 155 160

Asn Leu Pro Cys Gly Leu Asn Gly Ala Leu Tyr Phe Val Ala Met Asp
165 170 175

Ala Asp Gly Gly Met Ser Lys Tyr Pro Thr Asn Lys Ala Gly Ala Lys
180 185 190

Tyr Gly Thr Gly Tyr Cys Asp Ser Gln Cys Pro Arg Asp Leu Lys Phe
195 200 205

Ile Asn Gly Gln Ala Asn Val Glu Gly Trp Gln Pro Ser Ser Asn Asp
210 215 220

Ala Asn Ala Gly Thr Gly Asn His Gly Ser Cys Cys Ala Glu Met Asp
225 230 235 240

Ile Trp Glu Ala Asn Ser Ile Ser Thr Ala Phe Thr Pro His Pro Cys
245 250 255

Asp Thr Pro Gly Gln Val Met Cys Thr Gly Asp Ala Cys Gly Gly Thr
260 265 270

Tyr Ser Ser Asp Arg Tyr Gly Gly Thr Cys Asp Pro Asp Gly Cys Asp
275 280 285

-continued

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
    450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Thr Ala Gly Asn Pro Gly Gly Thr Gly
                485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
        515                 520                 525

Ser Gln Cys Leu
    530

<210> SEQ ID NO 18
<211> LENGTH: 454
<212> TYPE: PRT
<213> ORGANISM: Aspergillus fumigatus

<400> SEQUENCE: 18

Met Lys His Leu Ala Ser Ser Ile Ala Leu Thr Leu Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

```
Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
        435                 440                 445

Asn Ala Asn Pro Ser Phe
    450
```

<210> SEQ ID NO 19
<211> LENGTH: 459
<212> TYPE: PRT
<213> ORGANISM: Trichoderma reesei

<400> SEQUENCE: 19

```
Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
```

```
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
    370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
    450                 455
```

<210> SEQ ID NO 20
<211> LENGTH: 515
<212> TYPE: PRT
<213> ORGANISM: Bacillus stearothermophilus

<400> SEQUENCE: 20

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
```

```
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515


<210> SEQ ID NO 21
<211> LENGTH: 177
<212> TYPE: PRT
<213> ORGANISM: Thermoascus aurantiacus

<400> SEQUENCE: 21

Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Ala Asp Ala Ala
            20                  25                  30

Gln Ser Gly Ser Ala Ser Lys Phe Ser Glu Tyr Phe Lys Thr Thr Ser
        35                  40                  45

Ser Ser Thr Arg Gln Thr Val Ala Ala Arg Leu Arg Ala Val Ala Arg
    50                  55                  60

Glu Ala Ser Ser Ser Ser Ser Gly Ala Thr Thr Tyr Tyr Cys Asp Asp
65                  70                  75                  80

Pro Tyr Gly Tyr Cys Ser Ser Asn Val Leu Ala Tyr Thr Leu Pro Ser
                85                  90                  95

Tyr Asn Ile Ile Ala Asn Cys Asp Ile Phe Tyr Thr Tyr Leu Pro Ala
            100                 105                 110

Leu Thr Ser Thr Cys His Ala Gln Asp Gln Ala Thr Thr Ala Leu His
        115                 120                 125

Glu Phe Thr His Ala Pro Gly Val Tyr Ser Pro Gly Thr Asp Asp Leu
    130                 135                 140

Ala Tyr Gly Tyr Gln Ala Ala Met Gly Leu Ser Ser Ser Gln Ala Val
145                 150                 155                 160

Met Asn Ala Asp Thr Tyr Ala Leu Tyr Ala Asn Ala Ile Tyr Leu Gly
                165                 170                 175

Cys


<210> SEQ ID NO 22
<211> LENGTH: 412
<212> TYPE: PRT
<213> ORGANISM: Pyrococcus furiosus

<400> SEQUENCE: 22
```

-continued

```
Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
        35                  40                  45

Ile Gly Trp Val Asp Phe Val Asn Gly Arg Ser Tyr Pro Tyr Asp Asp
    50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
    130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
    210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
    290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
        355                 360                 365

Asp Phe Glu Lys Val Gly Tyr Tyr Asn Pro Thr Asp Gly Thr Trp Thr
    370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser
                405                 410
```

<210> SEQ ID NO 23
<211> LENGTH: 325
<212> TYPE: PRT
<213> ORGANISM: Palaeococcus ferrophilus

<400> SEQUENCE: 23

```
Gly Lys Pro Lys Pro Ser Gln Pro Pro Gln Glu Val Pro Trp Gly Ile
1               5                   10                  15

Glu Arg Val Lys Ala Pro Ser Val Trp Ser Thr Thr Asp Gly Ser Ser
            20                  25                  30

Asn Gly Val Ile Gln Val Ala Ile Leu Asp Thr Gly Ile Asp Tyr Asp
        35                  40                  45

His Pro Asp Leu Ala Ala Asn Leu Ala Trp Gly Val Ser Thr Leu Arg
    50                  55                  60

Gly Arg Val Ser Thr Lys Pro Lys Asp Tyr Arg Asp Gln Asn Gly His
65                  70                  75                  80

Gly Thr His Val Ala Gly Thr Ile Ala Ala Leu Asn Asn Asp Ile Gly
                85                  90                  95

Val Val Gly Val Ala Pro Gly Val Gln Ile Tyr Ala Ile Arg Val Leu
            100                 105                 110

Asp Ala Ser Gly Arg Gly Ser Tyr Ser Asp Ile Ala Ile Gly Ile Glu
        115                 120                 125

Gln Ala Ile Leu Gly Pro Asp Gly Val Ala Asp Lys Asp Gly Asp Gly
    130                 135                 140

Ile Ile Ala Gly Asp Pro Asp Asp Asp Ala Ala Glu Val Ile Ser Met
145                 150                 155                 160

Ser Leu Gly Gly Ser Ala Asp Asp Ser Tyr Leu His Asp Met Ile Ile
                165                 170                 175

Gln Ala Tyr Asn Ala Gly Ile Val Ile Val Ala Ala Ser Gly Asn Glu
            180                 185                 190

Gly Ala Ser Ser Pro Ser Tyr Pro Ala Ala Tyr Pro Glu Val Ile Ala
        195                 200                 205

Val Gly Ala Ser Asp Ile Asn Asp Asn Ile Ala Ser Phe Ser Asn Arg
    210                 215                 220

Gln Pro Glu Val Ser Ala Pro Gly Val Asp Val Leu Ser Thr Tyr Pro
225                 230                 235                 240

Asp Asp Thr Tyr Lys Thr Leu Ser Gly Thr Ser Met Ala Thr Pro His
                245                 250                 255

Val Ser Gly Val Val Ala Leu Ile Gln Ala Ala His Phe Asn Lys Tyr
            260                 265                 270

Gly Thr Ile Leu Pro Val Gly Thr Phe Asp Asp Met Ser Lys Asn Thr
        275                 280                 285

Val Arg Gly Ile Leu His Ile Thr Ala Asp Asp Leu Gly Ser Pro Gly
    290                 295                 300

Trp Asp Val Asp Tyr Gly Tyr Gly Ile Val Arg Ala Asp Leu Ala Val
305                 310                 315                 320

Gln Ala Ala Leu Gly
                325
```

<210> SEQ ID NO 24
<211> LENGTH: 595
<212> TYPE: PRT
<213> ORGANISM: Penicillium oxalicum

<400> SEQUENCE: 24

-continued

```
Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
            20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
    50                  55                  60

Thr Ala Lys Cys Leu Ile Asp Leu Phe Glu Asp Ser Arg Ala Lys Phe
65                  70                  75                  80

Pro Ile Asp Arg Lys Tyr Leu Glu Thr Gly Ile Arg Asp Tyr Lys Ser
                85                  90                  95

Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
    130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
        195                 200                 205

Leu Val Glu Gly Ser Gln Leu Ala Lys Lys Leu Gly Lys Ser Cys Asp
    210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
    290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
            340                 345                 350

Leu Gly Lys Leu Glu Val Ser Glu Thr Ser Leu Ser Phe Phe Lys Asp
        355                 360                 365

Phe Asp Ala Thr Val Lys Ile Gly Ser Tyr Ser Arg Asn Ser Lys Thr
    370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415

Tyr Asp Arg Asn Thr Ala Ala Pro Leu Ser Ala Asn Asp Leu Thr Trp
```

```
            420                 425                 430

Ser Phe Ala Ser Phe Leu Thr Ala Thr Gln Arg Arg Asp Ala Val Val
        435                 440                 445

Pro Pro Ser Trp Gly Ala Lys Ser Ala Asn Lys Val Pro Thr Thr Cys
    450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                485                 490                 495

Phe Tyr Leu Ile Glu Asn Thr Tyr Tyr Gly Glu Asn Val Phe Met Ser
            500                 505                 510

Gly Asn Ile Thr Ala Leu Gly Asn Trp Asp Ala Lys Lys Gly Phe Pro
        515                 520                 525

Leu Thr Ala Asn Leu Tyr Thr Gln Asp Gln Asn Leu Trp Phe Ala Ser
    530                 535                 540

Val Glu Phe Ile Pro Ala Gly Thr Pro Phe Glu Tyr Lys Tyr Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
            580                 585                 590

Trp Gln Phe
        595


<210> SEQ ID NO 25
<211> LENGTH: 556
<212> TYPE: PRT
<213> ORGANISM: Trametes cingulata

<400> SEQUENCE: 25

Gln Ser Ser Ala Ala Asp Ala Tyr Val Ala Ser Glu Ser Pro Ile Ala
1               5                   10                  15

Lys Ala Gly Val Leu Ala Asn Ile Gly Pro Ser Gly Ser Lys Ser Asn
            20                  25                  30

Gly Ala Lys Ala Gly Ile Val Ile Ala Ser Pro Ser Thr Ser Asn Pro
        35                  40                  45

Asn Tyr Leu Tyr Thr Trp Thr Arg Asp Ser Ser Leu Val Phe Lys Ala
    50                  55                  60

Leu Ile Asp Gln Phe Thr Thr Gly Glu Asp Thr Ser Leu Arg Thr Leu
65                  70                  75                  80

Ile Asp Glu Phe Thr Ser Ala Glu Ala Ile Leu Gln Gln Val Pro Asn
                85                  90                  95

Pro Ser Gly Thr Val Ser Thr Gly Gly Leu Gly Glu Pro Lys Phe Asn
            100                 105                 110

Ile Asp Glu Thr Ala Phe Thr Asp Ala Trp Gly Arg Pro Gln Arg Asp
        115                 120                 125

Gly Pro Ala Leu Arg Ala Thr Ala Ile Ile Thr Tyr Ala Asn Trp Leu
    130                 135                 140

Leu Asp Asn Lys Asn Thr Thr Tyr Val Thr Asn Thr Leu Trp Pro Ile
145                 150                 155                 160

Ile Lys Leu Asp Leu Asp Tyr Val Ala Ser Asn Trp Asn Gln Ser Thr
                165                 170                 175

Phe Asp Leu Trp Glu Glu Ile Asn Ser Ser Ser Phe Phe Thr Thr Ala
            180                 185                 190
```

-continued

```
Val Gln His Arg Ala Leu Arg Glu Gly Ala Thr Phe Ala Asn Arg Ile
        195                 200                 205

Gly Gln Thr Ser Val Val Ser Gly Tyr Thr Thr Gln Ala Asn Asn Leu
    210                 215                 220

Leu Cys Phe Leu Gln Ser Tyr Trp Asn Pro Thr Gly Gly Tyr Ile Thr
225                 230                 235                 240

Ala Asn Thr Gly Gly Gly Arg Ser Gly Lys Asp Ala Asn Thr Val Leu
                245                 250                 255

Thr Ser Ile His Thr Phe Asp Pro Ala Ala Gly Cys Asp Ala Val Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Ser Ile Asn Ser Gly Ile Ala Ser Asn
    290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Ile Val Trp Asn Lys Leu Gly Ala Leu Asn Val Thr Ser Thr
            340                 345                 350

Ser Leu Pro Phe Phe Gln Gln Phe Ser Ser Gly Val Thr Val Gly Thr
        355                 360                 365

Tyr Ala Ser Ser Ser Ser Thr Phe Lys Thr Leu Thr Ser Ala Ile Lys
    370                 375                 380

Thr Phe Ala Asp Gly Phe Leu Ala Val Asn Ala Lys Tyr Thr Pro Ser
385                 390                 395                 400

Asn Gly Gly Leu Ala Glu Gln Tyr Ser Arg Ser Asn Gly Ser Pro Val
                405                 410                 415

Ser Ala Val Asp Leu Thr Trp Ser Tyr Ala Ala Ala Leu Thr Ser Phe
            420                 425                 430

Ala Ala Arg Ser Gly Lys Thr Tyr Ala Ser Trp Gly Ala Ala Gly Leu
        435                 440                 445

Thr Val Pro Thr Thr Cys Ser Gly Ser Gly Gly Ala Gly Thr Val Ala
    450                 455                 460

Val Thr Phe Asn Val Gln Ala Thr Thr Val Phe Gly Glu Asn Ile Tyr
465                 470                 475                 480

Ile Thr Gly Ser Val Pro Ala Leu Gln Asn Trp Ser Pro Asp Asn Ala
                485                 490                 495

Leu Ile Leu Ser Ala Ala Asn Tyr Pro Thr Trp Ser Ile Thr Val Asn
            500                 505                 510

Leu Pro Ala Ser Thr Thr Ile Glu Tyr Lys Tyr Ile Arg Lys Phe Asn
        515                 520                 525

Gly Ala Val Thr Trp Glu Ser Asp Pro Asn Asn Ser Ile Thr Thr Pro
    530                 535                 540

Ala Ser Gly Thr Phe Thr Gln Asn Asp Thr Trp Arg
545                 550                 555
```

<210> SEQ ID NO 26
<211> LENGTH: 591
<212> TYPE: PRT
<213> ORGANISM: Talaromyces emersonii

<400> SEQUENCE: 26

```
Ala Thr Gly Ser Leu Asp Ser Phe Leu Ala Thr Glu Thr Pro Ile Ala
1               5                   10                  15
```

-continued

```
Leu Gln Gly Val Leu Asn Asn Ile Gly Pro Asn Gly Ala Asp Val Ala
            20                  25                  30

Gly Ala Ser Ala Gly Ile Val Val Ala Ser Pro Ser Arg Ser Asp Pro
        35                  40                  45

Asn Tyr Phe Tyr Ser Trp Thr Arg Asp Ala Ala Leu Thr Ala Lys Tyr
    50                  55                  60

Leu Val Asp Ala Phe Ile Ala Gly Asn Lys Asp Leu Glu Gln Thr Ile
65                  70                  75                  80

Gln Gln Tyr Ile Ser Ala Gln Ala Lys Val Gln Thr Ile Ser Asn Pro
                85                  90                  95

Ser Gly Asp Leu Ser Thr Gly Gly Leu Gly Glu Pro Lys Phe Asn Val
            100                 105                 110

Asn Glu Thr Ala Phe Thr Gly Pro Trp Gly Arg Pro Gln Arg Asp Gly
        115                 120                 125

Pro Ala Leu Arg Ala Thr Ala Leu Ile Ala Tyr Ala Asn Tyr Leu Ile
    130                 135                 140

Asp Asn Gly Glu Ala Ser Thr Ala Asp Glu Ile Ile Trp Pro Ile Val
145                 150                 155                 160

Gln Asn Asp Leu Ser Tyr Ile Thr Gln Tyr Trp Asn Ser Ser Thr Phe
                165                 170                 175

Asp Leu Trp Glu Glu Val Glu Gly Ser Ser Phe Phe Thr Thr Ala Val
            180                 185                 190

Gln His Arg Ala Leu Val Glu Gly Asn Ala Leu Ala Thr Arg Leu Asn
        195                 200                 205

His Thr Cys Ser Asn Cys Val Ser Gln Ala Pro Gln Val Leu Cys Phe
    210                 215                 220

Leu Gln Ser Tyr Trp Thr Gly Ser Tyr Val Leu Ala Asn Phe Gly Gly
225                 230                 235                 240

Ser Gly Arg Ser Gly Lys Asp Val Asn Ser Ile Leu Gly Ser Ile His
                245                 250                 255

Thr Phe Asp Pro Ala Gly Gly Cys Asp Asp Ser Thr Phe Gln Pro Cys
            260                 265                 270

Ser Ala Arg Ala Leu Ala Asn His Lys Val Val Thr Asp Ser Phe Arg
        275                 280                 285

Ser Ile Tyr Ala Ile Asn Ser Gly Ile Ala Glu Gly Ser Ala Val Ala
    290                 295                 300

Val Gly Arg Tyr Pro Glu Asp Val Tyr Gln Gly Gly Asn Pro Trp Tyr
305                 310                 315                 320

Leu Ala Thr Ala Ala Ala Ala Glu Gln Leu Tyr Asp Ala Ile Tyr Gln
                325                 330                 335

Trp Lys Lys Ile Gly Ser Ile Ser Ile Thr Asp Val Ser Leu Pro Phe
            340                 345                 350

Phe Gln Asp Ile Tyr Pro Ser Ala Ala Val Gly Thr Tyr Asn Ser Gly
        355                 360                 365

Ser Thr Thr Phe Asn Asp Ile Ile Ser Ala Val Gln Thr Tyr Gly Asp
    370                 375                 380

Gly Tyr Leu Ser Ile Val Glu Lys Tyr Thr Pro Ser Asp Gly Ser Leu
385                 390                 395                 400

Thr Glu Gln Phe Ser Arg Thr Asp Gly Thr Pro Leu Ser Ala Ser Ala
                405                 410                 415

Leu Thr Trp Ser Tyr Ala Ser Leu Leu Thr Ala Ser Ala Arg Arg Gln
            420                 425                 430
```

-continued

Ser Val Val Pro Ala Ser Trp Gly Glu Ser Ser Ala Ser Ser Val Pro
        435                 440                 445

Ala Val Cys Ser Ala Thr Ser Ala Thr Gly Pro Tyr Ser Thr Ala Thr
    450                 455                 460

Asn Thr Val Trp Pro Ser Ser Gly Ser Gly Ser Ser Thr Thr Thr Ser
465                 470                 475                 480

Ser Ala Pro Cys Thr Thr Pro Thr Ser Val Ala Val Thr Phe Asp Glu
                485                 490                 495

Ile Val Ser Thr Ser Tyr Gly Glu Thr Ile Tyr Leu Ala Gly Ser Ile
            500                 505                 510

Pro Glu Leu Gly Asn Trp Ser Thr Ala Ser Ala Ile Pro Leu Arg Ala
        515                 520                 525

Asp Ala Tyr Thr Asn Ser Asn Pro Leu Trp Tyr Val Thr Val Asn Leu
    530                 535                 540

Pro Pro Gly Thr Ser Phe Glu Tyr Lys Phe Phe Lys Asn Gln Thr Asp
545                 550                 555                 560

Gly Thr Ile Val Trp Glu Asp Asp Pro Asn Arg Ser Tyr Thr Val Pro
                565                 570                 575

Ala Tyr Cys Gly Gln Thr Thr Ala Ile Leu Asp Asp Ser Trp Gln
            580                 585                 590

<210> SEQ ID NO 27
<211> LENGTH: 555
<212> TYPE: PRT
<213> ORGANISM: Pycnoporus sanguineus

<400> SEQUENCE: 27

Gln Ser Ser Ala Val Asp Ala Tyr Val Ala Ser Glu Ser Pro Ile Ala
1               5                   10                  15

Lys Gln Gly Val Leu Asn Asn Ile Gly Pro Asn Gly Ser Lys Ala His
            20                  25                  30

Gly Ala Lys Ala Gly Ile Val Val Ala Ser Pro Ser Thr Glu Asn Pro
        35                  40                  45

Asp Tyr Leu Tyr Thr Trp Thr Arg Asp Ser Ser Leu Val Phe Lys Leu
    50                  55                  60

Leu Ile Asp Gln Phe Thr Ser Gly Asp Asp Thr Ser Leu Arg Gly Leu
65                  70                  75                  80

Ile Asp Asp Phe Thr Ser Ala Glu Ala Ile Leu Gln Gln Val Ser Asn
                85                  90                  95

Pro Ser Gly Thr Val Ser Thr Gly Gly Leu Gly Glu Pro Lys Phe Asn
            100                 105                 110

Ile Asp Glu Thr Ala Phe Thr Gly Ala Trp Gly Arg Pro Gln Arg Asp
        115                 120                 125

Gly Pro Ala Leu Arg Ala Thr Ser Ile Ile Arg Tyr Ala Asn Trp Leu
    130                 135                 140

Leu Asp Asn Gly Asn Thr Thr Tyr Val Ser Asn Thr Leu Trp Pro Val
145                 150                 155                 160

Ile Gln Leu Asp Leu Asp Tyr Val Ala Asp Asn Trp Asn Gln Ser Thr
                165                 170                 175

Phe Asp Leu Trp Glu Glu Val Asp Ser Ser Ser Phe Phe Thr Thr Ala
            180                 185                 190

Val Gln His Arg Ala Leu Arg Glu Gly Ala Thr Phe Ala Ser Arg Ile
        195                 200                 205

Gly Gln Ser Ser Val Val Ser Gly Tyr Thr Thr Gln Ala Asp Asn Leu
    210                 215                 220

```
Leu Cys Phe Leu Gln Ser Tyr Trp Asn Pro Ser Gly Gly Tyr Val Thr
225                 230                 235                 240

Ala Asn Thr Gly Gly Gly Arg Ser Gly Lys Asp Ser Asn Thr Val Leu
                245                 250                 255

Thr Ser Ile His Thr Phe Asp Pro Ala Ala Gly Cys Asp Ala Ala Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Thr Ile Asn Asn Gly Ile Ala Ser Asn
    290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Tyr Val Trp Asp Gln Leu Gly Gly Leu Asn Val Thr Ser Thr
            340                 345                 350

Ser Leu Ala Phe Phe Gln Gln Phe Ala Ser Gly Leu Ser Thr Gly Thr
        355                 360                 365

Tyr Ser Ala Ser Ser Ser Thr Tyr Ala Thr Leu Thr Ser Ala Ile Arg
    370                 375                 380

Ser Phe Ala Asp Gly Phe Leu Ala Ile Asn Ala Lys Tyr Thr Pro Ala
385                 390                 395                 400

Asp Gly Gly Leu Ala Glu Gln Tyr Ser Arg Asn Asp Gly Thr Pro Leu
                405                 410                 415

Ser Ala Val Asp Leu Thr Trp Ser Tyr Ala Ala Ala Leu Thr Ala Phe
            420                 425                 430

Ala Ala Arg Glu Gly Lys Thr Tyr Gly Ser Trp Gly Ala Ala Gly Leu
        435                 440                 445

Thr Val Pro Ala Ser Cys Ser Gly Gly Gly Gly Ala Thr Val Ala Val
    450                 455                 460

Thr Phe Asn Val Gln Ala Thr Thr Val Phe Gly Glu Asn Ile Tyr Ile
465                 470                 475                 480

Thr Gly Ser Val Ala Ala Leu Gln Asn Trp Ser Pro Asp Asn Ala Leu
                485                 490                 495

Ile Leu Ser Ala Ala Asn Tyr Pro Thr Trp Ser Ile Thr Val Asn Leu
            500                 505                 510

Pro Ala Asn Thr Val Val Gln Tyr Lys Tyr Ile Arg Lys Phe Asn Gly
        515                 520                 525

Gln Val Thr Trp Glu Ser Asp Pro Asn Asn Gln Ile Thr Thr Pro Ser
    530                 535                 540

Gly Gly Ser Phe Thr Gln Asn Asp Val Trp Arg
545                 550                 555
```

<210> SEQ ID NO 28
<211> LENGTH: 556
<212> TYPE: PRT
<213> ORGANISM: Gloeophyllum sepiarium

<400> SEQUENCE: 28

```
Gln Ser Val Asp Ser Tyr Val Ser Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ser Ala Gly Val Val Val Ala Ser Pro Ser Thr Ser Asp Pro Asp Tyr
```

-continued

```
        35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Thr Leu
65                  70                  75                  80

Ile Asp Asp Phe Val Thr Ala Glu Ala Asn Leu Gln Gln Val Ser Asn
                85                  90                  95

Pro Ser Gly Thr Leu Thr Thr Gly Gly Leu Gly Glu Pro Lys Phe Asn
            100                 105                 110

Val Asp Glu Thr Ala Phe Thr Gly Ala Trp Gly Arg Pro Gln Arg Asp
        115                 120                 125

Gly Pro Ala Leu Arg Ser Thr Ala Leu Ile Thr Tyr Gly Asn Trp Leu
    130                 135                 140

Leu Ser Asn Gly Asn Thr Ser Tyr Val Thr Ser Asn Leu Trp Pro Ile
145                 150                 155                 160

Ile Gln Asn Asp Leu Gly Tyr Val Val Ser Tyr Trp Asn Gln Ser Thr
                165                 170                 175

Tyr Asp Leu Trp Glu Glu Val Asp Ser Ser Ser Phe Phe Thr Thr Ala
            180                 185                 190

Val Gln His Arg Ala Leu Arg Glu Gly Ala Ala Phe Ala Thr Ala Ile
        195                 200                 205

Gly Gln Thr Ser Gln Val Ser Ser Tyr Thr Thr Gln Ala Asp Asn Leu
    210                 215                 220

Leu Cys Phe Leu Gln Ser Tyr Trp Asn Pro Ser Gly Gly Tyr Ile Thr
225                 230                 235                 240

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Ala Thr
            260                 265                 270

Phe Gln Pro Cys Ser Asp Lys Ala Leu Ser Asn Leu Lys Val Tyr Val
        275                 280                 285

Asp Ser Phe Arg Ser Val Tyr Ser Ile Asn Ser Gly Val Ala Ser Asn
    290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Glu Ser Gln Gly Ser Leu Glu Val Thr Ser Thr
            340                 345                 350

Ser Leu Ala Phe Phe Gln Gln Phe Ser Ser Gly Val Thr Ala Gly Thr
        355                 360                 365

Tyr Ser Ser Ser Ser Ser Thr Tyr Ser Thr Leu Thr Ser Ala Ile Lys
    370                 375                 380

Asn Phe Ala Asp Gly Phe Val Ala Ile Asn Ala Lys Tyr Thr Pro Ser
385                 390                 395                 400

Asn Gly Gly Leu Ala Glu Gln Tyr Ser Lys Ser Asp Gly Ser Pro Leu
                405                 410                 415

Ser Ala Val Asp Leu Thr Trp Ser Tyr Ala Ser Ala Leu Thr Ala Phe
            420                 425                 430

Glu Ala Arg Asn Asn Thr Gln Phe Ala Gly Trp Gly Ala Ala Gly Leu
        435                 440                 445

Thr Val Pro Ser Ser Cys Ser Gly Asn Ser Gly Gly Pro Thr Val Ala
    450                 455                 460
```

```
Val Thr Phe Asn Val Asn Ala Glu Thr Val Trp Gly Glu Asn Ile Tyr
465                 470                 475                 480

Leu Thr Gly Ser Val Asp Ala Leu Glu Asn Trp Ser Ala Asp Asn Ala
                485                 490                 495

Leu Leu Leu Ser Ser Ala Asn Tyr Pro Thr Trp Ser Ile Thr Val Asn
            500                 505                 510

Leu Pro Ala Ser Thr Ala Ile Glu Tyr Lys Tyr Ile Arg Lys Asn Asn
        515                 520                 525

Gly Ala Val Thr Trp Glu Ser Asp Pro Asn Asn Ser Ile Thr Thr Pro
    530                 535                 540

Ala Ser Gly Ser Thr Thr Glu Asn Asp Thr Trp Arg
545                 550                 555


<210> SEQ ID NO 29
<211> LENGTH: 559
<212> TYPE: PRT
<213> ORGANISM: Gloeophyllum trabeum

<400> SEQUENCE: 29

Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ala Ala Gly Val Val Val Ala Ser Pro Ser Lys Ser Asp Pro Asp Tyr
        35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Ser Leu
65                  70                  75                  80

Ile Asp Ser Phe Val Ile Ala Glu Ala Asn Ile Gln Gln Val Ser Asn
                85                  90                  95

Pro Ser Gly Thr Leu Thr Thr Gly Gly Leu Gly Glu Pro Lys Phe Asn
            100                 105                 110

Val Asp Glu Thr Ala Phe Thr Gly Ala Trp Gly Arg Pro Gln Arg Asp
        115                 120                 125

Gly Pro Ala Leu Arg Ala Thr Ala Leu Ile Thr Tyr Gly Asn Trp Leu
    130                 135                 140

Leu Ser Asn Gly Asn Thr Thr Trp Val Thr Ser Thr Leu Trp Pro Ile
145                 150                 155                 160

Ile Gln Asn Asp Leu Asn Tyr Val Val Gln Tyr Trp Asn Gln Thr Thr
                165                 170                 175

Phe Asp Leu Trp Glu Glu Val Asn Ser Ser Ser Phe Phe Thr Thr Ala
            180                 185                 190

Val Gln His Arg Ala Leu Arg Glu Gly Ala Ala Phe Ala Thr Lys Ile
        195                 200                 205

Gly Gln Thr Ser Ser Val Ser Ser Tyr Thr Thr Gln Ala Ala Asn Leu
    210                 215                 220

Leu Cys Phe Leu Gln Ser Tyr Trp Asn Pro Thr Ser Gly Tyr Ile Thr
225                 230                 235                 240

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Thr Thr
            260                 265                 270

Phe Gln Pro Cys Ser Asp Lys Ala Leu Ser Asn Leu Lys Val Tyr Val
```

```
        275                 280                 285

Asp Ser Phe Arg Ser Val Tyr Ser Ile Asn Ser Gly Ile Ala Ser Asn
    290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Ala Ala Gln Gly Ser Leu Asn Val Thr Ser Ile
            340                 345                 350

Ser Leu Pro Phe Phe Gln Gln Phe Ser Ser Ser Val Thr Ala Gly Thr
        355                 360                 365

Tyr Ala Ser Ser Ser Thr Thr Tyr Thr Thr Leu Thr Ser Ala Ile Lys
    370                 375                 380

Ser Phe Ala Asp Gly Phe Val Ala Ile Asn Ala Gln Tyr Thr Pro Ser
385                 390                 395                 400

Asn Gly Gly Leu Ala Glu Gln Phe Ser Arg Ser Asn Gly Ala Pro Val
                405                 410                 415

Ser Ala Val Asp Leu Thr Trp Ser Tyr Ala Ser Ala Leu Thr Ala Phe
            420                 425                 430

Glu Ala Arg Asn Asn Thr Gln Phe Ala Gly Trp Gly Ala Val Gly Leu
        435                 440                 445

Thr Val Pro Thr Ser Cys Ser Ser Asn Ser Gly Gly Gly Gly Gly Ser
    450                 455                 460

Thr Val Ala Val Thr Phe Asn Val Asn Ala Gln Thr Val Trp Gly Glu
465                 470                 475                 480

Asn Ile Tyr Ile Thr Gly Ser Val Asp Ala Leu Ser Asn Trp Ser Pro
                485                 490                 495

Asp Asn Ala Leu Leu Leu Ser Ser Ala Asn Tyr Pro Thr Trp Ser Ile
            500                 505                 510

Thr Val Asn Leu Pro Ala Ser Thr Ala Ile Gln Tyr Lys Tyr Ile Arg
        515                 520                 525

Lys Asn Asn Gly Ala Val Thr Trp Glu Ser Asp Pro Asn Asn Ser Ile
    530                 535                 540

Thr Thr Pro Ala Ser Gly Ser Val Thr Glu Asn Asp Thr Trp Arg
545                 550                 555


<210> SEQ ID NO 30
<211> LENGTH: 583
<212> TYPE: PRT
<213> ORGANISM: Rhizomucor pusillus

<400> SEQUENCE: 30

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95
```

-continued

```
Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
    290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
    370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Thr Ala Thr Pro
        435                 440                 445

Thr Gly Ser Gly Ser Val Thr Ser Thr Ser Lys Thr Thr Ala Thr Ala
    450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
```

-continued 515 520 525

Leu Trp Tyr Val Thr Val Thr Leu Pro Ala Gly Glu Ser Phe Glu Tyr
530 535 540

Lys Phe Ile Arg Ile Glu Ser Asp Asp Ser Val Glu Trp Glu Ser Asp
545 550 555 560

Pro Asn Arg Glu Tyr Thr Val Pro Gln Ala Cys Gly Thr Ser Thr Ala
565 570 575

Thr Val Thr Asp Thr Trp Arg
580

<210> SEQ ID NO 31
<211> LENGTH: 1020
<212> TYPE: PRT
<213> ORGANISM: Talaromyces funiculosus

<400> SEQUENCE: 31

Leu Pro Phe Asn Glu Arg Val Asp Gln Val Leu Arg Ser Tyr Glu Val
1 5 10 15

Thr Ser Lys Leu Asp Ser Arg Ser Thr Lys Pro Ser Lys His Gly His
20 25 30

Thr Tyr Gln Thr Gln Phe Leu Gly Val Thr Trp Asp Gln Arg Asn Trp
35 40 45

Arg Leu Gln Ser Thr Val Leu Asp Gln Gly His Tyr Glu Ser Arg Gly
50 55 60

Ser Ile Ala Asn Gly Tyr Ile Gly Leu Asn Val Ala Gly Ala Gly Pro
65 70 75 80

Leu Phe Glu Leu Asp Ser Pro Val Asp Gly Asp Val Ile Asn Gly Trp
85 90 95

Pro Leu Phe Ser Arg Arg Gln Thr Phe Ala Gly Leu Ala Gly Phe Tyr
100 105 110

Asp Leu Gln Pro Arg Thr Asn Gly Thr Asn Phe Pro Trp Leu Ser Gln
115 120 125

Tyr Gly Asp Asp Ser Ala Ile Ser Gly Val Pro His Trp Gly Gly Met
130 135 140

Val Leu Asp Leu Gly Asp Gly Glu Tyr Leu Asp Ala Thr Val Asp Asn
145 150 155 160

Ser Thr Ile Ser Asp Tyr Thr Thr Thr Tyr Asp Tyr Lys Ala Gly Val
165 170 175

Leu Ser Trp Asp Tyr Lys Trp Thr Pro Lys Asn Ala Asn Gly Ser Phe
180 185 190

Gly Ile Ser Tyr Lys Ile Phe Ala Asn Lys Leu Asp Val Asn Gln Ala
195 200 205

Val Val Gln Leu Ser Ile Thr Pro Ser Thr Asn Gly Ser Ala Ser Val
210 215 220

Val Asn Val Ile Asp Gly Tyr Ala Ala Val Arg Thr Asp Phe Val Ser
225 230 235 240

Ser Gly Asn Glu Ser Asp Val Val Tyr Thr Ala Val Lys Pro Asn Gly
245 250 255

Val Thr Asn Val Thr Ala Trp Ile Tyr Thr Ala Leu Asp Gly Asp Asp
260 265 270

Ala Phe Asp Ile Ser Ser Ala Ala Leu Val Asn Asp Lys Pro Tyr Val
275 280 285

His Gln Asn Asp Ser Ser Ile Ala Gln Ser Val Asn Val Thr Phe Thr
290 295 300

-continued

```
Ala Gly Thr Thr Ile Thr Ile Asn Lys Phe Val Gly Ala Ala Ser Thr
305                 310                 315                 320

Asp Ala Phe Pro Asp Pro Gln Ser Thr Ala Arg Glu Ala Ala Leu Ser
                325                 330                 335

Ala Arg Arg Arg Gly Phe Asp Asp Leu Phe Arg Ser His Ile Ser Glu
            340                 345                 350

Trp Ala Gln Val Met Pro Asp Asp Ser Val Asp Asp Phe Thr Leu Ala
        355                 360                 365

Asn Gly Thr Leu Pro Asn Asp Thr Phe Ile Ile Glu Ser Ala Val Met
    370                 375                 380

Ala Val Val Asn Pro Tyr Tyr Leu Leu Gln Asn Thr Val Gly Pro Asn
385                 390                 395                 400

Ala Leu Arg Arg Val Asn Asn Ala Pro Val Asn Asp Trp Ser Ile Pro
                405                 410                 415

Val Gly Gly Leu Thr Ser Asp Ser Tyr Ala Gly Gln Ile Phe Trp Asp
            420                 425                 430

Ala Asp Val Trp Met Gln Pro Gly Leu Val Ala Ala Phe Pro Glu Ser
        435                 440                 445

Ala Lys Arg Ile Thr Asn Tyr Arg Ala Ala Lys Tyr Ser Gln Ala Leu
    450                 455                 460

Glu Asn Ala Lys Thr Ala Tyr Thr Ser Ser Gln Asn Gln Thr Trp Phe
465                 470                 475                 480

Ser Pro Asp Ala Ala Ile Tyr Ser Trp Thr Ser Gly Arg Val Gly Asn
                485                 490                 495

Cys Thr Ala Thr Gly Pro Cys Trp Asp Tyr Glu Tyr His Leu Asn Gly
            500                 505                 510

Asp Ile Gly Ile Ser Leu Val Asn Glu Trp Val Val Ser Gly Asp Asn
        515                 520                 525

Glu Thr Phe Lys Asn Lys His Phe Pro Ile Tyr Asn Ser Ile Ala Thr
    530                 535                 540

Leu Tyr Gly Asp Leu Leu Lys Lys Asn Gly Ser Tyr Tyr Thr Leu Thr
545                 550                 555                 560

Asn Met Thr Asp Pro Asp Glu Tyr Ala Asn Asn Val Asp Ala Gly Gly
                565                 570                 575

Tyr Thr Met Thr Leu Ile Ser Gln Thr Leu Ser Asn Ala Asn Ala Phe
            580                 585                 590

Arg Lys Gln Phe Gly Met Asn Glu Asn Thr Thr Trp Thr Glu Met Ala
        595                 600                 605

Asp Asn Ile Leu Leu Ile Arg Glu Asn Asp Val Thr Leu Glu Tyr Thr
    610                 615                 620

Thr Met Asn Asn Ser Val Ala Val Lys Gln Ala Asp Val Ile Leu Ser
625                 630                 635                 640

Thr Phe Pro Leu Asp Tyr Thr Lys Asn Tyr Thr Thr Ser Ala Ala Leu
                645                 650                 655

Asn Asp Leu Asp Tyr Tyr Ala Leu Lys Gln Ser Pro Asp Gly Pro Gly
            660                 665                 670

Met Thr Tyr Ala Ile Phe Ser Ile Val Ala Asn Asp Val Ser Pro Ser
        675                 680                 685

Gly Cys Ser Ala Tyr Thr Tyr Ala Gln Tyr Ser Tyr Asp Pro Tyr Ile
    690                 695                 700

Arg Gly Pro Phe Phe Gln Phe Ser Glu Gln Leu Leu Asp Asp Tyr Thr
705                 710                 715                 720

Ile Asn Gly Gly Thr His Pro Ala Phe Pro Phe Leu Thr Gly His Gly
```

```
                725                 730                 735

Gly Ala Asn Gln Val Val Leu Tyr Gly Tyr Leu Gly Leu Arg Leu Leu
            740                 745                 750

Pro Asp Asp Met Leu His Ile Asp Pro Asn Leu Pro Pro Gln Ile Pro
        755                 760                 765

Ser Ile Lys Tyr Arg Thr Phe Tyr Trp Arg Gly Trp Pro Ile Gln Ala
    770                 775                 780

Ala Ser Asn Tyr Thr His Thr Thr Ile Gln Arg Ala Thr Thr Val Ala
785                 790                 795                 800

Pro Leu Ser Thr Ala Asp Pro Thr Tyr Ala Asn Lys Ser Ile His Val
                805                 810                 815

Ser Val Gly His Asn Thr Val Asn Ser Thr Thr Tyr Ser Leu Ser Ala
            820                 825                 830

Asn Gly Ser Ala Leu Val Val Pro Asn Arg Gln Ile Gly Ser Ile Asn
        835                 840                 845

Thr Val Ala Gly Asn Val Val Gln Cys Lys Ser Val Leu Ser Thr Asp
    850                 855                 860

Ala Tyr Gln Lys Gly Gln Tyr Pro Ile Ser Ala Val Asp Gly Ala Ala
865                 870                 875                 880

Ser Thr Lys Trp Gln Pro Glu Phe Ala Ala Asn Ile Ser Ser Leu Thr
                885                 890                 895

Val Asp Leu Thr Gly Ser Asn Val Ser Ser Val Ser Gly Phe Tyr Phe
            900                 905                 910

Asp Trp Ala Gln Ala Pro Pro Thr Asn Ile Thr Val Leu Leu His Asn
        915                 920                 925

Ser Ser Ser Ala Ala Leu Ala Ser Ser Gly Asp Lys Pro Gly Ser Ser
    930                 935                 940

Ala Val Thr Leu Asn Ile Thr Ile Ser Asn Pro Tyr Asn Ala Ser Thr
945                 950                 955                 960

Tyr Asn Ala Asn Ile Ile Ala Leu Pro Ser Ser Asn Ser Thr Asn Tyr
                965                 970                 975

Thr Phe Pro Ala Pro Val Pro Lys Pro Arg Tyr Ala Thr Leu Phe Val
            980                 985                 990

Gln Gly Asn Gln Ala Leu Asp Glu  Thr Asp Thr Lys Ser  Gly Asn Gly
        995                 1000                1005

Thr Gly  Ala Thr Val Ala Glu  Trp Ala Ile Leu Ser
    1010                1015                1020


<210> SEQ ID NO 32
<211> LENGTH: 694
<212> TYPE: PRT
<213> ORGANISM: Myceliophthora sepedonium

<400> SEQUENCE: 32

Met Ala Leu Arg His Ile Ala Ala Ala Ala Ile Ala Gly Leu Ala Ser
1               5                   10                  15

Arg Thr Ala Ala Leu Tyr Ile Asn Gly Ser Val Thr Ala Pro Cys Asp
            20                  25                  30

Ser Pro Ile Tyr Cys Gln Gly Glu Leu Leu Lys Ala Val Glu Leu Ala
        35                  40                  45

Arg Pro Phe Val Asp Ser Lys Thr Phe Val Asp Met Pro Thr Ile Lys
    50                  55                  60

Pro Val Asp Glu Val Leu Ala Ala Phe Ser Lys Leu Ser Leu Pro Leu
65                  70                  75                  80
```

-continued

```
Ser Asn Asn Ser Glu Leu Asn Ala Phe Leu Tyr Glu Asn Phe Ala Gln
                85                  90                  95

Ala Gly His Glu Leu Glu Glu Val Pro Asp Ser Glu Leu Glu Thr Asp
            100                 105                 110

Ala Lys Phe Leu Asp Lys Leu Glu Asp Arg Thr Ile Lys Glu Phe Val
        115                 120                 125

Gly Lys Val Ile Asp Ile Trp Pro Asp Leu Thr Arg Arg Tyr Ala Gly
    130                 135                 140

Pro Ser Asn Cys Thr Glu Cys Ala Asn Ser Phe Ile Pro Val Asn Arg
145                 150                 155                 160

Thr Phe Val Val Ala Gly Gly Arg Phe Arg Glu Pro Tyr Tyr Trp Asp
                165                 170                 175

Ser Tyr Trp Ile Val Glu Gly Leu Leu Arg Thr Gly Gly Ala Phe Thr
            180                 185                 190

His Ile Ser Lys Asn Ile Ile Glu Asn Phe Leu Asp Phe Val Asp Thr
        195                 200                 205

Ile Gly Phe Ile Pro Asn Gly Ala Arg Ile Tyr Tyr Leu Asn Arg Ser
    210                 215                 220

Gln Pro Pro Leu Leu Thr Leu Met Val Lys Ser Tyr Val Asp Tyr Thr
225                 230                 235                 240

Asn Asp Thr Ser Ile Leu Asp Arg Ala Leu Pro Leu Leu Ile Lys Glu
                245                 250                 255

His Glu Phe Phe Met Asn Asn Arg Thr Val Ser Ile Thr Gly Ser Asn
            260                 265                 270

Gly Lys Glu Tyr Thr Leu Asn Arg Tyr His Val Glu Asn Asn Gln Pro
        275                 280                 285

Arg Pro Glu Ser Phe Arg Glu Asp Tyr Ile Thr Ala Asn Asn Gly Ser
    290                 295                 300

Tyr Tyr Ala Ser Ser Gly Ile Ile Tyr Pro Val Lys Thr Pro Leu Asn
305                 310                 315                 320

Glu Thr Glu Lys Ala Ala Leu Tyr Ser Asn Leu Ala Thr Gly Ala Glu
                325                 330                 335

Ser Gly Trp Asp Tyr Thr Ser Arg Trp Leu Gly Val Pro Ser Asp Ala
            340                 345                 350

Ala Arg Asp Val Tyr Phe Pro Leu Arg Ser Leu Asn Val Arg Asp Ile
        355                 360                 365

Val Pro Val Asp Leu Asn Ser Ile Leu Tyr Gln Asn Glu Val Ile Ile
    370                 375                 380

Ala Glu Tyr Leu Glu Lys Ala Gly Asn Ser Ser Ala Ala Lys Arg Phe
385                 390                 395                 400

Ala Thr Ala Ala Glu Gln Arg Ser Glu Ala Met Tyr Ser Leu Met Trp
                405                 410                 415

Asn Ala Thr His Trp Ser Tyr Phe Asp Tyr Asn Leu Thr Asp Asn Thr
            420                 425                 430

Gln His Ile Phe Val Pro Ala Asp Glu Asp Thr Ala Pro Gln Asp Arg
        435                 440                 445

Ile Glu Ala Pro Pro Gly Gln Gln Val Phe Phe His Ile Ala Gln Leu
    450                 455                 460

Tyr Pro Phe Trp Thr Gly Ala Ala Pro Ala Ser Leu Lys Ala Asn Pro
465                 470                 475                 480

Leu Ala Val Gln Gln Ala Tyr Ala Arg Val Ala Arg Met Leu Asp Ile
                485                 490                 495

Lys Lys Gly Ala Ile Pro Ala Thr Asn Tyr Arg Thr Gly Gln Gln Trp
```

-continued

```
            500                 505                 510

Asp Gln Pro Asn Val Trp Pro Pro Leu Gln His Ile Leu Met Lys Gly
        515                 520                 525

Leu Leu Asn Thr Pro Ala Thr Phe Gly Lys Ser Asp Pro Ala Tyr Gln
    530                 535                 540

Ser Val Gln Asn Leu Ala Leu Arg Leu Ala Gln Arg Tyr Leu Asp Ser
545                 550                 555                 560

Thr Phe Cys Thr Trp Tyr Ala Thr Gly Gly Ser Thr Ser Asp Phe Pro
                565                 570                 575

Gln Leu Glu Gly Val Thr Pro Gly Ala Thr Gly Val Met Phe Glu Lys
            580                 585                 590

Tyr Ala Asp Asn Ala Thr Asn Val Ala Gly Gly Gly Gly Glu Tyr Glu
        595                 600                 605

Val Val Glu Gly Phe Gly Trp Thr Asn Gly Val Leu Ile Trp Ala Ala
    610                 615                 620

Asp Val Phe Gly Asn Lys Leu Lys Arg Pro Asp Cys Gly Asn Ile Thr
625                 630                 635                 640

Ala Ala His Thr His Ser Ser Ala Lys Arg Gly Leu Glu Glu Asn Lys
                645                 650                 655

Leu Pro Arg Arg Ala Val Glu Leu Asp Pro Trp Asp Ala Ala Trp Thr
            660                 665                 670

Lys Met Phe Gly Arg Ser Lys Leu Arg Arg Arg Glu Ala Glu Asp Val
        675                 680                 685

Arg Lys Arg Trp Met Ser
    690


<210> SEQ ID NO 33
<211> LENGTH: 186
<212> TYPE: PRT
<213> ORGANISM: Thermobifida cellulosilytica

<400> SEQUENCE: 33

Ala Asp Val Ile Gly Gly Asn Pro Tyr Tyr Phe Gly Gly Tyr Arg Cys
1               5                   10                  15

Ser Ile Gly Phe Ser Val Arg Lys Gly Ser Asp Thr Gly Phe Ala Thr
            20                  25                  30

Ala Gly His Cys Gly Glu Thr Gly Thr Leu Thr Arg Ser Pro Glu Gly
        35                  40                  45

Val Val Ala Gly Ser Tyr Phe Pro Gly Arg Asp Met Gly Trp Val Arg
    50                  55                  60

Leu Thr Gly Ala Asp Thr Val Thr Pro Leu Val Asn Arg Tyr Asp Gly
65                  70                  75                  80

Gly Thr Val Thr Val Thr Gly Ser Gln Glu Ala Val Thr Gly Ser Ser
                85                  90                  95

Val Cys Arg Ser Gly Ser Thr Thr Gly Trp Arg Cys Gly Ile Ile Gln
            100                 105                 110

Ser Lys Asn Gln Thr Val Arg Tyr Ala Glu Gly Thr Val Thr Gly Leu
        115                 120                 125

Thr Arg Thr Thr Ala Cys Ala Glu Ala Gly Asp Ser Gly Gly Pro Trp
    130                 135                 140

Leu Thr Gly Ser Gln Ala Gln Gly Val Thr Ser Gly Gly Ser Gly Asn
145                 150                 155                 160

Cys Arg Thr Gly Gly Ile Thr Tyr Phe Gln Pro Ile Asn Pro Leu Leu
                165                 170                 175
```

```
Ser Tyr Phe Gly Leu Glu Leu Val Thr Gly
            180                 185


<210> SEQ ID NO 34
<211> LENGTH: 186
<212> TYPE: PRT
<213> ORGANISM: Thermobifida fusca

<400> SEQUENCE: 34

Ala Ala Ile Ile Gly Gly Asn Pro Tyr Tyr Phe Gly Asn Tyr Arg Cys
1               5                   10                  15

Ser Ile Gly Phe Ser Val Arg Gln Gly Ser Gln Thr Gly Phe Ala Thr
            20                  25                  30

Ala Gly His Cys Gly Ser Thr Gly Thr Arg Val Ser Ser Pro Ser Gly
        35                  40                  45

Thr Val Ala Gly Ser Tyr Phe Pro Gly Arg Asp Met Gly Trp Val Arg
    50                  55                  60

Ile Thr Ser Ala Asp Thr Val Thr Pro Leu Val Asn Arg Tyr Asn Gly
65                  70                  75                  80

Gly Thr Val Thr Val Thr Gly Ser Gln Glu Ala Ala Thr Gly Ser Ser
                85                  90                  95

Val Cys Arg Ser Gly Ala Thr Thr Gly Trp Arg Cys Gly Thr Ile Gln
            100                 105                 110

Ser Lys Asn Gln Thr Val Arg Tyr Ala Glu Gly Thr Val Thr Gly Leu
        115                 120                 125

Thr Arg Thr Thr Ala Cys Ala Glu Gly Gly Asp Ser Gly Gly Pro Trp
    130                 135                 140

Leu Thr Gly Ser Gln Ala Gln Gly Val Thr Ser Gly Gly Thr Gly Asp
145                 150                 155                 160

Cys Arg Ser Gly Gly Ile Thr Phe Phe Gln Pro Ile Asn Pro Leu Leu
                165                 170                 175

Ser Tyr Phe Gly Leu Gln Leu Val Thr Gly
            180                 185


<210> SEQ ID NO 35
<211> LENGTH: 186
<212> TYPE: PRT
<213> ORGANISM: Thermobifida halotolerans

<400> SEQUENCE: 35

Thr Asp Ile Ile Gly Gly Asn Pro Tyr Tyr Phe Asp Gly Tyr Arg Cys
1               5                   10                  15

Ser Ile Gly Phe Ser Val Arg Arg Gly Ser Glu Ser Gly Phe Ala Thr
            20                  25                  30

Ala Gly His Cys Gly Glu Glu Gly Thr Glu Thr Ser Asp Pro Glu Gly
        35                  40                  45

Thr Val Ala Gly Ala Tyr Phe Pro Gly Arg Asp Met Gly Trp Val Arg
    50                  55                  60

Ile Thr Asp Ala Asp Thr Val Thr Pro Leu Val Asn Arg Tyr Asn Gly
65                  70                  75                  80

Glu Asn Val Thr Val Ala Gly Ser Arg Glu Ala Ala Thr Gly Ser Ser
                85                  90                  95

Val Cys Arg Ser Gly Ser Thr Thr Gly Trp Arg Cys Gly Thr Ile Arg
            100                 105                 110

Ser Lys Asn Gln Thr Val Arg Tyr Ile Glu Gly Thr Val Thr Gly Leu
        115                 120                 125
```

-continued

```
Thr Arg Thr Thr Ala Cys Ala Glu Gly Gly Asp Ser Gly Gly Pro Trp
    130                 135                 140

Leu Thr Gly Ser Gln Gly Gln Gly Val Thr Ser Gly Gly Ser Gly Asn
145                 150                 155                 160

Cys Thr Leu Gly Gly Val Thr Tyr Phe Gln Pro Leu Asn Pro Leu Leu
                165                 170                 175

Ser His Phe Asp Leu Asp Leu Val Thr Gly
            180                 185


<210> SEQ ID NO 36
<211> LENGTH: 325
<212> TYPE: PRT
<213> ORGANISM: Thermococcus nautili

<400> SEQUENCE: 36

Leu Val Pro Glu Pro Thr Gln Pro Ala Gln Glu Ile Pro Trp Gly Ile
1               5                   10                  15

Glu Arg Val Lys Ala Pro Asp Thr Trp Ser Ile Thr Thr Gly Ala Ser
            20                  25                  30

Asn Gly Val Ile Glu Val Ala Ile Leu Asp Thr Gly Ile Asp Trp Asp
        35                  40                  45

His Pro Asp Leu Lys Asp Asn Ile Ala Trp Gly Val Ser Thr Ile Gly
    50                  55                  60

Gly Glu Val Ser Thr Asp Pro Ala Asp Trp Tyr Asp Gly Asn Gly His
65                  70                  75                  80

Gly Thr His Val Ala Gly Thr Ile Ala Ala Leu Asn Asn Asp Ile Gly
                85                  90                  95

Val Val Gly Val Ala Pro Asn Val Glu Ile Tyr Ala Ile Lys Val Leu
            100                 105                 110

Asp Asp Arg Gly Ser Gly Ala Tyr Thr Asp Ile Ala Ile Gly Ile Glu
        115                 120                 125

Gln Ala Leu Leu Gly Pro Asp Gly Ile Leu Asp Lys Asp Gly Asp Gly
    130                 135                 140

Ile Ile Val Gly Asp Pro Asp Asp Asp Ala Ala Glu Val Ile Ser Met
145                 150                 155                 160

Ser Leu Gly Gly Pro Ser Asp Asp Glu Tyr Leu His Asp Met Ile Ile
                165                 170                 175

Lys Ala Tyr Asn Tyr Gly Val Val Ile Val Ala Ala Ser Gly Asn Glu
            180                 185                 190

Ala Ala Asp Gln Pro Ser Tyr Pro Ala Ile Tyr Pro Glu Val Ile Ala
        195                 200                 205

Val Gly Ala Thr Asp Ser Ser Asp Ala Val Ala Tyr Phe Ser Asn Leu
    210                 215                 220

Gln Pro Glu Val Ser Ala Pro Gly Val Asp Val Leu Ser Thr Tyr Pro
225                 230                 235                 240

Asp Asp Thr Tyr Glu Ser Leu Ser Gly Thr Ser Met Ala Thr Pro His
                245                 250                 255

Val Ser Gly Val Val Ala Leu Ile Gln Ala Ala Tyr Tyr Asn Lys Tyr
            260                 265                 270

Gly Lys Val Leu Pro Val Gly Thr Phe Asp Asp Met Asn Thr Asn Thr
        275                 280                 285

Val Arg Gly Ile Leu His Val Thr Ala Asp Asp Leu Gly Asp Pro Gly
    290                 295                 300

Trp Asp Ile Tyr Tyr Gly Tyr Gly Ile Val Arg Ala Asp Leu Ala Val
305                 310                 315                 320
```

Gln Ala Ala Leu Gly
325

<210> SEQ ID NO 37
<211> LENGTH: 484
<212> TYPE: PRT
<213> ORGANISM: Bacillus

<400> SEQUENCE: 37

Asn Thr Ala Pro Ile Asn Glu Thr Met Met Gln Tyr Phe Glu Trp Asp
1 5 10 15

Leu Pro Asn Asp Gly Thr Leu Trp Thr Lys Val Lys Asn Glu Ala Ala
20 25 30

Asn Leu Ser Ser Leu Gly Ile Thr Ala Leu Trp Leu Pro Pro Ala Tyr
35 40 45

Lys Gly Thr Ser Gln Ser Asp Val Gly Tyr Gly Val Tyr Asp Leu Tyr
50 55 60

Asp Leu Gly Glu Phe Asn Gln Lys Gly Thr Ile Arg Thr Lys Tyr Gly
65 70 75 80

Thr Lys Thr Gln Tyr Ile Gln Ala Ile Gln Ala Ala Lys Ala Ala Gly
85 90 95

Met Gln Val Tyr Ala Asp Val Val Phe Asn His Lys Ala Gly Ala Asp
100 105 110

Gly Thr Glu Phe Val Asp Ala Val Glu Val Asp Pro Ser Asn Arg Asn
115 120 125

Gln Glu Thr Ser Gly Thr Tyr Gln Ile Gln Ala Trp Thr Lys Phe Asp
130 135 140

Phe Pro Gly Arg Gly Asn Thr Tyr Ser Ser Phe Lys Trp Arg Trp Tyr
145 150 155 160

His Phe Asp Gly Thr Asp Trp Asp Glu Ser Arg Lys Leu Asn Arg Ile
165 170 175

Tyr Lys Phe Arg Ser Thr Gly Lys Ala Trp Asp Trp Glu Val Asp Thr
180 185 190

Glu Asn Gly Asn Tyr Asp Tyr Leu Met Phe Ala Asp Leu Asp Met Asp
195 200 205

His Pro Glu Val Val Thr Glu Leu Lys Asn Trp Gly Thr Trp Tyr Val
210 215 220

Asn Thr Thr Asn Ile Asp Gly Phe Arg Leu Asp Ala Val Lys His Ile
225 230 235 240

Lys Tyr Ser Phe Phe Pro Asp Trp Leu Thr Tyr Val Arg Asn Gln Thr
245 250 255

Gly Lys Asn Leu Phe Ala Val Gly Glu Phe Trp Ser Tyr Asp Val Asn
260 265 270

Lys Leu His Asn Tyr Ile Thr Lys Thr Asn Gly Ser Met Ser Leu Phe
275 280 285

Asp Ala Pro Leu His Asn Asn Phe Tyr Thr Ala Ser Lys Ser Ser Gly
290 295 300

Tyr Phe Asp Met Arg Tyr Leu Leu Asn Asn Thr Leu Met Lys Asp Gln
305 310 315 320

Pro Ser Leu Ala Val Thr Leu Val Asp Asn His Asp Thr Gln Pro Gly
325 330 335

Gln Ser Leu Gln Ser Trp Val Glu Pro Trp Phe Lys Pro Leu Ala Tyr
340 345 350

Ala Phe Ile Leu Thr Arg Gln Glu Gly Tyr Pro Cys Val Phe Tyr Gly

```
        355                 360                 365

Asp Tyr Tyr Gly Ile Pro Lys Tyr Asn Ile Pro Gly Leu Lys Ser Lys
    370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
        435                 440                 445

Val Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Ala Lys


<210> SEQ ID NO 38
<211> LENGTH: 485
<212> TYPE: PRT
<213> ORGANISM: Bacillus

<400> SEQUENCE: 38

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
```

```
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485


<210> SEQ ID NO 39
<211> LENGTH: 485
<212> TYPE: PRT
<213> ORGANISM: Cytophaga

<400> SEQUENCE: 39

Ala Ala Thr Asn Gly Thr Met Met Gln Tyr Phe Glu Trp Tyr Val Pro
1               5                   10                  15

Asn Asp Gly Gln Gln Trp Asn Arg Leu Arg Thr Asp Ala Pro Tyr Leu
            20                  25                  30

Ser Ser Val Gly Ile Thr Ala Val Trp Thr Pro Pro Ala Tyr Lys Gly
        35                  40                  45

Thr Ser Gln Ala Asp Val Gly Tyr Gly Pro Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Gly Glu Leu Lys Ser Ala Val Asn Thr Leu His Ser Asn Gly Ile Gln
                85                  90                  95

Val Tyr Gly Asp Val Val Met Asn His Lys Ala Gly Ala Asp Tyr Thr
            100                 105                 110

Glu Asn Val Thr Ala Val Glu Val Asn Pro Ser Asn Arg Asn Gln Glu
        115                 120                 125
```

```
Thr Ser Gly Glu Tyr Asn Ile Gln Ala Trp Thr Gly Phe Asn Phe Pro
    130                 135                 140

Gly Arg Gly Thr Thr Tyr Ser Asn Phe Lys Trp Gln Trp Phe His Phe
145                 150                 155                 160

Asp Gly Thr Asp Trp Asp Gln Ser Arg Ser Leu Ser Arg Ile Phe Lys
                165                 170                 175

Phe Arg Gly Thr Gly Lys Ala Trp Asp Trp Glu Val Ser Ser Glu Asn
            180                 185                 190

Gly Asn Tyr Asp Tyr Leu Met Tyr Ala Asp Ile Asp Tyr Asp His Pro
        195                 200                 205

Asp Val Val Asn Glu Met Lys Lys Trp Gly Val Trp Tyr Ala Asn Glu
    210                 215                 220

Val Gly Leu Asp Gly Tyr Arg Leu Asp Ala Val Lys His Ile Lys Phe
225                 230                 235                 240

Ser Phe Leu Lys Asp Trp Val Asp Asn Ala Arg Ala Ala Thr Gly Lys
                245                 250                 255

Glu Met Phe Thr Val Gly Glu Tyr Trp Gln Asn Asp Leu Gly Ala Leu
            260                 265                 270

Asn Asn Tyr Leu Ala Lys Val Asn Tyr Asn Gln Ser Leu Phe Asp Ala
        275                 280                 285

Pro Leu His Tyr Asn Phe Tyr Ala Ala Ser Thr Gly Gly Gly Tyr Tyr
    290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                325                 330                 335

Leu Glu Ser Thr Val Gln Pro Trp Phe Lys Pro Leu Ala Tyr Ala Phe
            340                 345                 350

Ile Leu Thr Arg Ser Gly Gly Tyr Pro Ser Val Phe Tyr Gly Asp Met
        355                 360                 365

Tyr Gly Thr Lys Gly Thr Thr Thr Arg Glu Ile Pro Ala Leu Lys Ser
    370                 375                 380

Lys Ile Glu Pro Leu Leu Lys Ala Arg Lys Asp Tyr Ala Tyr Gly Thr
385                 390                 395                 400

Gln Arg Asp Tyr Ile Asp Asn Pro Asp Val Ile Gly Trp Thr Arg Glu
                405                 410                 415

Gly Asp Ser Thr Lys Ala Lys Ser Gly Leu Ala Thr Val Ile Thr Asp
            420                 425                 430

Gly Pro Gly Gly Ser Lys Arg Met Tyr Val Gly Thr Ser Asn Ala Gly
        435                 440                 445

Glu Ile Trp Tyr Asp Leu Thr Gly Asn Arg Thr Asp Lys Ile Thr Ile
    450                 455                 460

Gly Ser Asp Gly Tyr Ala Thr Phe Pro Val Asn Gly Gly Ser Val Ser
465                 470                 475                 480

Val Trp Val Gln Gln
                485
```

<210> SEQ ID NO 40
<211> LENGTH: 328
<212> TYPE: PRT
<213> ORGANISM: Thermotoga maritima

<400> SEQUENCE: 40

```
Met Gln Asn Val Ser Leu Arg Glu Leu Ala Glu Lys Leu Asn Ile Tyr
1               5                   10                  15
```

```
Ile Gly Phe Ala Ala Ile Asn Asn Phe Trp Ser Leu Ser Asp Ala Glu
            20                  25                  30

Lys Tyr Met Glu Val Ala Arg Arg Glu Phe Asn Ile Leu Thr Pro Glu
        35                  40                  45

Asn Gln Met Lys Trp Asp Thr Ile His Pro Glu Arg Asp Arg Tyr Asn
    50                  55                  60

Phe Thr Pro Ala Glu Lys His Val Glu Phe Ala Glu Glu Asn Asp Met
65                  70                  75                  80

Ile Val His Gly His Thr Leu Val Trp His Asn Gln Leu Pro Gly Trp
                85                  90                  95

Ile Thr Gly Arg Glu Trp Thr Lys Glu Glu Leu Leu Asn Val Leu Glu
            100                 105                 110

Asp His Ile Lys Thr Val Val Ser His Phe Lys Gly Arg Val Lys Ile
        115                 120                 125

Trp Asp Val Val Asn Glu Ala Val Ser Asp Ser Gly Thr Tyr Arg Glu
    130                 135                 140

Ser Val Trp Tyr Lys Thr Ile Gly Pro Glu Tyr Ile Glu Lys Ala Phe
145                 150                 155                 160

Arg Trp Ala Lys Glu Ala Asp Pro Asp Ala Ile Leu Ile Tyr Asn Asp
                165                 170                 175

Tyr Ser Ile Glu Glu Ile Asn Ala Lys Ser Asn Phe Val Tyr Asn Met
            180                 185                 190

Ile Lys Glu Leu Lys Glu Lys Gly Val Pro Val Asp Gly Ile Gly Phe
        195                 200                 205

Gln Met His Ile Asp Tyr Arg Gly Leu Asn Tyr Asp Ser Phe Arg Arg
    210                 215                 220

Asn Leu Glu Arg Phe Ala Lys Leu Gly Leu Gln Ile Tyr Ile Thr Glu
225                 230                 235                 240

Met Asp Val Arg Ile Pro Leu Ser Gly Ser Glu Glu Tyr Tyr Leu Lys
                245                 250                 255

Lys Gln Ala Glu Val Cys Ala Lys Ile Phe Asp Ile Cys Leu Asp Asn
            260                 265                 270

Pro Ala Val Lys Ala Ile Gln Phe Trp Gly Phe Thr Asp Lys Tyr Ser
        275                 280                 285

Trp Val Pro Gly Phe Phe Lys Gly Tyr Gly Lys Ala Leu Leu Phe Asp
    290                 295                 300

Glu Asn Tyr Asn Pro Lys Pro Cys Tyr Tyr Ala Ile Lys Glu Val Leu
305                 310                 315                 320

Glu Lys Lys Ile Glu Glu Arg Lys
                325


<210> SEQ ID NO 41
<211> LENGTH: 354
<212> TYPE: PRT
<213> ORGANISM: Thermotoga neapolitana

<400> SEQUENCE: 41

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Ser Gln Asp Val Pro
            20                  25                  30

Leu Arg Val Leu Ala Glu Lys Leu Asn Ile His Ile Gly Phe Ala Ala
        35                  40                  45

Gly Asn Asn Phe Trp Ser Leu Pro Asp Ala Glu Lys Tyr Met Glu Val
```

```
    50                  55                  60

Ala Lys Arg Glu Phe Asn Ile Leu Thr Pro Gly Asn Gln Met Lys Trp
65                  70                  75                  80

Asp Thr Ile His Pro Glu Arg Asn Arg Tyr Asn Phe Glu Pro Ala Glu
                85                  90                  95

Lys His Val Glu Phe Ala Leu Lys Asn Asp Met Ile Val His Gly His
            100                 105                 110

Thr Leu Val Trp His Asn Gln Leu Pro Gly Trp Leu Thr Gly Gln Glu
        115                 120                 125

Trp Ser Lys Glu Glu Leu Leu Asn Ile Leu Glu Asp His Val Lys Thr
    130                 135                 140

Val Val Ser His Phe Arg Gly Arg Val Lys Ile Trp Asp Val Val Asn
145                 150                 155                 160

Glu Ala Val Ser Asp Ser Gly Thr Tyr Arg Glu Ser Ile Trp Tyr Arg
                165                 170                 175

Thr Ile Gly Pro Glu Tyr Ile Glu Lys Ala Leu Ile Trp Ala Lys Glu
            180                 185                 190

Ala Asp Pro Asp Ala Ile Leu Ile Tyr Asn Asp Tyr Asn Ile Glu Glu
        195                 200                 205

Ile Asn Ala Lys Ser Asn Phe Val Tyr Asn Met Ile Lys Asn Leu Arg
    210                 215                 220

Glu Lys Gly Val Pro Ile Asp Gly Ile Gly Phe Gln Met His Ile Asp
225                 230                 235                 240

Tyr Arg Gly Ile Asn Tyr Glu Ser Phe Lys Lys Asn Leu Glu Arg Phe
                245                 250                 255

Ala Glu Leu Gly Leu Gln Ile Tyr Ile Thr Glu Met Asp Arg Gly Phe
            260                 265                 270

Pro Leu Gly Gly Ser Val Gly Tyr Tyr Leu Lys Lys Gln Ala Glu Val
        275                 280                 285

Tyr Arg Arg Ile Phe Glu Ile Cys Leu Asp Asn Pro Ala Val Arg Ala
    290                 295                 300

Ile Gln Phe Trp Gly Phe Thr Asp Lys Tyr Ser Trp Val Pro Gly Phe
305                 310                 315                 320

Phe Lys Gly Tyr Gly Lys Ala Leu Ile Phe Asp Glu Asn Tyr Asn Pro
                325                 330                 335

Lys Pro Cys Tyr Phe Ala Ile Arg Glu Leu Met Glu Glu Lys Leu Lys
            340                 345                 350

Glu Arg


<210> SEQ ID NO 42
<211> LENGTH: 344
<212> TYPE: PRT
<213> ORGANISM: Thermotoga naphthophila

<400> SEQUENCE: 42

Met Lys Ile Leu Pro Ser Val Leu Ile Leu Leu Leu Gly Cys Val Pro
1               5                   10                  15

Val Phe Ser Ser Gln Asn Val Ser Leu Arg Glu Leu Ala Glu Lys Leu
            20                  25                  30

Asn Ile Tyr Ile Gly Phe Ala Ala Val Asn Asn Phe Trp Ser Leu Pro
        35                  40                  45

Asp Ala Glu Lys Tyr Met Glu Ile Ala Arg Arg Glu Phe Asn Ile Leu
    50                  55                  60

Thr His Glu Asn Gln Met Lys Trp Asp Thr Ile His Pro Glu Arg Asp
```

-continued

| | | | | | | | | | | | | | | | |
|---|---|---|---|---|---|---|---|---|---|---|---|---|---|---|---|
| 65 | | | | | 70 | | | | | 75 | | | | | 80 |
| Arg | Tyr | Asn | Phe | Thr | Pro | Ala | Glu | Lys | His | Val | Glu | Phe | Ala | Glu | Glu |
| | | | | 85 | | | | | 90 | | | | | 95 | |
| Asn | Gly | Met | Ile | Val | His | Gly | His | Thr | Leu | Val | Trp | His | Asn | Gln | Leu |
| | | | 100 | | | | | 105 | | | | | 110 | | |
| Pro | Gly | Trp | Leu | Thr | Gly | Arg | Glu | Trp | Thr | Arg | Glu | Glu | Leu | Leu | Asn |
| | | 115 | | | | | 120 | | | | | 125 | | | |
| Val | Leu | Glu | Asp | His | Ile | Lys | Thr | Val | Val | Ser | His | Phe | Lys | Gly | Arg |
| | 130 | | | | | 135 | | | | | 140 | | | | |
| Val | Lys | Ile | Trp | Asp | Val | Val | Asn | Glu | Ala | Val | Ser | Asp | Ser | Gly | Thr |
| 145 | | | | | 150 | | | | | 155 | | | | | 160 |
| Tyr | Arg | Glu | Ser | Val | Trp | Tyr | Lys | Thr | Ile | Gly | Pro | Glu | Tyr | Ile | Glu |
| | | | | 165 | | | | | 170 | | | | | 175 | |
| Lys | Ala | Phe | Arg | Trp | Ala | Lys | Glu | Ala | Asp | Pro | Asp | Ala | Ile | Leu | Ile |
| | | | 180 | | | | | 185 | | | | | 190 | | |
| Tyr | Asn | Asp | Tyr | Ser | Ile | Glu | Glu | Ile | Asn | Ala | Lys | Ser | Asn | Phe | Val |
| | | 195 | | | | | 200 | | | | | 205 | | | |
| Tyr | Asn | Met | Ile | Lys | Glu | Leu | Lys | Glu | Lys | Gly | Val | Pro | Val | Asp | Gly |
| | 210 | | | | | 215 | | | | | 220 | | | | |
| Ile | Gly | Phe | Gln | Met | His | Ile | Asp | His | Arg | Gly | Leu | Asn | Tyr | Asp | Ser |
| 225 | | | | | 230 | | | | | 235 | | | | | 240 |
| Phe | Arg | Arg | Asn | Leu | Glu | Arg | Phe | Ala | Glu | Leu | Gly | Leu | Gln | Ile | Tyr |
| | | | | 245 | | | | | 250 | | | | | 255 | |
| Ile | Thr | Glu | Met | Asp | Val | Arg | Ile | Pro | Leu | Ser | Gly | Ser | Glu | Glu | Tyr |
| | | | 260 | | | | | 265 | | | | | 270 | | |
| Tyr | Leu | Lys | Lys | Gln | Ala | Glu | Val | Cys | Ala | Lys | Ile | Phe | Glu | Ile | Cys |
| | | 275 | | | | | 280 | | | | | 285 | | | |
| Leu | Lys | Asn | Pro | Ala | Val | Lys | Ala | Ile | Gln | Phe | Trp | Gly | Phe | Thr | Asp |
| | 290 | | | | | 295 | | | | | 300 | | | | |
| Lys | Tyr | Ser | Trp | Val | Pro | Gly | Phe | Phe | Lys | Gly | Tyr | Gly | Lys | Ala | Leu |
| 305 | | | | | 310 | | | | | 315 | | | | | 320 |
| Leu | Phe | Asp | Glu | Asn | Tyr | Asn | Pro | Lys | Pro | Cys | Tyr | Tyr | Ala | Ile | Lys |
| | | | | 325 | | | | | 330 | | | | | 335 | |
| Glu | Val | Leu | Glu | Lys | Lys | Arg | Lys | | | | | | | | |
| | | | 340 | | | | | | | | | | | | |

GLUCOAMYLASE VARIANTS AND POLYNUCLEOTIDES ENCODING SAME

CROSS-REFERENCE TO RELATED APPLICATIONS

This application is a 35 U.S.C. 371 national application of international application no. PCT/EP2021/080338 filed Nov. 2, 2021, which claims priority or the benefit under 35 U.S.C. 119 of Danish application no. PA 2020 01234 filed Nov. 2, 2020, the disclosure of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to glucoamylase variants and compositions comprising such variants. The present invention further relates to polynucleotides encoding such variants, vectors and host cells comprising genes encoding such variants, which may also enable the production of such variants. The present invention also relates to methods of liquefying and/or saccharifying starch-containing materials using or applying the variants or compositions. The present invention further relates to processes for producing fermentation products from starch-containing or cellulosic-containing material, as well as an enzyme blend or composition, or a recombinant host cell or fermenting organism suitable for use in processes of the invention.

Description of the Related Art

Glucoamylase (1,4-alpha-D-glucan glucohydrolase, EC 3.2.1.3) is an enzyme, which catalyzes the release of D-glucose from the non-reducing ends of starch or related oligo- and polysaccharide molecules. Glucoamylases are produced by several filamentous fungi and yeast, with those from *Aspergillus* being commercially most important.

Commercially, glucoamylases are used to convert starchy material, which is already partially hydrolyzed by an alpha-amylase, to glucose. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones, and other compounds which are difficult to produce synthetically. Fermentation processes are also commonly used in the consumable alcohol (e.g., beer and wine), dairy (e.g., in the production of yogurt and cheese) industries.

It is an object of the present invention to provide polypeptides having glucoamylase activity and polynucleotides encoding the polypeptides and which provide a high yield in fermentation product production processes, such as ethanol production processes.

SUMMARY OF THE INVENTION

The present invention provides a glucoamylase variants with improved properties compared to parent glucoamylase.

The present invention relates to glucoamylase variants comprising a substitution at one or more positions corresponding to positions: 6, 7, 31, 34, 50, 132, 447, 481, 484, 501, 539, 568, 595 of SEQ ID NO: 1; and optionally further comprises substitution in one or more positions corresponding to positions 11, 75, 77, 78, 79, 80, 103, 105, 107, 110, 135, 138, 379, 445, 504, 566, 568, 594 of SEQ ID NO: 1, and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13.

The present invention relates to glucoamylase variants comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13.

The present invention relates to glucoamylase variants comprising a substitution at one or more positions corresponding to positions: 6, 7, 31, 34, 50, 132, 447, 481, 484, 501, 539, 568, 595 of SEQ ID NO: 1; and optionally further comprises substitution in one or more positions corresponding to positions 11, 75, 77, 78, 79, 80, 103, 105, 107, 110, 135, 138, 379, 445, 504, 566, 568, 594 of SEQ ID NO: 1, and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13 and wherein said variant has glucoamylase activity and wherein the glucoamylase variant has an increased thermostability compared to parent glucoamylase.

The present invention also relates to glucoamylase variants comprising a substitution at one or more positions corresponding to 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and, wherein the variant has glucoamylase activity and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13, and wherein said variant has glucoamylase activity and wherein the glucoamylase variant has an increased thermostability compared to parent glucoamylase.

The present invention relates also relates to a composition comprising the variant polypeptide of the invention.

The present invention also relates to a polynucleotide encoding a variant according to the invention, a nucleic acid construct comprising the polynucleotide encoding the variant according to the invention, an expression vector comprising the polynucleotide encoding the variant according to the invention, and a host cell comprising the polynucleotide encoding the variant according to the invention.

The present invention also relates to a method of producing a glucoamylase variant, comprising (a) cultivating the host cell of the invention under conditions suitable for expression of the variant, and (b) recovering the variant.

The present invention further relates to a method of obtaining a glucoamylase variant of a parent glucoamylase comprising the steps of: introducing a substitution at one or more positions corresponding to positions: 6, 7, 31, 34, 50, 132, 447, 481, 484, 501, 539, 568, 595 of SEQ ID NO: 1; and optionally further comprises introducing a substitution in one or more positions corresponding to positions 11, 75, 77, 78, 79, 80, 103, 105, 107, 110, 135, 138, 379, 445, 504, 566, 568, 594 of SEQ ID NO: 1, said method thereby providing glucoamylase variant of said parent glucoamylase, wherein said variant has at least 60%, such as at least 65%, such as at least 70%, such as at least 75%, such as at least 80%, such as about 85%, about 90%, about 91%, about 92%, about 93%, about 94%, about 95%, about 96%, about 97%, about 98%, about 99%, but less than 100%, sequence identity to the amino acid sequence to the polypeptide of SEQ ID Nos: 1-13, and wherein said variant has glucoamylase activity and wherein the glucoamylase variant has an increased thermostability compared to the parent glucoamylase.

The present invention further relates to a method of obtaining a glucoamylase variant of a parent glucoamylase comprising the steps of: introducing a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, said method thereby providing glucoamylase variant of said parent glucoamylase, wherein said variant has at least 60%, such as at least 65%, such as at least 70%, such as at least 75%, such as at least 80%, such as about 85%, about 90%, about 91%, about 92%, about 93%, about 94%, about 95%, about 96%, about 97%, about 98%, about 99%, but less than 100%, sequence identity to the amino acid sequence to the polypeptide of SEQ ID Nos: 1-13, and wherein said variant has glucoamylase activity and wherein the glucoamylase variant has an increased thermostability compared to the parent glucoamylase.

The present invention relates to processes of producing fermentation products, such as ethanol, from starch-containing material or cellulosic-containing material, using a fermenting organism.

In an aspect, the invention relates to a process for producing fermentation products from starch-containing material comprising the steps of:

i) saccharifying the starch-containing material using a carbohydrate-source generating enzyme at a temperature below the initial gelatinization temperature;

ii) fermenting using a fermenting organism;

wherein at least one or more glucoamylase variant(s) of the invention is present or added during fermentation or simultaneous saccharification and fermentation.

In an aspect, the invention relates to a process for producing fermentation products from starch-containing material comprising the steps of:

i) liquefying the starch-containing material at a temperature above the initial gelatinization temperature using an alpha-amylase;

ii) saccharifying using a carbohydrate-source generating enzyme;

iii) fermenting using a fermenting organism;

wherein at least one or more glucoamylase variant(s) of the present invention is present or added during liquefying step i), saccharifying step ii), fermenting step iii), or simultaneous saccharification and fermentation ("SSF").

In an aspect, the invention relates to a process for producing fermentation products from cellulosic-containing material comprising the steps of:

i) optionally pretreating a cellulosic-containing material;

ii) saccharifying a cellulosic-containing material and/or pretreated cellulosic-containing material using a carbohydrate-source generating enzyme; and iii) fermenting using a fermenting organism;

wherein at least one or more glucoamylase variant(s) of the present invention is present or added during saccharifying step ii) or fermenting step iii).

In an aspect, the present invention relates to an enzyme blend or composition comprising at least one or more glucoamylase variant(s) of the present invention.

In an aspect, the invention relates to a recombinant host cell comprising a heterologous polynucleotide encoding at least one or more glucoamylase variant(s) of the present invention.

In an aspect, the invention relates to a composition (e.g., fermenting or fermented mash composition) comprising: (i) a recombinant host cell or fermenting organism comprising a heterologous polynucleotide encoding an alpha-amylase and/or protease, and at least one or more glucoamylase variant(s) of the invention.

FIGURES

FIG. 1 shows a multiple alignment of the amino acid sequences of the mature proteins of:

Wildtype AMG from *Penicillium oxalicum* (PoAMG) of SEQ ID NO:6;

PoAMG variant denoted 'AMG NL' of SEQ ID NO:8;

PoAMG variant denoted 'AMG anPAV498' of SEQ ID NO:4;

PoAMG variant denoted 'AMG JPO001' of SEQ ID NO:1;

Wildtype AMG from *Penicillium miczynskii* (PmAMG) of SEQ ID NO:13;

Wildtype AMG from *Penicillium russellii* (PrAMG) of SEQ ID NO:12; and

Wildtype AMG from *Penicillium glabrum* (PgAMG) of SEQ ID NO:9.

DETAILED DESCRIPTION OF THE INVENTION

Definitions

In accordance with this detailed description, the following definitions apply. Note that the singular forms "a," "an," and "the" include plural references unless the context clearly dictates otherwise.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1 percent to about 5 percent" or "about 0.1 percent to 5 percent" should be interpreted to include not just about 0.1 percent to about 5 percent, but also the individual values (e.g., 1 percent, 2 percent, 3 percent, and 4 percent) and the sub-ranges (e.g., 0.1 percent to 0.5 percent, 1.1 percent to 2.2 percent, 3.3 percent to 4.4 percent) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

Unless defined otherwise or clearly indicated by context, all technical and scientific terms used herein have the same meaning as commonly understood by one of ordinary skill in the art to which this invention belongs.

Aldose reductase: The term "aldose reductase" or "AR" is classified as E.C. 1.1.1.21 and means an enzyme that catalyzes the conversion of L-arabinose to L-arabitol. Some aldose reductase genes may be unspecific and have activity on D-xylose to produce xylitol (AKA, D-xylose reductase; classified as E.C. 1.1.1.307). Aldose reductase activity can be determined using methods known in the art (e.g., Kuhn, et al., 1995, *Appl. Environ. Microbiol.* 61 (4), 1580-1585).

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

L-arabinitol dehydrogenase: The term "L-arabinitol dehydrogenase" or "LAD" is classified as E.C. 1.1.1.12 and means an enzyme that catalyzes the conversion of L-arabitol to L-xylulose. L-arabinitol dehydrogenase activity can be determined using methods known in the art (e.g., as described in U.S. Pat. No. 7,527,951).

Alpha-Amylases: Alpha-amylases (E.C. 3.2.1.1) are a group of enzymes which catalyze the hydrolysis of starch and other linear and branched 1,4 glucosidic oligo- and polysaccharides. The skilled person will know how to determine alpha-amylase activity.

Auxiliary Activity 9 polypeptide (previously named GH61): The term "Auxiliary Activity 9 polypeptide" or "AA9 polypeptide" means a polypeptide classified as a lytic polysaccharide monooxygenase (Quinlan et al., 2011, Proc. Natl. Acad. Sci. USA 208: 15079-15084; Phillips et al., 2011, *ACS Chem. Biol.* 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

AA9 polypeptides enhance the hydrolysis of a cellulosic material by an enzyme having cellulolytic activity. Cellulolytic enhancing activity can be determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40° C.-80° C., e.g., 40° C., 45° C., 50° C., 55° C., 60° C., 65° C., 70° C., 75° C., or 80° C. and a suitable pH, such as 4-9, e.g., 4.5, 5.0, 5.5, 6.0, 6.5, 7.0, 7.5, 8.0, 8.5, or 9.0, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST™ 1.5L (Novozymes A/S, Bagsværd, Denmark) and beta-glucosidase as the source of the cellulolytic activity, wherein the beta-glucosidase is present at a weight of at least 2-5% protein of the cellulase protein loading. In one aspect, the beta-glucosidase is an *Aspergillus oryzae* beta-glucosidase (e.g., recombinantly produced in *Aspergillus oryzae* according to WO 02/095014). In another aspect, the beta-glucosidase is an *Aspergillus fumigatus* beta-glucosidase (e.g., recombinantly produced in *Aspergillus oryzae* as described in WO 02/095014).

AA9 polypeptide enhancing activity can also be determined by incubating an AA9 polypeptide with 0.5% phosphoric acid swollen cellulose (PASC), 100 mM sodium acetate pH 5, 1 mM $MnSO_4$, gallic acid, 0.025 mg/ml of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO 2013/028928 for high temperature compositions.

AA9 polypeptides enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

The AA9 polypeptide can also be used in the presence of a soluble activating divalent metal cation according to WO 2008/151043 or WO 2012/122518, e.g., manganese or copper.

The AA9 polypeptide can be used in the presence of a dioxy compound, a bicyclic compound, a heterocyclic compound, a nitrogen-containing compound, a quinone compound, a sulfur-containing compound, or a liquor obtained from a pretreated cellulosic or hemicellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

Family 61 glycoside hydrolase (now known as AA9): The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Beta-glucanase: The term "beta-glucanase" encompasses polypeptides that hydrolyse cellulose to glucose requires the use of endo beta-glucanases (e.g. EC 3.2.1.4), cellobiohydrolases (e.g. EC 3.2.1.91) and beta-glucosidases (e.g. EC 3.2.1.21). A subgroup of beta-glucanases, also known as a licheninases (or lichenases) (EC 3.2.1.73), can be used to catalyse the hydrolysis of the beta-1, 4-glucosidic bonds to give beta-glucans. Licheninases (or lichenases) (e.g. EC 3.2.1.73) hydrolyse (1,4)-beta-D-glucosidic linkages in beta-D-glucans containing (1,3)- and (1,4)-bonds and can act on lichenin and cereal beta-D-glucans, but not on beta-D-glucans containing only 1,3- or 1 ,4-bonds. Other beta-glucanases (e.g. EC 3.2.1.4) can, for example, perform endohydrolysis of (1 ,4)-beta-D-glucosidic linkages in cellulose, lichenin and cereal beta-D-glucans and will also hydrolyze 1,4-linkages in beta-D-glucans containing 1,3-linkages.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In an aspect, a mixture of CELLUCLAST® 1.5L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptide having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20 (polyoxyethylene sorbitan monolaurate).

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 μmole of p-nitrophenolate anion produced per minute at 40° C., pH 5 from 1 mM p-nitrophenyl-beta-D-xyloside in 100 mM sodium citrate containing 0.01% TWEEN® 20.

Binding module: The term "carbohydrate binding module" means the region within a carbohydrate-active enzyme that provides carbohydrate-binding activity (Boraston et al., 2004, *Biochem. J.* 383: 769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose. Carbohydrate binding modules of the present invention have cellulose binding (A-type) specificity.

Catalase: The term "catalase" means a hydrogen-peroxide:hydrogen-peroxide oxidoreductase (EC 1.11.1.6) that catalyzes the conversion of $2H_2O_2$ to $O_2$+2 $H_2O$. For purposes of the present invention, catalase activity is determined according to U.S. Pat. No. 5,646,025. One unit of catalase activity equals the amount of enzyme that catalyzes the oxidation of 1 μmole of hydrogen peroxide under the assay conditions.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178).

Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Cellulolytic enzyme, cellulolytic composition, or cellulase: Cellulolytic enzyme, cellulolytic composition, or cellulase: The term "cellulolytic enzyme", "cellulolytic composition", or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman NW1 filter paper, microcrystalline cellulose, bacterial cellulose, algal cellulose, cotton, pretreated lignocellulose, etc. The most common total cellulolytic activity assay is the filter paper assay using Whatman NW1 filter paper as the substrate. The assay was established by the International Union of Pure and Applied Chemistry (IUPAC) (Ghose, 1987, Measurement of cellulase activities, *Pure Appl. Chem.* 59: 257-68).

Cellulolytic enzyme activity is determined by measuring the increase in hydrolysis of a cellulosic material by cellulolytic enzyme(s) under the following conditions: 1-50 mg of cellulolytic enzyme protein/g of cellulose in Pretreated Corn Stover ("PCS") (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX@ HPX-87H column (Bio-Rad Laboratories, Inc., Hercules, CA, USA).

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Corresponding to: The term "corresponding to" as used herein, refers to a way of determining the specific amino acid of a sequence wherein reference is made to a specific amino acid sequence. E.g. for the purposes of the present invention, when references are made to specific amino acid positions, the skilled person would be able to align another amino acid sequence to said amino acid sequence that reference has been made to, in order to determine which specific amino acid may be of interest in said another amino acid sequence. Alignment of another amino acid sequence with e.g. the sequence as set forth in SEQ ID NO: 3 or any other sequence listed herein, has been described elsewhere herein. Alternative alignment methods may be used, and are well-known for the skilled person.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, Bioresource Technology 50: 3-16; Lynd, 1990, Applied Biochemistry and Biotechnology 24/25: 695-719; Mosier et al., 1999, Recent Progress in Bioconversion of Lignocellulosics, in Advances in Biochemical Engineering/Biotechnology, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one aspect, the cellulosic material is any biomass material. In another aspect, the cellulosic material is lignocellulose, which comprises cellulose, hemicelluloses, and lignin.

Disruption: The term "disruption" means that a coding region and/or control sequence of a referenced gene is partially or entirely modified (such as by deletion, insertion, and/or substitution of one or more nucleotides) resulting in the absence (inactivation) or decrease in expression, and/or the absence or decrease of enzyme activity of the encoded polypeptide. The effects of disruption can be measured using techniques known in the art such as detecting the absence or decrease of enzyme activity using from cell-free extract measurements referenced herein; or by the absence or decrease of corresponding mRNA (e.g., at least 25% decrease, at least 50% decrease, at least 60% decrease, at least 70% decrease, at least 80% decrease, or at least 90% decrease); the absence or decrease in the amount of corresponding polypeptide having enzyme activity (e.g., at least 25% decrease, at least 50% decrease, at least 60% decrease, at least 70% decrease, at least 80% decrease, or at least 90% decrease); or the absence or decrease of the specific activity of the corresponding polypeptide having enzyme activity (e.g., at least 25% decrease, at least 50% decrease, at least 60% decrease, at least 70% decrease, at least 80% decrease, or at least 90% decrease). Disruptions of a particular gene of interest can be generated by methods known in the art, e.g., by directed homologous recombination (see *Methods in Yeast Genetics* (1997 edition), Adams, Gottschling, Kaiser, and Stems, Cold Spring Harbor Press (1998)).

Endogenous gene: The term "endogenous gene" means a gene that is native to the referenced host cell. "Endogenous gene expression" means expression of an endogenous gene.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components.

Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a variant including, but not limited to, transcription, post-transcriptional modification, translation, post-translational modification, and secretion. Expression can be measured—for example, to detect increased expression—by techniques known in the art, such as measuring levels of mRNA and/or translated polypeptide.

Expression vector: The term "expression vector" means a linear or circular DNA molecule that comprises a polynucleotide encoding a variant and is operably linked to control sequences that provide for its expression.

Fragment: The term "fragment" as used herein, refers to a polypeptide having one or more (e.g., several) amino acids absent from the amino and/or carboxyl terminus of the mature polypeptide of any one of the parent sequences herein disclosed, such as SEQ ID NOs: 1-13; wherein the fragment has glucoamylase activity. In one aspect, a fragment contains at least 200 contiguous amino acid residues of SEQ ID NOs: 1-13, for example at least 300 contiguous amino acid residues, or at least 350 contiguous amino acid residues, or at least 400 contiguous amino acid residues, or at least 450 contiguous amino acid residues of SEQ ID NOs: 1-13.

Fermentable medium: The term "fermentable medium" or "fermentation medium" refers to a medium comprising one or more (e.g., two, several) sugars, such as glucose, fructose, sucrose, cellobiose, xylose, xylulose, arabinose, mannose, galactose, and/or soluble oligosaccharides, wherein the medium is capable, in part, of being converted (fermented) by a host cell into a desired product, such as ethanol. In some instances, the fermentation medium is derived from a natural source, such as sugar cane, starch, or cellulose. The term fermentation medium is understood herein to refer to a medium before the fermenting organism is added, such as, a medium resulting from a saccharification process, as well as a medium used in a simultaneous saccharification and fermentation process (SSF).

Fusion polypeptide: The term "fusion polypeptide" is a polypeptide in which one polypeptide is fused at the N-terminus or the C-terminus of a polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, *Science* 266: 776-779). A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Glucoamylase: The term glucoamylase (1,4-alpha-D-glucan glucohydrolase, EC 3.2.1.3) is defined as an enzyme, which catalyzes the release of D-glucose from the non-reducing ends of starch or related oligo- and polysaccharide molecules. The Glucoamylase Unit (AGU) is defined as the amount of enzyme, which hydrolyses 1 micromole maltose per minute under the standard conditions 37° C., pH 4.3, substrate: maltose 23.2 mM, buffer: acetate 0.1 M, reaction time 5 minutes.

Hemicellulolytic enzyme or hemicellulase: The term "hemicellulolytic enzyme" or "hemicellulase" means one or more enzymes that hydrolyze a hemicellulosic material. See, for example, Shallom and Shoham, 2003, *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 40° C., 45° C., 50° C., 55° C., 60° C., 65° C., 70° C., 75° C., or 80° C., and a suitable pH such as 4-9, e.g., 4.0, 4.5, 5.0, 5.5, 6.0, 6.5, 7.0, 7.5, 8.0, 8.5, or 9.0.

Heterologous: The term "heterologous" means, with respect to a host cell, that a polypeptide or nucleic acid does not naturally occur in the host cell. The term "heterologous" means, with respect to a polypeptide or nucleic acid, that a control sequence, e.g., promoter, or domain of a polypeptide or nucleic acid is not naturally associated with the polypeptide or nucleic acid, i.e., the control sequence is from a gene other than the gene encoding the variants.

Host cell: The term "host cell" means any microbial or plant cell into which a nucleic acid construct or expression vector comprising a polynucleotide of the present invention has been introduced. Methods for introduction include but are not limited to protoplast fusion, transfection, transformation, electroporation, conjugation, and transduction. In some embodiments, the host cell is an isolated recombinant host cell that is partially or completely separated from at least one other component with, including but not limited to, proteins, nucleic acids, cells, etc.

Heterologous polynucleotide: The term "heterologous polynucleotide" is defined herein as a polynucleotide that is not native to the host cell; a native polynucleotide in which structural modifications have been made to the coding region; a native polynucleotide whose expression is quantitatively altered as a result of a manipulation of the DNA by recombinant DNA techniques, e.g., a different (foreign) promoter; or a native polynucleotide in a host cell having one or more extra copies of the polynucleotide to quantitatively alter expression. A "heterologous gene" is a gene comprising a heterologous polynucleotide.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Hybrid polypeptide: The term "hybrid polypeptide" means a polypeptide comprising domains from two or more polypeptides, e.g., a binding module from one polypeptide and a catalytic domain from another polypeptide. The domains may be fused at the N-terminus or the C-terminus.

Hybridization: The term "hybridization" means the pairing of substantially complementary strands of nucleic acids, using standard Southern blotting procedures. Hybridization may be performed under medium, medium-high, high or very high stringency conditions. Medium stringency conditions means prehybridization and hybridization at 42° C. in 5×SSPE, 0.3% SDS, 200 micrograms/ml sheared and denatured salmon sperm DNA, and 35% formamide for 12 to 24 hours, followed by washing three times each for 15 minutes using 0.2×SSC, 0.2% SDS at 55° C. Medium-high stringency conditions means prehybridization and hybridization at 42° C. in 5×SSPE, 0.3% SDS, 200 micrograms/ml sheared and denatured salmon sperm DNA, and 35% formamide for 12 to 24 hours, followed by washing three times each for 15 minutes using 0.2×SSC, 0.2% SDS at 60° C. High stringency conditions means prehybridization and hybridization at 42° C. in 5×SSPE, 0.3% SDS, 200 micrograms/ml sheared and denatured salmon sperm DNA, and 50% formamide for 12 to 24 hours, followed by washing three times each for 15 minutes using 0.2×SSC, 0.2% SDS at 65° C. Very high stringency conditions means prehybridization and hybridization at 42° C. in 5×SSPE, 0.3% SDS, 200 micrograms/ml sheared and denatured salmon sperm DNA, and 50% formamide for 12 to 24 hours, followed by washing three times each for 15 minutes using 0.2×SSC, 0.2% SDS at 70° C.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Improved property: The term "improved property" means a characteristic associated with a variant that is improved compared to the parent. Such improved properties include, but are not limited to, improved thermostability.

Non-phosphorylating NADP-dependent glyceraldehyde-3-phosphate dehydrogenase (GAPN): The term "non-phosphorylating NADP-dependent glyceraldehyde-3-phosphate dehydrogenase", "NADP-dependent glyceraldehyde-3-phosphate dehydrogenase" or "GAPN" is defined herein as an enzyme that catalyzes the chemical reaction of glyceraldehyde-3-phosphate and NADP+ to 3-phosphoglycerate and NADPH (e.g., EC 1.2.1.9). GAPN activity may be determined from cell-free extracts as described in the art, e.g., as described in Tamoi et al., 1996, Biochem. J. 316, 685-690. For example, GAPN activity may be measured spectrophotometrically by monitoring the absorbance change following NADPH oxidation at 340 nm in a reaction mixture containing 100 mM Tris/HCl buffer (pH 8.0), 10 mM $MgCl_2$, 10 mM GSH, 5 mM ATP, 0.2 mM NADPH, 2 units of 3-phosphoglyceric phosphokinase, 2 mM 3-phosphoglyceric acid and the enzyme.

Phospholipase: The term "phospholipase" means an enzyme that catalyzes the conversion of phospholipids into fatty acids and other lipophilic substances, such as phospholipase A (EC numbers 3.1.1.4, 3.1.1.5 and 3.1.1.32) or phospholipase C (EC numbers 3.1.4.3 and 3.1.4.11). Phospholipase activity may be determined using activity assays known in the art.

Pullulanase: The term "pullulanase" means a starch debranching enzyme having pullulan 6-glucano-hydrolase activity (EC 3.2.1.41) that catalyzes the hydrolysis the α-1,6-glycosidic bonds in pullulan, releasing maltotriose with reducing carbohydrate ends. For purposes of the present invention, pullulanase activity can be determined according to a PHADEBAS assay or the sweet potato starch assay described in WO2016/087237.

Mature polypeptide: The term "mature polypeptide" is defined herein as a polypeptide having biological activity that is in its final form following translation and any post-translational modifications, such as N-terminal processing, C-terminal truncation, glycosylation, phosphorylation, etc. The mature polypeptide sequence lacks a signal sequence, which may be determined using techniques known in the art (See, e.g., Zhang and Henzel, 2004, Protein Science 13: 2819-2824). The term "mature polypeptide coding sequence" means a polynucleotide that encodes a mature polypeptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Mature polypeptide coding sequence: The term "mature polypeptide coding sequence" means a polynucleotide that encodes a mature polypeptide having glucoamylase activity.

Mutant: The term "mutant" means a polynucleotide encoding a variant.

Native: The term "native" means a nucleic acid or polypeptide naturally occurring in a host cell.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Non-phosphorylating NADP-dependent glyceraldehyde-3-phosphate dehydrogenase (GAPN): The term "non-phosphorylating NADP-dependent glyceraldehyde-3-phosphate dehydrogenase", "NADP-dependent glyceraldehyde-3-phosphate dehydrogenase" or "GAPN" is defined herein as an enzyme that catalyzes the chemical reaction of glyceraldehyde-3-phosphate and NADP+ to 3-phosphoglycerate and NADPH (e.g., EC 1.2.1.9). GAPN activity may be determined from cell-free extracts as described in the art, e.g., as described in Tamoi et al., 1996, Biochem. J. 316, 685-690. For example, GAPN activity may be measured spectrophotometrically by monitoring the absorbance change following NADPH oxidation at 340 nm in a reaction mixture containing 100 mM Tris/HCl buffer (pH 8.0), 10 mM $MgCl_2$, 10 mM GSH, 5 mM ATP, 0.2 mM NADPH, 2 units of 3-phosphoglyceric phosphokinase, 2 mM 3-phosphoglyceric acid and the enzyme.

Operably linked: The term "operably linked" means a configuration in which a control sequence is placed at an appropriate position relative to the coding sequence of a polynucleotide such that the control sequence directs expression of the coding sequence.

Purified: The term "purified" means a nucleic acid or polypeptide that is substantially free from other components as determined by analytical techniques well known in the art (e.g., a purified polypeptide or nucleic acid may form a discrete band in an electrophoretic gel, chromatographic eluate, and/or a media subjected to density gradient centrifugation). A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

Parent or parent glucoamylase: The term "parent" glucoamylase as used herein means a glucoamylase to which modifications are made to produce the variant glucoamylase of the present invention. This term also refers to the polypeptide with which a variant of the invention is compared. The parent may be a naturally occurring (wild type) polypeptide, or it may even be a variant thereof, prepared by any suitable means. For instance, the parent protein may be a variant of a naturally occurring polypeptide which has been modified or altered in the amino acid sequence. Thus, the parent glucoamylase may have one or more (or one or several) amino acid substitutions, deletions and/or insertions. Thus, the parent glucoamylase may be a variant of a parent glucoamylase. A parent may also be an allelic variant which is a polypeptide encoded by any of two or more alternative forms of a gene occupying the same chromosomal locus. The term "parent" or "parent glucoamylase" as used herein, refers to the alpha-amylase of SEQ ID NOs: SEQ ID NOs: 1-13, or any glucoamylase having at least 60% sequence identity to any of the polypeptides of SEQ ID NOs: 1-13. The parent amylase may also be a polypeptide comprising a fragment of SEQ ID NOs: 1-13. The parent may be a bacterial or a fungal glucoamylase, preferably a fungal glucoamylase. In one aspect, the parent fungal glucoamylase, may be a *Penicillium* glucoamylase such as, e.g., a *Penicillium oxalicum* glucoamylase, *Penicillum glabrum* glucoamylase, *Penicillium brasilianum* glucoamylase, *Penicillium russellii* glucoamylase, *Penicillium miczynskii* glucoamylase.

Active pentose fermentation pathway: As used herein, a host cell or fermenting organism having an "active pentose fermentation pathway" produces active enzymes necessary to catalyze each reaction of a metabolic pathway in a sufficient amount to produce a fermentation product (e.g., ethanol) from pentose, and therefore is capable of producing the fermentation product in measurable yields when cultivated under fermentation conditions in the presence of pentose. A host cell or fermenting organism having an active pentose fermentation pathway comprises one or more active pentose fermentation pathway genes. A "pentose fermentation pathway gene" as used herein refers to a gene that encodes an enzyme involved in an active pentose fermentation pathway. In some embodiments, the active pentose fermentation pathway is an "active xylose fermentation pathway" (i.e., produces a fermentation product, such as ethanol, from xylose) or an "active arabinose fermentation pathway (i.e., produces a fermentation product, such as ethanol, from arabinose).

The active enzymes necessary to catalyze each reaction in an active pentose fermentation pathway may result from activities of endogenous gene expression, activities of heterologous gene expression, or from a combination of activities of endogenous and heterologous gene expression, as described in more detail herein.

Phospholipase: The term "phospholipase" means an enzyme that catalyzes the conversion of phospholipids into fatty acids and other lipophilic substances, such as phospholipase A (EC numbers 3.1.1.4, 3.1.1.5 and 3.1.1.32) or phospholipase C (EC numbers 3.1.4.3 and 3.1.4.11). Phospholipase activity may be determined using activity assays known in the art.

Pretreated corn stover: The term "Pretreated Corn Stover" or "PCS" means a cellulosic-containing material derived from corn stover by treatment with heat and dilute sulfuric acid, alkaline pretreatment, neutral pretreatment, or any pretreatment known in the art.

Protease: The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, California, including supplements 1-5 published in *Eur. J. Biochem.* 223: 1-5 (1994); *Eur. J. Biochem.* 232: 1-6 (1995); *Eur. J. Biochem.* 237: 1-5 (1996); *Eur. J. Biochem.* 250: 1-6 (1997); and *Eur. J.*

*Biochem.* 264: 610-650 (1999); respectively. The term "subtilases" refer to a sub-group of serine protease according to Siezen et al., 1991, *Protein Engng.* 4: 719-737 and Siezen et al., 1997, *Protein Science* 6: 501-523.

Proteases are classified on the basis of their catalytic mechanism into the following groups: Serine proteases (S), Cysteine proteases (C), Aspartic proteases (A), Metalloproteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

Polypeptides having protease activity, or proteases, are sometimes also designated peptidases, proteinases, peptide hydrolases, or proteolytic enzymes. Proteases may be of the exo-type (exopeptidases) that hydrolyse peptides starting at either end thereof, or of the endo-type that act internally in polypeptide chains (endopeptidases).

In particular embodiments, the proteases for use in the processes of the invention are selected from the group consisting of:

(a) proteases belonging to the EC 3.4.24 metalloendopeptidases;
(b) metalloproteases belonging to the M group of the above Handbook;
(c) metalloproteases not yet assigned to clans (designation: Clan MX), or belonging to either one of clans MA, MB, MC, MD, ME, MF, MG, MH (as defined at pp. 989-991 of the above Handbook);
(d) other families of metalloproteases (as defined at pp. 1448-1452 of the above Handbook);
(e) metalloproteases with a HEXXH motif;
(f) metalloproteases with an HEFTH motif;
(g) metalloproteases belonging to either one of families M3, M26, M27, M32, M34, M35, M36, M41, M43, or M47 (as defined at pp. 1448-1452 of the above Handbook); and
(h) metalloproteases belonging to family M35 (as defined at pp. 1492-1495 of the above Handbook).

Protease activity: The term "protease activity" means proteolytic activity (EC 3.4). There are several protease activity types such as trypsin-like proteases cleaving at the carboxyterminal side of Arg and Lys residues and chymotrypsin-like proteases cleaving at the carboxyterminal side of hydrophobic amino acid residues.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 15, 20, 25, 30, 35, 37, 40, 45, 50, 55, 60, 65, 70, 80, 90, or 95° C. Examples of general protease substrates are casein, bovine serum albumin and haemoglobin. In the classical Anson and Mirsky method, denatured haemoglobin is used as substrate and after the assay incubation with the protease in question, the amount of trichloroacetic acid soluble haemoglobin is determined as a measurement of protease activity (Anson, M. L. and Mirsky, A. E., 1932, *J. Gen. Physiol.* 16: 59 and Anson, M. L., 1938, *J. Gen. Physiol.* 22: 79).

Pullulanase: The term "pullulanase" means a starch debranching enzyme having pullulan 6-glucano-hydrolase activity (EC 3.2.1.41) that catalyzes the hydrolysis the α-1,6-glycosidic bonds in pullulan, releasing maltotriose with reducing carbohydrate ends. For purposes of the present invention, pullulanase activity can be determined according to a PHADEBAS assay or the sweet potato starch assay described in WO2016/087237.

Recombinant: The term "recombinant," when used in reference to a cell, nucleic acid, protein or vector, means that it has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. A vector comprising a nucleic acid encoding a polypeptide is a recombinant vector. The term "recombinant" is synonymous with "genetically modified" and "transgenic".

Starch binding domain: The terms "starch binding domain (SBD) or carbohydrate binding module (CBM)" are used interchangeably herein. SBDs can be divided into nine CBM families. As a source of energy, starch is degraded by a large number of various amylolytic enzymes. However, only about 10 percent of them are capable of binding and degrading raw starch. These enzymes usually possess a distinct sequence-structural module called the starch-binding domain that mediates attachment to starch granules. SBD refers to an amino acid sequence that binds preferentially to a starch (polysaccharide) substrate or a maltosaccharide, alpha-, beta and gamma-cyclodextrin and the like. They are usually motifs of approximately 100 amino acid residues found in about 10 percent of microbial amylolytic enzymes.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having glucoamylase activity.

Signal peptide: The term "signal peptide" is defined herein as a peptide linked (fused) in frame to the amino terminus of a polypeptide having biological activity and directs the polypeptide into the cell's secretory pathway. Signal sequences may be determined using techniques known in the art (See, e.g., Zhang and Henzel, 2004, Protein Science 13: 2819-2824).

Trehalase: The term "trehalase" means an enzyme which degrades trehalose into its unit monosaccharides (i.e., glucose). Trehalases are classified in EC 3.2.1.28 (alpha, alpha-trehalase) and EC. 3.2.1.93 (alpha, alpha-phosphotrehalase). The EC classes are based on recommendations of the Nomenclature Committee of the International Union of Biochemistry and Molecular Biology (IUBMB). Description of EC classes can be found on the internet. Trehalases are enzymes that catalyze the following reactions:
Trehalases are enzymes that catalyze the following reactions:

EC 3.2.1.28:

Alpha,alpha-trehalose+$H_2O$⇔2 D-glucose;

EC 3.2.1. 93:

Alpha,alpha-trehalose 6-phosphate+$H_2O$⇔D-glucose+D-glucose 6-phosphate.

For purposes of the present invention, trehalase activity may be determined according to the trehalase assay procedure described below.
PRINCIPLE:

Trehalose+$H_2O$ $\xrightarrow{Trehalase}$ 2Glucose

T=37° C., pH=5.7, A340 nm, Light path=1 cm
Spectrophotometric Stop Rate Determination
Unit Definition:

One unit will convert 1.0 mmole of trehalose to 2.0 mmoles of glucose per minute at pH 5.7 at 37° C. (liberated glucose determined at pH 7.5).
(See Dahlqvist, A. (1968) Analytical Biochemistry 22, 99-107)

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

Variant: The term "variant" means a polypeptide having glucoamylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the glucoamylase activity of polypeptide of SEQ ID NOs: 1-13.

Wild-type: The term "wild-type" in reference to an amino acid sequence or nucleic acid sequence means that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant nucleic acids and protein sequences produced in the laboratory or modification of the wild-type sequence). The term "wild-type" glucoamylase means a glucoamylase expressed by a naturally occurring microorganism, such as a bacterium, yeast, or filamentous fungus found in nature.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Xylitol dehydrogenase: The term "xylitol dehydrogenase" or "XDH" (AKA D-xylulose reductase) is classified as E.C. 1.1.1.9 and means an enzyme that catalyzes the conversion of xylitol to D-xylulose. Xylitol dehydrogenase activity can be determined using methods known in the art (e.g., Richard et al., 1999, *FEBS Letters* 457, 135-138).

Xylose isomerase: The term "xylose isomerase" or "XI" means an enzyme which can catalyze D-xylose into D-xylulose in vivo, and convert D-glucose into D-fructose in vitro. Xylose isomerase is also known as "glucose isomerase" and is classified as E.C. 5.3.1.5. As the structure of the enzyme is very stable, the xylose isomerase is a good model for studying the relationships between protein structure and functions (Karimaki et al., Protein Eng Des Sel, 12004, 17 (12):861-869). Xylose Isomerase activity may be determined using techniques known in the art (e.g., a coupled enzyme assay using D-sorbitol dehygrogenase, as described by Verhoeven et. al., 2017, Sci Rep 7, 46155).

Xylulokinase: The term "xylulokinase" or "XK" is classified as E.C. 2.7.1.17 and means an enzyme that catalyzes the conversion of D-xylulose to D-xylulose 5-phosphate. Xylulokinase activity can be determined using methods known in the art (e.g., Richard et al., 2000, *FEBS Microbiol. Letters* 190, 39-43) L-xylulose reductase: The term "L-xylulose reductase" or "LXR" is classified as E.D. 1.1.1.10 and means an enzyme that catalyzes the conversion of L-xylulose to xylitol. L-xylulose reductase activity can be determined using methods known in the art (e.g., as described in U.S. Pat. No. 7,527,951).

Reference to "about" a value or parameter herein includes embodiments that are directed to that value or parameter per se. For example, description referring to "about X" includes the embodiment "X". When used in combination with measured values, "about" includes a range that encompasses at least the uncertainty associated with the method of measuring the particular value, and can include a range of plus or minus two standard deviations around the stated value.

Likewise, reference to a gene or polypeptide that is "derived from" another gene or polypeptide X, includes the gene or polypeptide X.

As used herein and in the appended claims, the singular forms "a," "or," and "the" include plural referents unless the context clearly dictates otherwise.

It is understood that the embodiments described herein include "consisting" and/or "consisting essentially of" embodiments. As used herein, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments.

Nomenclature

For purposes of the present invention, the nomenclature [Y/F] means that the amino acid at this position may be a tyrosine (Try, Y) or a phenylalanine (Phe, F). Likewise, the nomenclature [V/G/A/I] means that the amino acid at this position may be a valine (Val, V), glycine (Gly, G), alanine (Ala, A) or isoleucine (lie, 1), and so forth for other combinations as described herein. The amino acid X is defined such that it may be any of the 20 natural amino acids, unless otherwise stated.

Conventions for Designation of Variants

For purposes of the present invention, the polypeptide disclosed in SEQ ID NO: 1 is used to determine the corresponding amino acid residue in another glucoamylase. Thus, all mentioned positions and specific substitutions refer to the numbering used in SEQ ID NO: 1. However, the skilled person would recognize that the sequence of any other sequence herein disclosed may also be used to determine the corresponding amino acid residue in another glucoamylase polypeptide. The amino acid sequence of another glucoamylase is aligned with the polypeptide disclosed in SEQ ID NO: 1, and based on the alignment, the amino acid position number corresponding the any amino acid residue in the polypeptide disclosed in SEQ ID No: 1 is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another glucoamylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, Nucleic Acids Res. 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example, the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, Protein Engineering 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195<br>G | 195 195a 195b<br>G - K - A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr, Glu" represents a substitution of arginine at position 170 with tyrosine or glutamic acid. Thus, "Tyr167Gly, Ala+Arg170Gly, Ala" designates the following variants:
"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

Glucoamylase Variants

The present invention relates to glucoamylase variants comprising a substitution at one or more positions corresponding to positions: 6, 7, 31, 34, 50, 132, 447, 481, 484, 501, 539, 568, 595 of SEQ ID NO: 1; and optionally further comprises a substitution in one or more positions corresponding to positions 11, 75, 77, 78, 79, 80, 103, 105, 107, 110, 135, 138, 379, 445, 504, 566, 568, 594 of SEQ ID NO: 1, wherein the variant has glucoamylase activity The present invention relates to glucoamylase variants comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity.

The present invention relates to glucoamylase variants comprising a substitution at one or more positions corresponding to positions: 6, 7, 31, 34, 50, 132, 447, 481, 484, 501, 539, 568, 595 of SEQ ID NO: 1; and optionally further comprises a substitution in one or more positions corresponding to positions 11, 75, 77, 78, 79, 80, 103, 105, 107, 110, 135, 138, 379, 445, 504, 566, 568, 594 of SEQ ID NO: 1, and wherein said variant has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% but less than 100% sequence identity to the polypeptide of SEQ ID NOs: 1-13, and wherein said variant has glucoamylase activity and wherein the glucoamylase variant has an increased thermostability compared to parent glucoamylase.

The present invention relates to glucoamylase variants comprising a substitution at one or more positions corresponding to positions: 6, 7, 31, 34, 50, 132, 447, 481, 484, 501, 539, 568, 595 of SEQ ID NO: 1; and optionally further comprises a substitution in one or more positions corresponding to positions 11, 75, 77, 78, 79, 80, 103, 105, 107, 110, 135, 138, 379, 445, 504, 566, 568, 594 of SEQ ID NO: 1, and wherein said variant has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% but less than 100% sequence identity to the polypeptide of SEQ ID NOs: 1-13, and wherein said variant has glucoamylase activity and wherein the glucoamylase variant has an increased thermostability compared to parent glucoamylase.

The present invention relates to glucoamylase variants comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, and wherein said variant has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% but less than 100% sequence identity to the polypeptide of SEQ ID NOs: 1-13, and wherein said variant has glucoamylase activity and wherein the glucoamylase variant has an increased thermostability compared to parent glucoamylase.

The present invention relates to glucoamylase variants comprising a substitution at one or more positions corresponding to positions: 6, 7, 31, 34, 50, 132, 447, 481, 484, 501, 539, 568, 595 of SEQ ID NO: 1; and optionally further comprises a substitution in one or more positions corresponding to positions 11, 75, 77, 78, 79, 80, 103, 105, 107, 110, 135, 138, 379, 445, 504, 566, 568, 594 of SEQ ID NO: 1, and wherein said variant has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to the polypeptide of SEQ ID NOs: 1-13, and wherein said variant has glucoamylase activity and wherein the glucoamylase variant has an increased thermostability compared to the parent glucoamylase of SEQ ID NO: 1 or SEQ ID NO: 4.

In one aspect, present invention relates to glucoamylase variants comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, and wherein said variant has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to the polypeptide of SEQ ID NOs: 1-13, and wherein said variant has glucoamylase activity and wherein the glucoamylase variant has an increased thermostability compared to the parent glucoamylase of SEQ ID NO: 1 or SEQ ID NO: 4.

The invention relates to glucoamylase variants having one or more substitutions having an improved property, such as improved (increased) thermostability.

In another embodiment, the variant has at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the parent polypeptide.

In another embodiment, the variant has at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 1.

In another embodiment, the variant has at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 2.

In another embodiment, the variant has at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 3.

In another embodiment, the variant has at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 4.

In another embodiment, the variant has at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 5.

In another embodiment, the variant has at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 6.

In another embodiment, the variant has at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 7.

In another embodiment, the variant has at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 8.

In another embodiment, the variant has at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 9.

In another embodiment, the variant has at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 10.

In another embodiment, the variant has at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 11.

In another embodiment, the variant has at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 12.

In another embodiment, the variant has at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 13.

In one aspect, the substituted amino acid residue is different from the naturally-occurring amino acid residue in that position. In one embodiment, the substitution is selected from the group consisting of A, C, D, E, F, G, H, I, K, L, M, N, P, Q, R, S, T, V, W and Y, with the proviso that the substituted amino acid residue is different from the naturally-occurring amino acid residue in that position.

In one aspect, the number of substitutions is 1-50, e.g., 1-45, 1-40, 1-35, 1-30, 1-25, 1-20, 1-15, 1-10 or 1-5, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 substitutions.

The above-mentioned variants having substitutions should be understood as encompassing all possible combinations of one or more substitutions at the specified positions.

The present invention provides glucoamylase variants comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at one or more (e.g., several) positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at two positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at three positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at four positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at five positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at six positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at seven positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at eight positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at nine positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at ten positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at eleven positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at twelve positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at thirteen positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at fourteen positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at fifteen positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at sixteen positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at seventeen positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at eighteen positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, a variant comprises a substitution at each position corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1, wherein the variant has glucoamylase activity and wherein said variant has at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity sequence identity to the polypeptide of SEQ ID NOs: 1-13.

In another aspect, the variant comprises or consists of a substitution at a position corresponding to position 6 of SEQ ID NO: 1. In another aspect, the amino acid at a position corresponding to position 6 is substituted with Ala, Arg, Asn, Asp, Cys, Gln, Glu, His, lie, Leu, Lys, Met, Phe, Pro, Ser, Thr, Trp, Tyr, or Val, preferably with Ser. In another aspect, the variant comprises or consists of the substitution G6S of the polypeptide of SEQ ID NO: 1.

In another aspect, the variant comprises or consists of a substitution at a position corresponding to position 7 of SEQ ID NO: 1. In another aspect, the amino acid at a position corresponding to position 7 is substituted with Ala, Arg, Asn, Asp, Cys, Gln, Glu, His, lie, Leu, Lys, Met, Phe, Pro, Ser, Thr, Trp, Tyr, or Val, preferably with Thr. In another aspect, the variant comprises or consists of the substitution G7T of the polypeptide of SEQ ID NO: 1.

In another aspect, the variant comprises or consists of a substitution at a position corresponding to position 11 of SEQ ID NO: 1. In another aspect, the amino acid at a position corresponding to position 11 is substituted with Ala, Arg, Asn, Asp, Cys, Gln, Glu, His, lie, Leu, Lys, Met, Pro, Ser, Thr, Trp, Tyr, or Val, preferably with Phe. In another aspect, the variant comprises or consists of the substitution P11F of the polypeptide of SEQ ID NO: 1.

In another aspect, the variant comprises or consists of a substitution at a position corresponding to position 31 of SEQ ID NO: 1. In another aspect, the amino acid at a position corresponding to position 31 is substituted with Ala, Asn, Asp, Cys, Gln, Glu, Gly, His, lie, Leu, Lys, Met, Phe, Pro, Ser, Thr, Trp, Tyr, or Val, preferably with Phe. In another aspect, the variant comprises or consists of the substitution R31F of the polypeptide of SEQ ID NO: 1.

In another aspect, the variant comprises or consists of a substitution at a position corresponding to position 34 of SEQ ID NO: 1. In another aspect, the amino acid at a position corresponding to position 34 is substituted with Ala, Arg, Asn, Asp, Cys, Gln, Glu, Gly, His, lie, Leu, Met, Phe, Pro, Ser, Thr, Trp, Tyr, or Val, preferably with Tyr. In another aspect, the variant comprises or consists of the substitution K34Y of the polypeptide of SEQ ID NO: 1.

In another aspect, the variant comprises or consists of a substitution at a position corresponding to position 50 of SEQ ID NO: 1. In another aspect, the amino acid at a position corresponding to position 50 is substituted with Ala, Arg, Asn, Asp, Cys, Gln, Gly, His, lie, Leu, Lys, Met, Phe, Pro, Ser, Thr, Trp, Tyr, or Val, preferably with Arg. In another aspect, the variant comprises or consists of the substitution E50R of the polypeptide of SEQ ID NO: 1.

In another aspect, the variant comprises or consists of a substitution at a position corresponding to position 75 of SEQ ID NO: 1. In another aspect, the amino acid at a position corresponding to position 75 is substituted with Ala, Arg, Asn, Cys, Gln, Glu, Gly, His, lie, Leu, Lys, Met, Phe, Pro, Ser, Thr, Trp, Tyr, or Val, preferably with Asn or Ser. In another aspect, the variant comprises or consists of the substitutions D75N or D75S of the polypeptide of SEQ ID NO: 1.

In another aspect, the variant comprises or consists of a substitution at a position corresponding to position 77 of SEQ ID NO: 1. In another aspect, the amino acid at a position corresponding to position 77 is substituted with Ala, Asn, Asp, Cys, Gln, Glu, Gly, His, lie, Leu, Lys, Met, Phe, Pro, Ser, Thr, Trp, Tyr, or Val, preferably with Asp or Gly. In another aspect, the variant comprises or consists of the substitutions R77D or R77G of the polypeptide of SEQ ID NO: 1.

In another aspect, the variant comprises or consists of a substitution at a position corresponding to position 78 of SEQ ID NO: 1. In another aspect, the amino acid at a position corresponding to position 78 is substituted with Arg, Asn, Asp, Cys, Gln, Glu, Gly, His, lie, Leu, Lys, Met, Phe, Pro, Ser, Thr, Trp, Tyr, or Val, preferably with Gln or Trp. In another aspect, the variant comprises or consists of the substitutions A78Q or A78W of the polypeptide of SEQ ID NO: 1.

In another aspect, the variant comprises or consists of a substitution at a position corresponding to position 79 of SEQ ID NO: 1. In another aspect, the amino acid at a position corresponding to position 79 is substituted with Ala, Arg, Asn, Asp, Cys, Gln, Glu, Gly, His, lie, Leu, Lys, Met, Phe, Pro, Ser, Thr, Trp, or Tyr, preferably with Asp. In another aspect, the variant comprises or consists of the substitution V79D of the polypeptide of SEQ ID NO: 1.

In another aspect, the variant comprises or consists of a substitution at a position corresponding to position 80 of SEQ ID NO: 1. In another aspect, the amino acid at a position corresponding to position 80 is substituted with Ala, Arg, Asn, Asp, Cys, Gln, Glu, Gly, His, lie, Leu, Lys, Met, Pro, Ser, Thr, Trp, Tyr, or Val, preferably with Tyr. In another aspect, the variant comprises or consists of the substitution F80Y of the polypeptide of SEQ ID NO: 1.

In another aspect, the variant comprises or consists of a substitution at a position corresponding to position 103 of SEQ ID NO: 1. In another aspect, the amino acid at a position corresponding to position 103 is substituted with Ala, Arg, Asn, Asp, Cys, Gln, Glu, Gly, His, lie, Leu, Lys, Met, Phe, Pro, Thr, Trp, Tyr, or Val, preferably with Asn. In another aspect, the variant comprises or consists of the substitution S103N of the polypeptide of SEQ ID NO: 1.

In another aspect, the variant comprises or consists of a substitution at a position corresponding to position 105 of SEQ ID NO: 1. In another aspect, the amino acid at a position corresponding to position 105 is substituted with Ala, Arg, Asn, Asp, Cys, Gln, Glu, Gly, His, lie, Leu, Lys, Met, Phe, Pro, Thr, Trp, Tyr, or Val, preferably with Glu or Leu. In another aspect, the variant comprises or consists of the substitutions S105E or S105L of the polypeptide of SEQ ID NO: 1.

In another aspect, the variant comprises or consists of a substitution at a position corresponding to position 107 of SEQ ID NO: 1. In another aspect, the amino acid at a position corresponding to position 107 is substituted with Ala, Arg, Asn, Asp, Cys, Gln, Glu, Gly, His, lie, Leu, Lys, Met, Phe, Ser, Thr, Trp, Tyr, or Val, preferably with Leu. In another aspect, the variant comprises or consists of the substitution P107L of the polypeptide of SEQ ID NO: 1.

In another aspect, the variant comprises or consists of a substitution at a position corresponding to position 110 of SEQ ID NO: 1. In another aspect, the amino acid at a position corresponding to position 110 is substituted with Ala, Arg, Asn, Asp, Cys, Gln, Glu, Gly, His, lie, Leu, Lys, Met, Phe, Pro, Ser, Trp, Tyr, or Val, preferably with Trp. In another aspect, the variant comprises or consists of the substitution T110W of the polypeptide of SEQ ID NO: 1.

In another aspect, the variant comprises or consists of a substitution at a position corresponding to position 132 of SEQ ID NO: 1. In another aspect, the amino acid at a position corresponding to position 132 is substituted with Arg, Asn, Asp, Cys, Gln, Glu, Gly, His, lie, Leu, Lys, Met, Phe, Pro, Ser, Thr, Trp, Tyr, or Val, preferably with Pro or Arg. In another aspect, the variant comprises or consists of the substitutions A132P or A132R of the polypeptide of SEQ ID NO: 1.

In another aspect, the variant comprises or consists of a substitution at a position corresponding to position 135 of SEQ ID NO: 1. In another aspect, the amino acid at a position corresponding to position 135 is substituted with Ala, Asn, Asp, Cys, Gln, Glu, Gly, His, lie, Leu, Lys, Met, Phe, Pro, Ser, Thr, Trp, Tyr, or Val, preferably with Ser. In another aspect, the variant comprises or consists of the substitution R135S of the polypeptide of SEQ ID NO: 1.

In another aspect, the variant comprises or consists of a substitution at a position corresponding to position 138 of SEQ ID NO: 1. In another aspect, the amino acid at a position corresponding to position 138 is substituted with Ala, Asn, Asp, Cys, Gln, Glu, Gly, His, lie, Leu, Lys, Met, Phe, Pro, Ser, Thr, Trp, Tyr, or Val, preferably with Gly or Leu or Pro. In another aspect, the variant comprises or consists of the substitutions R138G or R138L or R138P of the polypeptide of SEQ ID NO: 1.

In another aspect, the variant comprises or consists of a substitution at a position corresponding to position 379 of SEQ ID NO: 1. In another aspect, the amino acid at a position corresponding to position 379 is substituted with Ala, Arg, Asn, Asp, Cys, Gln, Glu, Gly, His, lie, Leu, Lys, Met, Phe, Pro, Thr, Trp, Tyr, or Val, preferably with Pro. In another aspect, the variant comprises or consists of the substitution S379P of the polypeptide of SEQ ID NO: 1.

In another aspect, the variant comprises or consists of a substitution at a position corresponding to position 445 of SEQ ID NO: 1. In another aspect, the amino acid at a position corresponding to position 445 is substituted with Ala, Arg, Asn, Cys, Gln, Glu, Gly, His, lie, Leu, Lys, Met, Phe, Pro, Ser, Thr, Trp, Tyr, or Val, preferably with Asn. In another aspect, the variant comprises or consists of the substitution D445N of the polypeptide of SEQ ID NO: 1.

In another aspect, the variant comprises or consists of a substitution at a position corresponding to position 447 of SEQ ID NO: 1. In another aspect, the amino acid at a position corresponding to position 447 is substituted with Ala, Arg, Asn, Asp, Cys, Gln, Glu, Gly, His, lie, Leu, Lys, Met, Phe, Pro, Ser, Thr, Trp, or Tyr, preferably with Ser. In another aspect, the variant comprises or consists of the substitution V447S of the polypeptide of SEQ ID NO: 1.

In another aspect, the variant comprises or consists of a substitution at a position corresponding to position 481 of SEQ ID NO: 1. In another aspect, the amino acid at a position corresponding to position 481 is substituted with Ala, Arg, Asn, Asp, Cys, Gln, Glu, Gly, His, lie, Leu, Lys, Met, Phe, Pro, Thr, Trp, Tyr, or Val, preferably with Pro. In another aspect, the variant comprises or consists of the substitution S481P of the polypeptide of SEQ ID NO: 1.

In another aspect, the variant comprises or consists of a substitution at a position corresponding to position 484 of SEQ ID NO: 1. In another aspect, the amino acid at a position corresponding to position 484 is substituted with Ala, Arg, Asn, Asp, Cys, Gln, Glu, Gly, His, lie, Leu, Lys, Met, Phe, Pro, Ser, Trp, Tyr, or Val, preferably with Pro. In another aspect, the variant comprises or consists of the substitution T484P of the polypeptide of SEQ ID NO: 1.

In another aspect, the variant comprises or consists of a substitution at a position corresponding to position 501 of SEQ ID NO: 1. In another aspect, the amino acid at a position corresponding to position 501 is substituted with Ala, Arg, Asn, Asp, Cys, Gln, Gly, His, lie, Leu, Lys, Met, Phe, Pro, Ser, Thr, Trp, Tyr, or Val, preferably with Ala or Leu or Val. In another aspect, the variant comprises or consists of the substitutions E501A or E501L or E501V of the polypeptide of SEQ ID NO: 1.

In another aspect, the variant comprises or consists of a substitution at a position corresponding to position 504 of SEQ ID NO: 1. In another aspect, the amino acid at a position corresponding to position 504 is substituted with Ala, Arg, Asn, Asp, Cys, Gln, Glu, Gly, His, lie, Leu, Lys, Met, Phe, Pro, Ser, Thr, Trp, or Val, preferably with Thr. In another aspect, the variant comprises or consists of the substitution Y504T of the polypeptide of SEQ ID NO: 1.

In another aspect, the variant comprises or consists of a substitution at a position corresponding to position 539 of SEQ ID NO: 1. In another aspect, the amino acid at a position corresponding to position 539 is substituted with Ala, Arg, Asp, Cys, Gln, Glu, Gly, His, lie, Leu, Lys, Met, Phe, Pro, Ser, Thr, Trp, Tyr, or Val, preferably with Pro. In another aspect, the variant comprises or consists of the substitution N539P of the polypeptide of SEQ ID NO: 1.

In another aspect, the variant comprises or consists of a substitution at a position corresponding to position 566 of SEQ ID NO: 1. In another aspect, the amino acid at a position corresponding to position 566 is substituted with Ala, Arg, Asn, Cys, Gln, Glu, Gly, His, lie, Leu, Lys, Met, Phe, Pro, Ser, Thr, Trp, Tyr, or Val, preferably with Thr. In another aspect, the variant comprises or consists of the substitution D566T of the polypeptide of SEQ ID NO: 1.

In another aspect, the variant comprises or consists of a substitution at a position corresponding to position 568 of SEQ ID NO: 1. In another aspect, the amino acid at a position corresponding to position 568 is substituted with Ala, Arg, Asn, Asp, Cys, Gln, Glu, Gly, His, lie, Leu, Lys, Met, Phe, Pro, Ser, Trp, Tyr, or Val, preferably with Val. In another aspect, the variant comprises or consists of the substitution T568V of the polypeptide of SEQ ID NO: 1.

In another aspect, the variant comprises or consists of a substitution at a position corresponding to position 592 of SEQ ID NO: 1. In another aspect, the amino acid at a position corresponding to position 592 is substituted with Ala, Arg, Asn, Asp, Cys, Gln, Glu, Gly, His, lie, Leu, Lys, Met, Phe, Pro, Ser, Thr, Trp, or Tyr preferably with Thr. In another aspect, the variant comprises or consists of the substitution V592T of the polypeptide of SEQ ID NO: 1.

In another aspect, the variant comprises or consists of a substitution at a position corresponding to position 594 of SEQ ID NO: 1. In another aspect, the amino acid at a position corresponding to position 594 is substituted with Ala, Arg, Asn, Asp, Cys, Glu, Gly, His, lie, Leu, Lys, Met, Phe, Pro, Ser, Thr, Trp, Tyr, or Val, preferably with Arg. In another aspect, the variant comprises or consists of the substitution Q594R of the polypeptide of SEQ ID NO: 1.

In another aspect, the variant comprises or consists of a substitution at a position corresponding to position 595 of SEQ ID NO: 1. In another aspect, the amino acid at a position corresponding to position 595 is substituted with Ala, Arg, Asn, Asp, Cys, Gln, Glu, Gly, His, lie, Leu, Lys, Met, Pro, Ser, Thr, Trp, Tyr, or Val, preferably with Ser. In another aspect, the variant comprises or consists of the substitution F595S of the polypeptide of SEQ ID NO: 1.

The variants may further comprise one or more additional substitutions at one or more (e.g., several) other positions.

In one aspect, a variant comprises one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises one or more of the following substitutions at positions corresponding to positions: S105L, S105E, A132R, R135S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises one or more of the following substitutions at positions corresponding to positions selected from a group consisting of: K34Y+S103N, K34Y+Y504T, S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: D75N+R77D+A78Q, K34Y+D445N+V447S, S103N+D445N+V447S, D445N+V447S+Y504T, K34Y+S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: K34Y+S103N+D445N+V447S, K34Y+S103N+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: D75S+R77G+A78W+V79D+F80Y, K34Y+S103N+D445N+V447S+D566T, K34Y+S103N+Y504T+Q594R F595S, K34Y+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: K34Y+S103N+D445N+V447S+E501V+Y504T, K34Y+S103N+S105L+Y504T+Q594R+F595S, K34Y+S103N+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: K34Y+S103N+D445N+V447S+Y504T+Q594R+F595S, K34Y+S103N+S105L+Y504T+D566T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: K34Y+S103N+S105L+D445N+V447S+D566T+Q594R+F595S, G6S+G7T+R31F+K34Y+S103N+A132P+D445N+V447S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: K34Y+S103N+S105L+D445N+V447S+Y504T+D566T+Q594R+F595S, K34Y+S103N+A132R+D445N+V447S+Y504T+D566T+Q594R+F595S, K34Y+S103N+S105L+A132R+D445N+V447S+Y504T+D566T+V592T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: K34Y+S103N+S105L+A132R+D445N+V447S+Y504T+D566T+Q594R+F595S, K34Y+S103N+P107L+A132R+D445N+V447S+Y504T+D566T+Q594R+F595S, G6S+G7T+K34Y+S103N+P107L+A132P+D445N+V447S+E501V+Y504T, K34Y+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: K34Y+S103N+S105L+A132R+D445N+V447S+E501V+Y504T+D566T+Q594R+F595S, K34Y+D75N+R77D+A78Q+S103N+R138L+D445N+V447S+Y504T+Q594R+F595S, R31F+K34Y+D75N+R77D+A78Q+S103N+R138L+D445N+V447S+Y504T+Q594R+F595S, K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: G6S+G7T+K34Y+S103N+S105L+A132R+D445N+V447S+Y504T+D566T+Q594R+F595S, G6S+G7T+K34Y+S103N+P107L+A132R+D445N+V447S+Y504T+D566T+Q594R+F595S, G6S+G7T+K34Y+S103N+P107L+A132P+D445N+V447S+Y504T+D566T+Q594R+F595S, G6S+G7T+K34Y+S103N+P107L+A132P+D445N+V447S+D566T+T568V+Q594R+F595S, R31F+K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: G6S+G7T+K34Y+S103N+P107L+A132R+D445N+V447S+Y504T+D566T+V592T+Q594R+F595S, G6S+G7T+K34Y+S103N+P107L+A132R+D445N+V447S+Y504T+D566T+T568V+Q594R+F595S, G6S+G7T+K34Y+S103N+P107L+A132P+D445N+V447S+Y504T+D566T+T568V+Q594R+F595S, G6S+G7T+K34Y+S103N+P107L+A132R+D445N+V447S+S481P+Y504T+D566T+Q594R+F595S, G6S+G7T+K34Y+S103N+P107L+A132R+D445N+V447S+S481P+Y504T+D566T+T568V+Q594R+F595S, G6S+G7T+R31F+K34Y+S103N+P107L+A132P+D445N+V447S+Y504T+D566T+T568V+Q594R+F595S, G6S+G7T+R31F+K34Y+S103N+

A132P+D445N+V447S+S481P+D566T+T568V+Q594R+F595S, G6S+G7T+K34Y+E50R+S103N+A132P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: G6S+G7T+K34Y+S103N+P107L+T110W+A132P+D445N+V447S+Y504T+D566T+T568V+Q594R+F595S, G6S+G7T+K34Y+E50R+S103N+P107L+A132P+D445N+V447S+Y504T+D566T+T568V+Q594R+F595S, G6S+G7T+R31F+K34Y+S103N+P107L+A132P+D445N+V447S+S481P+D566T+T568V+Q594R+F595S, G6S+G7T+R31F+K34Y+E50R+S103N+A132P+D445N+V447S+S481P+D566T+T568V+Q594R+F595S, G6S+G7T+R31F+K34Y+S103N+A132P+R138G+D445N+V447S+S481P+D566T+T568V+Q594R+F595S, G6S+G7T+R31F+K34Y+S103N+A132P+R138L+D445N+V447S+S481P+D566T+T568V+Q594R+F595S, G6S+G7T+R31F+K34Y+S103N+A132P+R138P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: G6S+G7T+R31F+K34Y+S103N+P107L+A132P+D445N+V447S+S481P+Y504T+D566T+T568V+Q594R+F595S, G6S+G7T+K34Y+E50R+S103N+P107L+A132P+D445N+V447S+S481P+Y504T+D566T+T568V+Q594R+F595S, G6S+G7T+R31F+K34Y+E50R+S103N+A132P+D445N+V447S+S481P+E501L+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: G6S+G7T+R31F+K34Y+S103N+P107L+A132P+D445N+V447S+S481P+E501V+Y504T+D566T+T568V+Q594R+F595S, G6S+G7T+R31F+K34Y+E50R+D75N+R77D+A78Q+S103N+A132P+D445N+V447S+S481P+D566T+Q594R+F595S, G6S+G7T+R31F+K34Y+E50R+S103N+A132P+S379P+D445N+V447S+S481P+E501A+D566T+T568V+Q594R+F595S, G6S+G7T+R31F+K34Y+E50R+S103N+A132P+D445N+V447S+S481P+T484P+E501A+D566T+T568V+Q594R+F595S, G6S+G7T+R31F+K34Y+E50R+S103N+A132P+D445N+V447S+S481P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: G6S+G7T+R31F+K34Y+E50R+D75N+R77D+A78Q+S103N+A132P+R138L+D445N+V447S+S481P+D566T+Q594R+F595S, G6S+G7T+R31F+K34Y+E50R+S103N+A132P+S379P+D445N+V447S+S481P+T484P+E501A+D566T+T568V+Q594R+F595S, G6S+G7T+R31F+K34Y+E50R+S103N+A132P+D445N+V447S+S481P+T484P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, a variant comprises substitutions at positions corresponding to positions selected from a group consisting of: G6S+G7T+R31F+K34Y+D75N+R77D+A78Q+S103N+P107L+A132P+D445N+V447S+S481P+Y504T+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

In one aspect, the glucoamylase variants of the present invention have an improved property relative to the parent polypeptide, wherein the improved property is selected from the group consisting of increased catalytic efficiency, increased catalytic rate, increased chemical stability, increased oxidation stability, increased pH activity, increased pH stability, increased specific activity, increased stability under storage conditions, increased substrate binding, increased substrate cleavage, increased substrate specificity, increased substrate stability, increased surface properties, increased thermal activity, and increased thermostability.

In one aspect, the glucoamylase variants of the present invention have improved property relative to said parent polypeptide.

In one aspect, the glucoamylase variants of the present invention have improved property relative to said parent polypeptide and wherein said improved property is increased thermostability.

In one aspect, the glucoamylase variant has improved (increased) thermostability relative to the parent glucoamylase.

In one aspect, the glucoamylase variant has improved (increased) thermostability relative to SEQ ID NO: 1 and/or SEQ ID NO: 4.

In one aspect, the glucoamylase variant has increased thermostability measured as increased melting temperature using TSA.

In one aspect, the glucoamylase variant has increased thermostability measured as increased melting temperature using TSA relative to SEQ ID NO: 4 of at least 0.1° C., at least 0.2° C., at least 0.3° C., at least 0.4° C., at least 0.5° C., at least 0.6° C., at least 0.7° C., at least 0.8° C., at least 0.9°

C., at least 1° C., at least 1.5° C., at least 2° C., at least 2.5° C., at least 3° C., at least 3.5° C., at least 4.0° C., at least 4.5° C. or at least 5° C. or at least 5.5° C. or at least 6° C., or at least 6.5° C. or at least 7° C. or at least 7.5° C., or at least 8° C., or at least 8.5° C., or at least 9° C., or at least 9.5° C. or at least 9.9° C. In one aspect, the glucoamylase variant has relative activity at 91° C. of at least 150, preferably at least 200, more preferably at least 250, most preferably at least 300 compared to said parent glucoamylase.

In one aspect, the present invention relates to glucoamylase variants comprises at least one of the following substitutions or combinations of substitutions:

i. D75N+R77D+A78Q;
ii. D75S+R77G+A78W+V79D+F80Y;
iii. K34Y+S103N;
iv. K34Y+D445N+V447S;
v. K34Y+Y504T;
vi. S103N+D445N+V447S;
vii. S103N+Y504T;
viii. D445N+V447S+Y504T;
ix. K34Y+S103N+D445N+V447S;
x. K34Y+S103N+D445N+V447S+E501V+Y504T;
xi. K34Y+S103N+Y504T;
xii. K34Y+S103N+D445N+V447S+D566T;
xiii. K34Y+S103N+Q594R+F595S;
xiv. K34Y+S103N+Y504T+Q594R+F595S;
xv. K34Y+S103N+D445N+V447S+Y504T+Q594R+F595S;
xvi. S105L;
xvii. S105E;
xviii. A132R;
xix. K34Y+S105L+Y504T+Q594R+F595S;
xx. K34Y+S103N+S105L+Y504T+Q594R+F595S;
xxi. K34Y+S103N+S105L+Y504T+Q594R+F595S;
xxii. K34Y+S103N+S105L+Y504T D566T Q594R F595S;
xxiii. K34Y+S103N+S105L+D445N+V447S+Y504T+D566T+Q594R+F595S;
xxiv. K34Y+S103N+S105L+A132R+D445N+V447S+Y504T+D566T+Q594R+F595S; xxv. K34Y+S103N+S105L+D445N+V447S+D566T+Q594R+F595S;
xxvi. K34Y+S103N+S105L+A132R+D445N+V447S+E501V+Y504T+D566T+Q594R+F595S;
xxvii. K34Y+S103N+A132R+D445N+V447S+Y504T+D566T+Q594R+F595S;
xxviii. K34Y+S103N+S105L+A132R+D445N+V447S+Y504T+D566T+V592T;
xxix. G6S+G7T+K34Y+S103N+S105L+A132R+D445N+V447S+Y504T+D566T+Q594R+F595S;
xxx. K34Y+S103N+P107L+A132R+D445N+V447S+Y504T+D566T+Q594R+F595S;
xxxi. G6S+G7T+K34Y+S103N+P107L+A132R+D445N+V447S+Y504T+D566T+Q594R+F595S;
xxxii. G6S+G7T+K34Y+S103N+P107L+A132R+D445N+V447S+Y504T+D566T+V592T+Q594R+F595S;
xxxiii. G6S+G7T+K34Y+S103N+P107L+A132P+D445N+V447S+Y504T+D566T+Q594R+F595S;
xxxiv. G6S+G7T+K34Y+S103N+P107L+A132R+D445N+V447S+Y504T+D566T+T568V+Q594R+F595S;
xxxv. G6S+G7T+K34Y+S103N+P107L+A132P+D445N+V447S+Y504T+D566T+T568V+Q594R+F595S;
xxxvi. G6S+G7T+K34Y+S103N+P107L+A132R+D445N+V447S+S481P+Y504T+D566T+Q594R+F595S;
xxxvii. G6S+G7T+K34Y+S103N+P107L+A132R+D445N+V447S+S481P+Y504T+D566T+T568V+Q594R+F595S;
xxxviii. G6S+G7T+K34Y+S103N+P107L+A132P+D445N+V447S+D566T+T568V+Q594R+F595S;
xxxix. G6S+G7T+K34Y+S103N+P107L+T110W+A132P+D445N+V447S+Y504T+D566T+T568V+Q594R+F595S;
xl. G6S+G7T+K34Y+E50R+S103N+P107L+A132P+D445N+V447S+Y504T+D566T+T568V+Q594R+F595S;
xli. G6S+G7T+K34Y+S103N+P107L+A132P+D445N+V447S+E501V+Y504T;
xlii. G6S+G7T+R31F+K34Y+S103N+P107L+A132P+D445N+V447S+Y504T+D566T+T568V+Q594R+F595S;
xliii. G6S+G7T+R31F+K34Y+S103N+P107L+A132P+D445N+V447S+S481P+Y504T+D566T+T568V+Q594R+F595S;
xliv. G6S+G7T+K34Y+E50R+S103N+P107L+A132P+D445N+V447S+S481P+Y504T+D566T+T568V+Q594R+F595S;
xlv. G6S+G7T+R31F+K34Y+S103N+P107L+A132P+D445N+V447S+S481P+E501V+Y504T+D566T+T568V+Q594R+F595S;
xlvi. G6S+G7T+R31F+K34Y+S103N+P107L+A132P+D445N+V447S+S481P+D566T+T568V+Q594R+F595S;
xlvii. K34Y+D75N+R77D+A78Q+S103N+R138L+D445N+V447S+Y504T+Q594R+F595S;
xlviii. G6S+G7T+R31F+K34Y+D75N+R77D+A78Q+S103N+P107L+A132P+D445N+V447S+S481P+Y504T+D566T+T568V+Q594R+F595S;
xlix. G6S+G7T+R31F+K34Y+S103N+A132P+D445N+V447S+S481P+D566T+T568V+Q594R+F595S;
l. G6S+G7T+K34Y+E50R+S103N+A132P+D445N+V447S+S481P+D566T+T568V+Q594R+F595S;
li. R31F+K34Y+D75N+R77D+A78Q+S103N+R138L+D445N+V447S+Y504T+Q594R+F595S;
lii. K34Y+D75N+R77D+A78Q+S103N+R138L+D445N+V447S+Q594R+F595S;
liii. G6S+G7T+R31F+K34Y+S103N+A132P+D445N+V447S;
liv. G6S+G7T+R31F+K34Y+E50R+S103N+A132P+D445N+V447S+S481P+D566T+T568V+Q594R+F595S;
lv. K34Y+E50R+D75N+R77D+A78Q+S103N+R138L+D445N+V447S+Q594R+F595S;
lvi. G6S+G7T+R31F+K34Y+E50R+D75N+R77D+A78Q+S103N+A132P+D445N+V447S+S481P+D566T+Q594R+F595S;
lvii. R31F+K34Y+E50R+D75N+R77D+A78Q+S103N+R138L+D445N+V447S+Q594R+F595S;
lviii. G6S+G7T+R31F+K34Y+E50R+D75N+R77D+A78Q+S103N+A132P+R138L+D445N+V447S+S481P+D566T+Q594R+F595S;
lix. R135S;
lx. G6S+G7T+R31F+K34Y+E50R+S103N+A132P+D445N+V447S+S481P+E501L+D566T+T568V+Q594R+F595S;
lxi. G6S+G7T+R31F+K34Y+S103N+A132P+R138G+D445N+V447S+S481P+D566T+T568V+Q594R+F595S;
lxii. G6S+G7T+R31F+K34Y+S103N+A132P+R138L+D445N+V447S+S481P+D566T+T568V+Q594R+F595S;

lxiii. G6S+G7T+R31F+K34Y+S103N+A132P+R138P+D445N+V447S+S481P+D566T+T568V+Q594R+F595S;

lxiv. G6S+G7T+R31F+K34Y+E50R+S103N+A132P+S379P+D445N+V447S+S481P+E501A+D566T+T568V+Q594R+F595S;

lxv. G6S+G7T+R31F+K34Y+E50R+S103N+A132P+D445N+V447S+S481P+T484P+E501A+D566T+T568V+Q594R+F595S;

lxvi. G6S+G7T+R31F+K34Y+E50R+S103N+A132P+D445N+V447S+S481P+E501A+N539P+D566T+T568V+Q594R+F595S;

lxvii. G6S+G7T+R31F+K34Y+E50R+S103N+A132P+S379P+D445N+V447S+S481P+T484P+E501A+D566T+T568V+Q594R+F595S; +G6S+G7T+R31F+K34Y+E50R+S103N+A132P+D445N+V447S+S481P+T484P+E501A+N539P+D566T+T568V+Q594R+F595S, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for glucoamylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Parent Glucoamylases

The parent glucoamylase may be a polypeptide wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity with any one of the polypeptides of SEQ ID Nos: 1-13.

In one embodiment, the parent has a sequence identity to the polypeptide of SEQ ID NO: 1 of at least 60% e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, or 100%, which have glucoamylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 1.

The parent preferably comprises or consists of the amino acid sequence of SEQ ID NO: 1. In one embodiment the parent comprises or consists of the polypeptide of SEQ ID NO: 1. In another embodiment, the parent is an allelic variant of the polypeptide of SEQ ID NO: 1.

In one embodiment, the parent has a sequence identity to the polypeptide of SEQ ID NO: 2 of at least 60% e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, or 100%, which have glucoamylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 2.

The parent preferably comprises or consists of the amino acid sequence of SEQ ID NO: 2. In one embodiment the parent comprises or consists of the polypeptide of SEQ ID NO: 2. In another embodiment, the parent is an allelic variant of the polypeptide of SEQ ID NO: 2.

In one embodiment, the parent has a sequence identity to the polypeptide of SEQ ID NO: 3 of at least 60% e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, or 100%, which have glucoamylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 3.

The parent preferably comprises or consists of the amino acid sequence of SEQ ID NO: 3. In one embodiment the parent comprises or consists of the polypeptide of SEQ ID NO: 3. In another embodiment, the parent is an allelic variant of the polypeptide of SEQ ID NO: 3.

In one embodiment, the parent has a sequence identity to the polypeptide of SEQ ID NO: 4 of at least 60% e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, or 100%, which have glucoamylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 4.

The parent preferably comprises or consists of the amino acid sequence of SEQ ID NO: 4. In one embodiment the parent comprises or consists of the polypeptide of SEQ ID NO: 4. In another embodiment, the parent is an allelic variant of the polypeptide of SEQ ID NO: 4.

In one embodiment, the parent has a sequence identity to the polypeptide of SEQ ID NO: 5 of at least 60% e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, or 100%, which have glucoamylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 5.

The parent preferably comprises or consists of the amino acid sequence of SEQ ID NO: 5. In one embodiment the parent comprises or consists of the polypeptide of SEQ ID NO: 5. In another embodiment, the parent is an allelic variant of the polypeptide of SEQ ID NO: 5.

In one embodiment, the parent has a sequence identity to the polypeptide of SEQ ID NO: 6 of at least 60% e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, or 100%, which have glucoamylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 6.

The parent preferably comprises or consists of the amino acid sequence of SEQ ID NO: 6. In one embodiment the parent comprises or consists of the polypeptide of SEQ ID NO: 6. In another embodiment, the parent is an allelic variant of the polypeptide of SEQ ID NO: 6.

In one embodiment, the parent has a sequence identity to the polypeptide of SEQ ID NO: 7 of at least 60% e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, or 100%, which have glucoamylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 7.

The parent preferably comprises or consists of the amino acid sequence of SEQ ID NO: 7. In one embodiment the parent comprises or consists of the polypeptide of SEQ ID NO: 7. In another embodiment, the parent is an allelic variant of the polypeptide of SEQ ID NO: 7.

In one embodiment, the parent has a sequence identity to the polypeptide of SEQ ID NO: 8 of at least 60% e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, or 100%, which have glucoamylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 8.

The parent preferably comprises or consists of the amino acid sequence of SEQ ID NO: 8. In one embodiment the parent comprises or consists of the polypeptide of SEQ ID NO: 8. In another embodiment, the parent is an allelic variant of the polypeptide of SEQ ID NO: 8.

In one embodiment, the parent has a sequence identity to the polypeptide of SEQ ID NO: 9 of at least 60% e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, or 100%, which have glucoamylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 9.

The parent preferably comprises or consists of the amino acid sequence of SEQ ID NO: 9. In one embodiment the parent comprises or consists of the polypeptide of SEQ ID NO: 9. In another embodiment, the parent is an allelic variant of the polypeptide of SEQ ID NO: 9.

In one embodiment, the parent has a sequence identity to the polypeptide of SEQ ID NO: 10 of at least 60% e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, or 100%, which have glucoamylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 10.

The parent preferably comprises or consists of the amino acid sequence of SEQ ID NO: 10. In one embodiment the parent comprises or consists of the polypeptide of SEQ ID NO: 10. In another embodiment, the parent is an allelic variant of the polypeptide of SEQ ID NO: 10.

In one embodiment, the parent has a sequence identity to the polypeptide of SEQ ID NO: 11 of at least 60% e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, or 100%, which have glucoamylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 11.

The parent preferably comprises or consists of the amino acid sequence of SEQ ID NO: 11. In one embodiment the parent comprises or consists of the polypeptide of SEQ ID NO: 11. In another embodiment, the parent is an allelic variant of the polypeptide of SEQ ID NO: 11.

In one embodiment, the parent has a sequence identity to the polypeptide of SEQ ID NO: 12 of at least 60% e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, or 100%, which have glucoamylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 12.

The parent preferably comprises or consists of the amino acid sequence of SEQ ID NO: 12. In one embodiment the parent comprises or consists of the polypeptide of SEQ ID NO: 12. In another embodiment, the parent is an allelic variant of the polypeptide of SEQ ID NO: 12.

In one embodiment, the parent has a sequence identity to the polypeptide of SEQ ID NO: 13 of at least 60% e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, or 100%, which have glucoamylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 13.

The parent preferably comprises or consists of the amino acid sequence of SEQ ID NO: 13. In one embodiment the parent comprises or consists of the polypeptide of SEQ ID NO: 13. In another embodiment, the parent is an allelic variant of the polypeptide of SEQ ID NO: 13.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence, or (ii) the full-length complement of (i) or (ii) (Sambrook et al., 1989, *Molecular Cloning, A Laboratory Manual, 2d edition*, Cold Spring Harbor, New York).

The polynucleotide or a subsequence thereof, as well as the polypeptide of SEQ ID NO: 1 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with parent or a subsequence thereof, the carrier material is used in a Southern blot.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

In one particular embodiment the hybrid polypeptide comprises the variant glucoamylase catalytic domain fused to a linker and a carbohydrate binding domain.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

In one aspect, the parent fungal glucoamylase, may be a *Penicillium* glucoamylase such as, e.g., a *Penicillium oxalicum* glucoamylase, Penicillum *glabrum* glucoamylase,

*Penicillium brasilianum* glucoamylase, *Penicillium* russellii glucoamylase, *Penicillium* miczynskii glucoamylase.

In another aspect, the parent is a *Penicillium oxalicum*, e.g., the glucoamylase of SEQ ID NO: 1. In another aspect, the parent is a *Penicillium oxalicum*, e.g., the glucoamylase of SEQ ID NO: 2. In another aspect, the parent is a *Penicillium oxalicum*, e.g., the glucoamylase of SEQ ID NO: 3. In another aspect, the parent is a *Penicillium oxalicum*, e.g., the glucoamylase of SEQ ID NO: 4. In another aspect, the parent is a *Penicillium oxalicum*, e.g., the glucoamylase of SEQ ID NO: 5. In another aspect, the parent is a *Penicillium oxalicum*, e.g., the glucoamylase of SEQ ID NO: 6. In another aspect, the parent is a *Penicillium oxalicum*, e.g., the glucoamylase of SEQ ID NO: 7. In another aspect, the parent is a *Penicillium oxalicum*, e.g., the glucoamylase of SEQ ID NO: 8. In another aspect, the parent is a Penicillum *glabrum*, e.g., the glucoamylase of SEQ ID NO: 9. In another aspect, the parent is a *Penicillium brasilianum*, e.g., the glucoamylase of SEQ ID NO: 10. In another aspect, the parent is a *Penicillium* russellii, e.g., the glucoamylase of SEQ ID NO: 11. In another aspect, the parent is a *Penicillium* russellii, e.g., the glucoamylase of SEQ ID NO: 12. In another aspect, the parent is a *Penicillium* miczynskii, e.g., the glucoamylase of SEQ ID NO: 13.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and *Agricultural Research* Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The glucoamylase variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding glucoamylase variant(s) of the present invention.

The techniques used to isolate or clone a polynucleotide are known in the art and include isolation from genomic DNA or cDNA, or a combination thereof. The cloning of the polynucleotides from genomic DNA can be effected, e.g., by using the polymerase chain reaction (PCR) or antibody screening of expression libraries to detect cloned DNA fragments with shared structural features. See, e.g., Innis et al., 1990, *PCR: A Guide to Methods and Application, Academic Press*, New York. Other nucleic acid amplification procedures such as ligase chain reaction (LCR), ligation activated transcription (LAT) and polynucleotide-based amplification (NASBA) may be used. The polynucleotides may be cloned from a strain of *Trichoderma, Lecanicillium, Simplicillium, Aspergillus, Cornyascus, Acrophialophora, Rhinocladiella, Nemania, Talaromyces, Collariella, Rigidoporous*, and/or *Loramyces*, or a related organism and thus, for example, may be a species variant of the polypeptide encoding region of the polynucleotide.

Modification of a polynucleotide encoding glucoamylase variant(s) of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide encoding glucoamylase variant(s) of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xy/A and xy/B genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the polynucleotide of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase 1, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *J. Bacteriol.* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is heterologous to the coding sequence. A heterologous signal peptide coding sequence may be required where the coding sequence does not naturally contain a signal peptide coding sequence. Alternatively, a heterologous signal peptide coding sequence may simply replace the natural signal peptide coding sequence to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiol. Rev.* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), Rhizomucormiehei aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide encoding glucoamylase variant(s) of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding glucoamylase variant(s) of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of glucoamylase variant(s), e.g., a prokaryote or a eukaryote.

In some embodiments, the polypeptide is heterologous to the recombinant host cell.

In some embodiments, at least one of the one or more control sequences is heterologous to the polynucleotide encoding the glucoamylase variant(s).

In some embodiments, the recombinant host cell comprises at least two copies, e.g., three, four, or five, of the polynucleotide of the present invention.

The host cell may be any microbial or plant cell useful in the recombinant production of a polypeptide of the present invention, e.g., a prokaryotic cell or a fungal cell.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, J. *Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series No.* 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Talaromyces emersonii, Thielavia terrestris, Trametes villosa, Trametes*

*versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, Bio/Technology 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing glucoamylase variant(s) of the present invention, comprising (a) cultivating a cell, which in its wild-type form produces the glucoamylase variant(s), under conditions conducive for production of the glucoamylase variant(s); and optionally, (b) recovering the glucoamylase variant(s).

In one aspect, the cell is a *Trichoderma, Lecanicillium, Simplicillium, Aspergillus*, Cornyascus, *Acrophialophora, Rhinocladiella, Nemania, Talaromyces, Collariella, Rigidoporous, Loramyces, Fusarium, Gilmaniella, Gliomastix, Albifimbria, Rasamsonia, Hamigera* and/or *Acremonium* cell. In another aspect, the cell is a *Trichoderma harzianum, Trichoderma atroviride, Trichoderma reesei, Trichoderma longipile, Trichoderma koningiopsis, Trichoderma koningii, Trichoderma sinuosum, Lecanicillium primulinum, Simplicillium lameillicola, Aspergillus nidulans, Aspergillus wentii, Cornyascus sepedonium, Acrophialophora fusispora, Rhinocladiella* sp., *Nemania serpens, Talaromyces leycettanus, Collariella virescens, Rigidoporous* sp. 74222, and/or *Loramyces macrosporus, Fusarium solani, Gilmaniella humicola, Gliomastix murorum, Albifimbria verrucaria, Rasamsonia byssochlamydoides, Hamigera inflata* and/or *Acremonium exiguum* cell.

The present invention also relates to methods of producing a variant of the present invention, comprising (a) cultivating a recombinant host cell of the present invention under conditions conducive for production of the variant; and optionally, (b) recovering the polypeptide.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant.

Glucoamylase Variant Granules

The present invention also relates to enzyme granules/particles comprising the glucoamylase variant(s) of the invention. In an embodiment, the granule comprises a core, and optionally one or more coatings (outer layers) surrounding the core.

The core may have a diameter, measured as equivalent spherical diameter (volume based average particle size), of 20-2000 μm, particularly 50-1500 μm, 100-1500 μm or 250-1200 μm.

In an embodiment, the core comprises one or more glucoamylase variant of the present invention. In an embodiment, the core comprises one or more polypeptides having glucoamylase variant of the present invention. In an embodiment, the core comprises one or more polypeptides having glucoamylase variant and/or one or more polypeptides having glucoamylase variant of the present invention.

The core may include additional materials such as fillers, fiber materials (cellulose or synthetic fibers), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

The core may include an inert particle with the enzyme absorbed into it, or applied onto the surface, e.g., by fluid bed coating.

The core may have a diameter of 20-2000 μm, particularly 50-1500 μm, 100-1500 μm or 250-1200 μm.

The core may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA).

The coating may be applied in an amount of at least 0.1% by weight of the core, e.g., at least 0.5%, at least 1%, at least 5%, at least 10%, or at least 15%. The amount may be at most 100%, 70%, 50%, 40% or 30%.

The coating is preferably at least 0.1 μm thick, particularly at least 0.5 μm, at least 1 μm or at least 5 μm. In some embodiments, the thickness of the coating is below 100 μm, such as below 60 μm, or below 40 μm.

The coating should encapsulate the core unit by forming a substantially continuous layer. A substantially continuous layer is to be understood as a coating having few or no holes, so that the core unit it is encapsulating/enclosing has few or none uncoated areas. The layer or coating should, in particular, be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

To provide acceptable protection, the salt coating is preferably at least 0.1 μm thick, e.g., at least 0.5 μm, at least 1 μm, at least 2 μm, at least 4 μm, at least 5 μm, or at least 8 μm. In a particular embodiment, the thickness of the salt coating is below 100 μm, such as below 60 μm, or below 40 μm.

The salt may be added from a salt solution where the salt is completely dissolved or from a salt suspension wherein the fine particles are less than 50 μm, such as less than 10 μm or less than 5 μm.

The salt coating may comprise a single salt or a mixture of two or more salts. The salt may be water soluble, in particular, having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminum. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular, alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate).

The salt coating may be as described in WO 00/01793 or WO 2006/034710.

Specific examples of suitable salts are NaCl ($CH_{20° C.}$=76%), $Na_2CO_3$ ($CH_{20° C.}$=92%), $NaNO_3$ ($CH_{20° C.}$=73%), $Na_2HPO_4$ ($CH_{20° C.}$=95%), $Na_3PO_4$ ($CH_{20° C.}$=92%), $NH_4Cl$ ($CH_{20° C.}$=79.5%), $(NH_4)_2HPO_4$ ($CH_{20° C.}$=93.0%), $NH_4H_2PO_4$ ($CH_{20° C.}$=93.1%), $(NH_4)_2SO_4$ ($CH_{20° C.}$=81.1%), KCl ($CH_{20° C.}$=85%), $K_2HPO_4$ ($CH_{20° C.}$=92%), $KH_2PO_4$ ($CH_{20° C.}$=96.5%), $KNO_3$ ($CH_{20° C.}$=93.5%), $Na_2SO_4$ ($CH_{20° C.}$=93%), $K_2SO_4$ ($CH_{20° C.}$=98%), $KHSO_4$ ($CH_{20° C.}$=86%), $MgSO_4$ ($CH_{20° C.}$=90%), $ZnSO_4$ ($CH_{20° C.}$=90%) and sodium citrate ($CH_{25° C.}$=86%). Other examples include $NaH_2PO_4$, $(NH_4)H_2PO_4$, $CuSO_4$, $Mg(NO_3)_2$ and magnesium acetate.

The salt may be in anhydrous form, or it may be a hydrated salt, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4 \cdot 7H_2O$), zinc sulfate heptahydrate ($ZnSO_4 \cdot 7H_2O$), sodium phosphate dibasic heptahydrate ($Na_2HPO_4 \cdot 7H_2O$), magnesium nitrate hexahydrate ($Mg(NO_3)_2(6H_2O)$), sodium citrate dihydrate and magnesium acetate tetrahydrate.

Preferably the salt is applied as a solution of the salt, e.g., using a fluid bed.

The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The granule may optionally have one or more additional coatings. Examples of suitable coating materials are polyethylene glycol (PEG), methyl hydroxy-propyl cellulose (MHPC) and polyvinyl alcohol (PVA). Examples of enzyme granules with multiple coatings are described in WO 93/07263 and WO 97/23606.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in the Handbook of Powder Technology; Particle size enlargement by C. E. Capes; Volume 1; 1980; Elsevier. Preparation methods include known feed and granule formulation technologies, e.g.:

(a) Spray dried products, wherein a liquid enzyme-containing solution is atomized in a spray drying tower to form small droplets which during their way down the drying tower dry to form an enzyme-containing particulate material. Very small particles can be produced this way (Michael S. Showell (editor); Powdered detergents; Surfactant Science Series; 1998; vol. 71; page 140-142; Marcel Dekker).

(b) Layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606.

(c) Absorbed core particles, wherein rather than coating the enzyme as a layer around the core, the enzyme is absorbed onto and/or into the surface of the core. Such a process is described in WO 97/39116.

(d) Extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme (Michael S. Showell (editor); Powdered detergents; Surfactant Science Series; 1998; vol. 71; pages 140-142; Marcel Dekker).

(e) Prilled products, wherein an enzyme-containing powder is suspended in molten wax and the suspension is sprayed, e.g., through a rotating disk atomizer, into a cooling chamber where the droplets quickly solidify (Michael S. Showell (editor); Powdered detergents; Surfactant Science Series; 1998; vol. 71; page 140-142; Marcel Dekker). The product obtained is one wherein the enzyme is uniformly distributed throughout an inert material instead of being concentrated on its surface. U.S. Pat. Nos. 4,016,040 and 4,713,245 describe this technique.

(f) Mixer granulation products, wherein an enzyme-containing liquid is added to a dry powder composition of conventional granulating components. The liquid and the powder in a suitable proportion are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process, various high-shear mixers can be used as granulators. Granulates consisting of enzyme, fillers and binders etc. are mixed with cellulose fibers to reinforce the particles to produce a so-called T-granulate. Reinforced particles, are more robust, and release less enzymatic dust.

(g) Size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in Martin Rhodes (editor); Principles of Powder Technology; 1990; Chapter 10; John Wiley & Sons.

(h) Fluid bed granulation. Fluid bed granulation involves suspending particulates in an air stream and spraying a liquid onto the fluidized particles via nozzles. Particles hit by spray droplets get wetted and become tacky. The tacky particles collide with other particles and adhere to them to form a granule.

(i) The cores may be subjected to drying, such as in a fluid bed drier. Other known methods for drying granules in the feed or enzyme industry can be used by the skilled person. The drying preferably takes place at a product temperature of from 25 to 90° C. For some enzymes, it is important the cores comprising the enzyme contain a low amount of water before coating with the salt. If water sensitive enzymes are coated with a salt before excessive water is removed, it will be trapped within the core and may affect the activity of the enzyme negatively. After drying, the cores preferably contain 0.1-10% w/w water.

Non-dusting granulates may be produced, e.g., as disclosed in U.S. Pat. Nos. 4,106,991 and 4,661,452 and may optionally be coated by methods known in the art.

The granulate may further one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The present invention also relates to protected enzymes prepared according to the method disclosed in EP 238,216.

In an embodiment, the granule further comprises one or more additional enzymes, e.g., hydrolase, isomerase, ligase, lyase, oxidoreductase, and transferase. The one or more additional enzymes are preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectin esterase, triacylglycerol lipase, xylanase, beta-xylosidase or any combination thereof.

Liquid Formulations

The present invention also relates to liquid compositions comprising the glucoamylase variants of the invention. The composition may comprise an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials.

In an aspect, the present invention relates to liquid formulations comprising:

(A) 0.001% to 25% w/w of one or more glucoamylase variant(s) of the present invention; and (B) water.

In an aspect, the present invention relates to liquid formulations comprising:

(A) 0.001% to 25% w/w of one or more glucoamylase variant(s) of the present invention; and (B) water.

In an aspect, the present invention relates to liquid formulations comprising:

(A) 0.001% to 25% w/w of one or more glucoamylase variant(s) and/or one or more polypeptides having glucoamylase variant(s) of the present invention; and (B) water.

In another embodiment, the liquid formulation comprises 20% to 80% w/w of polyol. In one embodiment, the liquid formulation comprises 0.001% to 2.0% w/w preservative.

In another embodiment, the invention relates to liquid formulations comprising:

(A) 0.001% to 25% w/w of one or more glucoamylase variant(s) of the present invention;
(B) 20% to 80% w/w of polyol;
(C) optionally 0.001% to 2.0% w/w preservative; and
(D) water.

In another embodiment, the invention relates to liquid formulations comprising:

(A) 0.001% to 25% w/w of one or more glucoamylase variant(s) of the present invention;
(B) 20% to 80% w/w of polyol;
(C) optionally 0.001% to 2.0% w/w preservative; and
(D) water.

In another embodiment, the invention relates to liquid formulations comprising:

(A) 0.001% to 25% w/w of one or more glucoamylase variant(s) and/or one or more glucoamylase variant(s) of the present invention;
(B) 20% to 80% w/w of polyol;
(C) optionally 0.001% to 2.0% w/w preservative; and
(D) water.

In another embodiment, the invention relates to liquid formulations comprising:

(A) 0.001% to 25% w/w of one or more glucoamylase variant(s) of the present invention;
(B) 0.001% to 2.0% w/w preservative;
(C) optionally 20% to 80% w/w of polyol; and
(D) water.

In another embodiment, the invention relates to liquid formulations comprising:

(A) 0.001% to 25% w/w of one or more glucoamylase variant(s) of the present invention;
(B) 0.001% to 2.0% w/w preservative;
(C) optionally 20% to 80% w/w of polyol; and
(D) water.

In another embodiment, the invention relates to liquid formulations comprising:

(A) 0.001% to 25% w/w of one or more glucoamylase variant(s) and/or one or more glucoamylase variant(s) of the present invention;
(B) 0.001% to 2.0% w/w preservative;
(C) optionally 20% to 80% w/w of polyol; and
(D) water.

In another embodiment, the liquid formulation comprises one or more formulating agents, such as a formulating agent selected from the group consisting of polyol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, PVA, acetate and phosphate, preferably selected from the group consisting of sodium sulfate, dextrin, cellulose, sodium thiosulfate, kaolin and calcium carbonate. In one embodiment, the polyols is selected from the group consisting of glycerol, sorbitol, propylene glycol (MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600, more preferably selected from the group consisting of glycerol, sorbitol and propylene glycol (MPG) or any combination thereof.

In another embodiment, the liquid formulation comprises 20%-80% polyol (i.e., total amount of polyol), e.g., 25%-75% polyol, 30%-70% polyol, 35%-65% polyol, or 40%-60% polyol. In one embodiment, the liquid formulation comprises 20%-80% polyol, e.g., 25%-75% polyol, 30%-70% polyol, 35%-65% polyol, or 40%-60% polyol, wherein the polyol is selected from the group consisting of glycerol, sorbitol, propylene glycol (MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600. In one embodiment, the liquid formulation comprises 20%-80% polyol (i.e., total amount of polyol), e.g., 25%-75% polyol, 30%-70% polyol, 35%-65% polyol, or 40%-60% polyol, wherein the polyol is selected from the group consisting of glycerol, sorbitol and propylene glycol (MPG).

In another embodiment, the preservative is selected from the group consisting of sodium sorbate, potassium sorbate, sodium benzoate and potassium benzoate or any combination thereof. In one embodiment, the liquid formulation comprises 0.02% to 1.5% w/w preservative, e.g., 0.05% to 1.0% w/w preservative or 0.1% to 0.5% w/w preservative. In one embodiment, the liquid formulation comprises 0.001% to 2.0% w/w preservative (i.e., total amount of preservative), e.g., 0.02% to 1.5% w/w preservative, 0.05% to 1.0% w/w preservative, or 0.1% to 0.5% w/w preservative, wherein the preservative is selected from the group consisting of sodium sorbate, potassium sorbate, sodium benzoate and potassium benzoate or any combination thereof.

In another embodiment, the liquid formulation further comprises one or more additional enzymes, e.g., hydrolase, isomerase, ligase, lyase, oxidoreductase, and transferase. The one or more additional enzymes are preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectin esterase, triacylglycerol lipase, xylanase, beta-xylosidase or any combination thereof.

Fermentation Broth Formulations or Cell Compositions

The present invention also relates to a fermentation broth formulation or a cell composition comprising glucoamylase variant(s) of the present invention. The fermentation broth formulation or the cell composition further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In some embodiments, the fermentation broth formulation or the cell composition comprises a first organic acid component comprising at least one 1-5 carbon organic acid and/or a salt thereof and a second organic acid component comprising at least one 6 or more carbon organic acid and/or a salt thereof. In some embodiments, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid (s), and optionally further contains killed cells and/or cell debris. In some embodiments, the killed cells and/or cell debris are removed from a cell-killed whole broth to provide a composition that is free of these components.

The fermentation broth formulation or cell composition may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell composition of the present invention may be produced by a method described in WO 90/15861 or WO 2010/096673.

Uses

An aspect of the present invention relates to the use of a glucoamylase variant of the present invention for producing a fermentation product, such as ethanol, from a gelatinized starch-containing material, using a fermenting organism, such as yeast (e.g., a strain of *Saccharomyces*, such as *Saccharomyces cerevisiae*).

An aspect of the present invention relates to the use of a glucoamylase variant of the present invention for producing a fermentation product, such as ethanol, from an ungelatinized starch-containing material, using a fermenting organism, such as yeast (e.g., a strain of *Saccharomyces*, such as *Saccharomyces cerevisiae*).

Another aspect of the present invention relates to the use of a glucoamylase variant of the present invention for producing a fermentation product, such as ethanol, from a cellulosic-containing material, using a fermenting organism, such as yeast (e.g., a strain of *Saccharomyces*, such as *Saccharomyces cerevisiae*).

Another aspect of the present invention relates to the use of a glucoamylase variant of the present invention for liquefying a starch-containing material.

Another aspect of the present invention relates to the use of a glucoamylase variant of the present invention for saccharifying a starch-containing material.

Another aspect of the present invention relates to the use of a glucoamylase variant of the present invention for saccharifying a cellulosic-containing material.

Processes of the Invention

Processes for Producing Fermentation Products from Un-Gelatinized Starch-Containing Material.

The invention relates to processes for producing fermentation products from starch-containing material without gelatinization (i.e., without cooking) of the starch-containing material (often referred to as a "raw starch hydrolysis" process). The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of an alpha-amylase and carbohydrate-source generating enzyme(s) to produce sugars that can be fermented into the fermentation product by a suitable fermenting organism. In this embodiment the desired fermentation product, e.g., ethanol, is produced from un-gelatinized (i.e., uncooked), preferably milled, cereal grains, such as corn.

Processes for producing a fermentation product from starch-containing material may comprise simultaneously saccharifying and fermenting starch-containing material using a carbohydrate-source generating enzymes and a fermenting organism at a temperature below the initial gelatinization temperature of said starch-containing material in the presence of an alpha-amylase of the invention. Saccharification and fermentation may also be separate.

In an aspect, the invention relates to processes for producing fermentation products, preferably ethanol, from starch-containing material comprising the steps of:

i) saccharifying the starch-containing material using a carbohydrate-source generating enzyme at a temperature below the initial gelatination temperature; and ii) fermenting using a fermenting organism;

wherein at least one or more glucoamylase variant(s) are present or added during saccharification, fermentation or simultaneous saccharification and fermentation.

In some embodiments, at least two, at least three, at least four, or at least five glucoamylase variant(s) are present and/or added during saccharification, fermentation or simultaneous saccharification and fermentation.

The glucoamylase variant(s) are present or added in the above described processes for producing fermentation products from starch-containing material may be added exogenously during saccharification, fermentation or simultaneous saccharification and fermentation as mono-components, as enzyme blends or compositions comprising the glucoamylase variant(s), and/or via in-situ expression and secretion of the glucoamylase variant(s) by the fermenting organism, e.g., a recombinant host cell or fermenting organism described herein (e.g., yeast, such as from the genus *Saccharomyces*, preferably *Saccharomyces cerevisiae*).

Processes for Producing Fermentation Products from Gelatinized Starch-Containing Material In this aspect, the invention relates to processes for producing fermentation products, especially ethanol, from starch-containing material, which process includes a liquefaction step and sequentially or simultaneously performed saccharification and fermentation steps.

Consequently, the invention relates to processes for producing fermentation products from starch-containing material comprising the steps of:

i) liquefying the starch-containing material at a temperature above the initial gelatinization temperature using an alpha-amylase;

ii) saccharifying using a carbohydrate-source generating enzyme; and iii) fermenting using a fermenting organism;

wherein at least one or more glucoamylase variant(s) are present or added during saccharification, fermentation or simultaneous saccharification and fermentation.

In some embodiments, at least two, at least three, at least four, or at least five glucoamylase variant(s) are present and/or added during saccharification, fermentation or simultaneous saccharification and fermentation.

The glucoamylase variant(s) are present or added in the above described processes for producing fermentation products from starch-containing material may be added exogenously during saccharification, fermentation or simultaneous saccharification and fermentation as mono-components, as enzyme blends or compositions comprising the glucoamylase variant(s), and/or via in-situ expression and secretion of the glucoamylase variant(s) by the fermenting organism, e.g., a recombinant host cell or fermenting organism described herein (e.g., yeast, such as from the genus *Saccharomyces*, preferably *Saccharomyces cerevisiae*).

Processes for Producing Fermentation Products from Cellulosic-Containing Material In this aspect, the invention relates to processes for producing fermentation products, especially ethanol, from cellulosic-containing material, which process may include a pretreatment step and sequentially or simultaneously performed saccharification and fermentation steps.

Consequently, the invention relates to processes for producing fermentation products from cellulosic-containing material comprising the steps of:

i) optionally pretreating a cellulosic-containing material;

ii) saccharifying a cellulosic-containing material and/or pretreated cellulosic-containing material using a carbohydrate-source generating enzyme; and iii) fermenting using a fermenting organism;

wherein at least one or more glucoamylase variant(s) are present or added during saccharifying step ii) or fermenting step iii).

In some embodiments, at least two, at least three, at least four, or at least five glucoamylase variant(s) are present and/or added during saccharifying step ii) or fermenting step iii).

The glucoamylase variant(s) are present or added in the above described processes for producing fermentation products from cellulosic-containing material may be added exogenously during saccharification, fermentation or simultaneous saccharification and fermentation as mono-components, as enzyme blends or compositions comprising the glucoamylase variant(s), and/or via in-situ expression and secretion of the glucoamylase variant(s) by the fermenting organism, e.g., a recombinant host cell or fermenting organism described herein (e.g., yeast, such as from the genus *Saccharomyces*, preferably *Saccharomyces cerevisiae*).

Steps ii) and iii) are carried out either sequentially or simultaneously. In a preferred embodiment steps ii) and iii) are carried out simultaneously. The alpha-amylase, an optional thermostable protease, may be added before and/or during liquefaction step i).

A composition of the invention may suitably be used in a process of the invention. A recombinant host cell or fermenting organism of the invention may suitably be used in a process of the invention. However, the enzymes may also be added separately.

Whether the process of the invention includes or does not include a liquefaction step or pretreatment step, the essential feature of the invention is that at glucoamylase variant(s) are present or added during liquefaction, saccharification, fermentation or simultaneous saccharification and fermentation. In one embodiment, at least one glucoamylase variant of the present invention is present or added during liquefaction. In one embodiment, at least one glucoamylase variant of the present invention is present or added during fermentation or simultaneous saccharification and fermentation. As noted above, the glucoamylase variant(s) may be added exogenously as a standalone enzyme or an enzyme blend or composition comprising at least one, at least two, at least three, at least four, or at least five glucoamylase variant(s), or expressed and secreted in situ by a recombinant host cell or fermenting organism of the present invention comprising at least one, at least two, at least three, at least four, or at least five glucoamylase variant(s).

Examples of other enzymes that can be added in addition to one or more glucoamylase variant(s) of the present invention during saccharification/fermentation/SSF, or used as a component of an enzyme blend or composition of the invention include, without limitation, alpha-amylases, endoglucanase, peroxidases, catalases, cellobhiohydrolases, beta-glucosidases, glucoamylases, hemicellulases, cellulases, beta-glucanases, xylanases, phospholipases, trehalases, and/or proteases. Particularly, saccharification and/or fermentation or simultaneous saccharification and fermentation, is performed in the presence of at least one cellulase/cellulolytic composition. More particularly the cellulases/cellulolytic composition are derived from a strain of *Trichoderma*, in particular *Trichoderma reesei*, or a strain of *Humicola*, in particular *Humicola insolens*, or a strain of *Chrysosporium*, in particular *Chrysosporium lucknowense*. The cellulases/cellulolytic composition should at least comprise a beta-glucosidase, a cellobiohydrolase and an endoglucanase.

In one embodiment, the cellulases/cellulolytic composition comprises one or more polypeptides selected from the group consisting of:

GH61 polypeptide having cellulolytic enhancing activity, beta-glucosidase;

Cellobiohydrolase I;

Cellobiohydrolase II;

or a mixture of two, three, or four thereof.

In an embodiment, the cellulase/cellulolytic composition comprises a beta-glucosidase, a cellobiohydrolase I, and an endoglucanase I.

Cellulases are well known in the art, and many are derived from filamentous fungi. Particularly, according to the invention, the cellulases/cellulolytic composition comprises one or more of the following components:

(i) an *Aspergillus fumigatus* cellobiohydrolase I;

(ii) an *Aspergillus fumigatus* cellobiohydrolase II;

(iii) an *Aspergillus fumigatus* beta-glucosidase or variant thereof; and (iv) a *Penicillium* sp. GH61 polypeptide having cellulolytic enhancing activity; or homologs thereof.

More specifically the cellulases/cellulolytic composition is in one embodiment a *Trichoderma reesei* cellulolytic enzyme composition further comprising *Penicillium emersonii* GH61A polypeptide having cellulolytic enhancing activity disclosed in SEQ ID NO: 15, or a polypeptide having at least 80%, at least 85%, at least 90% identity, at least 95% identity, at least 96% identity, at least 97% identity, at least 99% identity to SEQ ID NO: 15 and an *Aspergillus fumigatus* beta-glucosidase disclosed in SEQ ID NO: 16 or a variant thereof with the following substitutions: F100D, S283G, N456E, F512Y having at least 90% identity, at least 95% identity, at least 96% identity, at least 97% identity, at least 99% identity to SEQ ID NO: 16. In one embodiment, the cellulolytic composition comprises a cellobiohydrolase I (CBH I), such as one derived from a strain of the genus *Aspergillus*, such as a strain of *Aspergillus fumigatus*, such as the CBHI disclosed as SEQ ID NO: 17, or CBH I having at least 80%, at least 85%, at least 90% identity, at least 95% identity, at least 96% identity, at least 97% identity, at least 99% identity to SEQ ID NO: 17.

In one embodiment, the cellulolytic composition comprises a cellobiohydrolase II (CBH II), such as one derived from a strain of the genus *Aspergillus*, such as a strain of *Aspergillus fumigatus*; such as the CBH II disclosed as SEQ ID NO: 18, or a CBH II having at least 80%, at least 85%, at least 90% identity, at least 95% identity, at least 96% identity, at least 97% identity, at least 99% identity to SEQ ID NO: 18.

In another embodiment, the cellulases/cellulolytic composition is a *Trichoderma reesei* cellulolytic enzyme composition further comprising an endoglucanase I (EGI), such as one derived from a strain of the genus *Trichoderma*, such as a strain of *Trichoderma reesei*, such as the EGI disclosed as SEQ ID NO: 19, or an EGI having at least 80%, at least 85%, at least 90% identity, at least 95% identity, at least 96% identity, at least 97% identity, at least 99% identity to SEQ ID NO: 19.

Examples of suitable cellulases can be found in "Cellulolytic Composition present and/or added during Saccharification and/or Fermentation"

Examples of alpha-amylases can be found in the "Alpha-Amylase Present and/or Added During Liquefaction"-section below. Examples of thermostable proteases can be found in the "Protease Present and/or Added During Liquefaction"-section below. Examples of suitable optional carbohydrate-source generating enzymes, preferably thermostable carbohydrate-source generating enzymes, in particular, a thermostable glucoamylase, can be found in the "Carbohydrate-Source Generating Enzymes Present and/or Added During Liquefaction"-section below.

The pH during liquefaction may be between 4-7. In an embodiment, the pH during liquefaction is from 4.5-5.0, such as between 4.5-4.8. In another embodiment liquefaction is carried out at a pH above 5.0-6.5, such as above 5.0-6.0, such as above 5.0-5.5, such as between 5.2-6.2, such as around 5.2, such as around 5.4, such as around 5.6, such as around 5.8.

According to the invention the temperature is above the initial gelatinization temperature. The term "initial gelatinization temperature" refers to the lowest temperature at which solubilization of starch, typically by heating, begins. The temperature can vary for different starches.

In an embodiment, the temperature during liquefaction step i) is in the range from 70-100° C., such as between 75-100° C., preferably between 80-100° C., such as between 85-95° C., such as around between 88 and 92° C. In an embodiment, the temperature during liquefaction step i) is at least 80° C. In an embodiment, the temperature during liquefaction step i) is at least 81° C. In an embodiment, the temperature during liquefaction step i) is at least 82° C. In an embodiment, the temperature during liquefaction step i) is at least 83° C. In an embodiment, the temperature during liquefaction step i) is at least 84° C. In an embodiment, the temperature during liquefaction step i) is at least 85° C. In an embodiment, the temperature during liquefaction step i) is at least 86° C. In an embodiment, the temperature during liquefaction step i) is at least 87° C. In an embodiment, the temperature during liquefaction step i) is at least 88° C. In an embodiment, the temperature during liquefaction step i) is at least 89° C. In an embodiment, the temperature during liquefaction step i) is at least 90° C. In an embodiment, the temperature during liquefaction step i) is at least 91° C. In an embodiment, the temperature during liquefaction step i) is at least 92° C. In an embodiment, the temperature during liquefaction step i) is at least 93° C. In an embodiment, the temperature during liquefaction step i) is at least 94° C. In an embodiment, the temperature during liquefaction step i) is at least 95° C. In an embodiment, the temperature during liquefaction step i) is at least 96° C. In an embodiment, the temperature during liquefaction step i) is at least 97° C. In an embodiment, the temperature during liquefaction step i) is at least 97° C. In an embodiment, the temperature during liquefaction step i) is at least 98° C. In an embodiment, the temperature during liquefaction step i) is at least 99° C. In an embodiment, the temperature during liquefaction step i) is at least 100° C.

In an embodiment, the process of the invention further comprises, prior to the step i), the steps of:

a) reducing the particle size of the starch-containing material, preferably by dry milling;
b) forming a slurry comprising the starch-containing material and water.

The starch-containing starting material, such as whole grains, may be reduced in particle size, e.g., by milling, in order to open up the structure, to increase surface area, and allowing for further processing. Generally, there are two types of processes: wet and dry milling. In dry milling whole kernels are milled and used. Wet milling gives a good separation of germ and meal (starch granules and protein). Wet milling is often applied at locations where the starch hydrolysate is used in production of, e.g., syrups. Both dry and wet milling are well known in the art of starch processing. According to the present invention dry milling is preferred. In an embodiment, the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In another embodiment, at least 50%, preferably at least 70%, more preferably at least 80%, especially at least 90% of the starch-containing material fit through a sieve with #6 screen.

The aqueous slurry may contain from 10-55 w/w-% dry solids (DS), preferably 25-45 w/w-% dry solids (DS), more preferably 30-40 w/w-% dry solids (DS) of starch-containing material.

The alpha-amylase, optional thermostable protease, optional carbohydrate-source generating enzyme, in particular thermostable glucoamylase, may initially be added to the aqueous slurry to initiate liquefaction (thinning). In an embodiment only a portion of the enzymes is added to the aqueous slurry, while the rest of the enzymes are added during liquefaction step i).

Liquefaction step i) is according to the invention carried out for 0.5-5 hours, such as 1-3 hours, such as typically around 2 hours.

The aqueous slurry may in an embodiment be jet-cooked to further gelatinize the slurry before being subjected to liquefaction in step i). The jet-cooking may be carried out at a temperature between 110-145° C., preferably 120-140° C., such as 125-135° C., preferably around 130° C. for about 1-15 minutes, preferably for about 3-10 minutes, especially around about 5 minutes.

Saccharification and Fermentation

One or more carbohydrate-source generating enzymes, in particular glucoamylase, may be present and/or added during saccharification step ii) and/or fermentation step iii). The carbohydrate-source generating enzyme may preferably be a glucoamylase, but may also be an enzyme selected from the group consisting of: beta-amylase, maltogenic amylase and alpha-glucosidase. The carbohydrate-source generating enzyme added during saccharification step ii) and/or fermentation step iii) is typically different from the optional carbohydrate-source generating enzyme, in particular thermostable glucoamylase, optionally added during liquefaction step i). In a preferred embodiment the carbohydrate-source generating enzymes, in particular glucoamylase, is added together with a fungal alpha-amylase.

Examples of carbohydrate-source generating enzymes, including glucoamylases, can be found in the "Carbohydrate-Source Generating Enzyme Present and/or Added During Saccharification and/or Fermentation"-section below.

One or more alpha-amylases may be present and/or added during saccharification step ii) and/or fermentation step iii). In an embodiment, the alpha-amylase is the *Rhizomucor pusillus* alpha-amylase with *Aspergillus niger glucoamylase* linker and SBD disclosed as SEQ ID NO: 30 with the following substitutions: G128D+D143N (activity ratio AGU:AGU:FAU(F): approx. 30:7:1).

One or more trehalases may be present and/or added during saccharification step ii) and/or fermentation step iii). In an embodiment, the trehalase is the *Talaromyces funiculosus* trehalase disclosed herein as SEQ ID NO: 31 or a polypeptide having at least 80%, at least 85%, at least 90% identity, at least 95% identity, at least 96% identity, at least 97% identity, at least 99% identity to SEQ ID NO: 31, which has trehalase activity.

In an embodiment, the trehalase is part of a blend comprising *Gloeophyllum sepiarium* glucoamylase disclosed in SEQ ID NO: 28 or a polypeptide having at least 80%, at least 85%, at least 90% identity, at least 95% identity, at least 96% identity, at least 97% identity, at least 99% identity to SEQ ID NO: 28, which has gluocamylase activity, *Talaromyces funiculosus* trehalase disclosed herein as SEQ ID NO: 31, or a polypeptide having at least 80%, at least 85%, at least 90% identity, at least 95% identity, at least 96% identity, at least 97% identity, at least 99% identity to SEQ ID NO: 31, which has trehalase activity, and *Rhizomucor pusillus* alpha-amylase with *Aspergillus niger* glucoamylase linker and SBD disclosed as SEQ ID NO: 30 with the following substitutions: G128D+D143N (activity ratio AGU:AGU:FAU(F): approx. 30:7:1), or a polypeptide having at least 80%, at least 85%, at least 90% identity, at least 95% identity, at least 96% identity, at least 97% identity, at least 99% identity to SEQ ID NO: 30, which has alpha-amylase activity.

When doing sequential saccharification and fermentation, saccharification step ii) may be carried out at conditions well-known in the art. For instance, the saccharification step ii) may last up to from about 24 to about 72 hours. In an embodiment, pre-saccharification is done. Pre-saccharification is typically done for 40-90 minutes at a temperature between 30-65° C., typically about 60° C. Pre-saccharification is in an embodiment followed by saccharification during fermentation in simultaneous saccharification and fermentation ("SSF). Saccharification is typically carried out at temperatures from 20-75° C., preferably from 40-70° C., typically around 60° C., and at a pH between 4 and 5, normally at about pH 4.5.

Simultaneous saccharification and fermentation ("SSF") is widely used in industrial scale fermentation product production processes, especially ethanol production processes. When doing SSF the saccharification step ii) and the fermentation step iii) are carried out simultaneously. There is no holding stage for the saccharification, meaning that a fermenting organism, such as yeast, and enzyme(s), may be added together. However, it is also contemplated to add the fermenting organism and enzyme(s) separately. SSF is according to the invention typically carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours. In an embodiment the pH is between 3.5-5, in particular between 3.8 and 4.3.

Methods Using a Cellulosic-Containing Material

In some aspects, the methods described herein produce a fermentation product from a cellulosic-containing material. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic-containing material can be, but is not limited to, agricultural residue, herbaceous material (including energy crops), municipal solid waste, pulp and paper mill residue, waste paper, and wood (including forestry residue) (see, for example, Wiselogel et al., 1995, in *Handbook on Bioethanol* (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one embodiment, the cellulosic-containing material is any biomass material. In another embodiment, the cellulosic-containing material is lignocellulose, which comprises cellulose, hemicelluloses, and lignin.

In one embodiment, the cellulosic-containing material is agricultural residue, herbaceous material (including energy crops), municipal solid waste, pulp and paper mill residue, waste paper, or wood (including forestry residue).

In another embodiment, the cellulosic-containing material is arundo, bagasse, bamboo, corn cob, corn fiber, corn stover, miscanthus, rice straw, switchgrass, or wheat straw.

In another embodiment, the cellulosic-containing material is aspen, eucalyptus, fir, pine, poplar, spruce, or willow.

In another embodiment, the cellulosic-containing material is algal cellulose, bacterial cellulose, cotton linter, filter paper, microcrystalline cellulose (e.g., AVICEL®), or phosphoric-acid treated cellulose.

In another embodiment, the cellulosic-containing material is an aquatic biomass. As used herein the term "aquatic biomass" means biomass produced in an aquatic environment by a photosynthesis process. The aquatic biomass can be algae, emergent plants, floating-leaf plants, or submerged plants.

In another embodiment, the cellulosic-containing material is a whole stillage byproduct from a process for producing a fermentation from a starch-containing material.

The cellulosic-containing material may be used as is or may be subjected to pretreatment, using conventional methods known in the art, as described herein. In a preferred embodiment, the cellulosic-containing material is pretreated.

The methods of using cellulosic-containing material can be accomplished using methods conventional in the art. Moreover, the methods of can be implemented using any conventional biomass processing apparatus configured to carry out the processes.

Cellulosic Pretreatment

In one embodiment the cellulosic-containing material is pretreated before saccharification in step (ii).

In practicing the processes described herein, any pretreatment process known in the art can be used to disrupt plant cell wall components of the cellulosic-containing material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technology* 100: 10-18; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic-containing material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

In a one embodiment, the cellulosic-containing material is pretreated before saccharification (i.e., hydrolysis) and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

In one embodiment, the cellulosic-containing material is pretreated with steam. In steam pretreatment, the cellulosic-containing material is heated to disrupt the plant cell wall components, including lignin, hemicellulose, and cellulose to make the cellulose and other fractions, e.g., hemicellulose, accessible to enzymes. The cellulosic-containing material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

In one embodiment, the cellulosic-containing material is subjected to a chemical pretreatment. The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, *Bioresource Technology* 855: 1-33; Schell et al., 2004, *Bioresource Technology* 91: 179-188; Lee et al., 1999, *Adv. Biochem. Eng. Biotechnol.* 65: 93-115). In a specific embodiment the dilute acid pretreatment of cellulosic-containing material is carried out using 4% w/w sulfuric acid at 180° C. for 5 minutes.

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment. Lime pretreatment is performed with calcium oxide or calcium hydroxide at temperatures of 85-150° C. and residence times from one hour to several days (Wyman et al., 2005, *Bioresource Technology* 96: 1959-1966; Mosier et al., 2005, *Bioresource Technology* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technology* 64: 139-151; Palonen et al., 2004, *Appl. Biochem.* Biotechnol. 117: 1-17; Varga et al., 2004, *Biotechnol. Bioeng.* 88: 567-574; Martin et al., 2006, *J. Chem.* Technol. Biotechnol. 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO2006/032282).

Ammonia fiber expansion (AFEX) involves treating the cellulosic-containing material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic-containing material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, Appl. Biochem. Biotechnol. 121: 219-230). Sulphuric acid is usually added as a catalyst. In organosolv pretreatment, the majority of hemicellulose and lignin is removed.

Other examples of suitable pretreatment methods are described by Schell et al., 2003, Appl. *Biochem. Biotechnol.* 105-108: 69-85, and Mosier et al., 2005, *Bioresource Technology* 96: 673-686, and U.S. Published Application 2002/0164730.

In one embodiment, the chemical pretreatment is carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic-containing material and held at a temperature in the range of preferably 140-200° C., e.g., 165-190° C., for periods ranging from 1 to 60 minutes.

In another embodiment, pretreatment takes place in an aqueous slurry. In preferred aspects, the cellulosic-containing material is present during pretreatment in amounts preferably between 10-80 wt. %, e.g., 20-70 wt. % or 30-60 wt. %, such as around 40 wt. %. The pretreated cellulosic-containing material can be unwashed or washed using any method known in the art, e.g., washed with water.

In one embodiment, the cellulosic-containing material is subjected to mechanical or physical pretreatment. The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic-containing material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator A B, Sweden. The physical and chemical pretreatments can be carried out sequentially or simultaneously, as desired.

Accordingly, in one embodiment, the cellulosic-containing material is subjected to physical (mechanical) or chemical pretreatment, or any combination thereof, to promote the separation and/or release of cellulose, hemicellulose, and/or lignin.

In one embodiment, the cellulosic-containing material is subjected to a biological pretreatment. The term "biological pretreatment" refers to any biological pretreatment that promotes the separation and/or release of cellulose, hemicellulose, and/or lignin from the cellulosic-containing material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. *E., ed., Taylor & Francis, Washington, DC,* 179-212; Ghosh and Singh, 1993, *Adv. Appl. Microbiol.* 39: 295-333; McMillan, J. D., 1994, Pretreating lignocellulosic biomass: a review, in Enzymatic Conversion of Biomass for Fuels Production, Himmel, M. E., Baker, J. O., and Overend, R. P., eds., *ACS Symposium Series* 566, American Chemical Society, Washington, DC, chapter 15; Gong, C. S., Cao, N. J., Du, J., and Tsao, G. T., 1999, Ethanol production from renewable resources, in *Advances in Biochemical Engineering/Biotechnology, Scheper, T., ed.*, Springer-Verlag Berlin Heidelberg, *Germany,* 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Saccharification and Fermentation of Cellulosic-Containing Material

Saccharification (i.e., hydrolysis) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF).

SHF uses separate process steps to first enzymatically hydrolyze the cellulosic-containing material to fermentable sugars, e.g., glucose, cellobiose, and pentose monomers, and then ferment the fermentable sugars to ethanol. In SSF, the enzymatic hydrolysis of the cellulosic-containing material and the fermentation of sugars to ethanol are combined in one step (Philippidis, G. P., 1996, Cellulose bioconversion technology, in *Handbook on Bioethanol: Production and Utilization*, Wyman, C. *E., ed., Taylor & Francis, Washing-*

*ton, DC,* 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation organismcan tolerate. It is understood herein that any method known in the art comprising pretreatment, enzymatic hydrolysis (saccharification), fermentation, or a combination thereof, can be used in the practicing the processes described herein.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

In the saccharification step (i.e., hydrolysis step), the cellulosic and/or starch-containing material, e.g., pretreated or liquified, is hydrolyzed to break down cellulose, hemicellulose, and/or starch to fermentable sugars, such as glucose, cellobiose, xylose, xylulose, arabinose, mannose, galactose, and/or soluble oligosaccharides. The hydrolysis is performed enzymatically e.g., by a cellulolytic enzyme composition. The enzymes of the compositions can be added simultaneously or sequentially.

Enzymatic hydrolysis may be carried out in a suitable aqueous environment under conditions that can be readily determined by one skilled in the art. In one aspect, hydrolysis is performed under conditions suitable for the activity of the enzymes(s), i.e., optimal for the enzyme(s). The hydrolysis can be carried out as a fed batch or continuous process where the cellulosic and/or starch-containing material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 4.5 to about 5.5. The dry solids content is in the range of preferably about 5 to about 50 wt. %, e.g., about 10 to about 40 wt. % or about 20 to about 30 wt. %.

Saccharification in step (ii) may be carried out using a cellulolytic enzyme composition. Such enzyme compositions are described below in the "Cellulolytic Enzyme Composition'—section below. The cellulolytic enzyme compositions can comprise any protein useful in degrading the cellulosic-containing material. In one aspect, the cellulolytic enzyme composition comprises or further comprises one or more (e.g., two, several) proteins selected from the group consisting of a cellulase, an AA9 (GH61) polypeptide, a hemicellulase, an esterase, an expansin, a ligninolytic enzyme, an oxidoreductase, a pectinase, a protease, and a swollenin.

In another embodiment, the cellulase is preferably one or more (e.g., two, several) enzymes selected from the group consisting of an endoglucanase, a cellobiohydrolase, and a beta-glucosidase.

In another embodiment, the hemicellulase is preferably one or more (e.g., two, several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another embodiment, the oxidoreductase is one or more (e.g., two, several) enzymes selected from the group consisting of a catalase, a laccase, and a peroxidase.

The enzymes or enzyme compositions used in a processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

In one embodiment, an effective amount of cellulolytic or hemicellulolytic enzyme composition to the cellulosic-containing material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic-containing material.

In one embodiment, such a compound is added at a molar ratio of the compound to glucosyl units of cellulose of about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound is about 0.1 μM to about 1 M, e.g., about 0.5 μM to about 0.75 M, about 0.75 μM to about 0.5 M, about 1 μM to about 0.25 M, about 1 μM to about 0.1 M, about 5 μM to about 50 mM, about 10 μM to about 25 mM, about 50 μM to about 25 mM, about 10 μM to about 10 mM, about 5 μM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described in WO 2012/021401, and the soluble contents thereof. A liquor for cellulolytic enhancement of an AA9 polypeptide (GH61 polypeptide) can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and an AA9 polypeptide during hydrolysis of a cellulosic substrate by a cellulolytic enzyme preparation. The liquor can be separated from the treated material using a method standard in the art, such as filtration, sedimentation, or centrifugation.

In one embodiment, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In the fermentation step, sugars, released from the cellulosic-containing material, e.g., as a result of the pretreatment and enzymatic hydrolysis steps, are fermented to ethanol, by a fermenting organism, such as yeast described herein. Hydrolysis (saccharification) and fermentation can be separate or simultaneous.

Any suitable hydrolyzed cellulosic-containing material can be used in the fermentation step in practicing the processes described herein. Such feedstocks include, but are not limited to carbohydrates (e.g., lignocellulose, xylans, cellulose, starch, etc.). The material is generally selected based on economics, i.e., costs per equivalent sugar potential, and recalcitrance to enzymatic conversion.

Production of ethanol by a fermenting organism using cellulosic-containing material results from the metabolism of sugars (monosaccharides). The sugar composition of the hydrolyzed cellulosic-containing material and the ability of the fermenting organism to utilize the different sugars has a direct impact in process yields.

Compositions of the fermentation media and fermentation conditions depend on the fermenting organism and can easily be determined by one skilled in the art. Typically, the fermentation takes place under conditions known to be suitable for generating the fermentation product. In some embodiments, the fermentation process is carried out under aerobic or microaerophilic (i.e., where the concentration of oxygen is less than that in air), or anaerobic conditions. In some embodiments, fermentation is conducted under anaerobic conditions (i.e., no detectable oxygen), or less than about 5, about 2.5, or about 1 mmol/L/h oxygen. In the absence of oxygen, the NADH produced in glycolysis cannot be oxidized by oxidative phosphorylation. Under anaerobic conditions, pyruvate or a derivative thereof may be utilized by the host cell as an electron and hydrogen acceptor in order to generate NAD+.

The fermentation process is typically run at a temperature that is optimal for the recombinant fungal cell. For example, in some embodiments, the fermentation process is performed at a temperature in the range of from about 25° C. to about 42° C. Typically the process is carried out a temperature that is less than about 38° C., less than about 35° C., less than about 33° C., or less than about 38° C., but at least about 20° C., 22° C., or 25° C.

A fermentation stimulator can be used in a process described herein to further improve the fermentation, and in particular, the performance of the fermenting organism, such as, rate enhancement and product yield (e.g., ethanol yield). A "fermentation stimulator" refers to stimulators for growth of the fermenting organisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Medium

"Fermentation media" or "fermentation medium" refers to the environment in which fermentation is carried out. The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "Fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as ethanol. Examples of fermenting organisms include fungal organisms, such as yeast. Preferred yeast includes strains of *Saccharomyces* spp., in particular, *Saccharomyces cerevisiae.*

Suitable concentrations of the viable fermenting organism during fermentation, such as SSF, are well known in the art or can easily be determined by the skilled person in the art. In one embodiment the fermenting organism, such as ethanol fermenting yeast, (e.g., *Saccharomyces cerevisiae*) is added to the fermentation medium so that the viable fermenting organism, such as yeast, count per mL of fermentation medium is in the range from $10^5$ to $10^{12}$, preferably from $10^7$ to $10^{10}$, especially about $5\times10^7$.

Examples of commercially available yeast includes, e.g., RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand A B, Sweden), and FERMIOL (available from DSM Specialties). Other useful yeast strains are available from biological depositories such as the American Type Culture Collection (ATCC) or the Deutsche Sammlung von Mikroorganismen und Zellkulturen GmbH (DSMZ), such as, e.g., BY4741 (e.g., ATCC 201388); Y108-1 (ATCC PTA.10567) and NRRL YB-1952 (ARS Culture Collection). Still other *S. cerevisiae* strains suitable as host cells DBY746, [Alpha][Eta]22, S150-2B, GPY55-15Ba, CEN.PK, USM21, TMB3500, TMB3400, VTT-A-63015, VTT-A-85068, VTT-c-79093 and their derivatives as well as *Saccharomyces* sp. 1400, 424A (LNH-ST), 259A (LNH-ST) and derivatives thereof.

As used herein, a "derivative" of strain is derived from a referenced strain, such as through mutagenesis, recombinant DNA technology, mating, cell fusion, or cytoduction between yeast strains. Those skilled in the art will understand that the genetic alterations, including metabolic modifications exemplified herein, may be described with reference to a suitable host organism and their corresponding metabolic reactions or a suitable source organism for desired genetic material such as genes for a desired metabolic pathway. However, given the complete genome sequencing of a wide variety of organisms and the high level of skill in the area of genomics, those skilled in the art can apply the teachings and guidance provided herein to other organisms. For example, the metabolic alterations exemplified herein can readily be applied to other species by incorporating the same or analogous encoding nucleic acid from species other than the referenced species.

The host cell or fermenting organism may be *Saccharomyces* strain, e.g., *Saccharomyces cerevisiae* strain produced using the method described and concerned in U.S. Pat. No. 8,257,959-BB. In one embodiment, the recombinant cell is a derivative of a strain *Saccharomyces cerevisiae* CIBTS1260 (deposited under Accession No. NRRL Y-50973 at the *Agricultural Research* Service Culture Collection (NRRL), Illinois 61604 U.S.A.).

The strain may also be a derivative of *Saccharomyces cerevisiae* strain NMI V14/004037 (See, WO2015/143324 and WO2015/143317 each incorporated herein by reference), strain nos. V15/004035, V15/004036, and V15/004037 (See, WO 2016/153924 incorporated herein by reference), strain nos. V15/001459, V15/001460, V15/001461 (See, WO2016/138437 incorporated herein by reference), strain no. NRRL Y67342 (See, WO2018/098381 incorporated herein by reference), strain nos. NRRL Y67549 and NRRL Y67700 (See, PCT/US2019/018249 incorporated herein by reference), or any strain described in WO2017/087330 (incorporated herein by reference).

The fermenting organisms may be a host cell that expresses a heterologous glucoamylase variant(s) (e.g., any glucoamylase variant(s) described herein). Any glucoamylase variant(s)contemplated for a process, method, enzyme blend, or composition described herein is also contemplated for expression by a fermenting organism or host cell.

In one embodiment is a recombinant host cell (e.g., yeast host cell, such as a strain of *Saccharomyces*, for example *Saccharomyces cerevisiae*) comprising a heterologous polynucleotide encoding glucoamylase variant(s) (e.g., glucoamylase) (e.g., any glucoamylase described herein).

In one embodiment, a recombinant yeast host cell comprising a heterologous polynucleotide encoding a glucoamylase variant(s), wherein the polynucleotide comprises, consists, or consists essentially of the nucleotide sequence, or is a polynucleotide comprising, consisting of, or consisting essentially of a nucleotide sequence having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the polypeptide of SEQ ID NO: 1, which has glucoamylase activity.

In one embodiment, a recombinant yeast host cell comprising a heterologous polynucleotide encoding a glucoamylase variant(s), wherein the polynucleotide comprises, consists, or consists essentially of the nucleotide sequence or is a polynucleotide comprising, consisting of, or consisting essentially of a nucleotide sequence having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the polypeptide of SEQ ID NO: 2, which has glucoamylase activity.

In one embodiment, a recombinant yeast host cell comprising a heterologous polynucleotide encoding a glucoamylase variant(s), wherein the polynucleotide comprises, consists, or consists essentially of the nucleotide sequence or is a polynucleotide comprising, consisting of, or consisting essentially of a nucleotide sequence having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the polypeptide of SEQ ID NO: 3, which has glucoamylase activity.

In one embodiment, a recombinant yeast host cell comprising a heterologous polynucleotide encoding a glucoamylase variant(s), wherein the polynucleotide comprises, consists, or consists essentially of the nucleotide sequence or is a polynucleotide comprising, consisting of, or consisting essentially of a nucleotide sequence having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the polypeptide of SEQ ID NO: 4, which has glucoamylase activity.

In one embodiment, a recombinant yeast host cell comprising a heterologous polynucleotide encoding a glucoamylase variant(s), wherein the polynucleotide comprises, consists, or consists essentially of the nucleotide sequence, or is a polynucleotide comprising, consisting of, or consisting essentially of a nucleotide sequence having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the polypeptide of SEQ ID NO: 5, which has glucoamylase activity.

In one embodiment, a recombinant yeast host cell comprising a heterologous polynucleotide encoding a glucoamylase variant(s), wherein the polynucleotide comprises, consists, or consists essentially of the nucleotide sequence, or is a polynucleotide comprising, consisting of, or consisting essentially of a nucleotide sequence having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the polypeptide of SEQ ID NO: 6, which has glucoamylase activity.

In one embodiment, a recombinant yeast host cell comprising a heterologous polynucleotide encoding a glucoamylase variant(s), wherein the polynucleotide comprises, consists, or consists essentially of the nucleotide sequence, or is a polynucleotide comprising, consisting of, or consisting essentially of a nucleotide sequence having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the polypeptide of SEQ ID NO: 7, which has glucoamylase activity.

In one embodiment, a recombinant yeast host cell comprising a heterologous polynucleotide encoding a glucoamylase variant(s), wherein the polynucleotide comprises, consists, or consists essentially of the nucleotide sequence or is a polynucleotide comprising, consisting of, or consisting essentially of a nucleotide sequence having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the polypeptide of SEQ ID NO: 8, which has glucoamylase activity.

In one embodiment, a recombinant yeast host cell comprising a heterologous polynucleotide encoding a glucoamylase variant(s), wherein the polynucleotide comprises, consists, or consists essentially of the nucleotide sequence, or is a polynucleotide comprising, consisting of, or consisting essentially of a nucleotide sequence having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the polypeptide of SEQ ID NO: 9, which has glucoamylase activity.

In one embodiment, a recombinant yeast host cell comprising a heterologous polynucleotide encoding a glucoamylase variant(s), wherein the polynucleotide comprises, consists, or consists essentially of the nucleotide sequence or is a polynucleotide comprising, consisting of, or consisting essentially of a nucleotide sequence having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the polypeptide of SEQ ID NO: 10, which has glucoamylase activity.

In one embodiment, a recombinant yeast host cell comprising a heterologous polynucleotide encoding a glucoamylase variant(s), wherein the polynucleotide comprises, consists, or consists essentially of the nucleotide sequence or is a polynucleotide comprising, consisting of, or consisting essentially of a nucleotide sequence having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the polypeptide of SEQ ID NO: 11, which has glucoamylase activity.

In one embodiment, a recombinant yeast host cell comprising a heterologous polynucleotide encoding a glucoamylase variant(s), wherein the polynucleotide comprises, consists, or consists essentially of the nucleotide sequence or is a polynucleotide comprising, consisting of, or consisting essentially of a nucleotide sequence having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the polypeptide of SEQ ID NO: 12, which has glucoamylase activity.

In one embodiment, a recombinant yeast host cell comprising a heterologous polynucleotide encoding a glucoamylase variant(s), wherein the polynucleotide comprises, consists, or consists essentially of the nucleotide sequence or is a polynucleotide comprising, consisting of, or consisting essentially of a nucleotide sequence having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the polypeptide of SEQ ID NO: 13, which has glucoamylase activity.

The fermenting organisms may be a host cell that expresses heterologous polynucleotides encoding enzymes other than the glucoamylase of the present invention, or that expresses such enzymes in addition to the glucoamylase of the present invention.

In some embodiments, the host cells and/or fermenting organisms comprise one or more heterologous polynucleotides encoding an alpha-amylase, glucoamylase, protease, GAPN (Non-phosphorylating NADP-dependent glyceraldehyde-3-phosphate dehydrogenases), phospholipase, trehalase, arabinase, xylosidase, catalase, and/or pullulanase. Examples of alpha-amylase, glucoamylase, protease, GAPN (Non-phosphorylating NADP-dependent glyceraldehyde-3-phosphate dehydrogenases), phospholipase, trehalase, arabinase, xylosidase, catalase, and/or pullulanase suitable for expression in the host cells and/or fermenting organisms are described in more detail herein. Thus, the present invention contemplates compositions (e.g., fermenting mash compositions) which comprise a recombinant host cell and/or fermenting organism comprising: (i) one or more heterologous polynucleotides encoding an alpha-amylase, glucoamylase, protease, GAPN (Non-phosphorylating NADP-dependent glyceraldehyde-3-phosphate dehydrogenases), phospholipase, trehalase, arabinase, xylosidase, catalase, and/or pullulanase, and (ii) at least one glucoamylase variant(s) of the present invention.

The host cells and fermenting organisms described herein may utilize expression vectors comprising the coding sequence of one or more (e.g., two, several) heterologous genes linked to one or more control sequences that direct expression in a suitable cell under conditions compatible with the control sequence(s). Such expression vectors may be used in any of the cells and methods described herein. The polynucleotides described herein may be manipulated in a variety of ways to provide for expression of a desired polypeptide. Manipulation of the polynucleotide prior to its insertion into a vector may be desirable or necessary depending on the expression vector. The techniques for modifying polynucleotides utilizing recombinant DNA methods are well known in the art.

A construct or vector (or multiple constructs or vectors) comprising the one or more (e.g., two, several) heterologous genes may be introduced into a cell so that the construct or vector is maintained as a chromosomal integrant or as a self-replicating extra-chromosomal vector as described earlier.

The various nucleotide and control sequences may be joined together to produce a recombinant expression vector that may include one or more (e.g., two, several) convenient restriction sites to allow for insertion or substitution of the polynucleotide at such sites. Alternatively, the polynucleotide(s) may be expressed by inserting the polynucleotide(s) or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the cell, or a transposon, may be used.

The expression vector may contain any suitable promoter sequence that is recognized by a cell for expression of a gene described herein. The promoter sequence contains transcriptional control sequences that mediate the expression of the polypeptide. The promoter may be any polynucleotide that shows transcriptional activity in the cell of choice including mutant, truncated, and hybrid promoters, and may be obtained from genes encoding extracellular or intracellular polypeptides either homologous or heterologous to the cell.

Each heterologous polynucleotide described herein may be operably linked to a promoter that is foreign to the polynucleotide. For example, in one embodiment, the nucleic acid construct encoding the fusion protein is operably linked to a promoter foreign to the polynucleotide. The promoters may be identical to or share a high degree of sequence identity (e.g., at least about 80%, at least about 85%, at least about 90%, at least about 95%, at least about 96%, at least about 97%, at least about 98%, or at least about 99%) with a selected native promoter.

Examples of suitable promoters for directing the transcription of the nucleic acid constructs in a yeast cells, include, but are not limited to, the promoters obtained from the genes for enolase, (e.g., *S. cerevisiae* enolase or *I. orientalis* enolase (ENO1)), galactokinase (e.g., *S. cerevisiae* galactokinase or *I. orientalis* galactokinase (GAL1)), alcohol dehydrogenase/glyceraldehyde-3-phosphate dehydrogenase (e.g., *S. cerevisiae* alcohol dehydrogenase/glyceraldehyde-3-phosphate dehydrogenase or *I. orientalis* alcohol dehydrogenase/glyceraldehyde-3-phosphate dehydrogenase (ADH1, ADH2/GAP)), triose phosphate isomerase (e.g., *S. cerevisiae* triose phosphate isomerase or *I. orientalis* triose phosphate isomerase (TPI)), metallothionein (e.g., *S. cerevisiae* metallothionein or *I. orientalis* metallothionein (CUP1)), 3-phosphoglycerate kinase (e.g., *S. cerevisiae* 3-phosphoglycerate kinase or *I. orientalis* 3-phosphoglycerate kinase (PGK)), PDC1, xylose reductase (XR), xylitol dehydrogenase (XDH), L-(+)-lactate-cytochrome c oxidoreductase (CYB2), translation elongation factor-1 (TEF1), translation elongation factor-2 (TEF2), glyceraldehyde-3-phosphate dehydrogenase (GAPDH), and orotidine 5'-phosphate decarboxylase (URA3) genes. Other suitable promoters may be obtained from *S. cerevisiae*

TDH3, HXT7, PGK1, RPL18B and CCW12 genes. Additional useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the yeast cell of choice may be used. The terminator may be identical to or share a high degree of sequence identity (e.g., at least about 80%, at least about 85%, at least about 90%, at least about 95%, at least about 96%, at least about 97%, at least about 98%, or at least about 99%) with the selected native terminator.

Suitable terminators for yeast host cells may be obtained from the genes for enolase (e.g., *S. cerevisiae* or *I. orientalis* enolase cytochrome C (e.g., *S. cerevisiae* or *I. orientalis* cytochrome (CYC1)), glyceraldehyde-3-phosphate dehydrogenase (e.g., *S. cerevisiae* or *I. orientalis* glyceraldehyde-3-phosphate dehydrogenase (gpd)), PDC1, XR, XDH, transaldolase (TAL), transketolase (TKL), ribose 5-phosphate ketol-isomerase (RKI), CYB2, and the galactose family of genes (especially the GAL10 terminator). Other suitable terminators may be obtained from *S. cerevisiae* ENO2 or TEF1 genes. Additional useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a suitable leader sequence, when transcribed is a non-translated region of an mRNA that is important for translation by the host cell. The leader sequence is operably linked to the 5'-terminus of the polynucleotide encoding the polypeptide. Any leader sequence that is functional in the yeast cell of choice may be used.

Suitable leaders for yeast host cells are obtained from the genes for enolase (e.g., *S. cerevisiae* or *I. orientalis* enolase (ENO-1)), 3-phosphoglycerate kinase (e.g., *S. cerevisiae* or *I. orientalis* 3-phosphoglycerate kinase), alpha-factor (e.g., *S. cerevisiae* or *I. orientalis* alpha-factor), and alcohol dehydrogenase/glyceraldehyde-3-phosphate dehydrogenase (e.g., *S. cerevisiae* or *I. orientalis* alcohol dehydrogenase/glyceraldehyde-3-phosphate dehydrogenase (ADH2/GAP)).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used. Useful polyadenylation sequences for yeast cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used. Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used.

The vectors may contain one or more (e.g., two, several) selectable markers that permit easy selection of transformed, transfected, transduced, or the like cells. A selectable marker is a gene the product of which provides for biocide or viral resistance, resistance to heavy metals, prototrophy to auxotrophs, and the like. Suitable markers for yeast host cells include, but are not limited to, ADE2, HIS3, LEU2, LYS2, MET3, TRP1, and URA3.

The vectors may contain one or more (e.g., two, several) elements that permit integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination. Potential integration loci include those described in the art (e.g., See US2012/0135481).

For autonomous replication, the vector may further comprise an origin of replication enabling the vector to replicate autonomously in the yeast cell. The origin of replication may be any plasmid replicator mediating autonomous replication that functions in a cell. The term "origin of replication" or "plasmid replicator" means a polynucleotide that enables a plasmid or vector to replicate in vivo. Examples of origins of replication for use in a yeast host cell are the 2 micron origin of replication, ARS1, ARS4, the combination of ARS1 and CEN3, and the combination of ARS4 and CEN6.

More than one copy of a polynucleotide described herein may be inserted into a host cell to increase production of a polypeptide. An increase in the copy number of the polynucleotide can be obtained by integrating at least one additional copy of the sequence into the yeast cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors described herein are well known to one skilled in the art (see, e.g., Sambrook et al., 1989, *Molecular Cloning, A Laboratory Manual,* 2d edition, Cold Spring Harbor, New York).

Additional procedures and techniques known in the art for the preparation of recombinant cells for ethanol fermentation, are described in, e.g., WO 2016/045569, the content of which is hereby incorporated by reference.

The host cell or fermenting organism may be in the form of a composition comprising a host cell or fermenting organism (e.g., a yeast strain described herein) and a naturally occurring and/or a non-naturally occurring component.

The host cell or fermenting organism described herein may be in any viable form, including crumbled, dry, including active dry and instant, compressed, cream (liquid) form etc. In one embodiment, the host cell or fermenting organism (e.g., a *Saccharomyces cerevisiae* yeast strain) is dry yeast, such as active dry yeast or instant yeast. In one embodiment, the host cell or fermenting organism (e.g., a *Saccharomyces cerevisiae* yeast strain) is crumbled yeast. In one embodiment, the host cell or fermenting organism (e.g., a *Saccharomyces cerevisiae* yeast strain) is compressed yeast. In one embodiment, the host cell or fermenting organism (e.g., a *Saccharomyces cerevisiae* yeast strain) is cream yeast.

In one embodiment is a composition comprising a host cell or fermenting organism described herein (e.g., a *Saccharomyces cerevisiae* yeast strain), and one or more of the component selected from the group consisting of: surfactants, emulsifiers, gums, swelling agent, and antioxidants and other processing aids.

The compositions described herein may comprise a host cell or fermenting organism described herein (e.g., a *Saccharomyces cerevisiae* yeast strain) and any suitable surfactants. In one embodiment, the surfactant(s) is/are an anionic surfactant, cationic surfactant, and/or nonionic surfactant.

The compositions described herein may comprise a host cell or fermenting organism described herein (e.g., a *Saccharomyces cerevisiae* yeast strain) and any suitable emulsifier. In one embodiment, the emulsifier is a fatty-acid ester of sorbitan. In one embodiment, the emulsifier is selected from the group of sorbitan monostearate (SMS), citric acid esters of monodiglycerides, polyglycerolester, fatty acid esters of propylene glycol.

In one embodiment, the composition comprises a host cell or fermenting organism described herein (e.g., a *Saccharomyces cerevisiae* yeast strain), and Olindronal SMS, Olindronal SK, or Olindronal SPL including composition concerned in European Patent No. 1,724,336 (hereby incorporated by reference). These products are commercially available from Bussetti, Austria, for active dry yeast.

The compositions described herein may comprise a host cell or fermenting organism described herein (e.g., a *Saccharomyces cerevisiae* yeast strain) and any suitable gum. In one embodiment, the gum is selected from the group of carob, guar, tragacanth, arabic, xanthan and acacia gum, in particular for cream, compressed and dry yeast.

The compositions described herein may comprise a host cell or fermenting organism described herein (e.g., a *Saccharomyces cerevisiae* yeast strain) and any suitable swelling agent. In one embodiment, the swelling agent is methyl cellulose or carboxymethyl cellulose.

The compositions described herein may comprise a host cell or fermenting organism described herein (e.g., a *Saccharomyces cerevisiae* yeast strain) and any suitable antioxidant. In one embodiment, the antioxidant is butylated hydroxyanisol (BHA) and/or butylated hydroxytoluene (BHT), or ascorbic acid (vitamin C), particular for active dry yeast.

The compositions described herein may comprise a host cell or fermenting organism described herein (e.g., a *Saccharomyces* yeast strain) and any suitable fermentation enzyme (e.g., alpha-amylase (e.g., a fungal alpha-amylase), glucoamylase, protease, and/or cellulase.

The compositions described herein may comprise a host cell or fermenting organism described herein (e.g., a *Saccharomyces* yeast strain) and at least a glucoamylase variant (s) of the present invention.

The compositions described herein may comprise a host cell or fermenting organism described herein (e.g., a *Saccharomyces* yeast strain), at least one a glucoamylase variant (s) of the present invention, and any suitable fermentation enzyme (e.g., alpha-amylase (e.g., a fungal alpha-amylase), glucoamylase, protease, and/or cellulase).

The host cells and fermenting organisms described herein may also comprise one or more (e.g., two, several) gene disruptions, e.g., to divert sugar metabolism from undesired products to ethanol. In some embodiments, the recombinant host cells produce a greater amount of ethanol compared to the cell without the one or more disruptions when cultivated under identical conditions. In some embodiments, one or more of the disrupted endogenous genes is inactivated.

In certain embodiments, the host cell or fermenting organism provided herein comprises a disruption of one or more endogenous genes encoding enzymes involved in producing alternate fermentative products such as glycerol or other byproducts such as acetate or diols. For example, the cells provided herein may comprise a disruption of one or more of glycerol 3-phosphate dehydrogenase (GPD, catalyzes reaction of dihydroxyacetone phosphate to glycerol 3-phosphate), glycerol 3-phosphatase (GPP, catalyzes conversion of glycerol-3 phosphate to glycerol), glycerol kinase (catalyzes conversion of glycerol 3-phosphate to glycerol), dihydroxyacetone kinase (catalyzes conversion of dihydroxyacetone phosphate to dihydroxyacetone), glycerol dehydrogenase (catalyzes conversion of dihydroxyacetone to glycerol), and aldehyde dehydrogenase (ALD, e.g., converts acetaldehyde to acetate).

Modeling analysis can be used to design gene disruptions that additionally optimize utilization of the pathway. One exemplary computational method for identifying and designing metabolic alterations favoring biosynthesis of a desired product is the OptKnock computational framework, Burgard et al., 2003, *Biotechnol. Bioeng.* 84: 647-657.

The host cells and fermenting organisms comprising a gene disruption may be constructed using methods well known in the art, including those methods described herein. A portion of the gene can be disrupted such as the coding region or a control sequence required for expression of the coding region. Such a control sequence of the gene may be a promoter sequence or a functional part thereof, i.e., a part that is sufficient for affecting expression of the gene. For example, a promoter sequence may be inactivated resulting in no expression or a weaker promoter may be substituted for the native promoter sequence to reduce expression of the coding sequence. Other control sequences for possible modification include, but are not limited to, a leader, propeptide sequence, signal sequence, transcription terminator, and transcriptional activator.

The host cells and fermenting organisms comprising a gene disruption may be constructed by gene deletion techniques to eliminate or reduce expression of the gene. Gene deletion techniques enable the partial or complete removal of the gene thereby eliminating their expression. In such methods, deletion of the gene is accomplished by homologous recombination using a plasmid that has been constructed to contiguously contain the 5' and 3' regions flanking the gene.

The host cells and fermenting organisms comprising a gene disruption may also be constructed by introducing, substituting, and/or removing one or more (e.g., two, several) nucleotides in the gene or a control sequence thereof required for the transcription or translation thereof. For example, nucleotides may be inserted or removed for the introduction of a stop codon, the removal of the start codon, or a frame-shift of the open reading frame. Such a modification may be accomplished by site-directed mutagenesis or PCR generated mutagenesis in accordance with methods known in the art. See, for example, Botstein and Shortle, 1985, *Science* 229: 4719; Lo et al., 1985, *Proc. Natl. Acad. Sci. U.S.A.* 81: 2285; Higuchi et al., 1988, *Nucleic Acids Res* 16: 7351; Shimada, 1996, *Meth. Mol. Biol.* 57: 157; Ho et al., 1989, *Gene* 77: 61; Horton et al., 1989, *Gene* 77: 61; and Sarkar and Sommer, 1990, *BioTechniques* 8: 404.

The host cells and fermenting organisms comprising a gene disruption may also be constructed by inserting into the gene a disruptive nucleic acid construct comprising a nucleic acid fragment homologous to the gene that will create a duplication of the region of homology and incorporate construct DNA between the duplicated regions. Such a gene disruption can eliminate gene expression if the inserted construct separates the promoter of the gene from the coding region or interrupts the coding sequence such that a non-functional gene product results. A disrupting construct may be simply a selectable marker gene accompanied by 5' and 3' regions homologous to the gene. The selectable marker enables identification of transformants containing the disrupted gene.

The host cells and fermenting organisms comprising a gene disruption may also be constructed by the process of gene conversion (see, for example, Iglesias and Trautner, 1983, *Molecular General Genetics* 189: 73-76). For example, in the gene conversion method, a nucleotide sequence corresponding to the gene is mutagenized in vitro to produce a defective nucleotide sequence, which is then transformed into the recombinant strain to produce a defective gene. By homologous recombination, the defective nucleotide sequence replaces the endogenous gene. It may be desirable that the defective nucleotide sequence also comprises a marker for selection of transformants containing the defective gene.

The host cells and fermenting organisms comprising a gene disruption may be further constructed by random or specific mutagenesis using methods well known in the art, including, but not limited to, chemical mutagenesis (see, for example, Hopwood, *The Isolation of Mutants in Methods in Microbiology* (J. R. Norris and D. W. Ribbons, eds.) pp. 363-433, Academic Press, New York, 1970). Modification of the gene may be performed by subjecting the parent strain to mutagenesis and screening for mutant strains in which expression of the gene has been reduced or inactivated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosogaunidine (NTG) O-methyl hydroxylamine, nitrous acid, ethyl methane sulphonate (EMS), sodium bisulphite, formic acid, and nucleotide analogues. When such agents are used, the mutagenesis is typically performed by incubating the parent strain to be mutagenized in the presence of the mutagenizing agent of choice under suitable conditions, and selecting for mutants exhibiting reduced or no expression of the gene.

A nucleotide sequence homologous or complementary to a gene described herein may be used from other microbial sources to disrupt the corresponding gene in a recombinant strain of choice.

In one embodiment, the modification of a gene in the recombinant cell is unmarked with a selectable marker. Removal of the selectable marker gene may be accomplished by culturing the mutants on a counter-selection medium. Where the selectable marker gene contains repeats flanking its 5' and 3' ends, the repeats will facilitate the looping out of the selectable marker gene by homologous recombination when the mutant strain is submitted to counter-selection. The selectable marker gene may also be removed by homologous recombination by introducing into the mutant strain a nucleic acid fragment comprising 5' and 3' regions of the defective gene, but lacking the selectable marker gene, followed by selecting on the counter-selection medium. By homologous recombination, the defective gene containing the selectable marker gene is replaced with the nucleic acid fragment lacking the selectable marker gene. Other methods known in the art may also be used.

Starch-Containing Material

Any suitable starch-containing material containing may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived there from, or cereals. Contemplated are also waxy and non-waxy types of corn and barley. In a preferred embodiment, the starch-containing material in a process for producing a fermentation product, wherein the fermentation product is ethanol, is corn or wheat.

Fermentation Products

The term "fermentation product" means a product produced by a process including a fermentation step using a fermenting organism. A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an (e.g., pentane, hexane, heptane, octane, nonane, decane, undecane, and dodecane), a cycloalkane (e.g., cyclopentane, cyclohexane, cycloheptane, and cyclooctane), an alkene (e.g., pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide.

In one embodiment, the fermentation product is an alcohol. The term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603. In one embodiment, the fermentation product is ethanol.

In another embodiment, the fermentation product is an alkane. The alkane may be an unbranched or a branched alkane. The alkane can be, but is not limited to, pentane, hexane, heptane, octane, nonane, decane, undecane, or dodecane. In another embodiment, the fermentation product is a cycloalkane. The cycloalkane can be, but is not limited to, cyclopentane, cyclohexane, cycloheptane, or cyclooctane. In another aspect, the fermentation product is an alkene. The alkene may be an unbranched or a branched alkene. The alkalkaneene can be, but is not limited to, pentene, hexene, heptene, or octene.

In another aspect, the fermentation product is an amino acid. The amino acid can be, but is not limited to, aspartic acid, glutamic acid, glycine, lysine, serine, or threonine. See, for example, Richard and Margaritis, 2004, *Biotechnology and Bioengineering* 87(4): 501-515.

In another embodiment, the fermentation product is a gas. The gas can be, but is not limited to, methane, $H_2$, $CO_2$, or CO. See, for example, Kataoka et al., 1997, *Water Science and Technology* 36(6-7): 41-47; and Gunaseelan, 1997, *Biomass and Bioenergy* 13(1-2): 83-114.

In another embodiment, the fermentation product is antibiotics (e.g., penicillin and tetracycline).

In another embodiment, the fermentation product is isoprene.

In another embodiment, the fermentation product is an enzyme.

In another embodiment, the fermentation product is a hormone.

In another embodiment, the fermentation product is a ketone. The term "ketone" encompasses a substance that contains one or more ketone moieties. The ketone can be, but is not limited to, acetone.

In another embodiment, the fermentation product is an organic acid. The organic acid can be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another embodiment, the fermentation product is polyketide.

In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferably processes of the invention are used for producing an alcohol, such as ethanol. The fermentation product, such as ethanol, obtained according to the invention, may be used as fuel, which is typically blended with gasoline. However, in the case of ethanol it may also be used as potable ethanol.

Recovery

The fermentation product, e.g., ethanol, can optionally be recovered from the fermentation medium using any method known in the art including, but not limited to, chromatography, electrophoretic procedures, differential solubility, distillation, or extraction. For example, alcohol is separated from the fermented cellulosic material or fermented starch-containing material and purified by conventional methods of distillation. As another example, the desired fermentation product may be extracted from the fermentation medium by micro or membrane filtration techniques. Ethanol with a purity of up to about 96 vol. % can be obtained, which can be used as, for example, fuel ethanol, drinking ethanol, i.e., potable neutral spirits, or industrial ethanol.

In some embodiments of the methods, the fermentation product after being recovered is substantially pure. With respect to the methods herein, "substantially pure" intends a recovered preparation that contains no more than 15% impurity, wherein impurity intends compounds other than the fermentation product (e.g., ethanol). In one variation, a substantially pure preparation is provided wherein the preparation contains no more than 25% impurity, or no more than 20% impurity, or no more than 10% impurity, or no more than 5% impurity, or no more than 3% impurity, or no more than 1% impurity, or no more than 0.5% impurity.

Suitable assays to test for the production of ethanol and contaminants, and sugar consumption can be performed using methods known in the art. For example, ethanol product, as well as other organic compounds, can be analyzed by methods such as HPLC (High Performance Liquid Chromatography), GC-MS (Gas Chromatography Mass Spectroscopy) and LC-MS (Liquid Chromatography-Mass Spectroscopy) or other suitable analytical methods using routine procedures well known in the art. The release of ethanol in the fermentation broth can also be tested with the culture supernatant. Byproducts and residual sugar in the fermentation medium (e.g., glucose or xylose) can be quantified by HPLC using, for example, a refractive index detector for glucose and alcohols, and a UV detector for organic acids (Lin et al., *Biotechnol. Bioeng.* 90:775-779 (2005)), or using other suitable assay and detection methods well known in the art.

Alpha-Amylase Present and/or Added During Liquefaction

According to the invention an alpha-amylase is present and/or added during liquefaction together with at least one glucoamylase variant of the present invention and optionally a thermostable protease, thermostable pullulanase, thermostable phytase, thermostable lipase, thermostable xylanase and/or thermostable endoglucanase.

The alpha-amylase added during liquefaction step i) may be any alpha-amylase. Preferred are bacterial alpha-amylases, which typically are stable at temperature used during liquefaction.

Any alpha-amylase herein contemplated as being present and/or added during liquefaction is also contemplated for expression by a fermenting organism or host cell.

The term "bacterial alpha-amylase" means any bacterial alpha-amylase classified under EC 3.2.1.1. A bacterial alpha-amylase used according to the invention may, e.g., be derived from a strain of the genus *Bacillus*, which is sometimes also referred to as the genus *Geobacillus*. In an embodiment the *Bacillus* alpha-amylase is derived from a strain of *Bacillus amyloliquefaciens, Bacillus licheniformis, Bacillus stearothermophilus*, or *Bacillus subtilis*, but may also be derived from other *Bacillus* sp.

Specific examples of bacterial alpha-amylases include the *Bacillus stearothermophilus* alpha-amylase of SEQ ID NO: 3 in WO 99/19467, the *Bacillus amyloliquefaciens* alpha-amylase of SEQ ID NO: 5 in WO 99/19467, and the *Bacillus licheniformis* alpha-amylase of SEQ ID NO: 4 in WO 99/19467 (all sequences are hereby incorporated by reference). In an embodiment the alpha-amylase may be an enzyme having a degree of identity of at least 60%, e.g., at least 70%, at least 80%, at least 90%, at least 95%, at least 96%, at least 97%, at least 98% or at least 99% identity to any of the sequences shown in SEQ ID NOS: 3, 4 or 5, respectively, in WO 99/19467.

In an embodiment the alpha-amylase may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99% identity to any of the sequences shown in SEQ ID NO: 3 in WO 99/19467 or SEQ ID NO: 20 herein.

In a preferred embodiment the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases may naturally be truncated during recombinant production. For instance, the *Bacillus stearothermophilus* alpha-amylase may be a truncated so it has around 491 amino acids compared to SEQ ID NO: 3 in WO 99/19467.

The *Bacillus* alpha-amylase may also be a variant and/or hybrid. Examples of such a variant can be found in any of WO 96/23873, WO 96/23874, WO 97/41213, WO 99/19467, WO 00/60059, and WO 02/10355 (all documents are hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at positions R179, G180, 1181 and/or G182, preferably a double deletion disclosed in WO 96/23873—see, e.g., page 20, lines 1-10 (hereby incorporated by reference), preferably corresponding to deletion of positions I181 and G182 compared to the amino acid sequence of *Bacillus stearothermophilus* alpha-amylase set forth in SEQ ID NO: 3 disclosed in WO 99/19467 or SEQ ID NO: 20 herein or the deletion of amino acids R179 and G180 using SEQ ID NO: 3 in WO 99/19467 or SEQ ID NO: 20 herein for numbering (which reference is hereby incorporated by reference). Even more preferred are *Bacillus* alpha-amylases, especially *Bacillus stearothermophilus* alpha-amylases, which have a double deletion corresponding to a deletion of positions 181 and 182 and further comprise a N193F substitution (also denoted I181*+G182*+N193F) compared to the wild-type BSG alpha-amylase amino acid sequence set forth in SEQ ID NO: 3 disclosed in WO 99/19467 or SEQ ID NO: 20 herein. The bacterial alpha-amylase may also have a substitution in a position corresponding to S239 in the *Bacillus licheniformis* alpha-amylase shown in SEQ ID NO: 4 in WO 99/19467, or a S242 variant of the *Bacillus stearothermophilus* alpha-amylase of SEQ ID NO: 3 in WO 99/19467 or SEQ ID NO: 30 herein.

In an embodiment the variant is a S242A, E or Q variant, preferably a S242Q variant, of the *Bacillus stearothermophilus* alpha-amylase (using SEQ ID NO: 20 herein for numbering).

In an embodiment, the variant is a position E188 variant, preferably E188P variant of the *Bacillus stearothermophilus* alpha-amylase (using SEQ ID NO: 20 herein for numbering).

The bacterial alpha-amylase may in an embodiment be a truncated alpha-amylase. Especially the truncation is so that the *Bacillus stearothermophilus* alpha-amylase shown in SEQ ID NO: 3 in WO 99/19467 or SEQ ID NO: 20 herein, is around 491 amino acids long, such as from 480 to 495 amino acids long.

Most importantly, a suitable alpha-amylase for use in liquefaction must have sufficient therm-stability, and thus accordingly any alpha-amylase having a T % (min) at pH 4.5, 85° C., 0.12 mM $CaCl_2$) of at least 10, such as at least 15, such as at least 20, such as at least 25, such as at least 30, such as at least 40, such as at least 50, such as at least 60, such as between $10^{-70}$, such as between 15-70, such as between 20-70, such as between 25-70, such as between 30-70, such as between 40-70, such as between 50-70, such as between 60-70, may be used.

According to the invention the alpha-amylase may be a thermostable alpha-amylase, such as a thermostable bacterial alpha-amylase, preferably from *Bacillus stearothermophilus*. In an embodiment the alpha-amylase used according to the invention has a T % (min) at pH 4.5, 85° C., 0.12 mM $CaCl_2$ of at least 10.

In an embodiment the thermostable alpha-amylase has a T % (min) at pH 4.5, 85° C., 0.12 mM $CaCl_2$, of at least 15.

In an embodiment the thermostable alpha-amylase has a T % (min) at pH 4.5, 85° C., 0.12 mM $CaCl_2$, of as at least 20.

In an embodiment the thermostable alpha-amylase has a T % (min) at pH 4.5, 85° C., 0.12 mM $CaCl_2$, of as at least 25.

In an embodiment the thermostable alpha-amylase has a T % (min) at pH 4.5, 85° C., 0.12 mM $CaCl_2$, of as at least 30.

In an embodiment the thermostable alpha-amylase has a T % (min) at pH 4.5, 85° C., 0.12 mM $CaCl_2$, of as at least 40.

In an embodiment the thermostable alpha-amylase has a T % (min) at pH 4.5, 85° C., 0.12 mM $CaCl_2$, of at least 50.

In an embodiment the thermostable alpha-amylase has a T % (min) at pH 4.5, 85° C., 0.12 mM $CaCl_2$, of at least 60.

In an embodiment the thermostable alpha-amylase has a T % (min) at pH 4.5, 85° C., 0.12 mM $CaCl_2$, between 10-70.

In an embodiment the thermostable alpha-amylase has a T % (min) at pH 4.5, 85° C., 0.12 mM $CaCl_2$, between 15-70.

In an embodiment the thermostable alpha-amylase has a T % (min) at pH 4.5, 85° C., 0.12 mM $CaCl_2$, between 20-70.

In an embodiment the thermostable alpha-amylase has a T % (min) at pH 4.5, 85° C., 0.12 mM $CaCl_2$, between 25-70.

In an embodiment the thermostable alpha-amylase has a T % (min) at pH 4.5, 85° C., 0.12 mM $CaCl_2$, between 30-70.

In an embodiment the thermostable alpha-amylase has a T % (min) at pH 4.5, 85° C., 0.12 mM $CaCl_2$, between 40-70.

In an embodiment the thermostable alpha-amylase has a T % (min) at pH 4.5, 85° C., 0.12 mM $CaCl_2$, between 50-70.

In an embodiment the thermostable alpha-amylase has a T % (min) at pH 4.5, 85° C., 0.12 mM $CaCl_2$, between 60-70.

In an embodiment of the invention the alpha-amylase is an bacterial alpha-amylase, preferably derived from the genus *Bacillus*, especially a strain of *Bacillus stearothermophilus*, in particular the *Bacillus stearothermophilus* as disclosed in WO 99/019467 as SEQ ID NO: 3 (SEQ ID NO: 20 herein) with one or two amino acids deleted at positions R179, G180, 1181 and/or G182, in particular with R179 and G180 deleted, or with I181 and G182 deleted, with mutations in below list of mutations.

In preferred embodiments, the *Bacillus stearothermophilus* alpha-amylases have double deletion I181+G182, and optional substitution N193F, further comprising mutations selected from below list.

In a preferred embodiment, the alpha-amylase is selected from the following group of *Bacillus stearothermophilus* alpha-amylase variants (using SEQ ID NO: 20 for numbering):

- I181*+G182*+N193F+E129V+$K_{177}$L+R179E;
- I181*+G182*+N193F+E129V+$K_{177}$L+R179S;
- I181*+G182*+N193F+V59A+Q89R+E129V+$K_{177}$L+R179E+H208Y+K220P+N224L+Q254S;
- I181*+G182*+N193F+V59A+Q89R+E129V+K177L+R179E+Q254S+M284V;
- I181*+G182*+N193F+V59A+Q89R+E129V+K177L+R179S+Q254S+M284V;
- I181*+G182*+N193F+V59A+E129V+K177L+R179E+Q254S+M284V;
- I181*+G182*+N193F+V59A+E129V+K177L+R179S+Q254S+M284V;
- I181*+G182*+N193F+E129V+K177L+R179E+K220P+N224L+S242Q+Q254S;
- I181*+G182*+N193F+E129V+K177L+R179S+K220P+N224L+S242Q+Q254S;
- I181*+G182*+V59A+E129V+K177L+R179E+Q254S+M284V+V212T+Y268G+N293Y+T297N;
- I181*+G182*+V59A+E129V+K177L+R179E+Q254S+M284V+V212T+Y268G+N293Y+T297N+S173N+E188P+H208Y+S242Y+K2791;
- I181*+G182*+V59A+E129V+K177L+R179S+Q254S+M284V+V212T+Y268G+N293Y+T297N+A184Q+E188P+T191N
- I181*+G182*+V59A+E129V+K177L+R179S+Q254S+M284V+V212T+Y268G+N293Y+T297N+A184Q+E188P+T191N+S242Y+K2791;
- I181*+G182*+V59A+E129V+K177L+R179E+Q254S+M284V+V212T+Y268G+N293Y+T297N+E188P+K279W;
- I181*+G182*+V59A+E129V+K177L+R179E+Q254S+M284V+V212T+Y268G+N293Y+T297N+W115D+D117Q+T133P; and wherein the variant has at least 85%, at least 90%, at least 95%, at least 96%, at least 97%, at least 98%, or at least 99% sequence identity to SEQ ID NO: 20.

It should be understood, that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467 or SEQ ID NO: 20 herein, or variants thereof, are truncated in the C-terminal and are typically around 491 amino acids long, such as from 480-495 amino acids long.

In a preferred embodiment the alpha-amylase variant may be an enzyme having a degree of identity of at least 60%, e.g., at least 70%, at least 80%, at least 90%, at least 95%, at least 91%, at least 92%, at least 93%, at least 94%, at least 95%, at least 96%, at least 97%, at least 98% or at least 99%, but less than 100% to the sequence shown in SEQ ID NO: 3 in WO 99/19467 or SEQ ID NO: 20 herein.

In a preferred embodiment the alpha-amylase variant may be an enzyme having a degree of identity of at least 60%, e.g., at least 70%, at least 80%, at least 90%, at least 95%, at least 91%, at least 92%, at least 93%, at least 94%, at least 95%, at least 96%, at least 97%, at least 98% or at least 99%, but less than 100% to the SEQ ID NO: 2 of WO 09/061380 or SEQ ID NO: 37 herein.

In a preferred embodiment the alpha-amylase variant may be an enzyme having a degree of identity of at least 60%, e.g., at least 70%, at least 80%, at least 90%, at least 95%, at least 91%, at least 92%, at least 93%, at least 94%, at least 95%, at least 96%, at least 97%, at least 98% or at least 99%, but less than 100% to the SEQ ID NO: 2 of WO 08/153815) or SEQ ID NO: 38 herein.

In a preferred embodiment the alpha-amylase variant may be an enzyme having a degree of identity of at least 60%, e.g., at least 70%, at least 80%, at least 90%, at least 95%, at least 91%, at least 92%, at least 93%, at least 94%, at least 95%, at least 96%, at least 97%, at least 98% or at least 99%, but less than 100% to the SEQ ID NO: 2 of WO 08/153815) or SEQ ID NO: 39 herein.

Protease Present and/or Added During Liquefaction

According to the invention a thermostable protease is optionally present and/or added during liquefaction together with at least one glucoamylase variant of the present invention and optionally a thermostable pullulanase, thermostable phytase, thermostable lipase, thermostable xylanase and/or thermostable endoglucanase.

Any protease herein contemplated as being present and/or added during liquefaction is also contemplated for expression by a fermenting organism or host cell.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J.

Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the protease activity of the Protease 196 variant or Protease Pfu determined by the AZCL-casein assay described in the "Materials & Methods" section.

There are no limitations on the origin of the protease used in a process of the invention as long as it fulfills the thermostability properties defined below.

In one embodiment the protease is of fungal origin.

The protease may be a variant of, e.g., a wild-type protease as long as the protease has the thermostability properties defined herein.

In a particular embodiment the thermostable protease is a variant of a metallo protease as defined above. In an embodiment the thermostable protease used in a process of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 21 herein further with mutations selected from below list:

S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L;
D79L+S87P+D142L.

In a preferred embodiment the thermostable protease is a variant of the metalloprotease disclosed as the mature part of SEQ ID NO: 2 disclosed in WO 2003/048353 or the mature part of SEQ ID NO: 1 in WO 2010/008841 or SEQ ID NO: 21 herein with the following mutations:

D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 21 herein.

The thermostable protease may also be derived from any bacterium as long as the protease has the thermostability properties defined according to the invention. In one embodiment the protease is a serine protease, particularly a S8 protease. Preferred proteases are, serine proteases, particularly an S8 serine protease derived from a strain of *Pyrococcus*, preferably a strain of *Pyrococcus furiosus*, or derived from a strain of *Thermococcus*, preferably Themococcus *thioreducens*, or derived from a strain of *Palaeococcus*, preferably *Palaeococcus ferrophilus*.

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-B1 (Takara Shuzo Company), SEQ ID NO: 22 herein.

In another embodiment the thermostable protease is one disclosed in SEQ ID NO: 22 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 22 herein.

The *Pyrococcus furiosus* protease is a thermostable protease according to the invention. The *Pyrococcus furiosus* protease (PfuS) was found to have a thermostability of 110% (80° C./70° C.) and 103% (90° C./70° C.) at pH 4.5.

In an embodiment the thermostable protease is derived from a strain of the bacterium *Palaeococcus*, such as a strain of *Palaeococcus ferrophilus*. In an embodiment the protease is the one shown as SEQ ID NO: 23 herein. In another embodiment the thermostable protease is one disclosed in SEQ ID NO: 23 herein or a protease having at least 80% identity, such as at least 85%, such as at least 90%, such as at least 95%, such as at least 96%, such as at least 97%, such as at least 98%, such as at least 99% identity to SEQ ID NO: 23.

In one embodiment a thermostable protease used in a process of the invention has a thermostability value of more than 20% determined as Relative Activity at 80° C./70° C.

In an embodiment the protease has a thermostability of more than 30%, more than 40%, more than 50%, more than 60%, more than 70%, more than 80%, more than 90%, more than 100%, such as more than $10^5$%, such as more than 110%, such as more than 115%, such as more than 120% determined as Relative Activity at 80° C./70° C.

In an embodiment protease has a thermostability of between 20 and 50%, such as between 20 and 40%, such as 20 and 30% determined as Relative Activity at 80° C./70° C.

In an embodiment the protease has a thermostability between 50 and 115%, such as between 50 and 70%, such as between 50 and 60%, such as between 100 and 120%, such as between $10^5$ and 115% determined as Relative Activity at 80° C./70° C.

In an embodiment the protease has a thermostability value of more than 10% determined as Relative Activity at 85° C./70° C.

In an embodiment the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

In an embodiment the protease has a thermostability of between 10 and 50%, such as between 10 and 30%, such as between 10 and 25% determined as Relative Activity at 85° C./70° C.

In an embodiment the protease has more than 20%, more than 30%, more than 40%, more than 50%, more than 60%, more than 70%, more than 80%, more than 90% determined as Remaining Activity at 80° C.; and/or In an embodiment the protease has more than 20%, more than 30%, more than 40%, more than 50%, more than 60%, more than 70%, more than 80%, more than 90% determined as Remaining Activity at 84° C.

In an embodiment the protease may have a thermostability for above 90, such as above 100 at 85° C. as determined using the Zein-BCA assay.

In an embodiment the protease has a thermostability above 60%, such as above 90%, such as above 100%, such as above 110% at 85° C. as determined using the Zein-BCA assay.

In an embodiment protease has a thermostability between 60-120, such as between 70-120%, such as between 80-120%, such as between 90-120%, such as between 100-120%, such as 110-120% at 85° C. as determined using the Zein-BCA assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the activity of the JTP196 protease variant or Protease Pfu determined by the AZCL-casein assay.

In an embodiment the protease is derived from a strain of Thermobifida, such as the *Thermobifida* cellulosytica protease shown in SEQ ID NO: 33 herein, or one having at least 60%, such as at least 70%, such as at least 75% identity, at least 76% identity, at least 77% identity, at least 78% identity, at least 79% identity, preferably at least 80%, at least 81% identity, at least 82% identity, at least 83% identity, at least 84% identity, more preferably at least 85% identity, at least 86% identity, at least 87% identity, at least 88% identity, at least 89% identity, more preferably at least 90% identity, more preferably at least 91% identity, more preferably at least 92% identity, at least 93% identity, at least 94% identity, or at least 95% identity, such as at least 96% identity, at least 97% identity, at least 98% identity, at least 99% identity to the amino acid sequence of SEQ ID NO: 33.

In an embodiment the protease is derived from a strain of *Thermobifida*, such as the *Thermobifida fusca* protease shown in SEQ ID NO: 34 herein (referred to as SEQ ID NO: 8 in WO2018/118815 A1, which is incorporated herein by reference in its entirety), or one having at least 60%, such as at least 70%, such as at least 75% identity, at least 76% identity, at least 77% identity, at least 78% identity, at least 79% identity, preferably at least 80%, at least 81% identity, at least 82% identity, at least 83% identity, at least 84% identity, more preferably at least 85% identity, at least 86% identity, at least 87% identity, at least 88% identity, at least 89% identity, more preferably at least 90% identity, more preferably at least 91% identity, more preferably at least 92% identity, at least 93% identity, at least 94% identity, or at least 95% identity, such as at least 96% identity, at least 97% identity, at least 98% identity, at least 99% identity to the amino acid sequence of SEQ ID NO: 34.

In an embodiment the protease is derived from a strain of *Thermobifida*, such as the *Thermobifida halotolerans* protease shown in SEQ ID NO: 35 herein (referred to as SEQ ID NO: 10 in WO2018/118815 A1, which is incorporated herein by reference in its entirety), or one having at least 60%, such as at least 70%, such as at least 75% identity, at least 76% identity, at least 77% identity, at least 78% identity, at least 79% identity, preferably at least 80%, at least 81% identity, at least 82% identity, at least 83% identity, at least 84% identity, more preferably at least 85% identity, at least 86% identity, at least 87% identity, at least 88% identity, at least 89% identity, more preferably at least 90% identity, more preferably at least 91% identity, more preferably at least 92% identity, at least 93% identity, at least 94% identity, or at least 95% identity, such as at least 96% identity, at least 97% identity, at least 98% identity, at least 99% identity to the amino acid sequence of SEQ ID NO: 35.

In an embodiment the protease is derived from a strain of *Thermococcus*, such as the *Thermococcus* nautili protease shown in SEQ ID NO: 36 herein (referred to as SEQ ID NO: 3 in WO2018/169780A1, which is incorporated herein by reference in its entirety), or one having at least 60%, such as at least 70%, such as at least 75% identity, at least 76% identity, at least 77% identity, at least 78% identity, at least 79% identity, preferably at least 80%, at least 81% identity, at least 82% identity, at least 83% identity, at least 84% identity, more preferably at least 85% identity, at least 86% identity, at least 87% identity, at least 88% identity, at least 89% identity, more preferably at least 90% identity, more preferably at least 91% identity, more preferably at least 92% identity, at least 93% identity, at least 94% identity, or at least 95% identity, such as at least 96% identity, at least 97% identity, at least 98% identity, at least 99% identity to the amino acid sequence of SEQ ID NO: 36.

Carbohydrate-Source Generating Enzyme Present and/or Added During Liquefaction

According to the invention a carbohydrate-source generating enzyme, in particular a glucoamylase, preferably a thermostable glucoamylase variant of the invention, may be present and/or added during liquefaction together with an alpha-amylase optionally with a thermostable protease, thermostable pullulanase, thermostable phytase, thermostable lipase, thermostable xylanase and/or thermostable endoglucanase.

Any carbohydrate-source generating enzymes (e.g., glucoamylase) herein contemplated as being present and/or added during liquefaction is also contemplated for expression by a fermenting organism or host cell.

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used. Specific examples include glucoamylase (being glucose generators), beta-amylase and maltogenic amylase (being maltose generators).

In a preferred embodiment the carbohydrate-source generating enzyme is thermostable. The carbohydrate-source generating enzyme, in particular thermostable glucoamylase, may be added together with or separately from the alpha-amylase and the thermostable protease.

In an embodiment, the carbohydrate-source generating enzyme is a thermostable glucoamylase, preferably of fungal origin, preferably a filamentous fungi, such as from a strain of the genus *Penicillium*, especially a strain of *Penicillium oxalicum*, in particular the *Penicillium oxalicum* glucoamylase disclosed as SEQ ID NO: 2 in PCT/CN10/071753 published as WO 2011/127802 (which is hereby incorporated by reference) and shown in SEQ ID NO: 24 herein.

In an embodiment, the thermostable glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 24 herein.

In an embodiment, the carbohydrate-source generating enzyme is a variant of the *Penicillium oxalicum* glucoamylase disclosed as SEQ ID NO: 2 in WO 2011/127802 and SEQ ID NO: 24 herein, having a K79V substitution (using the mature sequence shown in SEQ ID NO: 34 for numbering).

In an embodiment the carbohydrate-source generating enzyme, in particular thermostable glucoamylase, is derived from *Penicillium oxalicum.*

In an embodiment the thermostable glucoamylase is a variant of the *Penicillium oxalicum* glucoamylase disclosed as SEQ ID NO: 2 in WO 2011/127802 and shown in SEQ ID NO: 24 herein. In a preferred embodiment the *Penicillium oxalicum* glucoamylase is the one disclosed as SEQ ID NO: 2 in WO 2011/127802 and shown in SEQ ID NO: 24 herein having Val (V) in position 79 (using SEQ ID NO: 34 for numbering).

In an embodiment these variants have reduced sensitivity to protease degradation.

In an embodiment these variants have improved thermostability compared to the parent.

In an embodiment the glucoamylase has a K79V substitution (using SEQ ID NO: 24 for numbering), corresponding to the PE001 variant, and further comprises at least one of the following substitutions or combination of substitutions:

P11F+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
P2N+P4S+P11F+T65A+Q327F+E501V+Y504T; or
P11F+T65A+Q327W+E501V+Y504T.

In an embodiment, the glucoamylase has a P2N+P4S+P11F+T65A+K79V+Q327F substitution (using SEQ ID NO: 24 for numbering) and further comprises at least one of the following substitutions or combination of substitutions:

D75N+R77D+A78Q;
D75S+R77G+A78W+V79D+F80Y;
K34Y+S103N;
K34Y+D445N+V447S;
K34Y+Y504T;
S103N+D445N+V447S;
S103N+Y504T;
D445N+V447S+Y504T;
K34Y+S103N+D445N+V447S;
K34Y+S103N+D445N+V447S+E501V+Y504T;
K34Y+S103N+Y504T;
K34Y+S103N+D445N+V447S+D566T;
K34Y+S103N+Q594R+F595S;
K34Y+S103N+Y504T+Q594R+F595S;
K34Y+S103N+D445N+V447S+Y504T+Q594R+F595S;
S105L;
S105E;
A132R;
K34Y+S105L+Y504T+Q594R+F595S;
K34Y+S103N+S105L+Y504T+Q594R+F595S;
K34Y+S103N+S105L+Y504T+Q594R+F595S;
K34Y+S103N+S105L+Y504T D566T Q594R F595S;
K34Y+S103N+S105L+D445N+V447S+Y504T+D566T+Q594R+F595S;
K34Y+S103N+S105L+A132R+D445N+V447S+Y504T+D566T+Q594R+F595S;
K34Y+S103N+S105L+D445N+V447S+D566T+Q594R+F595S;
K34Y+S103N+S105L+A132R+D445N+V447S+E501V+Y504T+D566T+Q594R+F595S;
K34Y+S103N+A132R+D445N+V447S+Y504T+D566T+Q594R+F595S;
K34Y+S103N+S105L+A132R+D445N+V447S+Y504T+D566T+V592T;
G6S+G7T+K34Y+S103N+S105L+A132R+D445N+V447S+Y504T+D566T+Q594R+F595S;
K34Y+S103N+P107L+A132R+D445N+V447S+Y504T+D566T+Q594R+F595S;
G6S+G7T+K34Y+S103N+P107L+A132R+D445N+V447S+Y504T+D566T+Q594R+F595S;
G6S+G7T+K34Y+S103N+P107L+A132R+D445N+V447S+Y504T+D566T+V592T+Q594R+F595S;
G6S+G7T+K34Y+S103N+P107L+A132P+D445N+V447S+Y504T+D566T+Q594R+F595S;
G6S+G7T+K34Y+S103N+P107L+A132R+D445N+V447S+Y504T+D566T+T568V+Q594R+F595S;

G6S+G7T+K34Y+S103N+P107L+A132P+D445N+V447S+Y504T+D566T+T568V+Q594R+F595S;

G6S+G7T+K34Y+S103N+P107L+A132R+D445N+V447S+S481P+Y504T+D566T+Q594R+F595S;

G6S+G7T+K34Y+S103N+P107L+A132R+D445N+V447S+S481P+Y504T+D566T+T568V+Q594R+F595S;

G6S+G7T+K34Y+S103N+P107L+A132P+D445N+V447S+D566T+T568V+Q594R+F595S;

G6S+G7T+K34Y+S103N+P107L+T110W+A132P+D445N+V447S+Y504T+D566T+T568V+Q594R+F595S;

G6S+G7T+K34Y+E50R+S103N+P107L+A132P+D445N+V447S+Y504T+D566T+T568V+Q594R+F595S;

G6S+G7T+K34Y+S103N+P107L+A132P+D445N+V447S+E501V+Y504T; G6S+G7T+R31F+K34Y+S103N+P107L+A132P+D445N+V447S+Y504T+D566T+T568V+Q594R+F595S;

G6S+G7T+R31F+K34Y+S103N+P107L+A132P+D445N+V447S+S481P+Y504T+D566T+T568V+Q594R+F595S;

G6S+G7T+K34Y+E50R+S103N+P107L+A132P+D445N+V447S+S481P+Y504T+D566T+T568V+Q594R+F595S;

G6S+G7T+R31F+K34Y+S103N+P107L+A132P+D445N+V447S+S481P+E501V+Y504T+D566T+T568V+Q594R+F595S;

G6S+G7T+R31F+K34Y+S103N+P107L+A132P+D445N+V447S+S481P+D566T+T568V+Q594R+F595S; K34Y+D75N+R77D+A78Q+S103N+R138L+D445N+V447S+Y504T+Q594R+F595S;

G6S+G7T+R31F+K34Y+D75N+R77D+A78Q+S103N+P107L+A132P+D445N+V447S+S481P+Y504T+D566T+T568V+Q594R+F595S;

G6S+G7T+R31F+K34Y+S103N+A132P+D445N+V447S+S481P+D566T+T568V+Q594R+F595S;

G6S+G7T+K34Y+E50R+S103N+A132P+D445N+V447S+S481P+D566T+T568V+Q594R+F595S;

R31F+K34Y+D75N+R77D+A78Q+S103N+R138L+D445N+V447S+Y504T+Q594R+F595S;

K34Y+D75N+R77D+A78Q+S103N+R138L+D445N+V447S+Q594R+F595S;

G6S+G7T+R31F+K34Y+S103N+A132P+D445N+V447S;

G6S+G7T+R31F+K34Y+E50R+S103N+A132P+D445N+V447S+S481P+D566T+T568V+Q594R+F595S;

K34Y+E50R+D75N+R77D+A78Q+S103N+R138L+D445N+V447S+Q594R+F595S;

G6S+G7T+R31F+K34Y+E50R+D75N+R77D+A78Q+S103N+A132P+D445N+V447S+S481P+D566T+Q594R+F595S;

R31F+K34Y+E50R+D75N+R77D+A78Q+S103N+R138L+D445N+V447S+Q594R+F595S;

G6S+G7T+R31F+K34Y+E50R+D75N+R77D+A78Q+S103N+A132P+R138L+D445N+V447S+S481P+D566T+Q594R+F595S;

R135S;

G6S+G7T+R31F+K34Y+E50R+S103N+A132P+D445N+V447S+S481P+E501L+D566T+T568V+Q594R+F595S;

G6S+G7T+R31F+K34Y+S103N+A132P+R138G+D445N+V447S+S481P+D566T+T568V+Q594R+F595S;

G6S+G7T+R31F+K34Y+S103N+A132P+R138L+D445N+V447S+S481P+D566T+T568V+Q594R+F595S;

G6S+G7T+R31F+K34Y+S103N+A132P+R138P+D445N+V447S+S481P+D566T+T568V+Q594R+F595S;

G6S+G7T+R31F+K34Y+E50R+S103N+A132P+S379P+D445N+V447S+S481P+E501A+D566T+T568V+Q594R+F595S;

G6S+G7T+R31F+K34Y+E50R+S103N+A132P+D445N+V447S+S481P+T484P+E501A+D566T+T568V+Q594R+F595S;

G6S+G7T+R31F+K34Y+E50R+S103N+A132P+D445N+V447S+S481P+E501A+N539P+D566T+T568V+Q594R+F595S;

G6S+G7T+R31F+K34Y+E50R+S103N+A132P+S379P+D445N+V447S+S481P+T484P+E501A+D566T+T568V+Q594R+F595S;

G6S+G7T+R31F+K34Y+E50R+S103N+A132P+D445N+V447S+S481P+T484P+E501A+N539P+D566T+T568V+Q594R+F595S.

The carbohydrate-source generating enzyme, in particular, may be added in amounts from 0.1-100 micrograms EP/g, such as 0.5-50 micrograms EP/g, such as 1-25 micrograms EP/g, such as 2-12 micrograms EP/g DS.

Carbohydrate-Source Generating Enzyme Present and/or Added During Saccharification and/or Fermentation According to the invention a carbohydrate-source generating enzyme, preferably a glucoamylase, may be present and/or added during saccharification and/or fermentation.

In a preferred embodiment the carbohydrate-source generating enzyme is a glucoamylase, of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii*, or or a strain of *Trametes*, preferably *Trametes cingulata*, or a strain of Pycnoporus, or a strain of *Gloeophyllum*, such as a strain of *Gloeophyllum sepiarium* or *Gloeophyllum trabeum* or a strain of the *Nigrofomes*.

Any glucoamylase contemplated as being present and/or added during saccharification and/or fermentation is also contemplated for expression by a fermenting organism or host cell.

Glucoamylases

According to the invention, the glucoamylase variants of the present invention are present and/or added during saccharification and/or fermentation may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), *EMBO J.* 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (*Agric. Biol. Chem.* (1991), 55 (4), p. 941-949), or variants or fragments thereof. Other *Aspergillus* glucoamylase variants include variants with enhanced thermal stability: G137A and G139A (Chen et al. (1996), *Prot. Eng.* 9, 499-505); D257E and D293E/Q (Chen et al. (1995), *Prot. Eng.* 8, 575-582); N182 (Chen et al. (1994), *Biochem. J.* 301, 275-281); disulphide bonds, A246C (Fierobe et al. (1996), *Biochemistry,* 35, 8698-8704; and introduction of Pro residues in position A435 and S436 (Li et al. (1997), *Protein Eng.* 10, 1199-1204.

Other glucoamylases include *Athelia rolfsii*(previously denoted *Corticium rolfsii*) glucoamylase (see U.S. Pat. No. 4,727,026 and (Nagasaka et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (US patent no. Re. 32,153), *Talaromyces duponti, Talaromyces thermophilus* (U.S. Pat. No. 4,587,215). In a preferred embodiment the glucoamylase used during saccharification and/or fermentation is the *Talaromyces emersonii* glucoamylase disclosed in WO 99/28448.

Contemplated fungal glucoamylases include particularly glucoamylases derived from *Talaromyces*, preferably *T. emersonii*, or or a strain of *Trametes*, preferably *Trametes cingulata*, or a strain of Pycnoporus, or a strain of *Gloeophyllum*, such as a strain of *Gloeophyllum sepiarium* or *Gloeophyllum trabeum* or a strain of the *Nigrofomes*.

In one embodiment the glucoamylase is derived from a strain of the genus *Trametes*, in particular a strain of *Trametes cingulata*, disclosed in WO 2006/069289 or in SEQ ID NO: 25 herein. In one embodiment the glucoamylase is derived from a strain of the genus *Talaromyces*, in particular a strain of *Talaromyces emersonii* disclosed in SEQ ID NO: 26 herein.

In another embodiment the glucoamylase is derived from a strain of the genus Pycnoporus, in particular a strain of Pycnoporus *sanguineus* as described in WO 2011/066576 (SEQ ID NOs 2, 4 or 6) or SEQ ID NO: 27 herrein, or from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is SEQ ID NO: 28 herein. In another embodiment the glucoamylase is SEQ ID NO: 29 herein. In an embodiment the glucoamylase is derived from a strain of the genus *Nigrofomes*, in particular a strain of *Nigrofomes* sp. disclosed in WO 2012/064351 as SEQ ID NO: 2. Contemplated are also glucoamylases which exhibit a high identity to any of the above mentioned glucoamylases, i.e., at least 70%, at least 75%, at least 80%, at least 85%, at least 90%, at least 95%, at least 96%, at least 97%, at least 98%, at least 99% or even 100% identity to any one of the mature parts of the enzyme sequences mentioned above, such as any of SEQ ID NOs: 131, 132, 133, 134, or 135 herein.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

In an embodiment the glucoamylase is added as a blend further comprising an alpha-amylase. In a preferred embodiment the alpha-amylase is a fungal alpha-amylase, especially an acid fungal alpha-amylase. The alpha-amylase is typically a side activity.

In an embodiment the glucoamylase is a blend comprising *Talaromyces emersonii* glucoamylase disclosed in WO 99/28448 as SEQ ID NO: 7 or SEQ ID NO: 26 herein and *Trametes cingulata* glucoamylase disclosed in WO 06/069289 and SEQ ID NO: 25 herein.

In an embodiment the glucoamylase is a blend comprising *Talaromyces emersonii* glucoamylase disclosed SEQ ID NO: 26, *Trametes cingulata* glucoamylase disclosed as SEQ ID NO: 25, and *Rhizomucor pusillus* alpha-amylase with *Aspergillus niger* glucoamylase linker and SBD disclosed as V039 in Table 5 in WO 2006/069290 and as SEQ ID NO: 30 herein, preferably with the following substitutions: G128D+D143N.

In an embodiment the glucoamylase is a blend comprising *Gloeophyllum sepiarium* glucoamylase shown as SEQ ID NO: 2 in WO 2011/068803 (SEQ ID NO: 28 herein) and *Rhizomucor pusillus* with an *Aspergillus niger* glucoamylase linker and starch-binding domain (SBD), disclosed SEQ ID NO: 3 in WO 2013/006756 (SEQ ID NO: 30 herein) with the following substitutions: G128D+D143N.

In an embodiment the *Rhizomucor pusillus* alpha-amylase or the *Rhizomucor pusillus* alpha-amylase with an *Aspergillus niger glucoamylase* linker and starch-binding domain (SBD) has at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 3 in WO 2013/006756 for numbering).

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL, SPIRIZYME ACHIEVE and AMG™ E (from Novozymes A/S); OPTIDEX™ 300, GC480, GC417 (from DuPont-Genencor); AMIGASE™ and AMIGASE™ PLUS (from DSM); G-ZYME™ G900, G-ZYME™ and G990 ZR (from DuPont-Genencor).

Cellulolytic Composition Present and/or Added During Saccharification and/or Fermentation According to the invention a cellulolytic composition is present during fermentation or simultaneous saccharification and fermentation (SSF).

The cellulolytic composition may be any cellulolytic composition, comprising a beta-glucosidase, a cellobiohydrolase and an endoglucanase.

Any cellulase described herein contemplated as being present and/or added during saccharification and/or fermentation is also contemplated for expression by a fermenting organism or host cell.

Examples of suitable cellulolytic composition can be found in WO 2008/151079 and co-pending patent application PCT/US12/052163 published as WO 2013/028928 which are incorporated by reference.

In preferred embodiments the cellulolytic composition is derived from a strain of *Trichoderma, Humicola*, or *Chrysosporium.*

In an embodiment the cellulolytic composition is derived from a strain of *Trichoderma reesei, Humicola insolens* and/or *Chrysosporium lucknowense.*

In an embodiment the cellulolytic composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as one disclosed in WO 2005/047499 or SEQ ID NO: 27 herein or an *Aspergillus fumigatus* beta-glucosidase variant disclosed in WO 2012/044915 (Novozymes), such as one with the following substitutions F100D, S283G, N456E, F512Y; or a strain of the genus a strain *Penicillium*, such as a strain of the *Penicillium brasilianum* disclosed in WO 2007/019442, or a strain of the genus *Trichoderma*, such as a strain of *Trichoderma reesei.*

In an embodiment the cellulolytic composition comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 or SEQ ID NO: 15 herein.

In an embodiment the cellulolytic composition comprises a cellobiohydrolase I (CBH I), such as one derived from a strain of the genus *Aspergillus*, such as a strain of *Aspergillus fumigatus*, such as the Cel7a CBHI disclosed in SEQ ID NO: 2 in WO 2011/057140 or SEQ ID NO: 17 herein, or a strain of the genus *Trichoderma*, such as a strain of *Trichoderma reesei.*

In an embodiment the cellulolytic composition comprises a cellobiohydrolase II (CBH II, such as one derived from a strain of the genus *Aspergillus*, such as a strain of *Aspergillus fumigatus* or SEQ ID NO: 18 herein; or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris.*

In an embodiment the cellulolytic composition comprises a GH61 polypeptide having cellulolytic enhancing activity and a beta-glucosidase.

In an embodiment the cellulolytic composition comprises a GH61 polypeptide having cellulolytic enhancing activity, a beta-glucosidase, and a CBH I.

In an embodiment the cellulolytic composition comprises a GH61 polypeptide having cellulolytic enhancing activity, a beta-glucosidase, a CBH I, and a CBH II.

In an embodiment the cellulolytic composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656), and *Aspergillus oryzae* beta-glucosidase fusion protein (WO 2008/057637).

In an embodiment the cellulolytic composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656) and *Aspergillus fumigatus* beta-glucosidase (SEQ ID NO: 2 of WO 2005/047499) or SEQ ID NO: 16 herein.

In an embodiment the cellulolytic composition is a *Trichoderma reesei* cellulolytic enzyme composition further comprising *Penicillium emersonii* GH61A polypeptide having cellulolytic enhancing activity disclosed in WO 2011/041397 and *Aspergillus fumigatus* beta-glucosidase (SEQ ID NO: 2 of WO 2005/047499) or SEQ ID NO: 16 herein or a variant thereof with the following substitutions F100D, S283G, N456E, F512Y.

In an embodiment, the cellulolytic composition, for example a *Trichoderma reesei* cellulolytic enzyme composition, comprises one or more polypeptides selected from the group consisting of:

beta-glucosidase;

cellobiohydrolase I; and endoglucanase I, or a mixture of two or three thereof.

In an embodiment, the cellulolytic composition, for example a *Trichoderma reesei* cellulolytic enzyme composition, comprises one or more of the following components:

(i) an *Aspergillus fumigatus* beta-glucosidase or a variant thereof;

(ii) an *Aspergillus fumigatus* cellobiohydrolase I; and (iii) a *Trichoderma reesei* endoglucanase I.

In an embodiment, the cellulolytic composition is a *Trichoderma reesei* cellulolytic composition further comprising:

(i) an *Aspergillus fumigatus* beta-glucosidase disclosed in SEQ ID NO: 16 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 16;

(ii) a cellobiohydrolase I (CBH I), such as one derived from a strain of the genus *Aspergillus*, such as a strain of *Aspergillus fumigatus*, such as the CBHI disclosed as SEQ ID NO: 17, or a CBHI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 17; and (iii) an endoglucanase I (EGI), such as one derived from a strain of the genus *Trichoderma*, such as a strain of *Trichoderma reesei*, such as the EGI disclosed as SEQ ID NO: 19, or an EGI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 19.

In a preferred embodiment the cellulolytic composition comprising one or more of the following components:

(i) an *Aspergillus fumigatus* cellobiohydrolase I;

(ii) an *Aspergillus fumigatus* cellobiohydrolase II;

(iii) an *Aspergillus fumigatus* beta-glucosidase or variant thereof; and (iv) a *Penicillium* sp. GH61 polypeptide having cellulolytic enhancing activity; or homologs thereof.

In an preferred embodiment the cellulolytic composition is derived from *Trichoderma reesei* comprising GH61A polypeptide having cellulolytic enhancing activity derived from a strain of *Penicillium emersonii* (SEQ ID NO: 2 in WO 2011/041397 or SEQ ID NO: 15 herein), *Aspergillus fumigatus* beta-glucosidase (SEQ ID NO: 2 in WO 2005/047499 SEQ ID NO: 27 herein) variant F100D, S283G, N456E, F512Y) disclosed in WO 2012/044915; *Aspergillus fumigatus* Cel7A CBH1 disclosed as SEQ ID NO: 6 in WO2011/057140 (SEQ ID NO: 17 herein) and *Aspergillus fumigatus* CBH II disclosed as SEQ ID NO: 18 in WO 2011/057140 (SEQ ID NO: 18 herein).

In an embodiment the cellulolytic composition is dosed from 0.0001-3 mg EP/g DS, preferably, 0.0005-2 mg EP/g DS, preferably 0.001-1 mg/g DS, more preferably 0.005-0.5 mg EP/g DS, and even more preferably 0.01-0.1 mg EP/g DS.

Enzyme Blends or Compositions

Aspects of the invention relate to enzyme blends or compositions comprising at least one glucoamylase variant of the present invention. In some aspects, the enzyme blends or compositions comprise thermostable enzymes and are suitable for use in the liquefaction step of the processes described herein. In other aspects, the enzyme blends or compositions comprise enzymes that are suitable for use in the saccharification, fermentation, or simultaneous saccharification and fermentation steps of the processes described herein.

The compositions may comprise one or more glucoamylase variant(s) as the major enzymatic component, e.g., a mono-component composition.

The enzyme blends or compositions may further comprise additional enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, trehalase, or xylanase.

In an embodiment, an enzyme blend or composition of the present invention comprises a glucoamylase variant comprising one or more of the following substitutions at positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13 and a thermostable alpha-amylase, preferably a bacterial alpha-amylase.

In an embodiment, an enzyme blend or composition of the present invention comprises a glucoamylase variant comprising one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13 and a thermostable alpha-amylase, preferably a bacterial alpha-amylase In an embodiment, an enzyme blend or composition of the present invention comprises a glucoamylase variant comprising one or more of the following substitutions at positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13 and a thermostable xylanase.

In one aspect, thermostable xylanase has a Melting Point (DSC) above 80° C., preferably above 85° C., especially above 90° C., in particular above 95° C.

Examples of suitable thermostable xylanases, in particular xylanases from the genus *Thermotoga*, include the xylanase shown in SEQ ID NOs: 40 herein, e.g., derived from a strain of *Thermotoga maritima*; the xylanase shown in SEQ ID NO: 41 herein, e.g., derived from a strain of *Thermotoga neapolitana*; the xylanase shown in SEQ ID NO: 42 herein, e.g., derived from a strain of *Thermotoga naphthophila*; or polypeptides having at least 60%, such as at least 70%, such as at least 75% identity, at least 76% identity, at least 77% identity, at least 78% identity, at least 79% identity, preferably at least 80%, at least 81% identity, at least 82% identity, at least 83% identity, at least 84% identity, more preferably at least 85% identity, at least 86% identity, at least 87% identity, at least 88% identity, at least 89% identity, more preferably at least 90% identity, more preferably at least 91% identity, more preferably at least 92% identity, at least 93% identity, at least 94% identity, or at least 95% identity, such as at least 96% identity, at least 97% identity, at least 98% identity, at least 99% identity, such as 100% identity to the mature part of any of the polypeptides of SEQ ID NOs: 40, 41, and 42 herein, respectively.

In an embodiment, an enzyme blend or composition of the present invention comprises a glucoamylase variant comprising one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13 and a thermostable xylanase having at least 60%, such as at least 70%, such as at least 75% identity, at least 76% identity, at least 77% identity, at least 78% identity, at least 79% identity, preferably at least 80%, at least 81% identity, at least 82% identity, at least 83% identity, at least 84% identity, more preferably at least 85% identity, at least 86% identity, at least 87% identity, at least 88% identity, at least 89% identity, more preferably at least 90% identity, more preferably at least 91% identity, more preferably at least 92% identity, at least 93% identity, at least 94% identity, or at least 95% identity, such as at least 96% identity, at least 97% identity, at least 98% identity, at least 99% identity, such as 100% identity to the mature part of any of the polypeptides of SEQ ID NOs: 40, 41, and 42.

In an embodiment, the glucoamylase variant comprising one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13 with a thermostable alpha-amylase and a protease, preferably a bacterial or archael protease.

In an embodiment, the glucoamylase variant comprising one or more of the following substitutions at positions corresponding to positions: G6S, G7T, P11F, R31F, K34Y, E50R, T65A, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13 with a thermostable alpha-amylase, a protease and a xylanase, preferably a bacterial xylanase.

In an embodiment, the glucoamylase variant comprising one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13 with a thermostable alpha-amylase and a phytase.

In an embodiment, the glucoamylase variant comprising one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13 with a thermostable alpha-amylase, a protease, and a phytase.

In an embodiment, the glucoamylase variant comprising one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13 with a thermostable alpha-amylase, protease, xylanase and phytase.

In an embodiment, the glucoamylase variant comprising one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13 with a thermostable alpha-amylase, protease, xylanase and phytase.

In an embodiment, the glucoamylase variant comprising one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13 with a thermostable alpha-amylase, a phytase, a protease, a xylanase, and a phospholipase.

In an embodiment, the glucoamylase variant comprising one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13 in combination with at least one, at least two, or at least three thermostable enzymes selected from the group consisting of thermostable alpha-amylase, protease, xylanase, phytase, phospholipase, endoglucanase, and/or pullulanase during liquefaction or used as a component of an enzyme blend or composition of the invention.

In an embodiment, the enzyme blend or composition comprises one or more cellulases, e.g., a beta-glucosidase, a cellobiohydrolase and an endoglucanase.

In another aspect, the present invention relates to a composition comprising one or more glucoamylase variant(s), and/or a cellulolytic composition, and a recombinant host cell or fermenting organism comprising at least one heterologous polynucleotide (e.g., a recombinant yeast host cell or fermenting organism engineered to optimize production of the fermentation product or a byproduct or co-product of the process for producing the fermentation product).

As used in this section, "composition" encompasses process streams within processes for producing a fermentation product, such as ethanol, from a starch-containing material or cellulosic-containing material, such as a fermenting mash or fermented mash composition.

As used herein, "fermenting mash or fermented mash composition" refers to the composition formed by the constituent parts of the mash which are present during fermentation (fermenting mash composition) or after fermentation (fermented mash composition) fermentation, including any compounds (e.g., enzymes) or microorganisms (e.g., fermenting organism, such as a recombinant yeast host cell comprising at least one heterologous polynucleotide) that are exogenously added to a process stream for producing a fermentation product (e.g., enzymes added upstream from the fermentation step, e.g., during the liquefaction step of a conventional process for producing a fermentation product from a starch-containing material, during the pretreatment step of a process for producing a fermentation product from a cellulosic-containing material, or during the saccharification step of any process for producing a fermentation product, such as process for producing a fermentation product from a starch-containing material, a raw starch hydrolysis (RSH) process, and a process for producing a fermentation product from a cellulosic-containing material, chemical inputs (e.g., urea), etc.), and any compounds or microorganisms that are generated in situ in the process stream for producing a fermentation product (e.g., reaction products of enzymes and their substrates in the mash, enzymes secreted from the fermenting organism, etc.).

The at least one heterologous polynucleotide may encode polypeptides that are expressed intracellularly to enhance performance of the yeast or fermenting organism itself, polypeptides that are secreted into the fermenting or fermented mash composition to exert their effects on the mash or components of the mash to improve fermentation results, or both.

In some embodiments, the recombinant yeast host cell or fermenting organism comprises nucleotide sequences encoding glucoamylase variant(s) of the present invention, in addition to at least one other heterologous polynucleotide that optimizes production of the fermentation product or a byproduct or co-product of the process for producing the fermentation product.

Accordingly, in one aspect, the present invention relates to a composition comprising:

(a) a recombinant yeast host cell or fermenting organism; and/or (b) at least one or more glucoamylase variant(s) of the present invention, wherein the yeast host cell or fermenting organism comprises a heterologous polynucleotide encoding a glucoamylase, an alpha-amylase, protease, and/or one or more glucoamylase variant(s) of the present invention.

The present invention contemplates the use of any viable recombinant yeast host cell or fermenting organism in the compositions described herein. Examples of suitable recombinant yeast host cells or fermenting organisms can be found herein in the "Fermenting Organisms" section.

The present invention contemplates the use of any glucoamylase, alpha-amylase, protease, and/or one or more glucoamylase variant(s) of the present invention. Examples of suitable such enzymes can be found under the heading "Enzymes".

In an embodiment, the fermenting or fermented mash composition or the whole stillage composition comprises:

(i) a recombinant yeast host cell or fermenting organism, wherein the yeast host cell or fermenting organism comprises a heterologous polynucleotide encoding a glucoamylase variant(s), an alpha-amylase, protease, and/or one or more glucoamylase of the present invention.

The fermented or fermenting mash compositions and whole stillage compositions may further comprise a cellulases/cellulolytic composition comprising a beta-glucosidase, a cellobiohydrolase and an endoglucanase. In one embodiment, the cellulases/cellulolytic composition comprises one or more polypeptides selected from the group consisting of:

GH61 polypeptide having cellulolytic enhancing activity;

beta-glucosidase;

Cellobiohydrolase I;

Cellobiohydrolase II;

or a mixture of two, three, or four thereof.

In another embodiment, the cellulases/cellulolytic composition comprises one or more polypeptides selected from the group consisting of:

GH61 polypeptide having cellulolytic enhancing activity;

beta-glucosidase;

Cellobiohydrolase I;

Cellobiohydrolase II;

or a mixture of two, three, or four thereof.

In another embodiment, the cellulases/cellulolytic composition comprises one or more of the following components:

(i) an *Aspergillus fumigatus* cellobiohydrolase I;

(ii) an *Aspergillus fumigatus* cellobiohydrolase II;

(iii) an *Aspergillus fumigatus* beta-glucosidase or variant thereof; and (iv) a *Penicillium* sp. GH61 polypeptide having cellulolytic enhancing activity; or homologs thereof.

In an embodiment, the fermenting or fermented mash composition or the whole stillage composition comprises:

(i) a recombinant yeast host cell or fermenting organism, wherein the yeast host cell or fermenting organism comprises a heterologous polynucleotide encoding one or more glucoamylase variant(s), an alpha-amylase, protease, and/or cellulase; and (ii) a *Trichoderma reesei* cellulolytic enzyme composition further comprising:

an *Aspergillus fumigatus* beta-glucosidase disclosed in SEQ ID NO: 16 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 16;

a cellobiohydrolase I (CBH I), such as one derived from a strain of the genus *Aspergillus*, such as a strain of *Aspergillus fumigatus*, such as the CBHI disclosed as SEQ ID NO: 17, or a CBHI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 17; and an endoglucanase I (EGI), such as one derived from a strain of the genus *Trichoderma*, such as a strain of *Trichoderma reesei*, such as the EGI disclosed as SEQ ID NO: 19, or an EGI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 19.

In an embodiment, the fermenting or fermented mash composition or the whole stillage composition comprises:

(i) a recombinant yeast host cell or fermenting organism, wherein the yeast host cell or fermenting organism comprises a heterologous polynucleotide encoding one or more glucoamylase variant(s), an alpha-amylase, protease, and/or cellulase; and (ii) a *Trichoderma reesei* cellulolytic enzyme composition further comprising *Penicillium emersonii* GH61A polypeptide having cellulolytic enhancing activity disclosed in SEQ ID NO: 15, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 15, an *Aspergillus fumigatus* beta-glucosidase disclosed in SEQ ID NO: 16 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 16, a cellobiohydrolase I (CBH I), such as one derived from a strain of the genus *Aspergillus*, such as a strain of *Aspergillus fumigatus*, such as the CBHI disclosed as SEQ ID NO: 17, or CBH I having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 17, and a cellobiohydrolase II (CBH II), such as one derived from a strain of the genus *Aspergillus*, such as a strain of *Aspergillus fumigatus*; such as the CBH II disclosed as SEQ ID NO: 18, or a CBH II having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 18.

In an embodiment, the fermenting or fermented mash composition or the whole stillage composition comprises:

(i) a recombinant yeast host cell or fermenting organism, wherein the yeast host cell or fermenting organism comprises a heterologous polynucleotide encoding one or more glucoamylase variant(s), an alpha-amylase, protease, and/or cellulase;

(ii) a *Trichoderma reesei* cellulolytic enzyme composition further comprising:

an *Aspergillus fumigatus* beta-glucosidase disclosed in SEQ ID NO: 16 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 16;

a cellobiohydrolase I (CBH I), such as one derived from a strain of the genus *Aspergillus*, such as a strain of *Aspergillus fumigatus*, such as the CBHI disclosed as SEQ ID NO: 17, or a CBHI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 17; and an endoglucanase I (EGI), such as one derived from a strain of the genus *Trichoderma*, such as a strain of *Trichoderma reesei*, such as the EGI disclosed as SEQ ID NO: 19, or an EGI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 19.

In an embodiment, the fermenting or fermented mash composition or the whole stillage composition comprises:

(i) a recombinant yeast host cell or fermenting organism, wherein the yeast host cell or fermenting organism comprises a heterologous polynucleotide encoding one or more glucoamylase variant(s), an alpha-amylase, protease, and/or cellulase;

(ii) a *Trichoderma reesei* cellulolytic enzyme composition further comprising *Penicillium emersonii* GH61A polypeptide having cellulolytic enhancing activity disclosed in SEQ ID NO: 15, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 15, an *Aspergillus fumigatus* beta-glucosidase disclosed in SEQ ID NO: 16 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 16, a cellobiohydrolase I (CBH I), such as one derived from a strain of the genus *Aspergillus*, such as a strain of *Aspergillus fumigatus*, such as the CBHI disclosed as SEQ ID NO: 17, or CBH I having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 17, and a cellobiohydrolase II (CBH II), such as one derived from a strain of the genus *Aspergillus*, such as a strain of *Aspergillus fumigatus*; such as the CBH II disclosed as SEQ ID NO: 18, or a CBH II having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 18.

In an embodiment, the fermenting or fermented mash composition or the whole stillage composition comprises:

(i) a recombinant yeast host cell or fermenting organism, wherein the yeast host cell or fermenting organism comprises a heterologous polynucleotide encoding one or more glucoamylase variant(s), an alpha-amylase, protease, and/or cellulase; and (ii) a *Trichoderma reesei* cellulolytic enzyme composition further comprising:

an *Aspergillus fumigatus* beta-glucosidase disclosed in SEQ ID NO: 16 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 16;

a cellobiohydrolase I (CBH I), such as one derived from a strain of the genus *Aspergillus*, such as a strain of *Aspergillus fumigatus*, such as the CBHI disclosed as SEQ ID NO: 17, or a CBHI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 17; and an endoglucanase I (EGI), such as one derived from a strain of the genus *Trichoderma*, such as a strain of *Trichoderma reesei*, such as the EGI disclosed as SEQ ID NO: 19, or an EGI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 19.

In an embodiment, the fermenting or fermented mash composition or the whole stillage composition comprises:

(i) a recombinant yeast host cell or fermenting organism, wherein the yeast host cell or fermenting organism comprises a heterologous polynucleotide encoding one or more glucoamylase variant(s), an alpha-amylase, protease, and/or cellulase; and (ii) a *Trichoderma reesei* cellulolytic enzyme composition further comprising *Penicillium emersonii* GH61A polypeptide having cellulolytic enhancing activity disclosed in SEQ ID NO: 15, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 15, an *Aspergillus fumigatus* beta-glucosidase disclosed in SEQ ID NO: 16 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 16, a cellobiohydrolase I (CBH I), such as one derived from a strain of the genus *Aspergillus*, such as a strain of *Aspergillus fumigatus*, such as the CBHI disclosed as SEQ ID NO: 17, or CBH I having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 17, and a cellobiohydrolase II (CBH II), such as one derived from a strain of the genus *Aspergillus*, such as a strain of *Aspergillus fumigatus*; such as the CBH II disclosed as SEQ ID NO: 18, or a CBH II having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 18.

In an embodiment, the fermenting or fermented mash composition or the whole stillage composition comprises:

(i) a recombinant yeast host cell or fermenting organism, wherein the yeast host cell or fermenting organism comprises a heterologous polynucleotide encoding one or more glucoamylase variant(s), an alpha-amylase, protease, and/or cellulase;

(ii) a *Trichoderma reesei* cellulolytic enzyme composition further comprising:

an *Aspergillus fumigatus* beta-glucosidase disclosed in SEQ ID NO: 16 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 16;

a cellobiohydrolase I (CBH I), such as one derived from a strain of the genus *Aspergillus*, such as a strain of *Aspergillus fumigatus*, such as the CBHI disclosed as SEQ ID NO: 17, or a CBHI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 17; and an endoglucanase I (EGI), such as one derived from a strain of the genus *Trichoderma*, such as a strain of *Trichoderma reesei*, such as the EGI disclosed as SEQ ID NO: 19, or an EGI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 19.

In an embodiment, the fermenting or fermented mash composition or the whole stillage composition comprises:

(i) a recombinant yeast host cell or fermenting organism, wherein the yeast host cell or fermenting organism comprises a heterologous polynucleotide encoding one or more glucoamylase variant(s), an alpha-amylase, protease, and/or cellulase;

(ii) a *Trichoderma reesei* cellulolytic enzyme composition further comprising *Penicillium emersonii* GH61A polypeptide having cellulolytic enhancing activity disclosed in SEQ ID NO: 15, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 15, an *Aspergillus fumigatus* beta-glucosidase disclosed in SEQ ID NO: 16 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 16, a cellobiohydrolase I (CBH I), such as one derived from a strain of the genus *Aspergillus*, such as a strain of *Aspergillus fumigatus*, such as the CBHI disclosed as SEQ ID NO: 17, or CBH I having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 17, and a cellobiohydrolase II (CBH II), such as one derived from a strain of the genus *Aspergillus*, such as a strain of *Aspergillus fumigatus*; such as the CBH II disclosed as SEQ ID NO: 18, or a CBH II having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 18.

In an embodiment, the fermenting or fermented mash composition or the whole stillage composition comprises:

(i) a recombinant yeast host cell or fermenting organism, wherein the yeast host cell or fermenting organism comprises a heterologous polynucleotide encoding one or more glucoamylase variant(s), an alpha-amylase, protease, and/or cellulase;

(ii) a *Trichoderma reesei* cellulolytic enzyme composition further comprising:

an *Aspergillus fumigatus* beta-glucosidase disclosed in SEQ ID NO: 16 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 16;

a cellobiohydrolase I (CBH I), such as one derived from a strain of the genus *Aspergillus*, such as a strain of *Aspergillus fumigatus*, such as the CBHI disclosed as SEQ ID NO: 17, or a CBHI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 17; and an endoglucanase I (EGI), such as one derived from a strain of the genus *Trichoderma*, such as a strain of *Trichoderma reesei*, such as the EGI disclosed as SEQ ID NO: 19, or an EGI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 19;

(iii) a polypeptide having trehalase activity selected from the group consisting of:

a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the mature polypeptide of SEQ ID NO: 31 and having trehalase activity; and a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the mature polypeptide of SEQ ID NO: 32 and having trehalase activity; and (iv) a glucoamylase blend selected from the group consisting of:

a blend comprising *Gloeophyllum sepiarium* glucoamylase shown as SEQ ID NO: 28, or a glucoamylase having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 28, and an alpha-amylase from *Rhizomucor pusillus* with an *Aspergillus niger* glucoamylase linker and starch-binding domain (SBD), disclosed SEQ ID NO: 30 with the following substitutions: G128D+D143N, and having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 136; and a blend comprising *Talaromyces emersonii* glucoamylase of SEQ ID NO: 26, or glucoamylase having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 26, a *Trametes cingulata* glucoamylase of SEQ ID NO: 25, or glucoamylase having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 25, and a *Rhizomucor pusillus* alpha-amylase with an *Aspergillus niger* glucoamylase linker and starch-binding domain (SBD), of SEQ ID NO: 30, and comprising the following substitutions: G128D+D143N, and having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 136.

The compositions may be prepared in accordance with methods known in the art and may be in the form of a liquid or a dry composition. The compositions may be stabilized in accordance with methods known in the art.

The compositions may be used in a process of the invention, for example, for degrading a starch-containing material, such as for example by contacting a starch-containing material with the composition during the saccharification, fermentation, or SSF step of a process of producing a fermentation product (e.g., the production of fuel ethanol from corn).

Glucoamylase Variants Used in a Process, Enzyme Blend, or Composition of the Invention Aspects of the present invention relates to the inclusion of one or more enzymes. The composition may comprise one or more enzymes such as a protease, a glucoamylase, an alpha-amylase, beta-glucosidase, cellobiohydrolase, phytase, endoglucanase, cellulase, trehalase, or xylanase.

In one embodiment, glucoamylase variant(s) of the present invention is combined with one or more enzymes, such as at least two enzymes, more preferred at least three, four or five enzymes. Preferably, the enzymes have different substrate specificity, e.g., proteolytic activity, amylolytic activity, hemicellulolytic activity or cellulolytic activity.

In general the properties of the selected enzyme(s) should be compatible with the process conditions, (i.e., pH-optimum, compatibility with other enzymatic and non-enzymatic ingredients, etc.), and the enzyme(s) should be present in effective amounts.

Aspects of the present invention relates to the inclusion of one or more glucoamylase variant(s) of the present invention in a process, enzyme blend, or composition of the invention. The present disclosure contemplates processes and enzyme blends or compositions comprising one or more glucoamylase variant(s) that when used alone, or in combination with each other or other enzymes or compositions described herein (e.g., cellulases/cellulolytic composition) result in an improvement in fermentation product yield (e.g., ethanol yield) compared to similar processes and/or enzyme blends or compositions lacking the one or more glucoamylase variant(s). Any glucoamylase variant(s) described herein is also contemplated for expression by a fermenting organism or host cell.

In terms of dose ranges envisaged according to the invention, in one embodiment, the glucoamylase variant(s) are dosed in the range 0.1-1000 micro gram EP/g DS; 0.5-500 micro gram EP/g DS; 1-100 micro gram EP/g DS; such as 5-50 micro gram EP/g DS.

According to the invention, at least glucoamylase variant is present or added during liquefaction, saccharification, fermentation or simultaneous saccharification and fermentation, or used as a component of an enzyme blend or composition of the invention, however, preferred embodiments may also include the addition of other enzyme classes during liquefaction/saccharification/fermentation/SSF, or as a component of an enzyme blend or composition of the invention.

In one aspect, a glucoamylase variant comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13 are present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13 are present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: S105L, S105E, A132R, R135S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: K34Y+S103N, K34Y+Y504T, S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75N+R77D+A78Q, K34Y+D445N+V447S, S103N+D445N+V447S, D445N+V447S+Y504T, K34Y+S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S, K34Y+S103N+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75S+R77G+A78W+V79D+F80Y, K34Y+S103N+D445N+V447S+D566T, K34Y+S103N+Y504T+Q594R F595S, K34Y+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+E501V+Y504T, K34Y+S103N+S105L+Y504T+Q594R+F595S, K34Y+S103N+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+Y504T+Q594R+F595S, K34Y+S103N+S105L+Y504T+D566T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+D566T+Q594R+F595S, G6S+G7T+R31F+K34Y+S103N+A132P+D445N+V447S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+Y504T+D566T+Q594R+F595S, K34Y+S103N+A132R+D445N+V447S+Y504T+D566T+Q594R+F595S, K34Y+S103N+S105L+A132R+D445N+V447S+Y504T+D566T+V592T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+Y504T+D566T+Q594R+F595S, K34Y+S103N+P107L+A132R+D445N+V447S+Y504T+D566T+Q594R+F595S, G6S+G7T+K34Y+S103N+P107L+A132P+D445N+V447S+E501V+Y504T, K34Y+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+E501V+Y504T+D566T+Q594R+F595S, K34Y+D75N+R77D+A78Q+S103N+R138L+D445N+V447S+Y504T+Q594R+F595S, R31F+K34Y+D75N+R77D+A78Q+S103N+R138L+D445N+V447S+Y504T+Q594R+F595S, K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+S105L+A132R+D445N+V447S+Y504T+D566T+Q594R+F595S, G6S+G7T+K34Y+S103N+P107L+A132R+D445N+V447S+Y504T+D566T+Q594R+F595S, G6S+G7T+K34Y+S103N+P107L+A132P+D445N+V447S+Y504T+D566T+Q594R+F595S, G6S+G7T+K34Y+S103N+P107L+A132P+D445N+V447S+D566T+T568V+Q594R+F595S, R31F+K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+A132R+D445N+V447S+Y504T+D566T+V592T+Q594R+F595S, G6S+G7T+K34Y+S103N+P107L+A132R+D445N+V447S+Y504T+D566T+T568V+Q594R+F595S, G6S+G7T+K34Y+S103N+P107L+A132P+D445N+V447S+Y504T+D566T+T568V+Q594R+F595S, G6S+G7T+K34Y+S103N+P107L+A132R+D445N+V447S+S481P+Y504T+D566T+Q594R+F595S, G6S+G7T+K34Y+S103N+P107L+A132R+D445N+V447S+S481P+Y504T+D566T+T568V+Q594R+F595S, G6S+G7T+R31F+K34Y+S103N+P107L+A132P+D445N+V447S+Y504T+D566T+T568V+Q594R+F595S, G6S+G7T+R31F+K34Y+S103N+A132P+D445N+V447S+S481P+D566T+T568V+Q594R+F595S, G6S+G7T+K34Y+E50R+S103N+A132P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+T110W+A132P+D445N+V447S+Y504T+D566T+T568V+Q594R+F595S, G6S+G7T+K34Y+E50R+S103N+P107L+A132P+D445N+V447S+Y504T+D566T+T568V+Q594R+F595S, G6S+G7T+R31F+K34Y+S103N+P107L+A132P+D445N+V447S+S481P+D566T+T568V+Q594R+F595S, G6S+G7T+R31F+K34Y+E50R+S103N+A132P+D445N+V447S+S481P+D566T+T568V+Q594R+F595S, G6S+G7T+R31F+K34Y+S103N+A132P+R138G+D445N+V447S+S481P+D566T+T568V+Q594R+F595S, G6S+G7T+R31F+K34Y+S103N+A132P+R138L+D445N+V447S+S481P+D566T+T568V+Q594R+F595S, G6S+G7T+R31F+K34Y+S103N+A132P+R138P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprises substitutions at positions corresponding to positions selected from a group consisting of: G6S+G7T+R31F+K34Y+S103N+P107L+A132P+D445N+V447S+S481P+Y504T+D566T+T568V+Q594R+F595S, G6S+G7T+K34Y+E50R+S103N+P107L+A132P+D445N+V447S+S481P+Y504T+D566T+T568V+Q594R+F595S, G6S+G7T+R31F+K34Y+E50R+S103N+A132P+D445N+V447S+S481P+E501L+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+E501V+Y504T+D566T+T568V+Q594R+F595S, G6S+G7T+R31F+K34Y+E50R+D75N+R77D+A78Q+S103N+A132P+D445N+V447S+S481P+D566T+Q594R+F595S, G6S+G7T+R31F+K34Y+E50R+S103N+A132P+S379P+D445N+V447S+S481P+E501A+D566T+T568V+Q594R+F595S, G6S+G7T+R31F+K34Y+E50R+S103N+A132P+D445N+V447S+S481P+T484P+E501A+D566T+T568V+Q594R+F595S, G6S+G7T+R31F+K34Y+E50R+S103N+A132P+D445N+V447S+S481P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+E50R+D75N+R77D+A78Q+S103N+A132P+R138L+D445N+V447S+S481P+D566T+Q594R+F595S, G6S+G7T+R31F+K34Y+E50R+S103N+A132P+S379P+D445N+V447S+S481P+T484P+E501A+D566T+T568V+Q594R+F595S, G6S+G7T+R31F+K34Y+E50R+S103N+A132P+D445N+V447S+S481P+T484P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+D75N+R77D+A78Q+S103N+P107L+A132P+D445N+V447S+S481P+Y504T+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID Nos: 1-13 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: S105L, S105E, A132R, R135S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: K34Y+S103N, K34Y+Y504T, S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75N+R77D+A78Q, K34Y+D445N+V447S, S103N+D445N+V447S, D445N+V447S+Y504T, K34Y+S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S, K34Y+S103N+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75S+R77G+A78W+V79D+F80Y, K34Y+S103N+D445N+V447S+D566T, K34Y+S103N+Y504T+Q594R F595S, K34Y+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+E501V+Y504T, K34Y+S103N+S105L+Y504T+Q594R+F595S, K34Y+S103N+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+Y504T+Q594R+F595S, K34Y+S103N+S105L+Y504T+D566T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+D566T+Q594R+F595S, G6S+G7T+R31F+K34Y+S103N+A132P+D445N+V447S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+Y504T+D566T+Q594R+F595S, K34Y+S103N+A132R+D445N+V447S+Y504T+D566T+Q594R+F595S, K34Y+S103N+S105L+A132R+D445N+V447S+Y504T+D566T+V592T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+Y504T+D566T+Q594R+F595S, K34Y+S103N+P107L+A132R+D445N+V447S+Y504T+D566T+Q594R+F595S, G6S+G7T+K34Y+S103N+P107L+A132P+D445N+V447S+E501V+Y504T, K34Y+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+E501V+Y504T+D566T+Q594R+F595S, K34Y+D75N+R77D+A78Q+S103N+R138L+D445N+V447S+Y504T+Q594R+F595S, R31F+K34Y+D75N+R77D+A78Q+S103N+R138L+D445N+V447S+Y504T+Q594R+F595S, K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+S105L+A132R+D445N+V447S+Y504T+D566T+Q594R+F595S, G6S+G7T+K34Y+S103N+P107L+A132R+D445N+V447S+Y504T+D566T+Q594R+F595S, G6S+G7T+K34Y+S103N+P107L+A132P+D445N+V447S+Y504T+D566T+Q594R+F595S, G6S+G7T+K34Y+S103N+P107L+A132P+D445N+V447S+D566T+T568V+Q594R+

F595S, R31F+K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+A132R+D445N+V447S+Y504T+D566T+V592T+Q594R+F595S, G6S+G7T+K34Y+S103N+P107L+A132R+D445N+V447S+Y504T+D566T+T568V+Q594R+F595S, G6S+G7T+K34Y+S103N+P107L+A132P+D445N+V447S+Y504T+D566T+T568V+Q594R+F595S, G6S+G7T+K34Y+S103N+P107L+A132R+D445N+V447S+S481P+Y504T+D566T+Q594R+F595S, G6S+G7T+K34Y+S103N+P107L+A132R+D445N+V447S+S481P+Y504T+D566T+T568V+Q594R+F595S, G6S+G7T+R31F+K34Y+S103N+P107L+A132P+D445N+V447S+Y504T+D566T+T568V+Q594R+F595S, G6S+G7T+R31F+K34Y+S103N+A132P+D445N+V447S+S481P+D566T+T568V+Q594R+F595S, G6S+G7T+K34Y+E50R+S103N+A132P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+T110W+A132P+D445N+V447S+Y504T+D566T+T568V+Q594R+F595S, G6S+G7T+K34Y+E50R+S103N+P107L+A132P+D445N+V447S+Y504T+D566T+T568V+Q594R+F595S, G6S+G7T+R31F+K34Y+S103N+P107L+A132P+D445N+V447S+S481P+D566T+T568V+Q594R+F595S, G6S+G7T+R31F+K34Y+E50R+S103N+A132P+D445N+V447S+S481P+D566T+T568V+Q594R+F595S, G6S+G7T+R31F+K34Y+S103N+A132P+R138G+D445N+V447S+S481P+D566T+T568V+Q594R+F595S, G6S+G7T+R31F+K34Y+S103N+A132P+R138L+D445N+V447S+S481P+D566T+T568V+Q594R+F595S, G6S+G7T+R31F+K34Y+S103N+A132P+R138P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+Y504T+D566T+T568V+Q594R+F595S, G6S+G7T+K34Y+E50R+S103N+P107L+A132P+D445N+V447S+S481P+Y504T+D566T+T568V+Q594R+F595S, G6S+G7T+R31F+K34Y+E50R+S103N+A132P+D445N+V447S+S481P+E501L+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+E501V+Y504T+D566T+T568V+Q594R+F595S, G6S+G7T+R31F+K34Y+E50R+D75N+R77D+A78Q+S103N+A132P+D445N+V447S+S481P+D566T+Q594R+F595S, G6S+G7T+R31F+K34Y+E50R+S103N+A132P+S379P+D445N+V447S+S481P+E501A+D566T+T568V+Q594R+F595S, G6S+G7T+R31F+K34Y+E50R+S103N+A132P+D445N+V447S+S481P+T484P+E501A+D566T+T568V+Q594R+F595S, G6S+G7T+R31F+K34Y+E50R+S103N+A132P+D445N+V447S+S481P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+E50R+D75N+R77D+A78Q+S103N+A132P+R138L+D445N+V447S+S481P+D566T+Q594R+F595S, G6S+G7T+R31F+K34Y+E50R+S103N+A132P+S379P+D445N+V447S+S481P+T484P+E501A+D566T+T568V+Q594R+F595S, G6S+G7T+R31F+K34Y+E50R+S103N+A132P+D445N+V447S+S481P+T484P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+D75N+R77D+A78Q+S103N+P107L+A132P+D445N+V447S+S481P+Y504T+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 1 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: S105L, S105E, A132R, R135S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: K34Y+S103N, K34Y+Y504T, S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to SEQ ID NO: 2 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75N+R77D+A78Q, K34Y+D445N+V447S, S103N+D445N+V447S, D445N+V447S+Y504T, K34Y+S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S, K34Y+S103N+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75S+R77G+A78W+V79D+F80Y, K34Y+S103N+D445N+V447S+D566T, K34Y+S103N+Y504T+Q594R F595S, K34Y+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+E501V+Y504T, K34Y+S103N+S105L+Y504T+Q594R+F595S, K34Y+S103N+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+Y504T+Q594R+F595S, K34Y+S103N+S105L+Y504T+D566T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+D566T+Q594R+F595S, G6S+G7T+R31F+K34Y+S103N+A132P+D445N+V447S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+Y504T+D566T+Q594R+F595S, K34Y+S103N+A132R+D445N+V447S+Y504T+D566T+Q594R+F595S, K34Y+S103N+S105L+A132R+D445N+V447S+Y504T+D566T+V592T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+Y504T+D566T+Q594R+F595S, K34Y+S103N+P107L+A132R+D445N+V447S+Y504T+D566T+Q594R+F595S, G6S+G7T+K34Y+S103N+P107L+A132P+D445N+V447S+E501V+Y504T, K34Y+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+E501V+Y504T+D566T+Q594R+F595S, K34Y+D75N+R77D+A78Q+S103N+R138L+D445N+V447S+Y504T+Q594R+F595S, R31F+K34Y+D75N+R77D+A78Q+S103N+R138L+D445N+V447S+Y504T+Q594R+F595S, K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+S105L+A132R+D445N+V447S+Y504T+D566T+Q594R+F595S, G6S+G7T+K34Y+S103N+P107L+A132R+D445N+V447S+Y504T+D566T+Q594R+F595S, G6S+G7T+K34Y+S103N+P107L+A132P+D445N+V447S+Y504T+D566T+Q594R+F595S, G6S+G7T+K34Y+S103N+P107L+A132P+D445N+V447S+D566T+T568V+Q594R+F595S, R31F+K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+A132R+D445N+V447S+Y504T+D566T+V592T+Q594R+F595S, G6S+G7T+K34Y+S103N+P107L+A132R+D445N+V447S+Y504T+D566T+T568V+Q594R+F595S, G6S+G7T+K34Y+S103N+P107L+A132P+D445N+V447S+Y504T+D566T+T568V+Q594R+F595S, G6S+G7T+K34Y+S103N+P107L+A132R+D445N+V447S+S481P+Y504T+D566T+Q594R+F595S, G6S+G7T+K34Y+S103N+P107L+A132R+D445N+V447S+S481P+Y504T+D566T+T568V+Q594R+F595S, G6S+G7T+R31F+K34Y+S103N+P107L+A132P+D445N+V447S+Y504T+D566T+T568V+Q594R+F595S, G6S+G7T+

R31F+K34Y+S103N+A132P+D445N+V447S+S481P+D566T+T568V+Q594R+F595S, G6S+G7T+K34Y+E50R+S103N+A132P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+T110W+A132P+D445N+V447S+Y504T+D566T+T568V+Q594R+F595S, G6S+G7T+K34Y+E50R+S103N+P107L+A132P+D445N+V447S+Y504T+D566T+T568V+Q594R+F595S, G6S+G7T+R31F+K34Y+S103N+P107L+A132P+D445N+V447S+S481P+D566T+T568V+Q594R+F595S, G6S+G7T+R31F+K34Y+E50R+S103N+A132P+D445N+V447S+S481P+D566T+T568V+Q594R+F595S, G6S+G7T+R31F+K34Y+S103N+A132P+R138G+D445N+V447S+S481P+D566T+T568V+Q594R+F595S, G6S+G7T+R31F+K34Y+S103N+A132P+R138L+D445N+V447S+S481P+D566T+T568V+Q594R+F595S, G6S+G7T+R31F+K34Y+S103N+A132P+R138P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising at positions corresponding to positions selected from a group consisting of: G6S+G7T+R31F+K34Y+S103N+P107L+A132P+D445N+V447S+S481P+Y504T+D566T+T568V+Q594R+F595S, G6S+G7T+K34Y+E50R+S103N+P107L+A132P+D445N+V447S+S481P+Y504T+D566T+T568V+Q594R+F595S, G6S+G7T+R31F+K34Y+E50R+S103N+A132P+D445N+V447S+S481P+E501L+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+E501V+Y504T+D566T+T568V+Q594R+F595S, G6S+G7T+R31F+K34Y+E50R+D75N+R77D+A78Q+S103N+A132P+D445N+V447S+S481P+D566T+Q594R+F595S, G6S+G7T+R31F+K34Y+E50R+S103N+A132P+S379P+D445N+V447S+S481P+E501A+D566T+T568V+Q594R+F595S, G6S+G7T+R31F+K34Y+E50R+S103N+A132P+D445N+V447S+S481P+T484P+E501A+D566T+T568V+Q594R+F595S, G6S+G7T+R31F+K34Y+E50R+S103N+A132P+D445N+V447S+S481P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+E50R+D75N+R77D+A78Q+S103N+A132P+R138L+D445N+V447S+S481P+D566T+Q594R+F595S, G6S+G7T+R31F+K34Y+E50R+S103N+A132P+S379P+D445N+V447S+S481P+T484P+E501A+D566T+T568V+Q594R+F595S, G6S+G7T+R31F+K34Y+E50R+S103N+A132P+D445N+V447S+S481P+T484P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+D75N+R77D+A78Q+S103N+P107L+A132P+D445N+V447S+S481P+Y504T+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 2 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO:

3 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: S105L, S105E, A132R, R135S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: K34Y+S103N, K34Y+Y504T, S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75N+R77D+A78Q, K34Y+D445N+V447S, S103N+D445N+V447S, D445N+V447S+Y504T, K34Y+S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S, K34Y+S103N+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75S+R77G+A78W+V79D+F80Y, K34Y+S103N+D445N+V447S+D566T, K34Y+S103N+Y504T+Q594R F595S, K34Y+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+E501V+Y504T, K34Y+S103N+S105L+Y504T+Q594R+F595S, K34Y+S103N+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+Y504T+Q594R+F595S, K34Y+S103N+S105L+Y504T+D566T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+

V447S+D566T+Q594R+F595S, G6S+G7T+R31F+K34Y+S103N+A132P+D445N+V447S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+Y504T+D566T+Q594R+F595S, K34Y+S103N+A132R+D445N+V447S+Y504T+D566T+Q594R+F595S, K34Y+S103N+S105L+A132R+D445N+V447S+Y504T+D566T+V592T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+Y504T+D566T+Q594R+F595S, K34Y+S103N+P107L+A132R+D445N+V447S+Y504T+D566T+Q594R+F595S, G6S+G7T+K34Y+S103N+P107L+A132P+D445N+V447S+E501V+Y504T, K34Y+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+E501V+Y504T+D566T+Q594R+F595S, K34Y+D75N+R77D+A78Q+S103N+R138L+D445N+V447S+Y504T+Q594R+F595S, R31F+K34Y+D75N+R77D+A78Q+S103N+R138L+D445N+V447S+Y504T+Q594R+F595S, K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+S105L+A132R+D445N+V447S+Y504T+D566T+Q594R+F595S, G6S+G7T+K34Y+S103N+P107L+A132R+D445N+V447S+Y504T+D566T+Q594R+F595S, G6S+G7T+K34Y+S103N+P107L+A132P+D445N+V447S+Y504T+D566T+Q594R+F595S, G6S+G7T+K34Y+S103N+P107L+A132P+D445N+V447S+D566T+T568V+Q594R+F595S, R31F+K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+A132R+D445N+V447S+Y504T+D566T+V592T+Q594R+F595S, G6S+G7T+K34Y+S103N+P107L+A132R+D445N+V447S+Y504T+D566T+T568V+Q594R+F595S, G6S+G7T+K34Y+S103N+P107L+A132P+D445N+V447S+Y504T+D566T+T568V+Q594R+F595S, G6S+G7T+K34Y+S103N+P107L+A132R+D445N+V447S+S481P+Y504T+D566T+Q594R+F595S, G6S+G7T+K34Y+S103N+P107L+A132R+D445N+V447S+S481P+Y504T+D566T+T568V+Q594R+F595S, G6S+G7T+R31F+K34Y+S103N+P107L+A132P+D445N+V447S+Y504T+D566T+T568V+Q594R+F595S, G6S+G7T+R31F+K34Y+S103N+A132P+D445N+V447S+S481P+D566T+T568V+Q594R+F595S, G6S+G7T+K34Y+E50R+S103N+A132P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+T110W+A132P+D445N+V447S+Y504T+D566T+T568V+Q594R+F595S, G6S+G7T+K34Y+E50R+S103N+P107L+A132P+D445N+V447S+Y504T+D566T+T568V+Q594R+F595S, G6S+G7T+R31F+K34Y+S103N+P107L+A132P+D445N+V447S+S481P+D566T+T568V+Q594R+F595S, G6S+G7T+R31F+K34Y+E50R+S103N+A132P+D445N+V447S+S481P+D566T+T568V+Q594R+F595S, G6S+G7T+R31F+K34Y+S103N+A132P+R138G+D445N+V447S+S481P+D566T+T568V+Q594R+F595S, G6S+

G7T+R31F+K34Y+S103N+A132P+R138L+D445N+V447S+S481P+D566T+T568V+Q594R+F595S, G6S+G7T+R31F+K34Y+S103N+A132P+R138P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+Y504T+D566T+T568V+Q594R+F595S, G6S+G7T+K34Y+E50R+S103N+P107L+A132P+D445N+V447S+S481P+Y504T+D566T+T568V+Q594R+F595S, G6S+G7T+R31F+K34Y+E50R+S103N+A132P+D445N+V447S+S481P+E501L+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+E501V+Y504T+D566T+T568V+Q594R+F595S, G6S+G7T+R31F+K34Y+E50R+D75N+R77D+A78Q+S103N+A132P+D445N+V447S+S481P+D566T+Q594R+F595S, G6S+G7T+R31F+K34Y+E50R+S103N+A132P+S379P+D445N+V447S+S481P+E501A+D566T+T568V+Q594R+F595S, G6S+G7T+R31F+K34Y+E50R+S103N+A132P+D445N+V447S+S481P+T484P+E501A+D566T+T568V+Q594R+F595S, G6S+G7T+R31F+K34Y+E50R+S103N+A132P+D445N+V447S+S481P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+E50R+D75N+R77D+A78Q+S103N+A132P+R138L+D445N+V447S+S481P+D566T+Q594R+F595S, G6S+G7T+R31F+K34Y+E50R+S103N+A132P+S379P+D445N+V447S+S481P+T484P+E501A+D566T+T568V+Q594R+F595S, G6S+G7T+R31F+K34Y+E50R+S103N+A132P+D445N+V447S+S481P+T484P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+D75N+R77D+A78Q+S103N+P107L+A132P+D445N+V447S+S481P+Y504T+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 3 is present or added during liquefaction, saccharification, fermentation or simultaneous saccharification and fermentation, or used as a component of an enzyme blend or composition of the invention.

In one aspect, a glucoamylase variant comprising substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: S105L, S105E, A132R, R135S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: K34Y+S103N, K34Y+Y504T, S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75N+R77D+A78Q, K34Y+D445N+V447S, S103N+D445N+V447S, D445N+V447S+Y504T, K34Y+S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S, K34Y+S103N+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75S+R77G+A78W+V79D+F80Y, K34Y+S103N+D445N+V447S+D566T, K34Y+S103N+Y504T+Q594R F595S, K34Y+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+E501V+Y504T, K34Y+S103N+S105L+Y504T+Q594R+F595S, K34Y+S103N+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+Y504T+Q594R+F595S, K34Y+S103N+S105L+Y504T+D566T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+D566T+Q594R+F595S, G6S+G7T+R31F+K34Y+S103N+A132P+D445N+V447S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+Y504T+D566T+Q594R+F595S, K34Y+S103N+A132R+D445N+V447S+Y504T+D566T+Q594R+F595S, K34Y+S103N+S105L+A132R+D445N+V447S+Y504T+D566T+V592T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+Y504T+D566T+Q594R+F595S, K34Y+S103N+P107L+A132R+D445N+V447S+Y504T+D566T+Q594R+F595S, G6S+G7T+K34Y+S103N+P107L+A132P+D445N+V447S+E501V+Y504T, K34Y+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+E501V+Y504T+D566T+Q594R+F595S, K34Y+D75N+R77D+A78Q+S103N+R138L+D445N+V447S+Y504T+Q594R+F595S, R31F+K34Y+D75N+R77D+A78Q+S103N+R138L+D445N+V447S+Y504T+Q594R+F595S, K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+S105L+A132R+D445N+V447S+Y504T+D566T+Q594R+F595S, G6S+G7T+K34Y+S103N+P107L+A132R+D445N+V447S+Y504T+D566T+Q594R+F595S, G6S+G7T+K34Y+S103N+P107L+A132P+D445N+V447S+Y504T+D566T+Q594R+F595S, G6S+G7T+K34Y+S103N+P107L+A132P+D445N+V447S+D566T+T568V+Q594R+F595S, R31F+K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+A132R+D445N+V447S+Y504T+D566T+V592T+Q594R+F595S, G6S+G7T+K34Y+S103N+P107L+A132R+D445N+V447S+Y504T+D566T+T568V+Q594R+F595S, G6S+G7T+K34Y+S103N+P107L+A132P+D445N+V447S+Y504T+D566T+T568V+Q594R+F595S, G6S+G7T+K34Y+S103N+P107L+A132R+D445N+V447S+S481P+Y504T+D566T+Q594R+F595S, G6S+G7T+K34Y+S103N+P107L+A132R+D445N+V447S+S481P+Y504T+D566T+T568V+Q594R+F595S, G6S+G7T+R31F+K34Y+S103N+P107L+A132P+D445N+V447S+Y504T+D566T+T568V+Q594R+F595S, G6S+G7T+R31F+K34Y+S103N+A132P+D445N+V447S+S481P+D566T+T568V+Q594R+F595S, G6S+G7T+K34Y+E50R+S103N+A132P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+T110W+A132P+D445N+V447S+Y504T+D566T+T568V+Q594R+F595S, G6S+G7T+K34Y+E50R+S103N+P107L+A132P+D445N+V447S+Y504T+D566T+T568V+Q594R+F595S, G6S+G7T+R31F+K34Y+S103N+P107L+A132P+D445N+V447S+S481P+D566T+T568V+Q594R+F595S, G6S+G7T+R31F+K34Y+E50R+S103N+A132P+D445N+V447S+S481P+D566T+T568V+Q594R+F595S, G6S+G7T+R31F+K34Y+S103N+A132P+R138G+D445N+V447S+S481P+D566T+T568V+Q594R+F595S, G6S+G7T+R31F+K34Y+S103N+A132P+R138L+D445N+V447S+S481P+D566T+T568V+Q594R+F595S, G6S+G7T+R31F+K34Y+S103N+A132P+R138P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+Y504T+D566T+T568V+Q594R+F595S, G6S+G7T+K34Y+E50R+S103N+P107L+A132P+D445N+V447S+S481P+Y504T+D566T+T568V+Q594R+F595S, G6S+G7T+R31F+K34Y+E50R+S103N+A132P+D445N+V447S+S481P+E501L+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+E501V+Y504T+D566T+T568V+Q594R+F595S, G6S+G7T+R31F+K34Y+E50R+D75N+R77D+A78Q+S103N+A132P+D445N+V447S+S481P+D566T+Q594R+F595S, G6S+G7T+R31F+K34Y+E50R+S103N+A132P+S379P+D445N+V447S+S481P+E501A+D566T+T568V+Q594R+F595S, G6S+G7T+R31F+K34Y+E50R+S103N+A132P+D445N+V447S+S481P+T484P+E501A+D566T+T568V+Q594R+F595S, G6S+G7T+R31F+K34Y+E50R+S103N+A132P+D445N+V447S+S481P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+E50R+D75N+R77D+A78Q+S103N+A132P+R138L+D445N+V447S+S481P+D566T+Q594R+F595S, G6S+G7T+R31F+K34Y+E50R+S103N+A132P+S379P+D445N+V447S+S481P+T484P+E501A+D566T+T568V+Q594R+F595S, G6S+G7T+R31F+K34Y+E50R+S103N+A132P+D445N+V447S+S481P+T484P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+D75N+R77D+A78Q+S103N+P107L+A132P+D445N+V447S+S481P+Y504T+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 4 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: S105L, S105E, A132R, R135S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: K34Y+S103N, K34Y+Y504T, S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75N+R77D+A78Q, K34Y+D445N+V447S, S103N+D445N+V447S, D445N+V447S+Y504T, K34Y+S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S, K34Y+S103N+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75S+R77G+A78W+V79D+F80Y, K34Y+S103N+D445N+V447S+D566T, K34Y+S103N+Y504T+Q594R F595S, K34Y+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+E501V+Y504T, K34Y+S103N+S105L+Y504T+Q594R+F595S, K34Y+S103N+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+Y504T+Q594R+F595S, K34Y+S103N+S105L+Y504T+D566T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+D566T+Q594R+F595S, G6S+G7T+R31F+K34Y+S103N+A132P+D445N+V447S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+Y504T+D566T+Q594R+F595S, K34Y+S103N+A132R+D445N+V447S+Y504T+D566T+Q594R+F595S, K34Y+S103N+S105L+A132R+D445N+V447S+Y504T+D566T+V592T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+Y504T+D566T+Q594R+F595S, K34Y+S103N+P107L+A132R+D445N+V447S+Y504T+D566T+Q594R+F595S, G6S+G7T+K34Y+S103N+P107L+A132P+D445N+V447S+E501V+Y504T, K34Y+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+E501V+Y504T+D566T+Q594R+F595S, K34Y+D75N+R77D+A78Q+S103N+R138L+D445N+

V447S+Y504T+Q594R+F595S, R31F+K34Y+D75N+R77D+A78Q+S103N+R138L+D445N+V447S+Y504T+Q594R+F595S, K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+S105L+A132R+D445N+V447S+Y504T+D566T+Q594R+F595S, G6S+G7T+K34Y+S103N+P107L+A132R+D445N+V447S+Y504T+D566T+Q594R+F595S, G6S+G7T+K34Y+S103N+P107L+A132P+D445N+V447S+Y504T+D566T+Q594R+F595S, G6S+G7T+K34Y+S103N+P107L+A132P+D445N+V447S+D566T+T568V+Q594R+F595S, R31F+K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+A132R+D445N+V447S+Y504T+D566T+V592T+Q594R+F595S, G6S+G7T+K34Y+S103N+P107L+A132R+D445N+V447S+Y504T+D566T+T568V+Q594R+F595S, G6S+G7T+K34Y+S103N+P107L+A132P+D445N+V447S+Y504T+D566T+T568V+Q594R+F595S, G6S+G7T+K34Y+S103N+P107L+A132R+D445N+V447S+S481P+Y504T+D566T+Q594R+F595S, G6S+G7T+K34Y+S103N+P107L+A132R+D445N+V447S+S481P+Y504T+D566T+T568V+Q594R+F595S, G6S+G7T+R31F+K34Y+S103N+P107L+A132P+D445N+V447S+Y504T+D566T+T568V+Q594R+F595S, G6S+G7T+R31F+K34Y+S103N+A132P+D445N+V447S+S481P+D566T+T568V+Q594R+F595S, G6S+G7T+K34Y+E50R+S103N+A132P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+T110W+A132P+D445N+V447S+Y504T+D566T+T568V+Q594R+F595S, G6S+G7T+K34Y+E50R+S103N+P107L+A132P+D445N+V447S+Y504T+D566T+T568V+Q594R+F595S, G6S+G7T+R31F+K34Y+S103N+P107L+A132P+D445N+V447S+S481P+D566T+T568V+Q594R+F595S, G6S+G7T+R31F+K34Y+E50R+S103N+A132P+D445N+V447S+S481P+D566T+T568V+Q594R+F595S, G6S+G7T+R31F+K34Y+S103N+A132P+R138G+D445N+V447S+S481P+D566T+T568V+Q594R+F595S, G6S+G7T+R31F+K34Y+S103N+A132P+R138L+D445N+V447S+S481P+D566T+T568V+Q594R+F595S, G6S+G7T+R31F+K34Y+S103N+A132P+R138P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+Y504T+D566T+T568V+Q594R+F595S, G6S+G7T+K34Y+E50R+S103N+P107L+A132P+D445N+V447S+S481P+Y504T+D566T+T568V+Q594R+F595S, G6S+G7T+R31F+K34Y+E50R+S103N+A132P+D445N+V447S+S481P+E501L+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+E501V+Y504T+D566T+T568V+Q594R+F595S, G6S+G7T+R31F+K34Y+E50R+D75N+R77D+A78Q+S103N+A132P+D445N+V447S+S481P+D566T+Q594R+F595S, G6S+G7T+R31F+K34Y+E50R+S103N+A132P+S379P+D445N+V447S+S481P+E501A+D566T+T568V+Q594R+F595S, G6S+G7T+R31F+K34Y+E50R+S103N+A132P+D445N+V447S+S481P+T484P+E501A+D566T+T568V+Q594R+F595S, G6S+G7T+R31F+K34Y+E50R+S103N+A132P+D445N+V447S+S481P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising comprises substitutions at positions corresponding to positions selected from a group consisting of: G6S+G7T+R31F+K34Y+E50R+D75N+R77D+A78Q+S103N+A132P+R138L+D445N+V447S+S481P+D566T+Q594R+F595S, G6S+G7T+R31F+K34Y+E50R+S103N+A132P+S379P+D445N+V447S+S481P+T484P+E501A+D566T+T568V+Q594R+F595S, G6S+G7T+R31F+K34Y+E50R+S103N+A132P+D445N+V447S+S481P+T484P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+D75N+R77D+A78Q+S103N+P107L+A132P+D445N+V447S+S481P+Y504T+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 5 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitution at one or more positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: S105L, S105E, A132R, R135S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: K34Y+S103N, K34Y+Y504T, S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75N+R77D+A78Q, K34Y+D445N+V447S, S103N+D445N+V447S, D445N+V447S+Y504T, K34Y+S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S, K34Y+S103N+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75S+R77G+A78W+V79D+F80Y, K34Y+S103N+D445N+V447S+D566T, K34Y+S103N+Y504T+Q594R F595S, K34Y+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+E501V+Y504T, K34Y+S103N+S105L+Y504T+Q594R+F595S, K34Y+S103N+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+Y504T+Q594R+F595S, K34Y+S103N+S105L+Y504T+D566T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+D566T+Q594R+F595S, G6S+G7T+R31F+K34Y+S103N+A132P+D445N+V447S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+Y504T+D566T+Q594R+F595S, K34Y+S103N+A132R+D445N+V447S+Y504T+D566T+Q594R+F595S, K34Y+S103N+S105L+A132R+D445N+V447S+Y504T+D566T+V592T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+Y504T+D566T+Q594R+F595S, K34Y+S103N+P107L+A132R+D445N+V447S+Y504T+D566T+Q594R+F595S, G6S+G7T+K34Y+S103N+P107L+A132P+D445N+V447S+E501V+Y504T, K34Y+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+E501V+Y504T+D566T+Q594R+F595S, K34Y+D75N+R77D+A78Q+S103N+R138L+D445N+V447S+Y504T+Q594R+F595S, R31F+K34Y+D75N+R77D+A78Q+S103N+R138L+D445N+V447S+Y504T+Q594R+F595S, K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+S105L+A132R+D445N+V447S+Y504T+D566T+Q594R+F595S, G6S+G7T+K34Y+S103N+P107L+A132R+D445N+V447S+Y504T+D566T+Q594R+F595S, G6S+G7T+K34Y+S103N+P107L+A132P+D445N+V447S+Y504T+D566T+Q594R+F595S, G6S+G7T+K34Y+S103N+P107L+A132P+D445N+V447S+D566T+T568V+Q594R+F595S, R31F+K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+A132R+D445N+V447S+Y504T+D566T+V592T+Q594R+F595S, G6S+G7T+K34Y+S103N+P107L+A132R+D445N+V447S+Y504T+D566T+T568V+Q594R+F595S, G6S+G7T+K34Y+S103N+P107L+A132P+D445N+V447S+Y504T+D566T+T568V+Q594R+F595S, G6S+G7T+K34Y+S103N+P107L+A132R+D445N+V447S+S481P+Y504T+D566T+Q594R+F595S, G6S+G7T+K34Y+S103N+P107L+A132R+D445N+V447S+S481P+Y504T+D566T+T568V+Q594R+F595S, G6S+G7T+R31F+K34Y+S103N+P107L+A132P+D445N+V447S+Y504T+D566T+T568V+Q594R+F595S, G6S+G7T+R31F+K34Y+S103N+A132P+D445N+V447S+S481P+D566T+T568V+Q594R+F595S, G6S+G7T+K34Y+E50R+S103N+A132P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+T110W+A132P+D445N+V447S+Y504T+D566T+T568V+Q594R+F595S, G6S+G7T+K34Y+E50R+S103N+P107L+A132P+D445N+V447S+Y504T+D566T+T568V+Q594R+F595S, G6S+G7T+R31F+K34Y+S103N+P107L+A132P+D445N+V447S+S481P+D566T+T568V+Q594R+F595S, G6S+G7T+R31F+K34Y+E50R+S103N+A132P+D445N+V447S+S481P+D566T+T568V+Q594R+F595S, G6S+G7T+R31F+K34Y+S103N+A132P+R138G+D445N+V447S+S481P+D566T+T568V+Q594R+F595S, G6S+G7T+R31F+K34Y+S103N+A132P+R138L+D445N+V447S+S481P+D566T+T568V+Q594R+F595S, G6S+G7T+R31F+K34Y+S103N+A132P+R138P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+Y504T+D566T+T568V+Q594R+F595S, G6S+G7T+K34Y+E50R+S103N+P107L+A132P+D445N+V447S+S481P+Y504T+D566T+T568V+Q594R+F595S, G6S+G7T+R31F+K34Y+E50R+S103N+A132P+D445N+V447S+S481P+E501L+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+E501V+Y504T+D566T+T568V+Q594R+F595S, G6S+G7T+R31F+K34Y+E50R+D75N+R77D+A78Q+S103N+A132P+D445N+V447S+S481P+D566T+Q594R+F595S, G6S+G7T+R31F+K34Y+E50R+S103N+A132P+S379P+D445N+V447S+S481P+E501A+D566T+T568V+Q594R+F595S, G6S+G7T+R31F+K34Y+E50R+S103N+A132P+D445N+V447S+S481P+T484P+E501A+D566T+T568V+Q594R+F595S, G6S+G7T+R31F+K34Y+E50R+S103N+A132P+D445N+V447S+S481P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+E50R+D75N+R77D+A78Q+S103N+A132P+R138L+D445N+V447S+S481P+D566T+Q594R+F595S, G6S+G7T+R31F+K34Y+E50R+S103N+A132P+S379P+D445N+V447S+S481P+T484P+E501A+D566T+T568V+Q594R+F595S, G6S+G7T+R31F+K34Y+E50R+S103N+A132P+D445N+V447S+S481P+T484P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+D75N+R77D+A78Q+S103N+P107L+A132P+D445N+V447S+S481P+Y504T+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 6 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: S105L, S105E, A132R, R135S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: K34Y+S103N, K34Y+Y504T, S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75N+R77D+A78Q, K34Y+D445N+V447S, S103N+D445N+V447S, D445N+V447S+Y504T, K34Y+S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S, K34Y+S103N+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75S+R77G+A78W+V79D+F80Y, K34Y+S103N+D445N+V447S+D566T, K34Y+S103N+Y504T+Q594R F595S, K34Y+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+E501V+Y504T, K34Y+S103N+S105L+Y504T+Q594R+F595S, K34Y+S103N+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising at positions corresponding to positions selected from a group consisting of: K34Y+S103N+D445N+V447S+Y504T+Q594R+F595S, K34Y+S103N+S105L+Y504T+D566T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+D566T+Q594R+F595S, G6S+G7T+R31F+K34Y+S103N+A132P+D445N+V447S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+Y504T+D566T+Q594R+F595S, K34Y+S103N+A132R+D445N+V447S+Y504T+D566T+Q594R+F595S, K34Y+S103N+S105L+A132R+D445N+V447S+Y504T+D566T+V592T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+Y504T+D566T+Q594R+F595S, K34Y+S103N+P107L+A132R+D445N+V447S+Y504T+D566T+Q594R+F595S, G6S+G7T+K34Y+S103N+P107L+A132P+D445N+V447S+E501V+Y504T, K34Y+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+E501V+Y504T+D566T+Q594R+F595S, K34Y+D75N+R77D+A78Q+S103N+R138L+D445N+V447S+Y504T+Q594R+F595S, R31F+K34Y+D75N+R77D+A78Q+S103N+R138L+D445N+V447S+Y504T+Q594R+F595S, K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+S105L+A132R+D445N+V447S+Y504T+D566T+Q594R+F595S, G6S+G7T+K34Y+S103N+P107L+A132R+D445N+V447S+Y504T+D566T+Q594R+F595S, G6S+G7T+K34Y+S103N+P107L+A132P+D445N+V447S+Y504T+D566T+Q594R+F595S, G6S+G7T+K34Y+S103N+P107L+A132P+D445N+V447S+D566T+T568V+Q594R+F595S, R31F+K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+A132R+D445N+V447S+Y504T+D566T+V592T+Q594R+F595S, G6S+G7T+K34Y+S103N+P107L+A132R+D445N+V447S+Y504T+D566T+T568V+Q594R+F595S, G6S+G7T+K34Y+S103N+P107L+A132P+D445N+V447S+Y504T+D566T+T568V+Q594R+F595S, G6S+G7T+K34Y+S103N+P107L+A132R+D445N+V447S+S481P+Y504T+D566T+Q594R+F595S, G6S+G7T+K34Y+S103N+P107L+A132R+D445N+V447S+S481P+Y504T+D566T+T568V+Q594R+F595S, G6S+G7T+R31F+K34Y+S103N+P107L+A132P+D445N+V447S+Y504T+D566T+T568V+Q594R+F595S, G6S+G7T+R31F+K34Y+S103N+A132P+D445N+V447S+S481P+D566T+T568V+Q594R+F595S, G6S+G7T+K34Y+E50R+

S103N+A132P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+T110W+A132P+D445N+V447S+Y504T+D566T+T568V+Q594R+F595S, G6S+G7T+K34Y+E50R+S103N+P107L+A132P+D445N+V447S+Y504T+D566T+T568V+Q594R+F595S, G6S+G7T+R31F+K34Y+S103N+P107L+A132P+D445N+V447S+S481P+D566T+T568V+Q594R+F595S, G6S+G7T+R31F+K34Y+E50R+S103N+A132P+D445N+V447S+S481P+D566T+T568V+Q594R+F595S, G6S+G7T+R31F+K34Y+S103N+A132P+R138G+D445N+V447S+S481P+D566T+T568V+Q594R+F595S, G6S+G7T+R31F+K34Y+S103N+A132P+R138L+D445N+V447S+S481P+D566T+T568V+Q594R+F595S, G6S+G7T+R31F+K34Y+S103N+A132P+R138P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+Y504T+D566T+T568V+Q594R+F595S, G6S+G7T+K34Y+E50R+S103N+P107L+A132P+D445N+V447S+S481P+Y504T+D566T+T568V+Q594R+F595S, G6S+G7T+R31F+K34Y+E50R+S103N+A132P+D445N+V447S+S481P+E501L+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+E501V+Y504T+D566T+T568V+Q594R+F595S, G6S+G7T+R31F+K34Y+E50R+D75N+R77D+A78Q+S103N+A132P+D445N+V447S+S481P+D566T+Q594R+F595S, G6S+G7T+R31F+K34Y+E50R+S103N+A132P+S379P+D445N+V447S+S481P+E501A+D566T+T568V+Q594R+F595S, G6S+G7T+R31F+K34Y+E50R+S103N+A132P+D445N+V447S+S481P+T484P+E501A+D566T+T568V+Q594R+F595S, G6S+G7T+R31F+K34Y+E50R+S103N+A132P+D445N+V447S+S481P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+E50R+D75N+R77D+A78Q+S103N+A132P+R138L+D445N+V447S+S481P+D566T+Q594R+F595S, G6S+G7T+R31F+K34Y+E50R+S103N+A132P+S379P+D445N+V447S+S481P+T484P+E501A+D566T+T568V+Q594R+F595S, G6S+G7T+R31F+K34Y+E50R+S103N+A132P+D445N+V447S+S481P+T484P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+D75N+R77D+A78Q+S103N+P107L+A132P+D445N+V447S+S481P+Y504T+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 7 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: S105L, S105E, A132R, R135S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: K34Y+S103N, K34Y+Y504T, S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75N+R77D+A78Q, K34Y+D445N+V447S, S103N+D445N+V447S, D445N+V447S+Y504T, K34Y+S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S, K34Y+S103N+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75S+R77G+A78W+V79D+F80Y, K34Y+S103N+D445N+V447S+D566T, K34Y+S103N+Y504T+Q594R F595S, K34Y+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+E501V+Y504T, K34Y+S103N+S105L+Y504T+Q594R+F595S, K34Y+S103N+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+Y504T+Q594R+F595S, K34Y+S103N+S105L+Y504T+D566T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+D566T+Q594R+F595S, G6S+G7T+R31F+K34Y+S103N+A132P+D445N+V447S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+Y504T+D566T+Q594R+F595S, K34Y+S103N+A132R+D445N+V447S+Y504T+D566T+Q594R+F595S, K34Y+S103N+S105L+A132R+D445N+V447S+Y504T+D566T+V592T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+Y504T+D566T+Q594R+F595S, K34Y+S103N+P107L+A132R+D445N+V447S+Y504T+D566T+Q594R+F595S, G6S+G7T+K34Y+S103N+P107L+A132P+D445N+V447S+E501V+Y504T, K34Y+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+E501V+Y504T+D566T+Q594R+F595S, K34Y+D75N+R77D+A78Q+S103N+R138L+D445N+V447S+Y504T+Q594R+F595S, R31F+K34Y+D75N+R77D+A78Q+S103N+R138L+D445N+V447S+Y504T+Q594R+F595S, K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+S105L+A132R+D445N+V447S+Y504T+D566T+Q594R+F595S, G6S+G7T+K34Y+S103N+P107L+A132R+D445N+V447S+Y504T+D566T+Q594R+F595S, G6S+G7T+K34Y+S103N+P107L+A132P+D445N+V447S+Y504T+D566T+Q594R+F595S, G6S+G7T+K34Y+S103N+P107L+A132P+D445N+V447S+D566T+T568V+Q594R+F595S, R31F+K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+A132R+D445N+V447S+Y504T+D566T+V592T+Q594R+F595S, G6S+G7T+K34Y+S103N+P107L+A132R+D445N+V447S+Y504T+D566T+T568V+Q594R+F595S, G6S+G7T+K34Y+S103N+P107L+A132P+D445N+V447S+Y504T+D566T+T568V+Q594R+F595S, G6S+G7T+K34Y+S103N+P107L+A132R+D445N+V447S+S481P+Y504T+D566T+Q594R+F595S, G6S+G7T+K34Y+S103N+P107L+A132R+D445N+V447S+S481P+Y504T+D566T+T568V+Q594R+F595S, G6S+G7T+R31F+K34Y+S103N+P107L+A132P+D445N+V447S+Y504T+D566T+T568V+Q594R+F595S, G6S+G7T+R31F+K34Y+S103N+A132P+D445N+V447S+S481P+D566T+T568V+Q594R+F595S, G6S+G7T+K34Y+E50R+S103N+A132P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+T110W+A132P+D445N+V447S+Y504T+D566T+T568V+Q594R+F595S, G6S+G7T+K34Y+E50R+S103N+P107L+A132P+D445N+V447S+Y504T+D566T+T568V+Q594R+F595S, G6S+G7T+R31F+K34Y+S103N+P107L+A132P+D445N+V447S+S481P+D566T+T568V+Q594R+F595S, G6S+G7T+R31F+K34Y+E50R+S103N+A132P+D445N+V447S+S481P+D566T+T568V+Q594R+F595S, G6S+G7T+R31F+K34Y+S103N+A132P+R138G+D445N+V447S+S481P+D566T+T568V+Q594R+F595S, G6S+G7T+R31F+K34Y+S103N+A132P+R138L+D445N+V447S+S481P+D566T+T568V+Q594R+F595S, G6S+

G7T+R31F+K34Y+S103N+A132P+R138P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+Y504T+D566T+T568V+Q594R+F595S, G6S+G7T+K34Y+E50R+S103N+P107L+A132P+D445N+V447S+S481P+Y504T+D566T+T568V+Q594R+F595S, G6S+G7T+R31F+K34Y+E50R+S103N+A132P+D445N+V447S+S481P+E501L+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+E501V+Y504T+D566T+T568V+Q594R+F595S, G6S+G7T+R31F+K34Y+E50R+D75N+R77D+A78Q+S103N+A132P+D445N+V447S+S481P+D566T+Q594R+F595S, G6S+G7T+R31F+K34Y+E50R+S103N+A132P+S379P+D445N+V447S+S481P+E501A+D566T+T568V+Q594R+F595S, G6S+G7T+R31F+K34Y+E50R+S103N+A132P+D445N+V447S+S481P+T484P+E501A+D566T+T568V+Q594R+F595S, G6S+G7T+R31F+K34Y+E50R+S103N+A132P+D445N+V447S+S481P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+E50R+D75N+R77D+A78Q+S103N+A132P+R138L+D445N+V447S+S481P+D566T+Q594R+F595S, G6S+G7T+R31F+K34Y+E50R+S103N+A132P+S379P+D445N+V447S+S481P+T484P+E501A+D566T+T568V+Q594R+F595S, G6S+G7T+R31F+K34Y+E50R+S103N+A132P+D445N+V447S+S481P+T484P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+D75N+R77D+A78Q+S103N+P107L+A132P+D445N+V447S+S481P+Y504T+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 8 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: S105L, S105E, A132R, R135S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: K34Y+S103N, K34Y+Y504T, S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75N+R77D+A78Q, K34Y+D445N+V447S, S103N+D445N+V447S, D445N+V447S+Y504T, K34Y+S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S, K34Y+S103N+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75S+R77G+A78W+V79D+F80Y, K34Y+S103N+D445N+V447S+D566T, K34Y+S103N+Y504T+Q594R F595S, K34Y+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+E501V+Y504T, K34Y+S103N+S105L+Y504T+Q594R+F595S, K34Y+S103N+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+Y504T+Q594R+F595S, K34Y+S103N+S105L+Y504T+D566T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+D566T+Q594R+F595S, G6S+G7T+R31F+K34Y+S103N+A132P+D445N+V447S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+Y504T+D566T+Q594R+F595S, K34Y+S103N+A132R+D445N+V447S+Y504T+D566T+Q594R+F595S, K34Y+S103N+S105L+A132R+D445N+V447S+Y504T+D566T+V592T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+Y504T+D566T+Q594R+F595S, K34Y+S103N+P107L+A132R+D445N+V447S+Y504T+D566T+Q594R+F595S, G6S+G7T+K34Y+S103N+P107L+A132P+D445N+V447S+E501V+Y504T, K34Y+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+E501V+Y504T+D566T+Q594R+F595S, K34Y+D75N+R77D+A78Q+S103N+R138L+D445N+V447S+Y504T+Q594R+F595S, R31F+K34Y+D75N+R77D+A78Q+S103N+R138L+D445N+V447S+Y504T+Q594R+F595S, K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+S105L+A132R+D445N+V447S+Y504T+D566T+Q594R+F595S, G6S+G7T+K34Y+S103N+P107L+A132R+D445N+V447S+Y504T+D566T+Q594R+F595S, G6S+G7T+K34Y+S103N+P107L+A132P+D445N+V447S+Y504T+D566T+Q594R+F595S, G6S+G7T+K34Y+S103N+P107L+A132P+D445N+V447S+D566T+T568V+Q594R+F595S, R31F+K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+A132R+D445N+V447S+Y504T+D566T+V592T+Q594R+F595S, G6S+G7T+K34Y+S103N+P107L+A132R+D445N+V447S+Y504T+D566T+T568V+Q594R+F595S, G6S+G7T+K34Y+S103N+P107L+A132P+D445N+V447S+Y504T+D566T+T568V+Q594R+F595S, G6S+G7T+K34Y+S103N+P107L+A132R+D445N+V447S+S481P+Y504T+D566T+Q594R+F595S, G6S+G7T+K34Y+S103N+P107L+A132R+D445N+V447S+S481P+Y504T+D566T+T568V+Q594R+F595S, G6S+G7T+R31F+K34Y+S103N+P107L+A132P+D445N+V447S+Y504T+D566T+T568V+Q594R+F595S, G6S+G7T+R31F+K34Y+S103N+A132P+D445N+V447S+S481P+D566T+T568V+Q594R+F595S, G6S+G7T+K34Y+E50R+S103N+A132P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+T110W+A132P+D445N+V447S+Y504T+D566T+T568V+Q594R+F595S, G6S+G7T+K34Y+E50R+S103N+P107L+A132P+D445N+V447S+Y504T+D566T+T568V+Q594R+F595S, G6S+G7T+R31F+K34Y+S103N+P107L+A132P+D445N+V447S+S481P+D566T+T568V+Q594R+F595S, G6S+G7T+R31F+K34Y+E50R+S103N+A132P+D445N+V447S+S481P+D566T+T568V+Q594R+F595S, G6S+G7T+R31F+K34Y+S103N+A132P+R138G+D445N+V447S+S481P+D566T+T568V+Q594R+F595S, G6S+G7T+R31F+K34Y+S103N+A132P+R138L+D445N+V447S+S481P+D566T+T568V+Q594R+F595S, G6S+G7T+R31F+K34Y+S103N+A132P+R138P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+Y504T+D566T+T568V+Q594R+F595S, G6S+G7T+K34Y+E50R+S103N+P107L+A132P+D445N+V447S+S481P+Y504T+D566T+T568V+Q594R+F595S, G6S+G7T+R31F+K34Y+E50R+S103N+A132P+D445N+V447S+S481P+E501L+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+E501V+Y504T+D566T+T568V+Q594R+F595S, G6S+G7T+R31F+K34Y+E50R+D75N+R77D+A78Q+S103N+A132P+D445N+V447S+S481P+D566T+Q594R+F595S, G6S+G7T+R31F+K34Y+E50R+S103N+A132P+S379P+D445N+V447S+S481P+E501A+D566T+T568V+Q594R+F595S, G6S+G7T+R31F+K34Y+E50R+S103N+A132P+D445N+V447S+S481P+T484P+E501A+D566T+T568V+Q594R+F595S, G6S+G7T+R31F+K34Y+E50R+S103N+A132P+D445N+V447S+S481P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+E50R+D75N+R77D+A78Q+S103N+A132P+R138L+D445N+V447S+S481P+D566T+Q594R+F595S, G6S+G7T+R31F+K34Y+E50R+S103N+A132P+S379P+D445N+V447S+S481P+T484P+E501A+D566T+T568V+Q594R+F595S, G6S+G7T+R31F+K34Y+E50R+S103N+A132P+D445N+V447S+S481P+T484P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+D75N+R77D+A78Q+S103N+P107L+A132P+D445N+V447S+S481P+Y504T+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 9 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: S105L, S105E, A132R, R135S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: K34Y+S103N, K34Y+Y504T, S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75N+R77D+A78Q, K34Y+D445N+V447S, S103N+D445N+V447S, D445N+V447S+Y504T, K34Y+S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S, K34Y+S103N+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75S+R77G+A78W+V79D+F80Y, K34Y+S103N+D445N+V447S+D566T, K34Y+S103N+Y504T+Q594R F595S, K34Y+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+E501V+Y504T, K34Y+S103N+S105L+Y504T+Q594R+F595S, K34Y+S103N+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+Y504T+Q594R+F595S, K34Y+S103N+S105L+Y504T+D566T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+D566T+Q594R+F595S, G6S+G7T+R31F+K34Y+S103N+A132P+D445N+V447S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+Y504T+D566T+Q594R+F595S, K34Y+S103N+A132R+D445N+V447S+Y504T+D566T+Q594R+F595S, K34Y+S103N+S105L+A132R+D445N+V447S+Y504T+D566T+V592T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+Y504T+D566T+Q594R+F595S, K34Y+S103N+P107L+A132R+D445N+V447S+Y504T+D566T+Q594R+F595S, G6S+G7T+K34Y+S103N+P107L+A132P+D445N+V447S+E501V+Y504T, K34Y+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+E501V+Y504T+D566T+Q594R+F595S, K34Y+D75N+R77D+A78Q+S103N+R138L+D445N+

V447S+Y504T+Q594R+F595S, R31F+K34Y+D75N+R77D+A78Q+S103N+R138L+D445N+V447S+Y504T+Q594R+F595S, K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+S105L+A132R+D445N+V447S+Y504T+D566T+Q594R+F595S, G6S+G7T+K34Y+S103N+P107L+A132R+D445N+V447S+Y504T+D566T+Q594R+F595S, G6S+G7T+K34Y+S103N+P107L+A132P+D445N+V447S+Y504T+D566T+Q594R+F595S, G6S+G7T+K34Y+S103N+P107L+A132P+D445N+V447S+D566T+T568V+Q594R+F595S, R31F+K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+A132R+D445N+V447S+Y504T+D566T+V592T+Q594R+F595S, G6S+G7T+K34Y+S103N+P107L+A132R+D445N+V447S+Y504T+D566T+T568V+Q594R+F595S, G6S+G7T+K34Y+S103N+P107L+A132P+D445N+V447S+Y504T+D566T+T568V+Q594R+F595S, G6S+G7T+K34Y+S103N+P107L+A132R+D445N+V447S+S481P+Y504T+D566T+Q594R+F595S, G6S+G7T+K34Y+S103N+P107L+A132R+D445N+V447S+S481P+Y504T+D566T+T568V+Q594R+F595S, G6S+G7T+R31F+K34Y+S103N+P107L+A132P+D445N+V447S+Y504T+D566T+T568V+Q594R+F595S, G6S+G7T+R31F+K34Y+S103N+A132P+D445N+V447S+S481P+D566T+T568V+Q594R+F595S, G6S+G7T+K34Y+E50R+S103N+A132P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+T110W+A132P+D445N+V447S+Y504T+D566T+T568V+Q594R+F595S, G6S+G7T+K34Y+E50R+S103N+P107L+A132P+D445N+V447S+Y504T+D566T+T568V+Q594R+F595S, G6S+G7T+R31F+K34Y+S103N+P107L+A132P+D445N+V447S+S481P+D566T+T568V+Q594R+F595S, G6S+G7T+R31F+K34Y+E50R+S103N+A132P+D445N+V447S+S481P+D566T+T568V+Q594R+F595S, G6S+G7T+R31F+K34Y+S103N+A132P+R138G+D445N+V447S+S481P+D566T+T568V+Q594R+F595S, G6S+G7T+R31F+K34Y+S103N+A132P+R138L+D445N+V447S+S481P+D566T+T568V+Q594R+F595S, G6S+G7T+R31F+K34Y+S103N+A132P+R138P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+Y504T+D566T+T568V+Q594R+F595S, G6S+G7T+K34Y+E50R+S103N+P107L+A132P+D445N+V447S+S481P+Y504T+D566T+T568V+Q594R+F595S, G6S+G7T+R31F+K34Y+E50R+S103N+A132P+D445N+V447S+S481P+E501L+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+E501V+Y504T+D566T+T568V+Q594R+F595S, G6S+G7T+R31F+K34Y+E50R+D75N+R77D+A78Q+S103N+A132P+D445N+V447S+S481P+D566T+Q594R+F595S, G6S+G7T+R31F+K34Y+E50R+S103N+A132P+S379P+D445N+V447S+S481P+E501A+D566T+T568V+Q594R+F595S, G6S+G7T+R31F+K34Y+E50R+S103N+A132P+D445N+V447S+S481P+T484P+E501A+D566T+T568V+Q594R+F595S, G6S+G7T+R31F+K34Y+E50R+S103N+A132P+D445N+V447S+S481P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+E50R+D75N+R77D+A78Q+S103N+A132P+R138L+D445N+V447S+S481P+D566T+Q594R+F595S, G6S+G7T+R31F+K34Y+E50R+S103N+A132P+S379P+D445N+V447S+S481P+T484P+E501A+D566T+T568V+Q594R+F595S, G6S+G7T+R31F+K34Y+E50R+S103N+A132P+D445N+V447S+S481P+T484P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+D75N+R77D+A78Q+S103N+P107L+A132P+D445N+V447S+S481P+Y504T+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 10 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: S105L, S105E, A132R, R135S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising comprises one or more of the following substitutions at positions corresponding to positions: K34Y+S103N, K34Y+Y504T, S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75N+R77D+A78Q, K34Y+D445N+V447S, S103N+D445N+V447S, D445N+V447S+Y504T, K34Y+S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S, K34Y+S103N+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75S+R77G+A78W+V79D+F80Y, K34Y+S103N+D445N+V447S+D566T, K34Y+S103N+Y504T+Q594R F595S, K34Y+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+E501V+Y504T, K34Y+S103N+S105L+Y504T+Q594R+F595S, K34Y+S103N+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+Y504T+Q594R+F595S, K34Y+S103N+S105L+Y504T+D566T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+D566T+Q594R+F595S, G6S+G7T+R31F+K34Y+S103N+A132P+D445N+V447S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+Y504T+D566T+Q594R+F595S, K34Y+S103N+A132R+D445N+V447S+Y504T+D566T+Q594R+F595S, K34Y+S103N+S105L+A132R+D445N+V447S+Y504T+D566T+V592T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+Y504T+D566T+Q594R+F595S, K34Y+S103N+P107L+A132R+D445N+V447S+Y504T+D566T+Q594R+F595S, G6S+G7T+K34Y+S103N+P107L+A132P+D445N+V447S+E501V+Y504T, K34Y+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+E501V+Y504T+D566T+Q594R+F595S, K34Y+D75N+R77D+A78Q+S103N+R138L+D445N+V447S+Y504T+Q594R+F595S, R31F+K34Y+D75N+R77D+A78Q+S103N+R138L+D445N+V447S+Y504T+Q594R+F595S, K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+S105L+A132R+D445N+V447S+Y504T+D566T+Q594R+F595S, G6S+G7T+K34Y+S103N+P107L+A132R+D445N+V447S+Y504T+D566T+Q594R+F595S, G6S+G7T+K34Y+S103N+P107L+A132P+D445N+V447S+Y504T+D566T+Q594R+F595S, G6S+G7T+K34Y+S103N+P107L+A132P+D445N+V447S+D566T+T568V+Q594R+F595S, R31F+K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+A132R+D445N+V447S+Y504T+D566T+V592T+Q594R+F595S, G6S+G7T+K34Y+S103N+P107L+A132R+D445N+V447S+Y504T+D566T+T568V+Q594R+F595S, G6S+G7T+K34Y+S103N+P107L+A132P+D445N+V447S+Y504T+D566T+T568V+Q594R+F595S, G6S+G7T+K34Y+S103N+P107L+A132R+D445N+V447S+S481P+Y504T+D566T+Q594R+F595S, G6S+G7T+K34Y+S103N+P107L+A132R+D445N+V447S+S481P+Y504T+D566T+T568V+Q594R+F595S, G6S+G7T+R31F+K34Y+S103N+P107L+A132P+D445N+V447S+Y504T+D566T+T568V+Q594R+F595S, G6S+G7T+R31F+K34Y+S103N+A132P+D445N+V447S+S481P+D566T+T568V+Q594R+F595S, G6S+G7T+K34Y+E50R+S103N+A132P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+T110W+A132P+D445N+V447S+Y504T+D566T+T568V+Q594R+F595S, G6S+G7T+K34Y+E50R+S103N+P107L+A132P+D445N+V447S+Y504T+D566T+T568V+Q594R+F595S, G6S+G7T+R31F+K34Y+S103N+P107L+A132P+D445N+V447S+S481P+D566T+T568V+Q594R+F595S, G6S+G7T+R31F+K34Y+E50R+S103N+A132P+D445N+V447S+S481P+D566T+T568V+Q594R+F595S, G6S+G7T+R31F+K34Y+S103N+A132P+R138G+D445N+V447S+S481P+D566T+T568V+Q594R+F595S, G6S+G7T+R31F+K34Y+S103N+A132P+R138L+D445N+V447S+S481P+D566T+T568V+Q594R+F595S, G6S+G7T+R31F+K34Y+S103N+A132P+R138P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+Y504T+D566T+T568V+Q594R+F595S, G6S+G7T+K34Y+E50R+S103N+P107L+A132P+D445N+V447S+S481P+Y504T+D566T+T568V+Q594R+F595S, G6S+G7T+R31F+K34Y+E50R+S103N+A132P+D445N+V447S+S481P+E501L+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+E501V+Y504T+D566T+T568V+Q594R+F595S, G6S+G7T+R31F+K34Y+E50R+D75N+R77D+A78Q+S103N+A132P+D445N+V447S+S481P+D566T+Q594R+F595S, G6S+G7T+R31F+K34Y+E50R+S103N+A132P+S379P+D445N+V447S+S481P+E501A+D566T+T568V+Q594R+F595S, G6S+G7T+R31F+K34Y+E50R+S103N+A132P+D445N+V447S+S481P+T484P+E501A+D566T+T568V+Q594R+F595S, G6S+G7T+R31F+K34Y+E50R+S103N+A132P+D445N+V447S+S481P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+E50R+D75N+R77D+A78Q+S103N+A132P+R138L+D445N+V447S+S481P+D566T+Q594R+F595S, G6S+G7T+R31F+K34Y+E50R+S103N+A132P+S379P+D445N+V447S+S481P+T484P+E501A+D566T+T568V+Q594R+F595S, G6S+G7T+R31F+K34Y+E50R+S103N+A132P+D445N+V447S+S481P+T484P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+D75N+R77D+A78Q+S103N+P107L+A132P+D445N+V447S+S481P+Y504T+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 11 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: S105L, S105E, A132R, R135S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: K34Y+S103N, K34Y+Y504T, S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75N+R77D+A78Q, K34Y+D445N+V447S, S103N+D445N+V447S, D445N+V447S+Y504T, K34Y+S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S, K34Y+S103N+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75S+R77G+A78W+V79D+F80Y, K34Y+S103N+D445N+V447S+D566T, K34Y+S103N+Y504T+Q594R F595S, K34Y+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+E501V+Y504T, K34Y+S103N+S105L+Y504T+Q594R+F595S, K34Y+S103N+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+Y504T+Q594R+F595S, K34Y+S103N+S105L+Y504T+D566T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+D566T+Q594R+F595S, G6S+G7T+R31F+K34Y+S103N+A132P+D445N+V447S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+Y504T+D566T+Q594R+F595S, K34Y+S103N+A132R+D445N+V447S+Y504T+D566T+Q594R+F595S, K34Y+S103N+S105L+A132R+D445N+V447S+Y504T+D566T+V592T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+Y504T+D566T+Q594R+F595S, K34Y+S103N+P107L+A132R+D445N+V447S+Y504T+D566T+Q594R+F595S, G6S+G7T+K34Y+S103N+P107L+A132P+D445N+V447S+E501V+Y504T, K34Y+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+E501V+Y504T+D566T+Q594R+F595S, K34Y+D75N+R77D+A78Q+S103N+R138L+D445N+V447S+Y504T+Q594R+F595S, R31F+K34Y+D75N+R77D+A78Q+S103N+R138L+D445N+V447S+Y504T+Q594R+F595S, K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+S105L+A132R+D445N+V447S+Y504T+D566T+Q594R+F595S, G6S+G7T+K34Y+S103N+P107L+A132R+D445N+V447S+Y504T+D566T+Q594R+F595S, G6S+G7T+K34Y+S103N+P107L+A132P+D445N+V447S+Y504T+D566T+Q594R+F595S, G6S+G7T+K34Y+S103N+P107L+A132P+D445N+V447S+D566T+T568V+Q594R+F595S, R31F+K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+A132R+D445N+V447S+Y504T+D566T+V592T+Q594R+F595S, G6S+G7T+K34Y+S103N+P107L+A132R+D445N+V447S+Y504T+D566T+T568V+Q594R+F595S, G6S+G7T+K34Y+S103N+P107L+A132P+D445N+V447S+Y504T+D566T+T568V+Q594R+F595S, G6S+G7T+K34Y+S103N+P107L+A132R+D445N+V447S+S481P+Y504T+D566T+Q594R+F595S, G6S+G7T+K34Y+S103N+P107L+A132R+D445N+V447S+S481P+Y504T+D566T+T568V+Q594R+F595S, G6S+G7T+R31F+K34Y+S103N+P107L+A132P+D445N+V447S+Y504T+D566T+T568V+Q594R+F595S, G6S+G7T+R31F+K34Y+S103N+A132P+D445N+V447S+S481P+D566T+T568V+Q594R+F595S, G6S+G7T+K34Y+E50R+

S103N+A132P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+T110W+A132P+D445N+V447S+Y504T+D566T+T568V+Q594R+F595S, G6S+G7T+K34Y+E50R+S103N+P107L+A132P+D445N+V447S+Y504T+D566T+T568V+Q594R+F595S, G6S+G7T+R31F+K34Y+S103N+P107L+A132P+D445N+V447S+S481P+D566T+T568V+Q594R+F595S, G6S+G7T+R31F+K34Y+E50R+S103N+A132P+D445N+V447S+S481P+D566T+T568V+Q594R+F595S, G6S+G7T+R31F+K34Y+S103N+A132P+R138G+D445N+V447S+S481P+D566T+T568V+Q594R+F595S, G6S+G7T+R31F+K34Y+S103N+A132P+R138L+D445N+V447S+S481P+D566T+T568V+Q594R+F595S, G6S+G7T+R31F+K34Y+S103N+A132P+R138P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+Y504T+D566T+T568V+Q594R+F595S, G6S+G7T+K34Y+E50R+S103N+P107L+A132P+D445N+V447S+S481P+Y504T+D566T+T568V+Q594R+F595S, G6S+G7T+R31F+K34Y+E50R+S103N+A132P+D445N+V447S+S481P+E501L+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+E501V+Y504T+D566T+T568V+Q594R+F595S, G6S+G7T+R31F+K34Y+E50R+D75N+R77D+A78Q+S103N+A132P+D445N+V447S+S481P+D566T+Q594R+F595S, G6S+G7T+R31F+K34Y+E50R+S103N+A132P+S379P+D445N+V447S+S481P+E501A+D566T+T568V+Q594R+F595S, G6S+G7T+R31F+K34Y+E50R+S103N+A132P+D445N+V447S+S481P+T484P+E501A+D566T+T568V+Q594R+F595S, G6S+G7T+R31F+K34Y+E50R+S103N+A132P+D445N+V447S+S481P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+E50R+D75N+R77D+A78Q+S103N+A132P+R138L+D445N+V447S+S481P+D566T+Q594R+F595S, G6S+G7T+R31F+K34Y+E50R+S103N+A132P+S379P+D445N+V447S+S481P+T484P+E501A+D566T+T568V+Q594R+F595S, G6S+G7T+R31F+K34Y+E50R+S103N+A132P+D445N+V447S+S481P+T484P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+D75N+R77D+A78Q+S103N+P107L+A132P+D445N+V447S+S481P+Y504T+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 12 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising a substitution at one or more positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: S105L, S105E, A132R, R135S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising one or more of the following substitutions at positions corresponding to positions: K34Y+S103N, K34Y+Y504T, S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75N+R77D+A78Q, K34Y+D445N+V447S, S103N+D445N+V447S, D445N+V447S+Y504T, K34Y+S103N+Y504T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S, K34Y+S103N+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: D75S+R77G+A78W+V79D+F80Y, K34Y+S103N+D445N+V447S+D566T, K34Y+S103N+Y504T+Q594R F595S, K34Y+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+E501V+Y504T, K34Y+S103N+S105L+Y504T+Q594R+F595S, K34Y+S103N+S105L+Y504T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+D445N+V447S+Y504T+Q594R+F595S, K34Y+S103N+S105L+Y504T+D566T+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+D566T+Q594R+F595S, G6S+G7T+R31F+K34Y+S103N+A132P+D445N+V447S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+D445N+V447S+Y504T+D566T+Q594R+F595S, K34Y+S103N+A132R+D445N+V447S+Y504T+D566T+Q594R+F595S, K34Y+S103N+S105L+A132R+D445N+V447S+Y504T+D566T+V592T of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+Y504T+D566T+Q594R+F595S, K34Y+S103N+P107L+A132R+D445N+V447S+Y504T+D566T+Q594R+F595S, G6S+G7T+K34Y+S103N+P107L+A132P+D445N+V447S+E501V+Y504T, K34Y+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: K34Y+S103N+S105L+A132R+D445N+V447S+E501V+Y504T+D566T+Q594R+F595S, K34Y+D75N+R77D+A78Q+S103N+R138L+D445N+V447S+Y504T+Q594R+F595S, R31F+K34Y+D75N+R77D+A78Q+S103N+R138L+D445N+V447S+Y504T+Q594R+F595S, K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+S105L+A132R+D445N+V447S+Y504T+D566T+Q594R+F595S, G6S+G7T+K34Y+S103N+P107L+A132R+D445N+V447S+Y504T+D566T+Q594R+F595S, G6S+G7T+K34Y+S103N+P107L+A132P+D445N+V447S+Y504T+D566T+Q594R+F595S, G6S+G7T+K34Y+S103N+P107L+A132P+D445N+V447S+D566T+T568V+Q594R+F595S, R31F+K34Y+E50R+D75N+R77D+A78Q+S103N+R138L+D445N+V447S+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+A132R+D445N+V447S+Y504T+D566T+V592T+Q594R+F595S, G6S+G7T+K34Y+S103N+P107L+A132R+D445N+V447S+Y504T+D566T+T568V+Q594R+F595S, G6S+G7T+K34Y+S103N+P107L+A132P+D445N+V447S+Y504T+D566T+T568V+Q594R+F595S, G6S+G7T+K34Y+S103N+P107L+A132R+D445N+V447S+S481P+Y504T+D566T+Q594R+F595S, G6S+G7T+K34Y+S103N+P107L+A132R+D445N+V447S+S481P+Y504T+D566T+T568V+Q594R+F595S, G6S+G7T+R31F+K34Y+S103N+P107L+A132P+D445N+V447S+Y504T+D566T+T568V+Q594R+F595S, G6S+G7T+R31F+K34Y+S103N+A132P+D445N+V447S+S481P+D566T+T568V+Q594R+F595S, G6S+G7T+K34Y+E50R+S103N+A132P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+K34Y+S103N+P107L+T110W+A132P+D445N+V447S+Y504T+D566T+T568V+Q594R+F595S, G6S+G7T+K34Y+E50R+S103N+P107L+A132P+D445N+V447S+Y504T+D566T+T568V+Q594R+F595S, G6S+G7T+R31F+K34Y+S103N+P107L+A132P+D445N+V447S+S481P+D566T+T568V+Q594R+F595S, G6S+G7T+R31F+K34Y+E50R+S103N+A132P+D445N+V447S+S481P+D566T+T568V+Q594R+F595S, G6S+G7T+R31F+K34Y+S103N+A132P+R138G+D445N+V447S+S481P+D566T+T568V+Q594R+F595S, G6S+G7T+R31F+K34Y+S103N+A132P+R138L+D445N+V447S+S481P+D566T+T568V+Q594R+F595S, G6S+

G7T+R31F+K34Y+S103N+A132P+R138P+D445N+V447S+S481P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+Y504T+D566T+T568V+Q594R+F595S, G6S+G7T+K34Y+E50R+S103N+P107L+A132P+D445N+V447S+S481P+Y504T+D566T+T568V+Q594R+F595S, G6S+G7T+R31F+K34Y+E50R+S103N+A132P+D445N+V447S+S481P+E501L+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+S103N+P107L+A132P+D445N+V447S+S481P+E501V+Y504T+D566T+T568V+Q594R+F595S, G6S+G7T+R31F+K34Y+E50R+D75N+R77D+A78Q+S103N+A132P+D445N+V447S+S481P+D566T+Q594R+F595S, G6S+G7T+R31F+K34Y+E50R+S103N+A132P+S379P+D445N+V447S+S481P+E501A+D566T+T568V+Q594R+F595S, G6S+G7T+R31F+K34Y+E50R+S103N+A132P+D445N+V447S+S481P+T484P+E501A+D566T+T568V+Q594R+F595S, G6S+G7T+R31F+K34Y+E50R+S103N+A132P+D445N+V447S+S481P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+E50R+D75N+R77D+A78Q+S103N+A132P+R138L+D445N+V447S+S481P+D566T+Q594R+F595S, G6S+G7T+R31F+K34Y+E50R+S103N+A132P+S379P+D445N+V447S+S481P+T484P+E501A+D566T+T568V+Q594R+F595S, G6S+G7T+R31F+K34Y+E50R+S103N+A132P+D445N+V447S+S481P+T484P+E501A+N539P+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

In one aspect, a glucoamylase variant comprising substitutions at positions corresponding to positions selected from a group consisting of: G6S+G7T+R31F+K34Y+D75N+R77D+A78Q+S103N+P107L+A132P+D445N+V447S+S481P+Y504T+D566T+T568V+Q594R+F595S of SEQ ID NO: 1, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the polypeptide of SEQ ID NO: 13 is present or added during liquefaction, saccharification, fermentation or simultaneous saccharification and fermentation, or used as a component of an enzyme blend or composition of the invention.

Examples of other enzymes that can be added in addition to one or more glucoamylase variant(s) of the present invention during liquefaction or used as a component of an enzyme blend or composition of the invention include, without limitation, thermostable alpha-amylases, endoglucanases, xylanases, phytases, lipases (e.g., phospholipases), pullulanases, and/or proteases.

The invention is further defined in the following paragraphs:

1. A glucoamylase variant comprising a substitution at one or more positions corresponding to positions: 6, 7, 31, 34, 50, 132, 447, 481, 484, 501, 539, 568, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13.
2. The glucoamylase variant according to paragraph 1, wherein the variant optionally further comprises substitution in one or more positions corresponding to positions 11, 75, 77, 78, 79, 80, 103, 105, 107, 110, 135, 138, 379, 445, 504, 566, 594 of SEQ ID NO: 1.
3. The glucoamylase variant according to paragraphs 1-2, wherein the variant comprises a substitution at one or more positions corresponding to positions: 6, 7, 11, 31, 34, 50, 75, 77, 78, 79, 80, 103, 105, 107, 110, 132, 135, 138, 379, 445, 447, 481, 484, 501, 504, 539, 566, 568 592, 594, 595 of SEQ ID NO: 1; and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13.
4. The glucoamylase variant according to any of the preceding paragraphs, wherein the variant has an improved property relative to the parent, wherein the improved property is increased thermostability.

5. The glucoamylase variant according to any of the preceding paragraphs, wherein said improved property is increased thermostability is measured as increased melting temperature using TSA of at least 0.1° C., at least 0.2° C., at least 0.3° C., at least 0.4° C., at least 0.5° C., at least 0.6° C., at least 0.7° C., at least 0.8° C., at least 0.9° C., at least 1° C., at least 1.5° C., at least 2° C., at least 2.5° C., at least 3° C., at least 3.5° C., at least 4.0° C., at least 4.5° C. or of at least 1° C., at least 1.5° C., at least 2° C., at least 2.5° C., at least 3° C., at least 3.5° C., at least 4.0° C., at least 4.5° C. or at least 5° C. or at least 5.5° C. or at least 6° C. or at least 6.5° C. or at least 7° C. or at least 7.5° C. or at least 8° C. or at least 8.5° C. or at least 9° C. or at least 9.5° C. or at least 10° C. compared to said parent glucoamylase.
6. The glucoamylase variant according to any of the preceding paragraphs, wherein variant have a relative activity at 91° C. of at least 150, preferably at least 200, more preferably at least 250, most preferably at least 300 compared to said parent glucoamylase.
7. The glucoamylase variant of any of the preceding paragraphs, wherein said variant comprises one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13.
8. The glucoamylase variant of any of the preceding paragraphs, wherein said variant comprises one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NO: 1.
9. The glucoamylase variant of any of the preceding paragraphs, wherein said variant comprises one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NO: 2.
10. The glucoamylase variant of any of the preceding paragraphs, wherein said variant comprises one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NO: 3.
11. The glucoamylase variant of any of the preceding paragraphs, wherein said variant comprises one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NO: 4.
12. The glucoamylase variant of any of the preceding paragraphs, wherein said variant comprises one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NO: 5.
13. The glucoamylase variant of any of the preceding paragraphs, wherein said variant comprises one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NO: 6.
14. The glucoamylase variant of any of the preceding paragraphs, wherein said variant comprises one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NO: 7.

15. The glucoamylase variant of any of the preceding paragraphs, wherein said variant comprises one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NO: 8.

16. The glucoamylase variant of any of the preceding paragraphs, wherein said variant comprises one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NO: 9.

17. The glucoamylase variant of any of the preceding paragraphs, wherein said variant comprises one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NO: 10.

18. The glucoamylase variant of any of the preceding paragraphs, wherein said variant comprises one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NO: 11.

19. The glucoamylase variant of any of the preceding paragraphs, wherein said variant comprises one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NO: 12.

20. The glucoamylase variant of any of the preceding paragraphs, wherein said variant comprises one or more of the following substitutions at positions corresponding to positions: G6S, G7T, P11F, R31F, K34Y, E50R, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, T484P, E501A, E501L, E501V, Y504T, N539P, D566T, T568V, V592T, Q594R, F595S of SEQ ID NO: 1 and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NO: 13.

21. The variant according to any one of the preceding paragraphs, wherein the number of substitutions is 1-20, e.g., 1-10 and 1-5, such as 1, 2, 3, 4, 5, 6, 7, 8, 9 or 10 substitutions.

22. The variant according to any one of the preceding paragraphs, wherein the variant comprises at least one of the following substitutions or combinations of substitutions:

1. D75N+R77D+A78Q;
2. D75S+R77G+A78W+V79D+F80Y;
3. K34Y+S103N;
4. K34Y+D445N+V447S;
5. K34Y+Y504T;
6. S103N+D445N+V447S;
7. S103N+Y504T;
8. D445N+V447S+Y504T;
9. K34Y+S103N+D445N+V447S;
10. K34Y+S103N+D445N+V447S+E501V+Y504T;
11. K34Y+S103N+Y504T;
12. K34Y+S103N+D445N+V447S+D566T;
13. K34Y+S103N+Q594R+F595S;
14. K34Y+S103N+Y504T+Q594R+F595S;
15. K34Y+S103N+D445N+V447S+Y504T+Q594R+F595S;
16. S105L;
17. S105E;
18. A132R;
19. K34Y+S105L+Y504T+Q594R+F595S;
20. K34Y+S103N+S105L+Y504T+Q594R+F595S;
21. K34Y+S103N+S105L+Y504T+Q594R+F595S;
22. K34Y+S103N+S105L+Y504T D566T Q594R F595S;
23. K34Y+S103N+S105L+D445N+V447S+Y504T+D566T+Q594R+F595S;

24. K34Y+S103N+S105L+A132R+D445N+V447S+Y504T+D566T+Q594R+F595S;
25. K34Y+S103N+S105L+D445N+V447S+D566T+Q594R+F595S;
26. K34Y+S103N+S105L+A132R+D445N+V447S+E501V+Y504T+D566T+Q594R+F595S;
27. K34Y+S103N+A132R+D445N+V447S+Y504T+D566T+Q594R+F595S;
28. K34Y+S103N+S105L+A132R+D445N+V447S+Y504T+D566T+V592T;
29. G6S+G7T+K34Y+S103N+S105L+A132R+D445N+V447S+Y504T+D566T+Q594R+F595S;
30. K34Y+S103N+P107L+A132R+D445N+V447S+Y504T+D566T+Q594R+F595S;
31. G6S+G7T+K34Y+S103N+P107L+A132R+D445N+V447S+Y504T+D566T+Q594R+F595S;
32. G6S+G7T+K34Y+S103N+P107L+A132R+D445N+V447S+Y504T+D566T+V592T+Q594R+F595S;
33. G6S+G7T+K34Y+S103N+P107L+A132P+D445N+V447S+Y504T+D566T+Q594R+F595S;
34. G6S+G7T+K34Y+S103N+P107L+A132R+D445N+V447S+Y504T+D566T+T568V+Q594R+F595S;
35. G6S+G7T+K34Y+S103N+P107L+A132P+D445N+V447S+Y504T+D566T+T568V+Q594R+F595S;
36. G6S+G7T+K34Y+S103N+P107L+A132R+D445N+V447S+S481P+Y504T+D566T+Q594R+F595S;
37. G6S+G7T+K34Y+S103N+P107L+A132R+D445N+V447S+S481P+Y504T+D566T+T568V+Q594R+F595S;
38. G6S+G7T+K34Y+S103N+P107L+A132P+D445N+V447S+D566T+T568V+Q594R+F595S;
39. G6S+G7T+K34Y+S103N+P107L+T110W+A132P+D445N+V447S+Y504T+D566T+T568V+Q594R+F595S;
40. G6S+G7T+K34Y+E50R+S103N+P107L+A132P+D445N+V447S+Y504T+D566T+T568V+Q594R+F595S;
41. G6S+G7T+K34Y+S103N+P107L+A132P+D445N+V447S+E501V+Y504T;
42. G6S+G7T+R31F+K34Y+S103N+P107L+A132P+D445N+V447S+Y504T+D566T+T568V+Q594R+F595S;
43. G6S+G7T+R31F+K34Y+S103N+P107L+A132P+D445N+V447S+S481P+Y504T+D566T+T568V+Q594R+F595S;
44. G6S+G7T+K34Y+E50R+S103N+P107L+A132P+D445N+V447S+S481P+Y504T+D566T+T568V+Q594R+F595S;
45. G6S+G7T+R31F+K34Y+S103N+P107L+A132P+D445N+V447S+S481P+E501V+Y504T+D566T+T568V+Q594R+F595S;
46. G6S+G7T+R31F+K34Y+S103N+P107L+A132P+D445N+V447S+S481P+D566T+T568V+Q594R+F595S;
47. K34Y+D75N+R77D+A78Q+S103N+R138L+D445N+V447S+Y504T+Q594R+F595S;
48. G6S+G7T+R31F+K34Y+D75N+R77D+A78Q+S103N+P107L+A132P+D445N+V447S+S481P+Y504T+D566T+T568V+Q594R+F595S;
49. G6S+G7T+R31F+K34Y+S103N+A132P+D445N+V447S+S481P+D566T+T568V+Q594R+F595S;
50. G6S+G7T+K34Y+E50R+S103N+A132P+D445N+V447S+S481P+D566T+T568V+Q594R+F595S;
51. R31F+K34Y+D75N+R77D+A78Q+S103N+R138L+D445N+V447S+Y504T+Q594R+F595S;
52. K34Y+D75N+R77D+A78Q+S103N+R138L+D445N+V447S+Q594R+F595S;
53. G6S+G7T+R31F+K34Y+S103N+A132P+D445N+V447S;
54. G6S+G7T+R31F+K34Y+E50R+S103N+A132P+D445N+V447S+S481P+D566T+T568V+Q594R+F595S;
55. K34Y+E50R+D75N+R77D+A78Q+S103N+R138L+D445N+V447S+Q594R+F595S;
56. G6S+G7T+R31F+K34Y+E50R+D75N+R77D+A78Q+S103N+A132P+D445N+V447S+S481P+D566T+Q594R+F595S;
57. R31F+K34Y+E50R+D75N+R77D+A78Q+S103N+R138L+D445N+V447S+Q594R+F595S;
58. G6S+G7T+R31F+K34Y+E50R+D75N+R77D+A78Q+S103N+A132P+R138L+D445N+V447S+S481P+D566T+Q594R+F595S;
59. R135S;
60. G6S+G7T+R31F+K34Y+E50R+S103N+A132P+D445N+V447S+S481P+E501L+D566T+T568V+Q594R+F595S;
61. G6S+G7T+R31F+K34Y+S103N+A132P+R138G+D445N+V447S+S481P+D566T+T568V+Q594R+F595S;
62. G6S+G7T+R31F+K34Y+S103N+A132P+R138L+D445N+V447S+S481P+D566T+T568V+Q594R+F595S;
63. G6S+G7T+R31F+K34Y+S103N+A132P+R138P+D445N+V447S+S481P+D566T+T568V+Q594R+F595S;
64. G6S+G7T+R31F+K34Y+E50R+S103N+A132P+S379P+D445N+V447S+S481P+E501A+D566T+T568V+Q594R+F595S;
65. G6S+G7T+R31F+K34Y+E50R+S103N+A132P+D445N+V447S+S481P+T484P+E501A+D566T+T568V+Q594R+F595S;
66. G6S+G7T+R31F+K34Y+E50R+S103N+A132P+D445N+V447S+S481P+E501A+N539P+D566T+T568V+Q594R+F595S;
67. G6S+G7T+R31F+K34Y+E50R+S103N+A132P+S379P+D445N+V447S+S481P+T484P+E501A+D566T+T568V+Q594R+F595S;
68. G6S+G7T+R31F+K34Y+E50R+S103N+A132P+D445N+V447S+S481P+T484P+E501A+N539P+D566T+T568V+Q594R+F595S of SEQ ID NO: 1 and, wherein the variant has glucoamylase activity and wherein said variant has at least 60%, at least 65%, at least 70%, at least 75%, at least 80%, about 85%, about 90%, about 91%, about 92%, about 93%, about 94%, about 95%, about 96%, about 97%, about 98%, about 99%, but less than 100% sequence identity to the polypeptide of SEQ ID NOs: 1-13.

23. An isolated polynucleotide comprising glucoamylase variant of any one of paragraphs 1-22.

24. A nucleic acid construct or expression vector comprising the polynucleotide of paragraph 23, wherein the polynucleotide is operably linked to one or more control sequences that direct the production of the polypeptide in an expression host.

25. A recombinant host cell comprising the polynucleotide of paragraph 23 operably linked to one or more control sequences that direct the production of the polypeptide.
26. The recombinant host cell of paragraph 25, wherein the polypeptide is heterologous to the recombinant host cell.
27. The recombinant host cell of paragraphs 25 or 26, wherein at least one of the one or more control sequences is heterologous to the polynucleotide encoding the polypeptide.
28. The recombinant host cell of any one of paragraphs 25 to 27 which comprises at least two copies, e.g., three, four, or five, of the polynucleotide of paragraph 23.
29. The recombinant host cell of any one of paragraphs 25-28, which is a yeast recombinant host cell, e.g., a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.
30. The recombinant host cell of any one of paragraphs 25-29, which is a filamentous fungal recombinant host cell, e.g., an *Acremonium, Aspergillus*, Aureobasidium, *Bjerkandera, Ceriporiopsis, Chrysosporium, Coprinus, Coriolus*, Cryptococcus, Filibasidium, *Fusarium, Humicola, Magnaporthe, Mucor, Myceliophthora, Neocallimastix, Neurospora, Paecilomyces, Penicillium, Phanerochaete, Phlebia*, Piromyces, *Pleurotus, Schizophyllum, Talaromyces, Thermoascus, Thielavia, Tolypocladium, Trametes*, or *Trichoderma* cell, in particular, an *Aspergillus* awamori, *Aspergillus* foetidus, *Aspergillus* fumigatus, *Aspergillus* japonicus, *Aspergillus* nidulans, *Aspergillus* niger, *Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Talaromyces emersonii, Thielavia terrestris, Trametes villosa, Trametes versicolor, Trichoderma harzianum, Trichoderma koningii, Trichoderma longibrachiatum, Trichoderma reesei*, or *Trichoderma viride* cell.
31. The recombinant host cell of any one of paragraphs 25-30, which is a prokaryotic recombinant host cell, e.g., a Gram-positive cell selected from the group consisting of *Bacillus, Clostridium, Enterococcus, Geobacillus, Lactobacillus, Lactococcus, Oceanobacillus, Staphylococcus, Streptococcus*, or *Streptomyces* cells, or a Gram-negative bacteria selected from the group consisting of *Campylobacter, E. coli, Flavobacterium, Fusobacterium, Helicobacter, Ilyobacter, Neisseria, Pseudomonas, Salmonella*, and *Ureaplasma* cells, such as *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, Bacillus thuringiensis, Streptococcus equisimilis, Streptococcus pyogenes, Streptococcus uberis*, and *Streptococcus equi* subsp. *Zooepidemicus, Streptomyces achromogenes, Streptomyces avermitilis, Streptomyces coelicolor, Streptomyces griseus*, and *Streptomyces lividans* cells.
32. A method of producing the glucoamylase variants of any one of paragraphs 1-22, comprising cultivating a cell, which in its wild-type form produces the glucoamylase variants, under conditions conducive for production of the polypeptide.
33. The method of paragraph 32, further comprising recovering the glucoamylase variants.
34. A method of producing a glucoamylase variants, comprising cultivating the recombinant host cell of any one of paragraphs 25-31 under conditions conducive for production of the glucoamylase variants.
35. The method of paragraph 34, further comprising recovering the glucoamylase variants.
36. A method of producing a glucoamylase variant of any one of paragraphs 1-22, comprising cultivating the recombinant host cell under conditions conducive for production of the variant and optionally, recovering the variant.
37. A process of producing a fermentation product from starch-containing material comprising the steps of:
 (a) liquefying starch-containing material in the presence of an alpha amylase;
 (b) saccharifying the liquefied material; and
 (c) fermenting with a fermenting organism;

wherein step (a), step (b), and/or step (c) is carried out using at least a glucoamylase variant of any of paragraphs 1-22.

38. A process of producing a fermentation product from starch-containing material, comprising the steps of:
 (a) saccharifying starch-containing material at a temperature below the initial gelatinization temperature of said starch-containing material; and
 (b) fermenting with a fermenting organism, wherein step (a) and/or step (b) is carried out using at least a glucoamylase variant of any of paragraphs 1-22.
39. A process for producing a fermentation product from a cellulosic-containing material comprising:
 a. optionally pretreating a cellulosic-containing material;
 b. saccharifying a cellulosic-containing material and/or pretreated cellulosic-containing material using a carbohydrate-source generating enzyme; and
 c. fermenting using a fermenting organism;
 wherein at least one or more glucoamylase variant(s) of the present invention is present or added during saccharifying step (b) and/or fermenting step c).
40. The process of any one of paragraphs 37-39, wherein saccharifying step ii) and fermenting step iii) are per formed simultaneously in a simultaneous saccharification and fermentation.

41. The process of any one of paragraphs 37-40, wherein at least glucoamylase variant(s) are present or added during fermentation or simultaneous saccharification and fermentation.
42. The process of any one of paragraphs 37-41, wherein at least glucoamylase variant(s) is present or added during fermentation or simultaneous saccharification and fermentation.
43. The process of any one of paragraphs 37-42, wherein the at least glucoamylase variant(s) are dosed in the range 0.1-1000 micro gram EP/g DS; 0.5-500 micro gram EP/g DS; 1-100 micro gram EP/g DS; such as 5-50 micro gram EP/g DS.
44. The process of any one of paragraphs 37-43, wherein saccharification is performed in the presence of at least one cellulase/cellulolytic composition.
45. The process of paragraph 44, wherein the cellulases/cellulolytic composition are derived from a strain of *Trichoderma*, in particular *Trichoderma reesei*, or a strain of *Humicola*, in particular *Humicola insolens*, or a strain of *Chrysosporium*, in particular *Chrysosporium lucknowense.*
46. The process of paragraphs 44 or 45, wherein the cellulases/cellulolytic composition comprises a beta-glucosidase, a cellobiohydrolase and an endoglucanase.
47. The process of any one of paragraphs 44-46, wherein the cellulases/cellulolytic composition comprises one or more polypeptides selected from the group consisting of:
   beta-glucosidase;
   cellobiohydrolase I; and
   endoglucanase I, or a mixture of two or three thereof.
48. The process of any one of paragraphs 44-47, wherein the cellulases/cellulolytic composition comprises one or more of the following components:
   (i) an *Aspergillus fumigatus* beta-glucosidase or a variant thereof;
   d. (ii) an *Aspergillus fumigatus* cellobiohydrolase I; and
   e. (iii) a *Trichoderma reesei* endoglucanase I.
49. The process of any one of paragraphs 44-48, wherein the cellulases/cellulolytic composition is a *Trichoderma reesei* cellulolytic composition further comprising:
   (i) an *Aspergillus fumigatus* beta-glucosidase disclosed in SEQ ID NO: 16 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 16; (ii) a cellobiohydrolase I (CBH I), such as one derived from a strain of the genus *Aspergillus*, such as a strain of *Aspergillus fumigatus*, such as the CBHI disclosed as SEQ ID NO: 17, or a CBHI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 17; and
   f. (iii) an endoglucanase I (EGI), such as one derived from a strain of the genus *Trichoderma*, such as a strain of *Trichoderma reesei*, such as the EGI disclosed as SEQ ID NO: 19, or an EGI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 19.
50. The process of any one of paragraphs 44-49, wherein the cellulases/cellulolytic composition comprises a beta-glucosidase, a cellobiohydrolase and an endoglucanase.
51. The process of any one of paragraphs 44-50, wherein the cellulases/cellulolytic composition comprises one or more polypeptides selected from the group consisting of:
   GH61 polypeptide having cellulolytic enhancing activity;
   beta-glucosidase;
   Cellobiohydrolase I;
   Cellobiohydrolase II;
   or a mixture of two, three, or four thereof.
52. The process of any one of paragraphs 44-51, wherein the cellulases/cellulolytic composition comprises one or more polypeptides selected from the group consisting of:
   GH61 polypeptide having cellulolytic enhancing activity;
   beta-glucosidase;
   Cellobiohydrolase I;
   Cellobiohydrolase II;
   or a mixture of two, three, or four thereof.
53. The process of any one of paragraphs 44-52, wherein the cellulases/cellulolytic composition comprises one or more of the following components:
   (i) an *Aspergillus fumigatus* cellobiohydrolase I;
   g. (ii) an *Aspergillus fumigatus* cellobiohydrolase II;
   h. (iii) an *Aspergillus fumigatus* beta-glucosidase or variant thereof; and
   i. (iv) a *Penicillium* sp. GH61 polypeptide having cellulolytic enhancing activity;
   or homologs thereof.
54. The process of any one of paragraphs 44-53, wherein the cellulases/cellulolytic composition is a *Trichoderma reesei* cellulolytic enzyme composition further comprising *Penicillium emersonii* GH61A polypeptide having cellulolytic enhancing activity disclosed in SEQ ID NO: 121, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 121 and an *Aspergillus fumigatus* beta-glucosidase disclosed in SEQ ID NO: 16 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 16.

55. The process of any one of paragraphs 44-54, wherein the cellulolytic composition comprises a cellobiohydrolase I (CBH I), such as one derived from a strain of the genus *Aspergillus*, such as a strain of *Aspergillus fumigatus*, such as the CBHI disclosed as SEQ ID NO: 17, or CBH I having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 17.

56. The process of any one of paragraphs 44-55, wherein the cellulolytic composition comprises a cellobiohydrolase II (CBH II), such as one derived from a strain of the genus *Aspergillus*, such as a strain of *Aspergillus fumigatus*; such as the CBH II disclosed as SEQ ID NO: 18, or a CBH II having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 18.

57. The process of any one of paragraphs 44-56, wherein liquefaction is performed in the presence of a protease having a thermostability value of more than 20% determined as Relative Activity at 80° C./70° C.

58. The process of any one of paragraphs 44-57, wherein liquefaction is performed in the presence of a glucoamylase.

59. The process of any one of paragraphs 44-59, wherein the carbohydrate-source generating enzyme(s) is at least a glucoamylase and optionally in combination with a fungal acid alpha-amylase.

60. The process of any one of paragraphs 44-59, wherein the fermentation product is an alcohol, preferably ethanol, especially fuel ethanol, potable ethanol and/or industrial ethanol.

61. The process of any one of paragraphs 44-60, wherein the alpha-amylase is a bacterial or fungal alpha-amylase.

62. The process of any one of paragraphs 44-61, wherein the alpha-amylase is from the genus *Bacillus*, such as a strain of *Bacillus stearothermophilus*, in particular a variant of a *Bacillus stearothermophilus* alpha-amylase, such as the one shown in SEQ ID NO: 20, or alpha-amylase having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 126.

63. The process of any one of paragraphs 44-62, wherein the *Bacillus stearothermophilus* alpha-amylase comprises a deletion of two amino acids in the region corresponding to positions 179-182 using SEQ ID NO: 20 for numbering.

66. The process of paragraph 63, wherein the deletion is selected from the group consisting of 179*+180*, 179*+181*, 179*+182*, 180*+181*, 180*+182*, and 181*+182*, particularly I181*+G182*.

67. The process of any one of paragraphs 61-63, wherein the alpha-amylase comprises a substitution N193F using SEQ ID NO: 20 for numbering.

68. The process of any one of paragraphs 61-65, wherein the *Bacillus stearothermophilus* alpha-amylase has a substitution in position S242, preferably S242Q substitution using SEQ ID NO: 20 for numbering.

69. The process of any one of paragraphs 61-66, wherein the *Bacillus stearothermophilus* alpha-amylase has a substitution in position E188, preferably E188P substitution using SEQ ID NO: 20 for numbering.

70. The process of any one of paragraphs 59-67, wherein the alpha-amylase has a T % (min) at pH 4.5, 85° C., 0.12 mM $CaCl_2$) of at least 10, such as at least 15, such as at least 20, such as at least 25, such as at least 30, such as at least 40, such as at least 50, such as at least 60, such as between $10^{-70}$, such as between 15-70, such as between 20-70, such as between 25-70, such as between 30-70, such as between 40-70, such as between 50-70, such as between 60-70.

71. The process of any one of paragraphs 59-67, wherein the alpha-amylase is selected from the following group of *Bacillus stearothermophilus* alpha-amylase variants (using SEQ ID NO: 20 for numbering):
I181*+G182*+N193F+E129V+K177L+R179E;
181*+G182*+N193F+V59A+Q89R+E129V+K177L+R179E+H208Y+K220P+N224L+Q254S
I181*+G182*+N193F+V59A+Q89R+E129V+K177L+R179E+Q254S+M284V;
I181*+G182*+N193F+V59A+E129V+K177L+R179E+Q254S+M284V;
I181*+G182*+N193F+E129V+K177L+R179E+K220P+N224L+S242Q+Q254S;
I181*+G182*+V59A+E129V+K177L+R179E+Q254S+M284V+V212T+Y268G+N293Y+T297N;
I181*+G182*+V59A+E129V+K177L+R179E+Q254S+M284V+V212T+Y268G+N293Y+T297N+S173N+E188P+H208Y+S242Y+K2791;
I181*+G182*+V59A+E129V+K177L+R179S+Q254S+M284V+V212T+Y268G+N293Y+T297N+A184Q+E188P+T191N
I181*+G182*+V59A+E129V+K177L+R179S+Q254S+M284V+V212T+Y268G+N293Y+T297N+A184Q+E188P+T191N+S242Y+K2791;
I181*+G182*+V59A+E129V+K177L+R179E+Q254S+M284V+V212T+Y268G+N293Y+T297N+E188P+K279W;
I181*+G182*+V59A+E129V+K177L+R179E+Q254S+M284V+V212T+Y268G+N293Y+T297N+W115D+D117Q+T133P;
and wherein the variant has at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 20.

72. The process of any one of paragraphs 59-69, wherein a protease with a thermostability value of more than 25% determined as Relative Activity at 80° C./70° C. is present in liquefaction step i).

73. The process of any one of paragraphs 59-69, the protease has a thermostability of more than 30%, more than 40%, more than 50%, more than 60%, more than 70%, more than 80%, more than 90%, more than 100%, such as more than $10^5$%, such as more than 110%, such as more than 115%, such as more than 120% determined as Relative Activity at 80° C./70° C.

74. The process of any one of paragraphs 59-71, wherein the alpha-amylase has a T % (min) at pH 4.5, 85° C., 0.12 mM $CaCl_2$) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

75. The process of any one of paragraphs 59-72, wherein the protease has a thermostability of between 20% and 50%, such as between 20% and 40%, such as 20% and 30% determined as Relative Activity at 80° C./70° C.

76. The process of any one of paragraphs 59-73, wherein the protease has a thermostability between 50% and 115%, such as between 50% and 70%, such as between 50% and 60%, such as between 100% and 120%, such as between $10^5$% and 115% determined as Relative Activity at 80° C./70° C.

77. The process of any one of paragraphs 59-75, wherein the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

78. The process of any one of paragraphs 59-75, wherein the protease has thermostability of between 10% and 50%, such as between 10% and 30%, such as between 10% and 25% determined as Relative Activity at 85° C./70° C.

79. The process of any one of paragraphs 59-76, wherein the protease has a thermostability above 60%, such as above 90%, such as above 100%, such as above 110% at 85° C. as determined using the Zein-BCA assay.

81. The process of any one of paragraphs 73-77, wherein the protease has a thermostability between 60-120, such as between 70-120%, such as between 80-120%, such as between 90-120%, such as between 100-120%, such as 110-120% at 85° C. as determined using the Zein-BCA assay.

82. The process of any one of paragraphs 73-78, wherein the protease is of fungal or bacterial origin.

83. The process of any one of paragraphs 73-79, wherein the protease is a metallo protease or a serine protease.

84. The process of any one of paragraphs 73-80, wherein the protease is a variant of the metallo protease derived from a strain of the genus *Thermoascus*, preferably a strain of *Thermoascus aurantiacus*, especially *Thermoascus aurantiacus* CGMCC No. 0670.

85. The process of any one of paragraphs 73-81, wherein the protease is a variant of the metallo protease disclosed as SEQ ID NO: 20 with the following mutations:
j. D79L+S87P+A112P+D142L;
k. D79L+S87P+D142L; or
l. A27K+D79L+Y82F+S87G+D104P+A112P+A126V+D142L; and wherein the protease has at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 20.

86. The process of any one of paragraphs 73-82, wherein the protease is a serine protease, particularly an S8 serine protease derived from a strain of *Pyrococcus*, preferably a strain of *Pyrococcus furiosus*, or derived from a strain of *Thermococcus*, preferably Themococcus *thioreducens* or *Thermococcus* nautili, or derived from a strain of *Palaeococcus*, preferably *Palaeococcus ferrophilus*

87. The process of any one of paragraphs 73-83, wherein the protease is derived from a strain of *Pyrococcus*, preferably a strain of *Pyrococcus furiosus*.

88. The process of any one of paragraphs 73-84, wherein the protease is the one shown in SEQ ID NO: 21, or a protease having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 21.

89. The process of any one of paragraphs 73-85, wherein the protease is derived from a strain of *Thermobifida*, preferably a strain of *Thermobifida* cellulosytica.

90. The process of any one of paragraphs 73-86, wherein the protease is the one shown in SEQ ID NO: 33, or a protease having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 33.

91. The process of any one of paragraphs 73-87, wherein a glucoamylase is present and/or added during saccharification and/or fermentation.

92. The process of paragraphs 73-88, wherein the glucoamylase present and/or added during saccharification and/or fermentation is of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *Talaromyces emersonii*, or a strain of *Trametes*, preferably *Trametes cingulata*, or a strain of Pycnoporus, or a strain of *Gloeophyllum*, such as a strain of *Gloeophyllum sepiarium* or *Gloeophyllum trabeum* or a strain of the *Nigrofomes*.

93. The process of any one of paragraphs 73-89, wherein the glucoamylase present and/or added during saccharification and/or fermentation is a blend comprising *Talaromyces emersonii* glucoamylase of SEQ ID NO: 26, or glucoamylase having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 26, a *Trametes cingulata* glucoamylase of SEQ ID NO: 25, or glucoamylase having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 25, and a *Rhizomucor pusillus* alpha-amylase with an *Aspergillus niger* glucoamylase linker and starch-binding domain (SBD), of SEQ ID NO: 30, and comprising the following substitutions: G128D+D143N, and having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 30.

94. The process of any one of paragraphs 73-90, wherein the glucoamylase present and/or added during saccharification and/or fermentation is a blend comprising *Gloeophyllum sepiarium* glucoamylase shown as SEQ ID NO: 134, or a glucoamylase having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 134, and an alpha-amylase from *Rhizomucor pusillus* with an *Aspergillus niger* glucoamylase linker and starch-binding domain (SBD), disclosed SEQ ID NO: 30 with the following substitutions: G128D+D143N, and having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 30.

95. The process of any one of paragraphs 73-91, wherein a trehalase is present and/or added during saccharification and/or fermentation.

96. The process of paragraph 95, wherein the trehalase present and/or added during saccharification and/or fermentation is a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the mature polypeptide of SEQ ID NO: 31 and having trehalase activity.

97. The process of paragraph 95, wherein the trehalase present and/or added during saccharification and/or fermentation is a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the mature polypeptide of SEQ ID NO: 31 and having trehalase activity.

98. The process of any one of paragraphs 37-94, wherein fermentation or simultaneous saccharification and fermentation (SSF) are carried out at a temperature from 25° C. to 40° C., such as from 28° C. to 35° C., such as from 30° C. to 34° C., preferably around about 32° C.

99. The process of any one of paragraphs 37-98, wherein the fermentation product is recovered after fermentation, such as by distillation.

100. The process of any one of paragraphs 37-99, wherein the starch-containing starting material is whole grains.

101. The process of any one of paragraphs 37-100, wherein the starch-containing material is derived from corn, wheat, barley, rye, milo, sago, cassava, manioc, tapioca, sorghum, rice or potatoes.

102. The process of any one of paragraphs 37-101, wherein the cellulosic-containing material is selected from the group consisting of agricultural residue, herbaceous material (including energy crops), municipal solid waste, pulp and paper mill residue, waste paper, and wood (including forestry residue).

103. The process of any one of paragraphs 37-102, wherein the cellulosic-containing material is *arundo*, bagasse, bamboo, corn cob, corn fiber, corn stover, *miscanthus*, rice straw, switchgrass, and wheat straw.

104. The process of any one of paragraphs 37-103, wherein the cellulosic-containing material is selected from the group consisting of aspen, *eucalyptus*, fir, pine, poplar, spruce, or willow.

105. The process of any one of paragraphs 37-104, wherein the cellulosic-containing material is selected from the group consisting of algal cellulose, bacterial cellulose, cotton linter, filter paper, microcrystalline cellulose (e.g., AVICEL®), or phosphoric-acid treated cellulose 106. The process of any one of paragraphs 37-10$^5$, wherein the cellulosic-containing material is an aquatic biomass.

107. The process of any one of paragraphs 37-106, wherein the cellulosic-containing material is a whole stillage byproduct of a process for producing a fermentation product from a starch-contaning material.

108. The process of any one of paragraphs 37-10$^7$, wherein the organism applied in fermentation is a yeast, particularly a *Saccharomyces* spp., more particular *Saccharomyces cerevisiae.*

109. An enzyme blend or enzyme composition comprising at least comprising the variant of any of paragraphs 1-20 and one or more additional enzymes.

110. The blend or composition of paragraph 109, further comprising a carbohydrate-source generating enzyme, particularly a glucoamylase.

111. The blend or composition of any one of paragraphs 109-110, further comprising a cellulase/cellulolytic composition according to any one of paragraphs 86-98.

112. The composition of paragraphs 109-111, wherein the additional enzyme selected from the group consisting of an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, trehalase, and xylanase.

113. A composition comprising:

(i) a recombinant yeast host cell or fermenting organism, wherein the yeast host cell or fermenting organism comprises a heterologous polynucleotide encoding a glucoamylase, an alpha-amylase, protease, and/or cellulase; and m. (ii) a one or more glucoamylase variant(s) of any of paragraphs 1-22.

114. Use of glucoamylase variant of any of any of paragraphs 1-22.

115. A granule, which comprises:

n. a core comprising the glucoamylase variant of any one of paragraphs 1-22, and optionally, o. a coating consisting of one or more layer(s) surrounding the core.

116. A granule, which comprises:

p. a core, and q. a coating consisting of one or more layer(s) surrounding the core, wherein the coating comprises the glucoamylase variant of any one of paragraphs 1-22.

The present invention is further described by the following examples that should not be construed as limiting the scope of the invention.

EXAMPLES

Materials and Methods

Glucoamylase Activity

Glucoamylase activity may be measured in AGU Units.

Glucoamylase Activity (AGU)

The Glucoamylase Unit (AGU) is defined as the amount of enzyme, which hydrolyzes 1 micromole maltose per minute under the standard conditions (37° C., pH 4.3, substrate: maltose 100 mM, buffer: acetate 0.1 M, reaction time 6 minutes as set out in the glucoamylase incubation below), thereby generating glucose.

| glucoamylase incubation: | |
|---|---|
| Substrate: | maltose 100 mM |
| Buffer: | acetate 0.1M |
| pH: | 4.30 ± 0.05 |
| Incubation temperature: | 37° C. ± 1 |
| Reaction time: | 6 minutes |
| Enzyme working range: | 0.5-4.0 AGU/mL |

The analysis principle is described by 3 reaction steps:

Step 1 is an enzyme reaction:

Glucoamylase (AMG), EC 3.2.1.3 (exo-alpha-1,4-glucan-glucohydrolase), hydrolyzes maltose to form alpha-D-glucose. After incubation, the reaction is stopped with NaOH.

Steps 2 and 3 result in an endpoint reaction:

Glucose is phosphorylated by ATP, in a reaction catalyzed by hexokinase. The glucose-6-phosphate formed is oxidized to 6-phosphogluconate by glucose-6-phosphate dehydrogenase. In this same reaction, an equimolar amount of NAD+ is reduced to NADH with a resulting increase in absorbance at 340 nm. An autoanalyzer system such as Konelab 30 Analyzer (Thermo Fisher Scientific) may be used.

| Colour reaction | |
|---|---|
| Tris | approx. 35 mM |
| ATP | 0.7 mM |
| $NAD^+$ | 0.7 mM |
| $Mg^{2+}$ | 1.8 mM |
| Hexokinase | >850 U/L |
| Glucose-6-P-DH | >850 U/L |
| pH | approx. 7.8 |
| Temperature | 37.0° C. ± 1.0 ° C. |
| Reaction time | 420 sec |
| Wavelength | 340 nm |

Acid Alpha-Amylase Activity

When used according to the present invention the activity of any acid alpha-amylase may be measured in AFAU (Acid Fungal Alpha-amylase Units). Alternatively activity of acid alpha-amylase may be measured in KNU-s (Kilo Novozymes Units (Termamyl SC)).

Acid Alpha-Amylase Activity (AFAU)

Acid alpha-amylase activity may be measured in AFAU (Acid Fungal Alpha-amylase Units). 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

STARCH + IODINE —ALPHA-AMYLASE / 40°, pH 2.5 / t = 23 sec.→ DEXTRINS + OLIGOSACCHARIDES $\lambda$ = 590 nm blue/violet color less

| Standard conditions/reaction conditions: | |
|---|---|
| Substrate: | Soluble starch, approx. 0.17 g/L |
| Buffer: | Citrate, approx. 0.03M |
| Iodine ($I_2$): | 0.03 g/L |
| $CaCl_2$: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

Example 1: Construction of Glucoamylase Libraries

Glucoamylase libraries were constructed as follows: A forward or reverse primer having NNK or desired mutation(s) at target site(s) with 15 bp overlaps each other were designed. Inverse PCR, which means amplification of entire plasmid DNA sequences by inversely directed primers, were carried out with appropriate template plasmid DNA (e.g. plasmid DNA containing JPO-0001 gene (SEQ ID NO: 5) by the following conditions. The resultant PCR fragments were purified by QIAquick Gel extraction kit [QIAGEN], and then introduced into *Escherichia coli* ECOS Competent *E. coli* DH5a [NIPPON GENE CO., LTD.]. The plasmid DNAs were extracted from *E. coli* transformants by MagExtractor plasmid extraction kit [TOYOBO], and then introduced into *A. niger* competent cells.

PCR reaction mix:

PrimeSTAR Max DNA polymerase [TaKaRa]

Total 25 μl 1.0 μl Template DNA (1 ng/μl)

9.5 μl $H_2O$ 12.5 μl 2×PrimeSTAR Max pre-mix 1.0 μl Forward primer (5 μM)

1.0 μl Reverse primer (5 μM)

PCR program: 98° C./2 min, 25×(98° C./10 sec, 60° C./15 sec, 72° C./2 min); 10° C./hold

Example 2: Relative Activity of Variant(s) Compared to Parent

*Aspergillus niger* libraries constructed as in Example 1 were fermented in either 96-well or 24-well MTP containing COVE liquid medium (2.0 g/L sucrose, 2.0 g/L iso-maltose, 2.0 g/L maltose, 4.9 mg/L, 0.2 ml/L 5N NaOH, 10 ml/L COVE salt, 10 ml/L 1M acetamide), 32° C. for 3 days. Then, AMG activities in culture supernatants were measured at several temperatures by pNPG assay.

pNPG Thermostability Assay

The culture supernatants containing desired variants was mixed with same volume of pH 5.0 200 mM NaOAc buffer. Twenty microliters of this mixture were dispensed into either 96-well plate or 8-strip PCR tube, and then heated by thermal cycler at various temperatures for 30 min. These samples were mixed with 10 μl of substrate solution containing 0.1% (w/v) pNPG [wako] in pH 5.0 200 mM NaOAc buffer and incubated at 70° C. for 20 min for enzymatic reaction. After the reaction, 60 μl of 0.1M Borax buffer was added to stop the reaction. Eighty microliter of reaction supernatant was taken out and its $OD_{405}$ value was read by photometer to evaluate the enzyme activity.

All variants according to the present invention were derived from the PE001 as the parent glucoamylase and disclosed in SEQ ID NO: 1.

TABLE 1a

Relative activity of variants when compared with glucoamylase of SEQ ID NO: 1 and/or SEQ ID NO: 4.

| JPO-AMG | Variant | Relative activity of 80° C./75° C. (%) |
|---|---|---|
| AnPav498 (SEQ ID NO: 4) | — | 17% |
| JPO-004 | S103N | 32% |

| JPO-AMG | Variant | Relative activity of 80° C./75° C. (%) |
|---|---|---|
| AnPav498 (SEQ ID NO: 4) | — | 13% |
| JPO-009 | D445N + V447S | 16% |
| JPO-011 | K455N + A457T | 15% |
| JPO-012 | D566S | 15% |
| JPO-013 | D566T | 17% |
| JPO-020 | Y504T | 20% |

| JPO-AMG | Variant | Relative activity of 80° C./75° C. (%) |
|---|---|---|
| JPO-001 (SEQ ID NO: 1) | | 10% |
| JPO-004 | S103N | 29% |
| JPO-009 | D445N + V447S | 13% |
| JPO-014 | K34Y | 21% |
| JPO-020 | Y504T | 16% |
| JPO-021 | Q594R + F595S | 30% |
| JPO-052 | S105L | 33% |

| JPO-AMG | Variant | Relative activity of 79° C./70° C. (%) |
|---|---|---|
| JPO-001 (SEQ ID NO: 1) | | 23% |
| JPO-021 | Q594R + F595S | 46% |
| JPO-022 | K34Y + D445N + V447S | 39% |
| JPO-023 | K34Y + S103N | 44% |
| JPO-025 | K34Y Y504T | 51% |
| JPO-027 | S103N Y504T | 49% |
| JPO-029 | K34Y S103N D445N V447S | 37% |

TABLE 1a-continued

Relative activity of variants when compared with glucoamylase of SEQ ID NO: 1 and/or SEQ ID NO: 4.

| JPO-AMG | Variant | Relative activity of 77° C./70° C. (%) |
|---|---|---|
| JPO-001 (SEQ ID NO: 1) | | 72% |
| JPO-029 | K34Y + S103N + D445N + V447S | 82% |
| JPO-047 | K34Y + S103N +Y504T | 80% |
| JPO-048 | K34Y + S103N + D445N + V447S + D566T | 90% |
| JPO-049 | K34Y + S103N + Q594R + F595S | 84% |
| JPO-050 | K34Y + S103N + Y504T + Q594R + F595S | 86% |
| JPO-064 | K34Y + S103N + S105L + D445N + V447S + D566T + Q594R + F595S | 87% |

| JPO-AMG | Variant | Relative activity of 79° C./77° C. (%) |
|---|---|---|
| JPO-001 (SEQ ID NO: 1) | | 36% |
| JPO-029 | K34Y + S103N + D445N + V447S | 51% |
| JPO-047 | K34Y + S103N + Y504T | 45% |
| JPO-048 | K34Y + S103N + D445N + V447S + D566T | 81% |
| JPO-049 | K34Y + S103N + Q594R + F595S | 53% |
| JPO-050 | K34Y + S103N + Y504T + Q594R + F595S | 58% |
| JPO-064 | K34Y + S103N + S105L + D445N + V447S + D566T + Q594R + F595S | 65% |

| JPO-AMG | Variant | Relative activity of 79° C./77° C. (%) |
|---|---|---|
| JPO-001 (SEQ ID NO: 1) | | 41% |
| JPO-021 | Q594R + F595S | 60% |
| JPO-022 | K34Y + D445N + V447S | 48% |
| JPO-023 | K34Y + S103N | 57% |
| JPO-025 | K34Y + Y504T | 56% |
| JPO-027 | S103N +Y504T | 64% |
| JPO-029 | K34Y + S103N + D445N + V447S | 66% |
| JPO-047 | K34Y + S103N + Y504T | 50% |
| JPO-048 | K34Y + S103N + D445N + V447S + D566T | 72% |
| JPO-051 | K34Y + S103N + D445N + V447S + Y504T + Q594R + F595S | 82% |
| JPO-058 | K34Y + S105L + Y504T + Q594R + F595S | 73% |
| JPO-062 | K34Y + S103N + S105L + D445N + V447S + Y504T + D566T + Q594R + F595S | 72% |
| JPO-063 | K34Y + S103N + S105L + A132R + D445N + V447S + Y504T + D566T + Q594R + F595S | 85% |
| JPO-064 | K34Y + S103N + S105L + D445N + V447S + D566T + Q594R + F595S | 83% |

TABLE 1b

List of the relative activity of JPO-AMG variants when compared to JPO-022

| JPO-AMG | Variant | Relative activity of 77° C./70° C. (%) |
|---|---|---|
| JPO-022 | K34Y + D445N + V447S | 60% |
| JPO-027 | S103N + Y504T | 67% |

TABLE 1b-continued

List of the relative activity of JPO-AMG variants when compared to JPO-022

| | | |
|---|---|---|
| JPO-044 | K34Y + S103N + D445N + V447S + E501V + Y504T | 86% |
| JPO-045 | K34Y + 182E + D83T + R84V + K85T + Y86L + L87V + S103N + D445N + V447S | 67% |
| JPO-046 | K34Y + D75S + R77D + A78Q + V79Q + F80D + P81Y + D83S + S103N + D445N + V447S | 48% |
| JPO-022 | K34Y + D445N + V447S | 76% |
| JPO-025 | K34Y + Y504T | 80% |
| JPO-027 | S103N + Y504T | 84% |
| JPO-058 | K34Y + S105L + Y504T + Q594R + F595S | 92% |
| JPO-059 | K34Y + S103N + S105L + Y504T + Q594R + F595S | 88% |
| JPO-060 | K34Y + S103N + S105L + Y504T + Q594R + F595S | 86% |
| JPO-061 | K34Y + S103N + S105L + Y504T + D566T + Q594R + F595S | 83% |
| JPO-062 | K34Y + S103N + S105L + D445N + V447S + Y504T + D566T + Q594R + F595S | 87% |

| JPO-AMG | Variant | Relative activity of 79° C./77° C. (%) |
|---|---|---|
| JPO-022 | K34Y + D445N + V447S | 49% |
| JPO-023 | K34Y + S103N | 51% |
| JPO-025 | K34Y + Y504T | 52% |
| JPO-027 | S103N + Y504T | 58% |
| JPO-058 | K34Y + S105L + Y504T + Q594R + F595S | 69% |
| JPO-062 | K34Y + S103N + S105L + D445N + V447S + Y504T + D566T + Q594R + F595S | 57% |

TABLE 1c

List of the relative activity of JPO-AMG variants when compared to JPO-063

| JPO-AMG | Variant | Relative activity of 79° C./77° C. (%) |
|---|---|---|
| JPO-063 | K34Y + S103N + S105L + A132R + D445N + V447S + Y504T + D566T + Q594R + F595S | 91% |
| JPO-066 | K34Y + S103N + A132R + D445N + V447S + Y504T + D566T + Q594R + F595S | 96% |
| JPO-074 | K34Y + S103N + P107L + A132R + D445N + V447S + Y504T + D566T + Q594R + F595S | 103% |
| JPO-076 | K34Y + S103N + S105L + S130T + A132R + D445N + V447S + Y504T + D566T + Q594R + F595S | 92% |
| JPO-077 | K34Y + S103N + S105L + A132R + D445N + V447S + Y504T + A523T + K524N + K525N + D566T + Q594R + F595S | 95% |
| JPO-079 | K34Y + S103N + S105L + A132R + D445N + V447S + Y504T + D566T + T568V + Q594R + F595S | 100% |

| JPO-AMG | Variant | Relative activity of 84° C./80° C. (%) |
|---|---|---|
| JPO-063 | K34Y + S103N + S105L + A132R + D445N + V447S + Y504T + D566T + Q594R + F595S | 16% |
| JPO-065 | K34Y + S103N + S105L + A132R + D445N + V447S + E501V + Y504T + D566T + Q594R + F595S | 26% |
| JPO-067 | K34Y + S103N + S105L + A132R + K244S + D445N + V447S + Y504T + D566T + Q594R + F595S | 21% |
| JPO-074 | K34Y + S103N + P107L + A132R + D445N + V447S + Y504T + D566T Q594R + F595S | 32% |
| JPO-081 | K34Y + S103N + S105L + D445N + V447S + Y504T + D566T + Q594R + F595S | 17% |
| JPO-082 | K34Y + S103N + S105L + A132P + D445N + V447S + Y504T + D566T + Q594R + F595S | 24% |
| JPO-083 | G6S + G7T + K34Y + S103N + P107L A132R + D445N + V447S + Y504T D566T + Q594R + F595S | 46% |
| JPO-084 | G6S + G7T + K34Y + S103N + P107L A132R + D445N + V447S + Y504T D566T + V592T + Q594R + F595S | 26% |
| JPO-044 | K34Y + S103N + D445N + V447S + E501V + Y504T | 37% |

TABLE 1c-continued

List of the relative activity of JPO-AMG variants when compared to JPO-063

| JPO-AMG | Variant | Relative activity of 82° C./70° C. (%) |
|---|---|---|
| JPO-063 | K34Y + S103N + S105L + A132R + D445N + V447S + Y504T + D566T + Q594R + F595S | 21% |
| JPO-093 | G6S + G7T + K34Y + S103N + P107L A132P + D445N + V447S + Y504T D566T + T568V + Q594R + F595S | 43% |
| JPO-081 | K34Y + S103N + S105L + D445N + V447S + Y504T + D566T + Q594R + F595S | 25% |
| JPO-088 | G6S + G7T + K34Y + S103N + P107L A132R + D445N + V447S + S481P + Y504T+ D566T + Q594R + F595S | 39% |
| JPO-094 | G6S + G7T + K34Y + S103N + P107L A132R + D445N + V447S + S481P Y504T + D566T + Q594R + F595S | 38% |
| JPO-096 | G6S + G7T + K34Y + S103N + P107L + A132P + D445N + V447S + D566T T568V + Q594R + F595S | 38% |
| JPO-106 | G6S + G7T + R31F + K34Y + S103N P107L + A132P + D445N + V447S Y504T + D566T + T568V + Q594R + F595S | 53% |

| JPO-AMG | Variant | Relative activity of 83° C./80° C. (%) |
|---|---|---|
| JPO-063 | K34Y + S103N + S105L + A132R + D445N + V447S + Y504T + D566T + Q594R + F595S | 46% |
| JPO-096 | G6S + G7T + K34Y + S103N + P107L + A132P + D445N + V447S + D566T + T568V + Q594R + F595S | 64% |
| JPO-106 | G6S + G7T + R31F + K34Y + S103N + P107L + A132P + D445N + V447S + Y504T + D566T + T568V + Q594R + F595S | 88% |
| JPO-110 | G6S + G7T + K34Y + S103N + P107L + A132R + D445N + V447S + S481P + E501V + Y504T + D566T + T568V + Q594R + F595S | 81% |
| JPO-111 | G6S + G7T + R31F + K34Y + S103N + P107L + A132P + D445N + V447S + S481P + E501V + Y504T + D566T + T568V + Q594R + F595S | 100% |

TABLE 1c-continued

| List of the relative activity of JPO-AMG variants when compared to JPO-063 | | |
|---|---|---|
| JPO-112 | G6S + G7T + R31F + K34Y + S103N + P107L + A132P + D445N + V447S + S481P + D566T + T568V + Q594R + F595S | 86% |
| JPO-113 | G6S + G7T + K34Y + E50R + S103N + P107L + A132P + D445N + V447S + S481P + D566T + T568V + Q594R + F595S | 83% |
| JPO-114 | K34Y + D75N + R77D + A78Q + S103N + R138L + D445N + V447S + Y504T + Q594R + F595S | 47% |
| JPO-115 | G6S + G7T + R31F + K34Y + D75N + R77D + A78Q + S103N + P107L + A132P + D445N + V447S + S481P + Y504T+ D566T + T568V + Q594R + F595S | 90% |

TABLE 1e

Relative activity of JPO-AMG variants when compared to JPO-129

| JPO-AMG | Variant | Relative activity of 84° C./80° C. (%) |
|---|---|---|
| JPO-129 | G6S + G7T + R31F + K34Y + E50R + S103N + A132P + D445N + V447S + S481P + D566T + T568V + Q594R + F595S | 62% |
| JPO-156 | G6S + G7T + R31F + K34Y + S103N + A132P + R138P + D445N + V447S + S481P + D566T + T568V + Q594R + F595S | 51% |
| JPO-165 | G6S + G7T + R31F + K34Y + E50R + S103N + A132P + D445N + V447S + S481P + E501A + D566T + T568V + Q594R + F595S | 77% |

TABLE 1d

List of the relative activity of JPO-AMG variants when compared to JPO-096

| JPO-AMG | Variant | Relative activity of 83° C./70° C. (%) |
|---|---|---|
| JPO-088 | G6S + G7T + K34Y + S103N + P107L + A132R + D445N + V447S + S481P + Y504T + D566T + Q594R + F595S | 70% |
| JPO-091 | G6S + G7T + K34Y + S103N + P107L + A132P + D445N + V447S + Y504T + D566T + Q594R + F595S | 69% |
| JPO-092 | G6S + G7T + K34Y + S103N + P107L + A132R + D445N + V447S + Y504T + D566T + T568V + Q594R + F595S | 65% |
| JPO-093 | G6S + G7T + K34Y + S103N + P107L + A132P + D445N + V447S + Y504T + D566T + T568V + Q594R + F595S | 62% |
| JPO-094 | G6S + G7T + K34Y + S103N + P107L + A132R + D445N + V447S + S481P + Y504T + D566T + Q594R + F595S | 74% |
| JPO-095 | G6S + G7T + K34Y + S103N + P107L + A132R + D445N + V447S + S481P + Y504T + D566T + T568V + Q594R + F595S | 69% |
| JPO-096 | G6S + G7T + K34Y + S103N + P107L + A132P + D445N + V447S + D566T + T568V + Q594R + F595S | 67% |
| JPO-097 | G6S + G7T + K34Y + S103N + P107L + T110W + A132P + D445N + V447S + Y504T + D566T + T568V + Q594R + F595S | 65% |
| JPO-098 | G6S + G7T + K34Y + E50R + S103N + P107L + A132P + D445N + V447S + Y504T + D566T + T568V + Q594R + F595S | 65% |

| JPO-AMG | Variant | Relative activity of 83° C./80° C. (%) |
|---|---|---|
| JPO-096 | G6S + G7T + K34Y + S103N + P107L + A132P + D445N + V447S + D566T + T568V + Q594R + F595S | 43% |
| JPO-109 | G6S + G7T + K34Y + E50R + S103N + P107L + A132P + D445N + V447S + S481P + Y504T + D566T + T568V + Q594R + F595S | 51% |
| JPO-129 | G6S + G7T + R31F + K34Y + E50R + S103N +A132P + D445N +V447S + S481P + D566T + T568V + Q594R + F595S | 48% |
| JPO-131 | G6S + G7T + R31F + K34Y + E50R + D75N + R77D + A78Q + S103N + A132P + D445N + V447S + S481P + D566T + Q594R + F595S | 51% |

TABLE 1f

Relative activity of JPO-AMG variants when compared to JPO-166

| JPO-AMG | Variant | Relative activity of 84° C./75° C. (%) |
|---|---|---|
| JPO-166 | G6S + G7T + R31F + K33P + K34Y + E50R + S103N + A132P + D445N + V447S + S481P + D566T + T568V + Q594R + F595S | 19% |
| JPO-167 | G6S + G7T + R31F + K34Y + E50R + S103N + A132P + S379P + D445N + V447S + S481P + E501A + D566T + T568V + Q594R + F595S | 66% |
| JPO-168 | G6S + G7T + R31F + K34Y + E50R + S103N + A132P + D445N + V447S + S481P + T484P + E501A + D566T + T568V + Q594R + F595S | 58% |
| JPO-169 | G6S + G7T + R31F + K34Y + E50R + S103N + A132P + D445N + V447S + S481P + E501A + N539P + D566T + T568V + Q594R + F595S | 53% |
| JPO-171 | G6S + G7T + R31F + K34Y + E50R + S103N + A132P + S379P + D445N + V447S + S481P + T484P + E501A + D566T + T568V + Q594R + F595S | 47% |
| JPO-172 | G6S + G7T + R31F + K34Y + E50R + S103N + A132P + D445N + V447S + S481P + T484P + E501A + N539P + D566T + T568V + Q594R + F595S | 98% |

Example 3: Fermentation of the *Aspergillus* Niger

*Aspergillus niger* strains were fermented on a rotary shaking table in 500 ml baffled flasks containing 100 ml MU1 with 4 ml 50% urea at 220 rpm, 30° C. The culture broth was centrifuged (10,000×g, 20 min) and the supernatant was carefully decanted from the precipitates.

Example 4: Purification of JPO-AMG

PoAMG variant was purified by cation exchange chromatography. The peak fractions were pooled and dialyzed against 20 mM sodium acetate buffer pH 5.0, and then the sample was concentrated using a centrifugal filter unit (Vivaspin Turbo 15, Sartorius). Enzyme concentrations were determined by A280 value.

Example 5: Thermostability Determination (TSA, Thermal Shift Assay)

Purified variants were diluted with 50 mM sodium acetate buffer pH 5.0 to 0.5 mg/ml and mixed with equal volume of SYPRO Orange (Invitrogen) diluted with Milli-Q water. 18 ul of mixture solution were transfer to LightCycler 480 Multiwell Plate 384 (Roche Diagnostics) and the plate was sealed.

Equipment parameters of TSA:

Apparatus: LightCycler 480 Real-Time PCR System (Roche *Applied Science*)

Scan rate: 0.02° C./sec

Scan range: 37-96° C.

Integration time: 1.0 sec

Excitation wave length 465 nm

Emission wave length 580 nm

The obtained fluorescence signal was normalized into a range of 0 and 1. The Td was defined as the temperature at which the signal intensity was 0.5. The thermostability improvements are listed in TABLE 3 with Td of anPAV498 (SEQ ID NO: 4) as 0 and JPO-001 (SEQ ID NO:3) as 1.0.

Example 6: JPO-AMG Assay maltodextrin (DE11) assay by GOD-POD method: Substrate solution: 30 g maltodextrin (pindex #2 from MATSUTANI chemical industry Co., Ltd.). 100 ml 120 mM sodium acetate buffer, pH 5.0. Glucose CII test kit (Wako Pure Chemical Industries, Ltd.). 20 ul of enzyme samples were mixed with 100 ul of substrate solution and incubated at set temperatures for 2 hours. The samples were cooled down on the aluminum block for 3 min then 10 ul of the reaction solution was mixed with 590 ul of 1 M Tris-HCl pH 8.0 to stop reaction. 10 ul of the solution was mixed with 200 ul of the working solution of the test kit then stand at room temperature for 15 min. The absorbance at A505 was read. The activities are listed in TABLE 3 as relative activity to that of anPAV498 (SEQ ID NO:5).

TABLE 3

| JPO-AMG name | Variant | Td improvement [° C.] (pH5.0, anPAV498 as 0) | Activity at 91° C. (anPAV4 98 as 100) |
|---|---|---|---|
| anPAV498 (SEQ ID NO: 4) | — | — | 100 |
| JPO-001 | | 1.0 | 94 |
| JPO-004 | S103N | 2.2 | — |
| JPO-009 | D445N + V447S | 0.7 | — |
| JPO-013 | D566T | 1.5 | — |

TABLE 3-continued

| JPO-AMG name | Variant | Td improvement [° C.] (pH5.0, anPAV498 as 0) | Activity at 91° C. (anPAV498 as 100) |
|---|---|---|---|
| JPO-014 | K34Y | 2.3 | — |
| JPO-020 | Y504T | 1.4 | 74 |
| JPO-021 | Q594R + F595S | 2.5 | 113 |
| JPO-052 | S105L | 2.6 | 85 |
| JPO-055 | A132R | 1.6 | 85 |
| JPO-023 | K34Y + S103N | 3.6 | — |
| JPO-024 | K34Y + D445N + V447S | 2.5 | — |
| JPO-025 | K34Y + Y504T | 3.4 | — |
| JPO-027 | S103N + Y504T | 2.9 | — |
| JPO-029 | K34Y + S103N + D445N + V447S | 3.7 | 191 |
| JPO-048 | K34Y + S103N + D445N + V447S + D566T | 4.3 | 163 |
| JPO-051 | K34Y + S103N + D445N + V447S + Y504T + Q594R + F595S | 5.7 | 222 |
| JPO-058 | K34Y + S105L + Y504T + Q594R + F595S | 4.2 | 157 |
| JPO-062 | K34Y + S103N +S105L + D445N + V447S + Y504T + D566T + Q594R + F595S | 4.2 | 159 |
| JPO-063 | K34Y + S103N + S105L + A132R + D445N + V447S + Y504T + D566T + Q594R + F595S | 5.4 | 107 |
| JPO-064 | K34Y + S103N + S105L + D445N + V447S + D566T + Q594R + F595S | 4.9 | 178 |
| JPO-065 | K34Y + S103N + S105L + A132R + D445N + V447S + E501V + Y504T + D566T + Q594R + F595S | 7.0 | 127 |
| JPO-066 | K34Y + S103N + A132R + D445N + V447S + Y504T + D566T + Q594R + F595S | 6.5 | 178 |
| JPO-069 | K34Y + S103N + S105L + A132R + D445N + V447S + Y504T + D566T + V592T | 4.8 | 95 |
| JPO-071 | G6S + G7T + K34Y + S103N + S105L + A132R + D445N + V447S + Y504T + D566T + Q594R + F595S | 6.1 | 128 |
| JPO-074 | K34Y + S103N + P107L + A132R + D445N + V447S + Y504T + D566T + Q594R + F595S | 6.3 | 108 |
| JPO-081 | K34Y + S103N + S105L + D445N + V447S + Y504T + D566T + Q594R + F595S | 5.5 | 213 |
| JPO-082 | K34Y + S103N + S105L + A132P + D445N + V447S + Y504T + D566T + Q594R + F595S | 5.6 | 215 |
| JPO-089 | K34Y + S103N + T110W + A132R + D445N + V447S + Y504T + D566T + Q594R + F595S | 6.0 | 171 |
| JPO-090 | K34Y + E50R + S103N + S105L + A132R + D445N + V447S + Y504T + D566T + Q594R + F595S | 5.5 | 155 |
| JPO-018 | D75N + R77D + A78Q | 0.6 | 84 |
| JPO-019 | D75S + R77G + A78W + V79D + F80Y | 0.5 | 86 |
| JPO-044 | K34Y + S103N + D445N + V447S + E501V + Y504T | 6.3 | 225 |
| JPO-083 | G6S + G7T + K34Y + S103N + P107L + A132R + D445N + V447S + Y504T + D566T + Q594R + F595S | 6.1 | 103 |
| JPO-084 | G6S + G7T + K34Y + S103N + P107L + A132R + D445N + V447S + Y504T + D566T + V592T + Q594R + F595S | 4.4 | 66 |
| JPO-099 | R31F + K34Y + S103N + S105L + A132R + D445N + V447S + Y504T + D566T + Q594R + F595S | 6.8 | 156 |
| JPO-091 | G6S + G7T + K34Y + S103N + P107L + A132P + D445N + V447S + Y504T + D566T + Q594R + F595S | 6.6 | 130 |
| JPO-092 | G6S + G7T + K34Y + S103N + P107L + A132R + D445N + V447S + Y504T + D566T + T568V + Q594R + F595S | 6.7 | 113 |
| JPO-093 | G6S + G7T + K34Y + S103N + P107L + A132P + D445N + V447S + Y504T + D566T + T568V + Q594R + F595S | 6.8 | 132 |
| JPO-094 | G6S + G7T + K34Y + S103N + P107L + A132R + D445N + V447S + S481P + Y504T + D566T + Q594R + F595S | 6.6 | 126 |
| JPO-095 | G6S + G7T + K34Y + S103N + P107L + A132R + D445N + V447S + S481P + Y504T + D566T + T568V + Q594R + F595S | 6.9 | — |
| JPO-096 | G6S + G7T + K34Y + S103N + P107L + A132P + D445N + V447S + D566T + T568V + Q594R + F595S | 5.9 | — |
| JPO-097 | G6S + G7T + K34Y + S103N + P107L + T110W + A132P + D445N + V447S + Y504T + D566T + T568V + Q594R + F595S | 5.2 | — |

TABLE 3-continued

| JPO-AMG name | Variant | Td improvement [° C.] (pH5.0, anPAV498 as 0) | Activity at 91° C. (anPAV4 98 as 100) |
|---|---|---|---|
| JPO-098 | G6S + G7T + K34Y + E50R + S103N + P107L + A132P + D445N + V447S + Y504T + D566T + T568V + Q594R + F595S | 5.6 | — |
| JPO-112 | G6S + G7T + R31F + K34Y + S103N + P107L + A132P + D445N + V447S + S481P + D566T + T568V + Q594R + F595S | 8.2 | — |
| JPO-114 | K34Y + D75N + R77D + A78Q + S103N + R138L + D445N + V447S + Y504T + Q594R + F595S | 5.2 | 218 |
| JPO-115 | G6S + G7T + R31F + K34Y + D75N + R77D + A78Q + S103N + P107L + A132P + D445N + V447S + S481P + Y504T + D566T + T568V + Q594R + F595S | 8.0 | — |
| JPO-108 | G6S + G7T + R31F + K34Y + S103N + P107L + A132P + D445N + V447S + S481P + Y504T + D566T + T568V + Q594R + F595S | 8.5 | — |
| JPO-109 | G6S + G7T + K34Y + E50R + S103N + P107L + A132P + D445N + V447S + S481P + Y504T + D566T + T568V + Q594R + F595S | 7.2 | — |
| JPO-111 | G6S + G7T + R31F + K34Y + S103N + P107L + A132P + D445N + V447S + S481P + E501V + Y504T + D566T + T568V + Q594R + F595S | 8.4 | — |
| JPO-124 | G6S + G7T + R31F + K34Y + S103N + A132P + D445N + V447S + S481P + D566T + T568V + Q594R + F595S | 8.0 | 385 |
| JPO-125 | G6S + G7T + K34Y + E50R + S103N + A132P + D445N + V447S + S481P + D566T + T568V + Q594R + F595S | 6.8 | 324 |
| JPO-126 | R31F + K34Y + D75N + R77D + A78Q + S103N + R138L + D445N + V447S + Y504T + Q594R + F595S | 6.6 | 268 |
| JPO-127 | K34Y + D75N + R77D + A78Q + S103N + R138L + D445N + V447S + Q594R + F595S | 4.9 | 246 |
| JPO-129 | G6S + G7T + R31F + K34Y + E50R + S103N + A132P + D445N + V447S + S481P + D566T + T568V + Q594R + F595S | 8.2 | 399 |
| JPO-130 | K34Y + E50R + D75N + R77D + A78Q + S103N + R138L + D445N + V447S + Q594R + F595S | 5.3 | 278 |
| JPO-131 | G6S + G7T + R31F + K34Y + E50R + D75N + R77D + A78Q + S103N + A132P + D445N + V447S + S481P + D566T + Q594R + F595S | 7.9 | 367 |
| JPO-132 | R31F + K34Y + E50R + D75N + R77D + A78Q + S103N + R138L + D445N + V447S + Q594R + F595S | 6.6 | 336 |
| JPO-138 | G6S + G7T + K34Y + S103N + P107L + A132P + R135S + D445N + V447S + D566T + T568V + Q594R + F595S | 6.4 | 125 |
| JPO-133 | G6S + G7T + R31F + K34Y + E50R + D75N + R77D + A78Q + S103N + A132P + R138L + D445N + V447S + S481P + D566T + Q594R + F595S | 6.1 | 143 |
| JPO-143 | G6S + G7T +R31F +K34Y +E50R + S103N + A132P + D445N + V447S + S481P + E501L + D566T + T568V +Q594R + F595S | 8.8 | 280 |
| JPO-154 | G6S + G7T + R31F + K34Y + S103N + A132P + R138G + D445N + V447S + S481P + D566T + T568V + Q594R + F595S | 7.6 | 252 |
| JPO-155 | G6S + G7T + R31F + K34Y + S103N + A132P + R138L + D445N + V447S + S481P + D566T + T568V + Q594R + F595S | 8.3 | 282 |
| JPO-156 | G6S + G7T + R31F + K34Y + S103N + A132P + R138P + D445N + V447S + S481P + D566T + T568V + Q594R + F595S | 8.3 | 290 |
| JPO-145 | G6S + G7T + R31F + K34Y + S103N + A132P + A287P + D445N + V447S + S481P + D566T + T568V + Q594R + F595S | 8.2 | — |
| JPO-147 | G6S + G7T + R31F + K34Y + S103N + A132P + S364P + D445N + V447S + S481P + D566T + T568V + Q594R + F595S | 8.2 | — |
| JPO-150 | G6S + G7T + R31F + K34Y + S103N + A132P + S379P + D445N + V447S + S481P + D566T + T568V + Q594R + F595S | 8.2 | — |
| JPO-152 | G6S + G7T + R31F + K34Y + S103N + A132P + D445N + V447S + S481P + A523P + D566T + T568V + Q594R + F595S | 8.4 | — |

TABLE 3-continued

| JPO-AMG name | Variant | Td improvement [° C.] (pH5.0, anPAV498 as 0) | Activity at 91° C. (anPAV4 98 as 100) |
|---|---|---|---|
| JPO-153 | G6S + G7T + R31F + K34Y + S103N + A132P + D445N + V447S + S481P + N539P + D566T + T568V + Q594R + F595S | 9.0 | 399 |
| JPO-161 | G6S + G7T + R31F + K34Y + E50R + S103N + A132P + R138P + D445N + V447S + S481P + D566T + T568V + Q594R + F595S | 6.0 | 200 |
| JPO-165 | G6S + G7T + R31F + K34Y + E50R + S103N + A132P + D445N + V447S + S481P + E501A + D566T + T568V + Q594R + F595S | 8.9 | 403 |
| JPO-166 | G6S + G7T + R31F + K33P + K34Y + E50R + S103N + A132P + D445N + V447S + S481P + D566T + T568V + Q594R + F595S | 7.0 | 237 |
| JPO-167 | G6S + G7T + R31F + K34Y + E50R + S103N + A132P + S379P + D445N + V447S + S481P + E501A + D566T + T568V + Q594R + F595S | 9.1 | 387 |
| JPO-168 | G6S + G7T + R31F + K34Y + E50R + S103N + A132P + D445N + V447S + S481P + T484P + E501A + D566T + T568V + Q594R + F595S | 9.3 | 332 |
| JPO-169 | G6S + G7T + R31F + K34Y + E50R + S103N + A132P + D445N + V447S + S481P + E501A + N539P + D566T + T568V + Q594R + F595S | 9.6 | 269 |
| JPO-171 | G6S + G7T + R31F + K34Y + E50R + S103N + A132P + S379P + D445N + V447S + S481P + T484P + E501A + D566T + T568V + Q594R + F595S | 9.4 | 255 |
| JPO-172 | G6S + G7T + R31F + K34Y + E50R + S103N + A132P + D445N + V447S + S481P + T484P + E501A + N539P + D566T + T568V + Q594R + F595S | 9.9 | 432 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A glucoamylase variant having improved thermostability, comprising a substitution at one or more positions corresponding to positions: 50, 484, and 539 of SEQ ID NO: 1, wherein the substitution at position 50 is to an arginine, and wherein said variant has at least 80% but less than 100% sequence identity to the polypeptide of SEQ ID NOs: 1, 4, or 6.

2. The glucoamylase variant according to claim 1, wherein the variant further comprises a substitution in one or more positions corresponding to positions 11, 75, 77, 78, 79, 80, 103, 105, 107, 110, 135, 138, 379, 445, 504, 566, 594 of SEQ ID NO: 1.

3. The glucoamylase variant according to claim 1, wherein the variant further comprises a substitution at one or more positions corresponding to positions: 6, 7, 11, 31, 34, 75, 77, 78, 79, 80, 103, 105, 107, 110, 132, 135, 138, 379, 445, 447, 501, 504, 566, 568 592, 594, of SEQ ID NO: 1; and wherein said variant has at least 80% but less than 100% sequence identity to the polypeptide of SEQ ID NOs: 1, 4, or 6.

4. The glucoamylase variant according to claim 1, wherein said improved thermostability as measured by a Thermal Shift Assay (TSA) as increased melting temperature of at least 0.1° C., at least 0.2° C., at least 0.3° C., at least 0.4° C., at least 0.5° C., at least 0.6° C., at least 0.7° C., at least 0.8° C., at least 0.9° C., at least 1° C., at least 1.5° C., at least 2° C., at least 2.5° C., at least 3° C., at least 3.5° C., at least 4.0° C., at least 4.5° C. or of at least 1° C., at least 1.5° C., at least 2° C., at least 2.5° C., at least 3° C., at least 3.5° C., at least 4.0° C., at least 4.5° C. or at least 5° C. or at least 5.5° C. or at least 6° C. or at least 6.5° C. or at least 7° C. or at least 7.5° C. or at least 8° C. or at least 8.5° C. or at least 9° C. or at least 9.5° C. or at least 10° C. compared to said parent glucoamylase.

5. The glucoamylase variant according to claim 1, wherein variant have a relative activity at 91° C. of at least 150 compared to said parent glucoamylase.

6. The glucoamylase variant according to claim 1, wherein said further variant comprises one or more of the following substitutions at positions corresponding to positions: G6S, G7T, P11F, R31F, K34Y, D75N, D75S, R77D, R77G, A78Q, A78W, V79D, F80Y, S103N, S105E, S105L, P107L, T110W, A132P, A132R, R135S, R138G, R138L, R138P, S379P, D445N, V447S, S481P, E501A, E501L, E501V, Y504T, D566T, T568V, V592T, Q594R, F595S of SEQ ID NO: 1 and wherein said variant has at least 80% but less than 100% sequence identity to the polypeptide of SEQ ID NOs: 1, 4, or 6.

7. The variant according to claim 1, wherein the variant comprises at least one of the following substitutions or combinations of substitutions:

G6S+G7T+K34Y+E50R+S103N+P107L+A132P+D445N+V447S+Y504T+D566T+T568V+Q594R+F595S;

G6S+G7T+K34Y+E50R+S103N+P107L+A132P+D445N+V447S+S481P+Y504T+D566T+T568V+Q594R+F595S;

G6S+G7T+K34Y+E50R+S103N+A132P+D445N+V447S+S481P+D566T+T568V+Q594R+F595S;

G6S+G7T+R31F+K34Y+E50R+S103N+A132P+D445N+V447S+S481P+D566T+T568V+Q594R+F595S;

K34Y+E50R+D75N+R77D+A78Q+S103N+R138L+D445N+V447S+Q594R+F595S;

G6S+G7T+R31F+K34Y+E50R+D75N+R77D+A78Q+S103N+A132P+D445N+V447S+S481P+D566T+Q594R+F595S;

R31F+K34Y+E50R+D75N+R77D+A78Q+S103N+R138L+D445N+V447S+Q594R+F595S;

G6S+G7T+R31F+K34Y+E50R+D75N+R77D+A78Q+S103N+A132P+R138L+D445N+V447S+S481P+D566T+Q594R+F595S;

R135S;

G6S+G7T+R31F+K34Y+E50R+S103N+A132P+D445N+V447S+S481P+E501L+D566T+T568V+Q594R+F595S;

G6S+G7T+R31F+K34Y+E50R+S103N+A132P+S379P+D445N+V447S+S481P+E501A+D566T+T568V+Q594R+F595S;

G6S+G7T+R31F+K34Y+E50R+S103N+A132P+D445N+V447S+S481P+T484P+E501A+D566T+T568V+Q594R+F595S;

G6S+G7T+R31F+K34Y+E50R+S103N+A132P+D445N+V447S+S481P+E501A+N539P+D566T+T568V+Q594R+F595S;

G6S+G7T+R31F+K34Y+E50R+S103N+A132P+S379P+D445N+V447S+S481P+T484P+E501A+D566T+T568V+Q594R+F595S;

G6S+G7T+R31F+K34Y+E50R+S103N+A132P+D445N+V447S+S481P+T484P+E501A+N539P+D566T+T568V+Q594R+F595S of SEQ ID NO: 1 and, wherein the variant has glucoamylase activity and wherein said variant has at least 80% but less than 100% sequence identity to the polypeptide of SEQ ID NOs: 1, 4, or 6.

8. A polynucleotide or a nucleic acid construct or expression vector comprising glucoamylase variant of claim 1, wherein the polynucleotide is operably linked to one or more control sequences that direct the production of the polypeptide in an expression host.

9. A method of producing a glucoamylase variant of claim 1, comprising cultivating the recombinant host cell under conditions conducive for production of the variant and recovering the variant.

10. A composition comprising the variant of claim 1 and one or more additional enzymes.

11. A process of producing a fermentation product from starch-containing material comprising the steps of:

(a) liquefying starch-containing material in the presence of an alpha amylase;

(b) saccharifying the liquefied material; and (c) fermenting with a fermenting organism;

wherein step (a), step (b), and/or step (c) is carried out using at least a glucoamylase variant of claim 1.

12. A process of producing a fermentation product from starch-containing material, comprising the steps of:

(a) saccharifying starch-containing material at a temperature below the initial gelatinization temperature of said starch-containing material; and (b) fermenting with a fermenting organism, wherein step (a) and/or step (b) is carried out using at least a glucoamylase variant of claim 1.

13. A process for producing a fermentation product from a cellulosic-containing material comprising:

(a) pretreating a cellulosic-containing material;

(b) saccharifying a cellulosic-containing material and/or pretreated cellulosic-containing material using a carbohydrate-source generating enzyme; and (c) fermenting using a fermenting organism;

(d) wherein at least one or more glucoamylase variant(s) of claim 1 is present or added during saccharifying step (b) and/or fermenting step c).

14. The glucoamylase variant according to claim 1, wherein said variant comprises one or more of the following substitutions at positions corresponding to positions: T484P, and N539P of SEQ ID NO: 1 and wherein said variant has at least 80% but less than 100% sequence identity to the polypeptide of SEQ ID NOs: 1, 4, or 6.

15. The variant according to claim 1, wherein the variant has at least 85% but less than 100% sequence identity to the polypeptide of SEQ ID NOs: 1, 4, or 6.

16. The variant according to claim 1, wherein the variant has at least 90% but less than 100% sequence identity to the polypeptide of SEQ ID NOs: 1, 4, or 6.

* * * * *